US011866508B2

(12) United States Patent
Fanslow, III et al.

(10) Patent No.: US 11,866,508 B2
(45) Date of Patent: *Jan. 9, 2024

(54) ANTI-MESOTHELIN BINDING PROTEINS

(71) Applicant: AMGEN INC., Thousand Oaks, CA (US)

(72) Inventors: William Christian Fanslow, III, Normandy Park, WA (US); Carl Kozlosky, Bainbridge Island, WA (US); Jean Gudas, Fremont, CA (US)

(73) Assignee: AMGEN INC., Thousand Oaks, CA (US)

( * ) Notice: Subject to any disclaimer, the term of this patent is extended or adjusted under 35 U.S.C. 154(b) by 33 days.

This patent is subject to a terminal disclaimer.

(21) Appl. No.: 17/142,850

(22) Filed: Jan. 6, 2021

(65) Prior Publication Data

US 2021/0380714 A1 Dec. 9, 2021

Related U.S. Application Data

(63) Continuation of application No. 16/123,827, filed on Sep. 6, 2018, now Pat. No. 10,919,975, which is a continuation of application No. 15/141,463, filed on Apr. 28, 2016, now Pat. No. 10,100,121, which is a continuation of application No. 13/926,847, filed on Jun. 25, 2013, now abandoned.

(60) Provisional application No. 61/789,678, filed on Mar. 15, 2013, provisional application No. 61/665,139, filed on Jun. 27, 2012.

(51) Int. Cl.

| | |
|---|---|
| ***A61K 39/00*** | (2006.01) |
| ***C07K 16/30*** | (2006.01) |
| ***C07K 16/46*** | (2006.01) |
| ***G01N 33/68*** | (2006.01) |
| ***C07K 16/28*** | (2006.01) |

(52) U.S. Cl.

CPC .............. *C07K 16/30* (2013.01); *C07K 16/28* (2013.01); *C07K 16/2809* (2013.01); *C07K 16/3046* (2013.01); *C07K 16/468* (2013.01); *G01N 33/6893* (2013.01); *A61K 2039/505* (2013.01); *C07K 2317/21* (2013.01); *C07K 2317/31* (2013.01); *C07K 2317/33* (2013.01); *C07K 2317/622* (2013.01); *C07K 2317/72* (2013.01); *C07K 2317/732* (2013.01); *C07K 2317/734* (2013.01); *C07K 2317/92* (2013.01)

(58) Field of Classification Search

CPC .. C07K 16/30; C07K 2317/31; G01N 33/574; A61K 2039/505; A61P 35/00

See application file for complete search history.

(56) References Cited

U.S. PATENT DOCUMENTS

| | | | |
|---|---|---|---|
| 3,720,760 | A | 3/1973 | Bennich et al. |
| 4,179,337 | A | 12/1979 | Davis et al. |
| 4,301,144 | A | 11/1981 | Iwashita et al. |
| 4,331,647 | A | 5/1982 | Goldenberg |
| 4,464,456 | A | 8/1984 | Fujikawa et al. |
| 4,496,689 | A | 1/1985 | Mitra |
| 4,518,584 | A | 5/1985 | Mark et al. |
| 4,640,835 | A | 2/1987 | Shimizu et al. |
| 4,670,417 | A | 6/1987 | Iwasaki et al. |
| 4,675,187 | A | 6/1987 | Konishi et al. |
| 4,737,456 | A | 4/1988 | Weng et al. |
| 4,737,462 | A | 4/1988 | Mark et al. |
| 4,751,180 | A | 6/1988 | Cousens et al. |
| 4,791,192 | A | 12/1988 | Nakagawa et al. |
| 4,923,990 | A | 5/1990 | Nakano et al. |
| 4,935,233 | A | 6/1990 | Bell et al. |
| 4,946,778 | A | 8/1990 | Ladner et al. |
| 5,011,912 | A | 4/1991 | Hopp et al. |
| 5,223,409 | A | 6/1993 | Ladner et al. |
| 5,225,539 | A | 7/1993 | Winter |
| 5,457,035 | A | 10/1995 | Baum et al. |
| 5,474,981 | A | 12/1995 | Leder et al. |
| 5,545,806 | A | 8/1996 | Lonberg et al. |
| 5,569,825 | A | 10/1996 | Lonberg et al. |
| 5,624,821 | A | 4/1997 | Winter et al. |
| 5,627,052 | A | 5/1997 | Schrader |
| 5,698,426 | A | 12/1997 | Huse |
| 5,703,080 | A | 12/1997 | Nakakura et al. |
| 5,814,318 | A | 9/1998 | Lonberg et al. |
| 5,821,337 | A | 10/1998 | Carter et al. |

(Continued)

FOREIGN PATENT DOCUMENTS

| | | | |
|---|---|---|---|
| EP | 439095 | A2 | 7/1991 |
| EP | 1176195 | A1 | 1/2002 |

(Continued)

OTHER PUBLICATIONS

Aplin et al., Preparation, properties, and applications of carboydrate conugates of proteins and lipids. *CRC Crit. Rev. Biochem.* 259-306 (1981).

Arbones et al., Lymphocyte homing and leukocyte rolling and migration are impaired in L-selectin-deficient mice. *Immunity.* 1 : 247-60 (1994).

(Continued)

*Primary Examiner* — Sheela J. Huff

(74) *Attorney, Agent, or Firm* — MARSHALL, GERSTEIN & BORUN LLP

(57) ABSTRACT

The present disclosure provides compositions and methods relating to antigen binding proteins, in particular, antibodies and bispecific antibodies which specifically bind to mesothelin. The disclosure provides nucleic acids encoding such antigen binding proteins and antibodies and methods of making and using such antibodies, including methods of treating and preventing cancer or other hypoproliferative disorders and related disorders by administering such antigen binding proteins and antibodies to a subject in need of such treatment.

26 Claims, 30 Drawing Sheets

Specification includes a Sequence Listing.

(56) References Cited

U.S. PATENT DOCUMENTS

| | | | |
|---|---|---|---|
| 5,859,205 | A | 1/1999 | Adair et al. |
| 5,869,619 | A | 2/1999 | Studnicka |
| 5,877,293 | A | 3/1999 | Adair et al. |
| 5,877,397 | A | 3/1999 | Lonberg et al. |
| 5,886,152 | A | 3/1999 | Nakatani et al. |
| 6,054,297 | A | 4/2000 | Carter et al. |
| 6,083,502 | A | 7/2000 | Pastan et al. |
| 6,133,426 | A | 10/2000 | Gonzalez et al. |
| 6,153,430 | A | 11/2000 | Pastan et al. |
| 6,210,924 | B1 | 4/2001 | Hu et al. |
| 6,277,375 | B1 | 8/2001 | Ward |
| 6,395,272 | B1 | 5/2002 | Deo et al. |
| 6,602,684 | B1 | 8/2003 | Umana et al. |
| 6,696,245 | B2 | 2/2004 | Winter et al. |
| 6,703,199 | B1 | 3/2004 | Koide |
| 6,723,538 | B2 | 4/2004 | Mack et al. |
| 6,846,634 | B1 | 1/2005 | Tomlinson et al. |
| 6,881,557 | B2 | 4/2005 | Foote |
| 7,029,872 | B2 | 4/2006 | Gerngross |
| 7,064,244 | B2 | 6/2006 | Jakobovits et al. |
| 7,081,518 | B1 | 7/2006 | Pastan et al. |
| 7,112,324 | B1 | 9/2006 | Dorken et al. |
| 7,227,002 | B1 | 6/2007 | Kufer et al. |
| 7,235,641 | B2 | 6/2007 | Kufer et al. |
| 7,323,440 | B2 | 1/2008 | Zocher et al. |
| 7,332,168 | B2 | 2/2008 | Zocher et al. |
| 7,368,110 | B2 | 5/2008 | Pastan et al. |
| 7,375,183 | B1 | 5/2008 | Pastan et al. |
| 7,592,426 | B2 | 9/2009 | Ebel et al. |
| 7,635,472 | B2 | 12/2009 | Kufer et al. |
| 7,709,252 | B2 | 5/2010 | Pastan et al. |
| 7,820,166 | B2 | 10/2010 | Lanzavecchia |
| 7,919,089 | B2 | 4/2011 | Kufer et al. |
| 8,017,748 | B2 | 9/2011 | Raum et al. |
| 8,076,459 | B2 | 12/2011 | Hofmeister et al. |
| 8,101,722 | B2 | 1/2012 | Kufer et al. |
| 8,206,710 | B2 | 6/2012 | Ebel et al. |
| 8,236,308 | B2 | 8/2012 | Kischel et al. |
| 8,247,194 | B2 | 8/2012 | Raum et al. |
| 8,268,970 | B2 | 9/2012 | Terrett et al. |
| 8,383,779 | B2 | 2/2013 | Terrett et al. |
| 8,399,623 | B2 | 3/2013 | Terrett et al. |
| 8,425,904 | B2 | 4/2013 | Terrett et al. |
| 8,460,660 | B2 | 6/2013 | Ho et al. |
| 8,481,703 | B2 | 7/2013 | Ebel et al. |
| 10,100,121 | B2 | 10/2018 | Fanslow, III et al. |
| 2001/0036459 | A1 | 11/2001 | Ravetch |
| 2003/0003097 | A1 | 1/2003 | Reff et al. |
| 2003/0039958 | A1 | 2/2003 | Holt et al. |
| 2003/0115614 | A1 | 6/2003 | Kanda et al. |
| 2003/0157108 | A1 | 8/2003 | Presta |
| 2003/0157730 | A1 | 8/2003 | Walker et al. |
| 2004/0009507 | A1 | 1/2004 | Winter et al. |
| 2004/0038291 | A2 | 2/2004 | Tomlinson et al. |
| 2004/0072290 | A1 | 4/2004 | Umana et al. |
| 2004/0185045 | A1 | 9/2004 | Koenig et al. |
| 2004/0202995 | A1 | 10/2004 | de Wildt et al. |
| 2004/0261148 | A1 | 12/2004 | Dickey et al. |
| 2005/0079605 | A1 | 4/2005 | Umana et al. |
| 2005/0118643 | A1 | 6/2005 | Burgess et al. |
| 2005/0123546 | A1 | 6/2005 | Umana et al. |
| 2005/0202512 | A1 | 9/2005 | Tomlinson et al. |
| 2005/0238646 | A1 | 10/2005 | Ledbetter et al. |
| 2005/0272128 | A1 | 12/2005 | Umana et al. |
| 2006/0039904 | A1 | 2/2006 | Wu et al. |
| 2006/0040325 | A1 | 2/2006 | Wu et al. |
| 2006/0067930 | A1 | 3/2006 | Adams et al. |
| 2006/0257399 | A1 | 11/2006 | Gerngross et al. |
| 2007/0092521 | A1 | 4/2007 | McPherson et al. |
| 2009/0241202 | A1 | 9/2009 | Kufer et al. |
| 2009/0291072 | A1 | 11/2009 | Baeuerle et al. |
| 2010/0150918 | A1 | 6/2010 | Kufer et al. |
| 2011/0027268 | A1 | 2/2011 | Kahnert et al. |
| 2011/0262439 | A1 | 10/2011 | Kufer et al. |
| 2011/0293619 | A1 | 12/2011 | Kufer et al. |
| 2012/0034228 | A1 | 2/2012 | Kufer et al. |
| 2012/0189644 | A1 | 7/2012 | Kahnert et al. |
| 2012/0225013 | A1 | 9/2012 | Dennis et al. |
| 2012/0244162 | A1 | 9/2012 | Kufer et al. |
| 2013/0190481 | A1 | 7/2013 | Terrett et al. |
| 2015/0252118 | A1 | 9/2015 | Ho et al. |
| 2015/0274836 | A1 | 10/2015 | Ho et al. |

FOREIGN PATENT DOCUMENTS

| | | | |
|---|---|---|---|
| WO | WO-1987/005330 | A1 | 9/1987 |
| WO | WO-1992/02551 | A1 | 2/1992 |
| WO | WO-1993/10151 | A1 | 5/1993 |
| WO | WO-1993/21232 | A1 | 10/1993 |
| WO | WO-1994/010308 | A1 | 5/1994 |
| WO | WO-1997/25068 | A2 | 7/1997 |
| WO | WO-1997/34631 | A1 | 9/1997 |
| WO | WO-1998/23289 | A1 | 6/1998 |
| WO | WO-1998/24838 | A1 | 6/1998 |
| WO | WO-1999/28471 | A2 | 6/1999 |
| WO | WO-1999/51642 | A1 | 10/1999 |
| WO | WO-1999/54342 | A1 | 10/1999 |
| WO | WO-1999/58572 | A1 | 11/1999 |
| WO | WO-2000/61739 | A1 | 10/2000 |
| WO | WO-2000/73346 | A1 | 12/2000 |
| WO | WO-2000/76310 | A1 | 12/2000 |
| WO | WO-2001/29246 | A1 | 4/2001 |
| WO | WO-2001/79299 | A1 | 10/2001 |
| WO | WO-2002/30954 | A1 | 4/2002 |
| WO | WO-2002/31140 | A1 | 4/2002 |
| WO | WO-2003/11878 | A2 | 2/2003 |
| WO | WO-2003/35835 | A2 | 5/2003 |
| WO | WO-2004/16750 | A2 | 2/2004 |
| WO | WO-2004/29207 | A2 | 4/2004 |
| WO | WO-2004/63351 | A2 | 7/2004 |
| WO | WO-2005/014652 | A1 | 2/2005 |
| WO | WO-2005/44859 | A2 | 5/2005 |
| WO | WO-2005/94879 | A2 | 10/2005 |
| WO | WO-2006/71280 | A1 | 7/2006 |
| WO | WO-2006/71856 | A2 | 7/2006 |
| WO | WO-2006/099141 | A2 | 9/2006 |
| WO | WO-2006/124641 | A2 | 11/2006 |
| WO | WO-2008/119567 | A2 | 10/2008 |
| WO | WO-2009/09086 | A2 | 1/2009 |
| WO | WO-2009/045957 | A1 | 4/2009 |
| WO | WO-2009/068204 | A1 | 6/2009 |
| WO | WO-2009/120769 | A1 | 10/2009 |
| WO | WO-2010/111282 | A1 | 9/2010 |
| WO | WO-2010/124797 | A1 | 11/2010 |
| WO | WO-2012/087962 | A2 | 6/2012 |
| WO | WO-2014/031476 | A1 | 2/2014 |

OTHER PUBLICATIONS

Ashkenazi et al., Protection against endotoxic shock by a tumor necrosis factor receptor immunoadhesin. *Proc. Natl. Acad. Sci. USA.* 88: 10535 (1991).

Babcook et al., A novel strategy for generating monoclonal antibodies from single, isolated lymphocytes producing antibodies of defined specificities. *Proc. Natl. Acad. Sci. USA.* 93: 7843-48 (1996).

Baron et al., Co-regulation of two gene activities by tetracycline via a bidirectional promoter. *Nucleic Acids Res.* 23: 3605-06 (1995).

Bauer et al., A genetic enrichment for mutations constructed by oligodeoxynucleotide-directed mutage. *Gene.* 37: 73 (1985).

Baum et al., Molecular characterization of murine and human OX40/0X40 ligand systems: identification of a human OX40 ligand as the HTLV-1-regulated protein gp34. *EMBO J.* 13: 3992-4001 (1994).

Bera et al., Mesothelin is not required for normal mouse development and reproduction. *Mol. Cell. Biol.* 20: 2902-6 (2000).

Bird et al., Single-chain antigen-binding proteins. *Science.* 242: 423-26 (1988).

Boerner et al., Production of antigen-specific human monoclonal antibodies from in vitro-primed human splenocytes. *J. Immunol.* 147: 86-95 (1991).

(56) References Cited

OTHER PUBLICATIONS

Bowie et al., A method to identify protein sequences that fold into a known three-dimensional structure. *Science*. 253:164 (1991).
Brand et al., Prospect for anti-HER2 receptor therapy in breast cancer. *Anticancer Res.* 26:463-70 (2006).
Brenner et al., Population statistics of protein structures: lessons from structural classifications. *Curr. Op. Struct. Biol.* 7(3): 369-76 (1997).
Brown et al., Tolerance of single, but not multiple, amino acid replacements in antibody VH CDR 2: A means of minimizing B cell wastage from somatic hypermutation? *J. Immunol.* 156(9): 3285-91 (1996).
Bruggemann et al., Production of human antibody repertoires in transgenic mice. *Curr. Opin. Biotechnol.* 8: 455-58 (1997).
Burton et al., Human antibodies from combinatorial libraries. *Adv. Immunol.* 57: 191-280 (1994).
Byrn et al., Biological properties of a CD4 immunoadhesin. *Nature*. 344: 677 (1990).
Chang et al., Isolation and characterization of a monoclonal antibody, K1 , reactive with ovarian cancers and normal mesothelium. *Int. J. Cancer.* 50: 373-81 (1992).
Chang et al., Molecular cloning of mesothelin, a differentiation antigen present on mesothelium, mesotheliomas, and ovarian cancers. *Proc. Natl. Acad. Sci. USA*. 93: 136-40 (1996).
Chen et al., Immunoglobulin gene rearrangement in B-cell deficient mice generated by targeted deletion of the JH locus. *Int. Immunol.* 5: 647-56 (1993).
Cheung et al., Epitope-specific antibody response to the surface antigen of duck hepatitis B virus in infected ducks. *Virology.* 176: 546-52 (1990).
Choi et al., Transgenic mice containing a human heavy chain immunoglobulin gene fragment cloned in a yeast artificial chromosome. *Nat. Genet.* 4:117-23 (1993).
Chou et al., Conformation parameters for amino acids in helical beta-sheet and random coil regions calculated from proteins. *Biochemistry.* 113(2): 211-22 (1974).
Chou et al., Empirical predictions of protein conformation. *Ann. Rev. Biochem.* 47: 251-76 (1978).
Chou et al., Prediction of beta-turns. *Biophys. J.* 26: 367-84 (1979).
Chou et al., Prediction of protein conformation. *Biochemistry.* 13(2): 222-45 (1974).
Chou et al., Prediction of the secondary structure of proteins from their amino acid sequence. *Adv. Enzymol. Relat. Areas Mol. Biol.* 47: 145-8 (1978).
Clark, Antibody humanization: A case of Emperor's new clothes? *Immunol. Today.* 21(8): 397-402 (2000).
Cockett et al., High level expression of tissue inhibitor of metalloproteinases in Chinese hamster ovary cells using glutamine synthetase gene amplification. *Bio/Technology.* 8: 2 (1990).
Colberre-Garapin et al., A new dominant hybrid selective marker for higher eukaryotic cells. *J. Mol. Biol.* 150: 1 (1981).
Corso et al., Real-time detection of mesothelin in pancreatic cancer cell line supernatant using an acoustic wave immunoensor. *Cancer Detect. Prey.* 30: 180-7 (2006).
Craik, Use of oligonucleotides from site-specific mutagenesis. *BioTechniques.* 12-9 (1985).
Crameri et al., DNA shuffling of a family of genes from diverse species accelerates directed evolution. *Nature.* 391: 288-91 (1998).
Creaney et al., Detection of malignant mesothelioma in asbestos-exposed individuals: The potential role of soluble mesothelin-related protein. *Hematol. Oncol. Clin. North Am.* 19: 1025-40 (2005).
Cristaudo et al., Clinical significance of serum mesothelin in patients with mesothelioma and lung cancer. *Clin. Cancer Res.* 13: 5076-81 (2007).
Crouse et al., Expression and amplification of engineered mouse dihydrofolate reductase minigenes. *Mol. Cell. Biol.* 3: 257 (1983).
Dall'Acqua et al., Antibody humanization by framework shuffling. *Methods.* 36(1): 43-60 (2005).
Davies et al., Expression of GnTIII in a recombinant anti-CD20 CHO production cell line: Expression of antibodies with altered glycoforms leads to an increase in ADCC through higher affinity for FC RIII. *Biotechnol Bioeng.* 74: 288-94 (2001).
Davis et al., Transgenic mice as a source of fully human antibodies for the treatment of cancer. *Cancer Metastasis Rev.* 18: 421-5 (1999).
De Graaf et al., Expression of scFvs and scFv fusion proteins in eukaryotic cells. *Methods Mol Biol.* 178: 379-87 (2002).
Deutscher, Guide to Protein Purification, *Meth. Enzymol.* 182:738 (199).
Fanslow et al., Structural characteristics of CD40 ligand that determine biological function. *Semin. Immunol.* 6: 267-78 (1994).
Fell et al., Genetic construction and characterization of a fusion protein consisting of a chimeric F(ab') with specificity for carcinomas and human IL-2. *J. Immunol.* 146: 2446-52 (1991).
Fishwild et al., High-avidity human IgGk monoclonal antibodies from a novel strain of minilocus transgenic mice. *Nat. Biotechnol.* 14: 845-51 (1996).
Foecking et al., Powerful and versatile enhancer-promoter unit for mammalian expression vectors. *Gene.* 45: 101 (1986).
Gallo et al., The human immunoglobulin loci introduced into mice: V (D) and J gene segment usage similar to that of adult humans. *Eur. J. Immunol.* 30: 534-40 (2000).
Gentz et al., Bioassay for trans-activation using purified human immunodeficiency virus tat-encoded protein: trans-activation requires mRNA synthesis. *Proc. Natl. Acad. Sci. USA.* 86: 821-4 (1989).
George et al., Differential effects of anti-b2-glycoprotein I antibodies on endothelial cells and on the manifestations of experimental antiphospholipid syndrome. *Circulation.* 97: 900-6 (1998).
Gillies et al., Antibody-targeted interleukin 2 stimulates T-cell killing of autologous tumor cells. *Proc. Natl. Acad. Sci. USA.* 89: 1428-32 (1992).
Glasky et al., Stability of specific immunoglobulin secretion by EBV-transformed lymphoblastoid cells and human-murine heterohybridomas. *Hybridoma.* 8: 377-89 (1989).
Gluzman et al., SV40-transformed simian cells support the replication of early SV40 mutant. *Cell.* 23: 175 (1981).
Goldenberg et al., New developments in monoclonal antibodies for cancer detection and therapy. *Cancer J. Clinic.* 44: 43 (1994).
Green et al., Antigen-specific human monoclonal antibodies from mice engineered with human Ig heavy and light chain YACs. *Nat. Genet.* 7: 13-21 (1994).
Green et al., Regulation of B cell development by variable gene complexity in mice reconstituted with human immunoglobulin yeast artificial chromosomes. *J. Exp. Med.* 188: 483-9 (1998).
Green, Antibody engineering via genetic engineering of the mouse: XenoMouse strains are a vehicle for the facile generation of therapeutic human monoclonal antibodies. *J. Immunol. Methods.* 231: 11-23 (1999).
Gribskov et al., Profile analysis. *Meth. Enzymol.* 183: 146-59 (1990).
Gribskov et al., Profile analysis: Detection of distantly related proteins. *Proc. Nat. Acad. Sci. USA.* 84(13): 4355-8 (1987).
Gubbels et al., Mesothelin-MUC16 binding is a high affinity, N-glycan dependent interaction that facilitates peritoneal metastasis of ovarian tumors. *Mol. Cancer.* 5: 50 (2006).
Harris, Processing of C-terminal lysine and arginine residues of proteins isolated from mammalian cell culture. *J. Chromatography.* 705: 129-34 (1995).
Hassan et al., Detection and quantitation of serum mesothelin, a tumor marker for patients with mesothelioma and ovarian cancer. *Clin. Cancer Res.* 12: 447-53 (2006).
Hassan et al., Mesothelin targeted cancer immunotherapy. *Eur. J. Cancer.* 44: 46-53 (2008).
Hassan et al., Mesothelin: A new target for immunotherapy. *Clin. Cancer. Res.* 10: 3937-42 (2004).
Hellstrom et al., Mesothelin variant 1 is released from tumor cells as a diagnostic marker. *Cancer Epidemiol. Biomarkers Prey.* 15: 1014-20 (2006).
Ho et al., Mesothelin expression in lung cancer. *Clin. Cancer Res.* 13: 1571-5 (2007).

(56) References Cited

OTHER PUBLICATIONS

Ho et al., Mesothelin is shed from tumor cells. *Cancer Epidemiol. Biomarkers Prey.* 15: 1751 (2006).
Holliger et al., Diabodies: Small bivalent and bispecific antibody fragments. *Proc. Natl. Acad. Sci. USA.* 90: 6444-8 (1993).
Holliger et al., Engineered antibody fragments and the rise of single domains. *Nat. Biotechnol.* 23(9): 1126-36 (2005).
Holm et al., Protein folds and families: Sequence and structure alignments. *Nucl. Acid. Res.* 27(1): 244-7 (1999).
Hoogenboom et al., By-immunization: Human antibodies from synthetic repertoires of passing permline VH gene segments rearranged in vitro. *J. Molec. Biol.* 227: 381-8 (1992).
Hopp et al., A short polypeptide marker sequence useful for recombinant protein identification and purification. *Bio/Technology.* 6: 1204 (1988).
Hoppe et al., A parallel three stranded alpha-helical bundle at the nucleation site of collagen triple-helix formation. *FEBS Lett.* 344: 191 (1994).
Huse et al., Generation of a large combinatorial library of the immunoglobulin repertoire in phage lambda. *Science.* 246: 1275-81 (1989).
Huston et al., Protein engineering of antibody binding sites: recovery of specific activity in an anti-digoxin single-chain Fv analogue produced in *Escherichia coli. Proc. Natl. Acad. Sci. USA.* 85: 5879-83 (1988).
Hwang et al., Use of human germline genes in a CDR homology-based approach to antibody humanization. *Methods.* 36(1): 35-42 (2005).
Jakobovits et al., Analysis of homozygous mutant chimeric mice: Deletion of the immunoglobulin heavy-chain joining region blocks B-cell development and antibody production. *Proc. Natl. Acad. Sci. USA.* 90: 2551-5 (1993).
Jakobovits et al., Germ-line transmission and expression of a human-derived yeast artificial chromosome. *Nature.* 362: 255-58 (1993).
Jakobovits et al., Production of antigen-specific human antibodies from mice engineered with human heavy and light chain YACsa. *Ann. N. Y. Acad. Sci.* 764: 525-35 (1995).
Jakobovits, Production and selection of antigen-specific fully human monoclonal antibodies from mice engineered with human Ig loci. *Adv. Drug Deliv. Rev.* 31: 33-42 (1998).
Jakobovits, The long-awaited magic bullets: therapeutic human monoclonal antibodies from transgenic mice. *Exp. Opin. Invest. Drugs.* 7: 607-14 (1998).
Jakobovits, YAC vectors. Humanizing the mouse genome. *Curr Biol.* 4: 761-63 (1994).
Jones, Progress in protein structure prediction. *Curr. Opin. Struct. Biol.* 7(3): 377-87 (1997).
Kang et al., Linkage of recognition and replication functions by assembling combinatorial antibody Fab libraries along phage surfaces. *Proc. Natl. Acad. Sci. USA.* 88: 4363-6 (1991).
Kellermann et al., Antibody discovery: the use of transgenic mice to generate human monoclonal antibodies for therapeutics. *Curr. Opin. Biotechnol.* 13: 593-97 (2002).
Kelly et al., Mesothelin-targeted agents in clinical trials and in preclinical development. *Molec. Cancer Therapeut.* 11(3): 517-25 (2012).
Kirkland et al., Analysis of the fine specificity and cross-reactivity of monoclonal anti-lipid A antibodies. *J. Immunol.* 137: 3614 (1986).
Kohler, Immunoglobulin chain loss in hybridoma lines. *Proc. Natl. Acad. Sci. USA.* 77: 2197 (1980).
Kojima et al., Molecular cloning and expression of megakaryocyte potentiating factor cDNA. *J. Biol. Chem.* 270: 21984-90 (1995).
Korndorfer et al., Proteins: Structure, Function, and Bioinformatics, vol. 53, Issue 1:121129 (2003).
Kortt et al., Dimeric and trimeric antibodies: high avidity scFvs for cancer targeting. *Biomol. Eng.* 18: 95-108 (2001).
Kortt et al., Single-chain Fv fragments of anti-neuraminidase antibody NC10 containing five- and ten-residue linkers form dimers and with zero-residue linker a trimer. *Prot. Eng.* 10: 423 (1997).
Kriangkum et al., Bispecific and bifunctional signal chain recombinant antibodies. *Biomol. Eng.* 18: 31-40 (2001).
Landschulz et al., The leucine zipper: a hypothetical structure common to a new class of DNA binding proteins. *Science.* 240: 1759 (1988).
Lantto et al., Chain shuffling to modify properties of recombinant immunoglobulins. *Methods Mol. Biol.* 178: 303-16 (2002).
Larrick et al., PCR amplification of antibody genes. *Methods.* 2: 106 (1991).
Larrick et al., Polymemse chain reaction using mixed primers: Cloning of human monoclonal antibody variable region genes from single hybridoma cells. *Bio/Technology.* 7: 934 (1989).
Liu et al., Chimeric mouse-human IgG1 antibody that can mediate lysis of cancer cells. *Proc. Nat. Acad. Sci. USA.* 84: 3439 (1987).
Lonberg et al., Antigen-specific human antibodies from mice comprising four distinct genetic modifications. *Nature.* 368: 856-9 (1994).
Lonberg et al., Human antibodies from transgenic mice. *Int. Rev. Immunol.* 13: 65-93 (1995).
Lonberg, Transgenic Approaches to Human Monoclonal Antibodies in Handbook of Experimental Pharmacology, 113: 49-101 (1994).
Lowy et al., Isolation of transforming DNA: Cloning the hamster aprt gene. *Cell.* 22: 817 (1980).
Lunde et al., Troybodies and pepbodies. *Biochem. Soc. Trans.* 30: 500-06 (2002).
Lutterbuese et al., T cell-engaging BiTE antibodies specific for EGFR potently eliminate KRAS- and BRAF-mutated colorectal cancer cells. *Proc. Natl. Acad. Sci. USA.* 107(28): 12605-10 (2010).
Maniatis et al., Regulation of inducible and tissue-specific gene expression. *Science.* 236: 1237 (1987).
Marks et al., By-passing immunization: building high affinity human antibodies by chain shuffling. *Bio/Technology.* 10: 779-83 (1992).
Massey, Catalytic antibodies catching on. *Nature.* 328: 457-8 (1987).
McMahan et al., A novel IL-1 receptor, cloned from B cells by mammalian expression, is expressed in many cell types. *EMBO J.* 10: 2821 (1991).
Mendez et al., Functional transplant of megabase human immunoglobulin loci recapitulates human antibody response in mice. *Nat. Genet.* 15: 146-56 (1997).
Moldenhauer et al., Identity of HML-1 antigen on intestinal intraepithelial T cells and of B-1y7 antigen on hairy cell leukaemiam. *Scand. J. Immunol.* 32: 77-82 (1990).
Morel et al., Monoclonal antibodies to bovine serum albumin: affinity and specificity determinations. *Molec. Immunol.* 25: 7-15 (1988).
Moult, The current state of the art in protein structure prediction. *Curr. Op. Biotech.* 7(4): 422-7 (1996).
Mulligan et al., Selection for animal cells that express the *Escherichia coli* gene coding for xanthine-guanine phosphoribosyltransferase. *Proc. Natl. Acad. Sci. USA.* 78: 2072 (1981).
Naramura et al., Mechanisms of cellular cytotoxicity mediated by a recombinant antibody-IL2 fusion protein against human melanoma cells. *Immunol. Lett.* 39: 91-99 (1993).
Neuberger et al., Recombinant antibodies possessing novel effector functions. *Nature.* 312: 604-8 (1984).
Neuberger, Generating high-avidity human Mabs in mice. *Nat. Biotechnol.* 14: 826 (1996).
Nisonoff et al., Separation of univalent fragments from the bivalent rabbit antibody molecule by reduction of disulfide bonds. *Arch. Biochem. Biophys.* 89: 230 (1960).
Nygren et al., Scaffolds for engineering novel binding sites in proteins. *Curr. Opin. Struct. Biol.* 7: 463-9 (1997).
O'Hare et al., Transformation of mouse fibroblasts to methotrexate resistance by a recombinant plasmid expressing a prokaryotic dihydrofolate reductase. *Proc. Natl. Acad. Sci. USA.* 78: 1527 (1981).
Okazaki et al., Fucose depletion from human IgG1 oligosaccharide enhances binding enthalpy and association rate between IgG1 and FcgammacRIIIa. *J. Molec. Biol.* 336: 1239-49 (2004).

(56) References Cited

OTHER PUBLICATIONS

Ordonez, Application of mesothelin immunostaining in tumor diagnosis. *Am. J. Surg. Pathol.* 27: 1418-28 (2003).
Osada et al., Metastatic colorectal cancer cells from patients previously treated with chemotherapy are sensitive to T-cell killing mediated by CEA/CD3-bispecific T-cell-engaging BiTE antibody. *Br. J. Cancer.* 102: 124-33 (2010).
Padlan et al., Identification of specificity-determining residues in antibodies. *FASEB J.* 9: 133-39 (1995).
Pastan et al., Immunotoxins, *Cell.* 47: 641-8 (1986).
Patten et al., Applications of DNA shuffling to pharmaceuticals and vaccines. *Curr. Opin. Biotechnol.* 8: 724-33 (1997).
Poljak et al., Production and structure of diabodies. *Structure.* 2: 1121-23 (1994).
Porter, The hydrolysis of rabbit y-globulin and antibodies with crystalline papain. *Biochem. J.* 73: 119 (1959).
Proudfoot, Transcriptional interference and termination between duplicated α-globin gene constructs suggests a novel mechanism for gene regulation. *Nature.* 322: 562-5 (1986).
Rasmussen et al., Isolation, characterization and recombinant protein expression in Veggie-CHO: A serum-free CHO host cell line. *Cytotechnol.* 28: 31 (1998).
Riechmann et al., Reshaping human antibodies for therapy. *Nature.* 332: 323 (1988).
Roque et al., Antibodies and genetically engineered related molecules: production and purification. *Biotechnol. Prog.* 20: 639-54 (2004).
Rump et al., Binding of ovarian cancer antigen CA125/MUC16 to mesothelin mediates cell adhesion. *J. Biol. Chem.* 279: 9190-8 (2004).
Russel et al., Production of protective human antipneumococcal antibodies by transgenic mice with human immunoglobulin loci. *Infect. Immun.* 68: 1820-26 (2000).
Santerre et al., Expression of prokaryotic genes for hygromycin B and G418 resistance as dominant-selection markers in mouse L cells. *Gene.* 30: 147 (1984).
Sastry et al., Cloning of the immunological repertoire in *Escherichia coli* for generation of monoclonal catalytic antibodies: construction of a heavy chain variable region-specific cDNA library. *Proc. Natl. Acad. Sci. USA.* 86: 5728-32 (1989).
Schatz, Efficacy and candidate biomarker evaluation for the anti-mesothelin antibody drug conjugate (ADC) bay 94-9343, mesothelin-ADC in mesothelin-positive preclinical xenograft models. *Cancer Res.* 72(8): Supp. 1 (2012).
Schier et al., Isolation of picomolar affinity anti-c-erbB-2 single-chain Fv by molecular evolution of the complementarity determining regions in the center of the antibody binding site. *J. Mol. Biol.* 263: 551 (1996).
Schlebusch et al., Production of a single-chain fragment of the murine anti-idiotypic antibody ACA125 as phage-displayed and soluble antibody by recombinant phage antibody technique. *Hybridoma.* 16: 47-52 (1997).
Shields et al., Lack of fucose on human IgG1 N-linked oligosaccharide improves binding to human Fc gamma RIII and antibody-dependent cellular toxicity. *J. Biol. Chem.* 277: 26733-40 (2002).
Shinkawa et al., The absence of fucose but not the presence of galactose or bisecting N-acetylglucosamine of human IgG1 complex-type oligosaccharides shows the critical role of enhancing antibody-dependent cellular cytotoxicity. *J. Biol. Chem.* 278: 3466-73 (2003).
Sippl et al., Threading thrills and threats. *Structure.* 4(1): 15-9 (1996).
Stahli et al., Distinction of epitopes by monoclonal antibodies. *Meth. Enzymol.* 9: 242-53 (1983).
Strome et al., A mechanistic perspective of monoclonal antibodies in cancer therapy beyond target-related effects, *Oncologist.* 12:1084-95 (2007).
Szybalska et al., Genetics of human cell lines, IV. DNA-mediated heritable transformation of a biochemical trait. *Proc. Natl. Acad. Sci. USA.* 48: 202 (1962).
Tamura et al., Structural correlates of an anticarcinoma antibody: identification of specificity-determining residues (SDRs) and development of a minimally immunogenic antibody variant by retention of DSRs only. *J. Immunol.* 164: 1432-41 (2000).
Taylor et al., A transgenic mouse that expresses a diversity of human sequence heavy and light chain immunoglobulins. *Nucl. Acids Res.* 20: 6287-95 (1992).
Taylor et al., Human immunoglobulin transgenes undergo rearrangement, somatic mutation and class switching in mice that lack endogenous IgM. *Int. Immunol.* 6: 579-91 (1994).
Thompson et al., Affinity maturation of a high-affinity human monoclonal antibody against the third hypervariable loop of human immunodeficiency virus: Use of phage display to improve affinity and broaden strain reactivity. *J. Mol. Biol.* 256: 7-88 (1996).
Thornton et al., Prediction of progress at last. *Nature.* 354: 105 (1991).
Tomizuka et al., Double trans-chromosomic mice: maintenance of two individual human chromosome fragments containing Ig heavy and kappa loci and expression of fully human antibodies. *Proc. Natl. Acad. Sci. USA.* 97: 722-27 (2000).
Tomizuka et al., Functional expression and germline a transmission of a human chromosome fragment in chimeric mice. *Nat. Genet.* 16: 133-43 (1997).
Traunecker, Bispecific single chain molecules (Janusins) target cytotoxic lymphocytes on HIV infected cells. *EMBO J.* 10: 3655-9 (1991).
Tsuda et al., Inactivation of the Mouse HPRT Locus by a 203-bp retroposon insertion and a 55-kb gene-targeted deletion: establishment of new HPRT-deficient mouse embryonic stem cell lines. *Genomics.* 42: 413-21 (1997).
Tuaillon et al., Biased utilization of DHQ52 and JH4 gene segments in a human Ig transgenic minilocus is independent of antigenic selection. *J. Immunol.* 152: 2912-20 (1994).
Tuaillon et al., Human mice: immunoglobulin heavy-chain minilocus recombination in transgenic gene-segment use in mu and gamma transcripts. *Proc. Natl. Acad. Sci. USA.* 90: 3720-24 (1993).
Tunnacliffe, The majority of human CD3 epitopes are conferred by the epsilon chain. *Int. Immunol.* 1: 546-50 (1989).
Umana et al., Engineered glycoforms of an antineuroblastoma IgG1 with optimized antibody-dependent cellular cytotoxic activity. *Nat. Biotech.* 17: 176-80 (1999).
Urlaub et al., Isolation of Chinese hamster cell mutants deficient in dihydrofolate reductase activity. *Proc. Natl. Acad. Sci. USA.* 77: 4216-20 (1980).
Vajdos et al., Comprehensive functional maps of the antigen-binding site of an anti-ErbB2 antibody obtained with shotgun scanning mutagenesis. *J. Mol. Biol.* 320: 415-28 (2002).
Vaughan et al., Human antibodies by design. *Nat. Biotechnol.* 16: 535-9 (1998).
Voss et al., The role of enhancers in the regulation of cell-type-specific transcriptional control. *Trends Biochem. Sci.* 11: 287 (1986).
Walder et al., Oligodeoxynucleotide-directed mutagenesis using the yeast transformation system. *Gene.* 42: 133 (1986).
Ward et al., Binding activities of a repertoire of single immunoglobulin variable domains secreted from *Escherichia coli. Nature.* 341:544-6 (1989).
Wigler et al., Transfer of purified herpes virus thymidine kinase gene to cultured mouse cells. *Cell.* 11: 223 (1977).
Wigler et al., Transformation of mammalian cells with an amplifiable dominant-acting gene. *Proc. Natl. Acad. Sci. USA.* 77(6): 3567-70 (1980).
Wilson et al., The structure of an antigenic determinant in a protein. *Cell.* 37: 767 (1984).
Winter et al., Humanized antibodies. *TIPS.* 14: 139 (1993).
Winter et al., Making antibodies by phage display technology. *Annu. Rev. Immunol.* 12: 433-55 (1994).
Wu et al., Delivery systems for gene therapy. *Biotherapy.* 3: 87-95 (1991).
Yamaguchi et al., A novel cytokine exhibiting megakaryocyte potentiating activity from a human pancreatic tumor cell line HPC-Y5. *J. Biol. Chem.* 269: 805-8 (1994).

(56) References Cited

OTHER PUBLICATIONS

Yang et al., CDR walking mutagenesis for the affinity maturation of a potent human anti-HIV-1 antibody into the picomolar range. *J. Mol. Biol.* 254: 392-403 (1995).
Zhang et al., Humanization of an anti-human TNF-alphaA antibody by variable region resurfacing with the aid of molecular modeling. *Molec. Immunol.* 42(12): 1445-51 (2005).

MSLN mRNA is Abundantly Expressed in Ovarian Serous and Pancreatic Cancer but not Normal Ovary or Pancreas

FIG. 3

MSLN Expressing Tumors

| Cancer Type | Estimated New Cases (US) | Estimated Deaths (US) | MSLN Expression (mRNA) % Incidence | MSLN Expression (protein) % Incidence |
|---|---|---|---|---|
| Ovarian Serous Carcinoma | 21,900 | 13,900 | 33/35 (94%) | 76/77 (99%) |
| Pancreatic carcinoma | 43,100 | 36,800 | 8/9 (89%) | 39/42 (93%) |
| Mesothelioma | 2-3,000 | 2,700 | 123/131 (94%) | 44/44 (100%) |
| Lung<br>Adenocarcinoma<br>Squamous | <br>156,000<br>56,000 | <br>82,000<br>28,000 | <br>6/10 (60%)<br>3/10 (30%) | <br>78/148 (53%)<br>29/124 (23%) |
| Gastric | 37,000 | 25,000 | 19/41 (46%) | 156/621(25%) |

FIG. 4

Comparison of Xenomouse Derived anti MSLN antibodies to Morab-009

| mAb | Kd (Biacore, pM) Soluble human MSLN | Kd(Kinexa, pM) Native hu MSLN (cells) | Cyno MSLN Reactivity | Rat MSLN Reactivity | Mouse MSLN Reactivity |
| --- | --- | --- | --- | --- | --- |
| 237 | 120 | 3.5 | +++ | ++ | ++ |
| 158.3 | 2400 | 12.2 | no | not done | no |
| 151 | 17400 | 30 | + | not done | no |
| 1.12 | 282 | not done | yes | not done | not done |
| 1.33 | 965 | not done | yes | not done | not done |
| 1.68 | 9737 | not done | yes | not done | not done |
| 1.78 | 1277 | not done | yes | not done | not done |
| 1.119 | 112 | not done | yes | not done | not done |
| 2.69 LC2 | 228 | not done | yes | not done | not done |
| Morab-009 (ssl CDRs) | 160 (1500 published#) | 2.2 | +++ | No (Hassan 2007) | ++ |

FIG. 5

Antibody Binning Data

| Antibody coated on the bead | Antibody used for detection | | | | | | | | | | | | | | |
|---|---|---|---|---|---|---|---|---|---|---|---|---|---|---|---|
| | 1.5.1 | 1.5.2 | 1.58.3 g1 | 1.58.3 g2 | 1.1.2 | 1.33.1 | 1.68.1 | 1.78.1 | 1.119.1 | 1.80.3 | 2.37.1 | 2.69.2 | 2.85.3 | 2.26.1 | Bin Number |
| 1.51 | 940 | 842 | 1101 | 1032 | 3699 | 3379 | 4927 | 4140 | 3057 | 2992 | 7644 | 6060 | 7041 | 731 | 1 |
| 1.5.2 | 993 | 810 | 1201 | 1070 | 3590 | 3619 | 4726 | 4252 | 2961 | 2877 | 7353 | 6033 | 6227 | 801 | |
| 1.58.3 g1 | 919 | 956 | 849 | 918 | 4449 | 5168 | 7909 | 4933 | 4892 | 4846 | 11989 | 9754 | 10229 | 701 | |
| 1.58.3 g2 | 982 | 1001 | 1168 | 1074 | 3914 | 4677 | 6065 | 4836 | 3964 | 3665 | 9982 | 8061 | 8215 | 849 | |
| 1.1.2 | 4004 | 3735 | 6393 | 4149 | 838 | 603 | 936 | 827 | 737 | 4514 | 8901 | 7161 | 6445 | 825 | 2 |
| 1.33.1 | 5839 | 5575 | 8489 | 5762 | 768 | 709 | 914 | 788 | 730 | 5605 | 5976 | 7144 | 5291 | 746 | |
| 1.68.1 | 7424 | 7586 | 12054 | 7665 | 828 | 857 | 970 | 789 | 731 | 6147 | 8611 | 8713 | 5368 | 664 | |
| 1.78.1 | 4655 | 4539 | 6848 | 4733 | 960 | 914 | 1244 | 976 | 901 | 5898 | 10190 | 8084 | 7531 | 1116 | |
| 1.119.1 | 4323 | 4097 | 6645 | 4569 | 632 | 521 | 792 | 642 | 471 | 4071 | 4444 | 5349 | 3943 | 581 | |
| 1.80.3 | 2385 | 2384 | 6956 | 2310 | 6063 | 4281 | 3822 | 6205 | 3829 | 301 | 10454 | 9733 | 8792 | 494 | 3 |
| 2.37.1 | 6365 | 6175 | 11865 | 6271 | 7734 | 832 | 6364 | 8035 | 752 | 6865 | 3693 | 3902 | 1020 | 746 | 4 |
| 2.69.2 | 3672 | 3400 | 6428 | 3860 | 3507 | 2700 | 3599 | 3887 | 2187 | 4704 | 2936 | 685 | 3474 | 612 | 5 |
| 2.85.3 | 6039 | 5573 | 9382 | 5818 | 4527 | 3577 | 3797 | 5093 | 3038 | 5425 | 5107 | 4894 | 656 | 394 | 6 |
| 2.26.1 | 62 | 92 | 170 | 87 | 51 | 74 | 73 | 111 | 62 | 37 | 158 | 160 | 133 | 94 | N/A |

Ab binned against itself

Binning observed

No Binning observed

FIG. 6

Antibody Binning Data

| | Morab-009 | 237 | 158 | 151 | MN | MB | CA125 | OV569 | 4H3 |
|---|---|---|---|---|---|---|---|---|---|
| Morab-009 | (-) | (+) | (+) | (nd) | (-) | (+) | (-) | (nd) | (nd) |
| 237 | (+) | (-) | (+) | (nd) | (+) | (+) | (+) | (+) | (+) |
| 158 | (+) | (+) | (-) | (nd) | (+) | (+/-) | (nd) | (nd) | (nd) |
| 151 | (nd) | (nd) | (nd) | (-) | | | | | |
| MN | (-) | (+) | (+) | | | | | | |
| MB | (+) | (+) | (+/-) | | | | | | |
| CA125 | (-) | (+) | (nd) | | | | | | |
| OV569 | | (+) | | | | | | | |
| 4H3 | | (+) | | | | | | | |

*(-) = cross competition for binding to human MSLN observed*
*(+) = little to no cross competition for binding to human MSLN observed*
*(nd) = not done*

Anti-MSLN Antibody ADCC Mediated Cell Killing
158 FV
158 FF
Capan-2
40K
MSLN/cell
Ovcar-8
65-100K
MSLN/cell
A
B
C
D
% specific lysis
Concentration (ug/ml)
49 22hr ADCC
41,46 MORAb-009
39,40 MOA αCD16, deglyc.
48 sol.MSLN
hIgG1
αMSLN 237 WT
α MSLN 237 3X
α MSLN 237 low fucose
α MSLN 151 WT
α MSLN 151 3X
MORAb-009

Anti-MSLN Antibody ADCC Mediated Cell Killing

| Cell line | MSLN level (sites/cell) | ADCC(3x) |
|---|---|---|
| A2780 | < LLOQ | (-) |
| Caki-1 | 13 K | (-) |
| ASPC-1 | 20 K | (+) |
| CAPAN-2 | 40 K | (++) |
| Ovcar-8 | 65 K | (++) |

| sample | EC50 (nM) |
|---|---|
| 158.3 WT | >67 |
| 158.3 3x | 0.00031 |
| 151 WT | 21 |
| 151 3x | 0.0042 |
| Morab 009 | >67 |

| | 237 Wt | 237 3x | 237 low fuc | 237 3x degly | MORAb |
|---|---|---|---|---|---|
| EC50 (ug/ml) | 0.016 | 0.000056 | 0.0025 | > 10 | >10 |

- Neither deglycosylated 237 3x nor Morab-009 Mediate ADCC against N87 targets (both bind well to MSLN)

Anti-MSLN Antibody CDC Mediated Cell Killing

FIG. 13
Anti-MSLN Antibodies Induce Human Macrophages to Phagocytose Ovcar 8 Cells
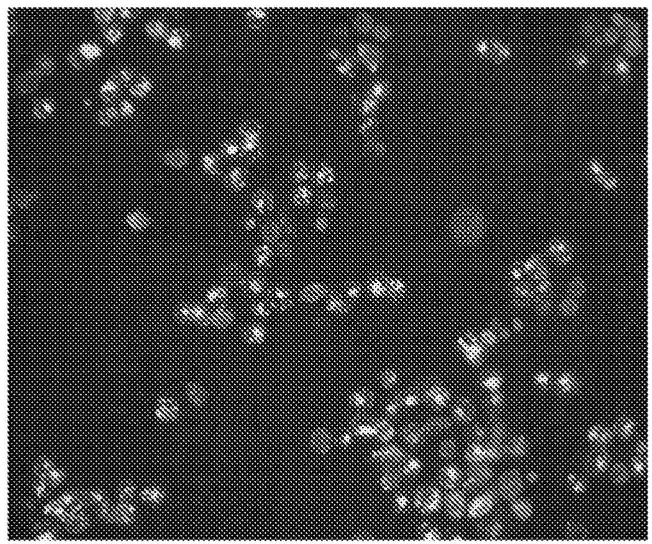
30 ng/ml hulgG1 Kappa
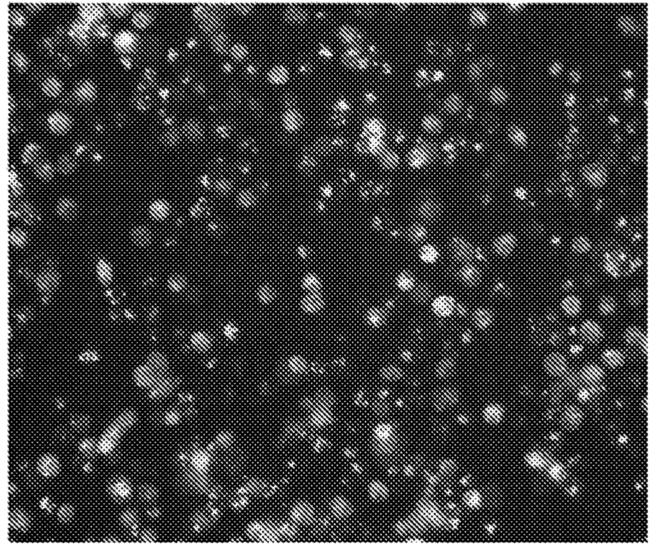
30 ng/ml 237 Low Fucose MSLN Anti-MSLN Antibody ADCP Mediated Cell Killing

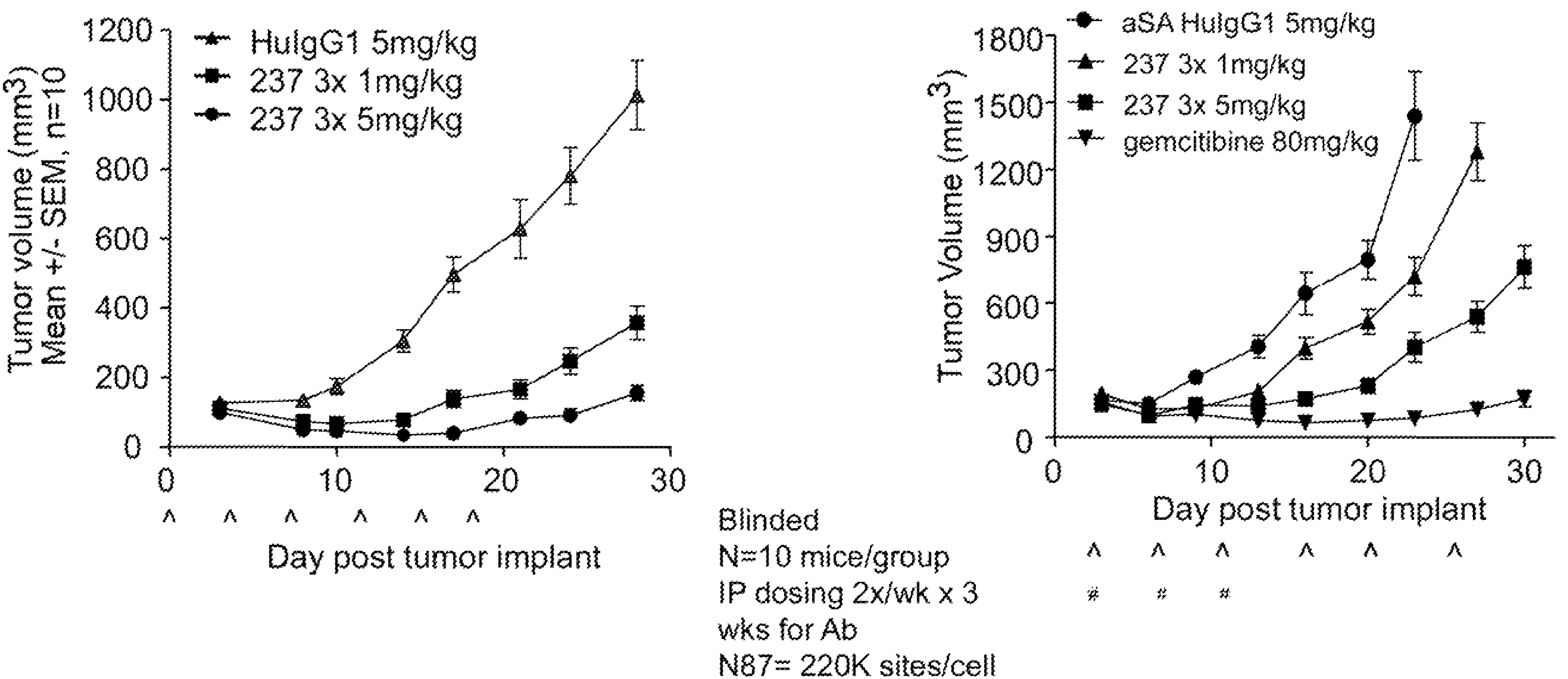
FIG. 15
Fc-Enhanced 237 3x anti MSLN huIgG1 Induces Dose-Dependent Anti-Tumor Activity in a MSLN+ve N87 Xenograft Model (CB-17/SCID mice)
Tumor volume (mm3) Mean +/- SEM, n=10
1200
1000
800
600
400
200
0
HuIgG1 5mg/kg
237 3x 1mg/kg
237 3x 5mg/kg
0
10
20
30
Day post tumor implant
Tumor Volume (mm3)
1800
1500
1200
900
600
300
0
aSA HuIgG1 5mg/kg
237 3x 1mg/kg
237 3x 5mg/kg
gemcitibine 80mg/kg
0
10
20
30
Day post tumor implant
Blinded
N=10 mice/group
IP dosing 2x/wk x 3 wks for Ab
N87= 220K sites/cell
• Increased response observed in MRD setting as compared to established tumor setting
• Able to evince robust anti tumor activity in standard mouse xenograft model Combining 237 3x anti Human MSLN and Gemcitabine Mediate Greater than Additive Anti-Tumor Activity in the N87 Xenograft Model Alignment of scFv for MSLN-BiTE molecules
Ab Bin
aMSLN 1.1.2 VH-VL_scFv
aMSLN 1.117 HL_VL_scFv
aMSLN 1.119 VH-VL_scFv
aMSLN 1.33 VH-VL_scFv
aMSLN 1.68 VH-VL_scFv
aMSLN 1.78 VH-VL_scFv
aMSLN 2.37 VH-VL_scFv
aMSLN 2.69.2 VH-VL_scFv
Consensus
Section 2
Section 3

Antibody binning

Antibody bins were determined by competitive binding of an anti-mesothelin antibody to a labeled anti-mesothelin antibody with known epitope. Sequence comparison was used to generate the dendrogram.

MSLN-BiTE molecules bind human MSLN and CD3

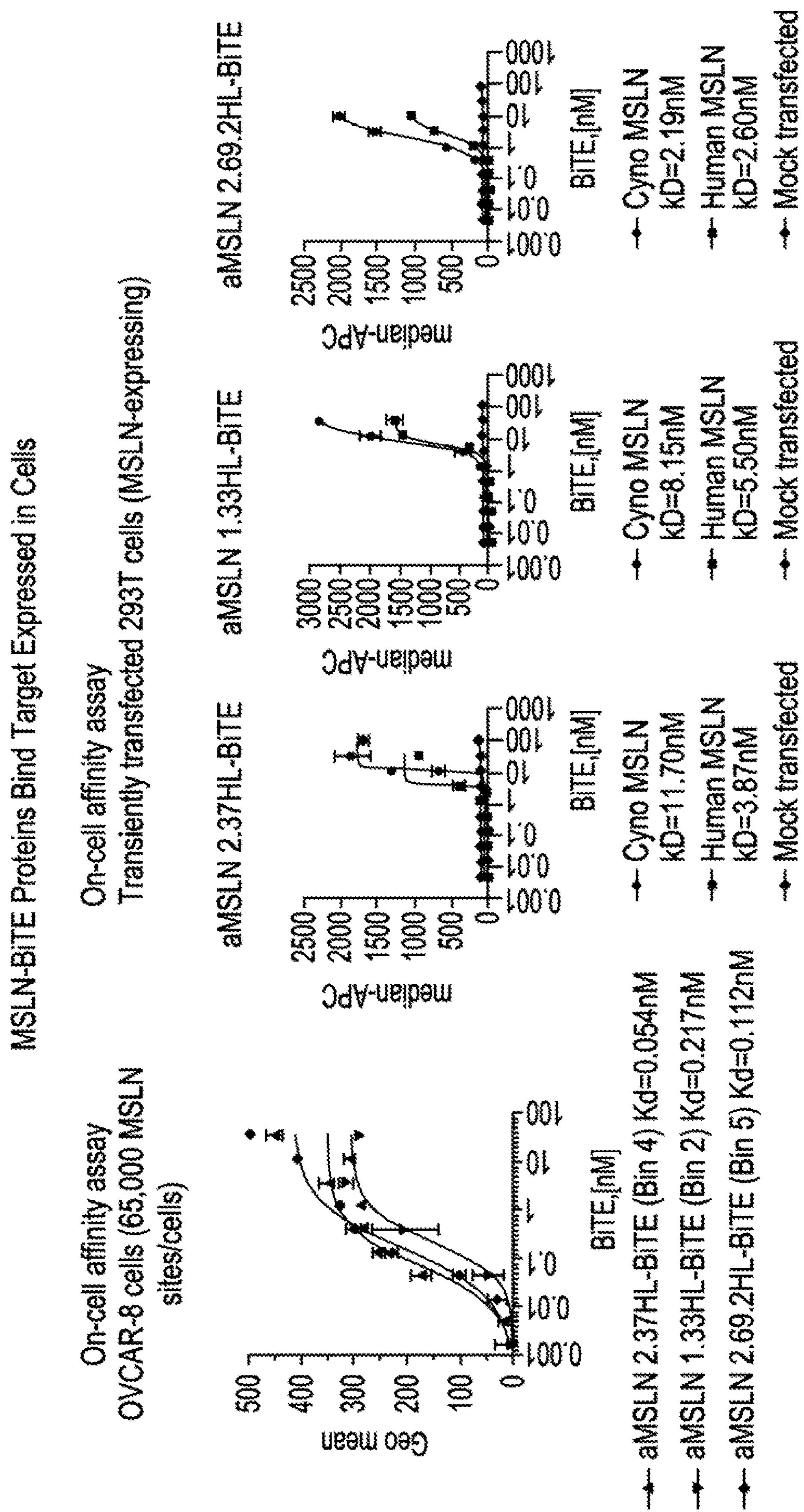
FIG. 21
MSLN-BiTE Proteins Bind Target Expressed in Cells
On-cell affinity assay
OVCAR-8 cells (65,000 MSLN sites/cells)
Geo mean
500
400
300
200
100
0
0.001
0.01
0.1
1
10
100
BiTE,[nM]
aMSLN 2.37HL-BiTE (Bin 4) Kd=0.054nM
aMSLN 1.33HL-BiTE (Bin 2) Kd=0.217nM
aMSLN 2.69.2HL-BiTE (Bin 5) Kd=0.112nM
On-cell affinity assay
Transiently transfected 293T cells (MSLN-expressing)
aMSLN 2.37HL-BiTE
median-APC
2500
2000
1500
1000
500
0
0.001
0.01
0.1
1
10
100
1000
BiTE,[nM]
Cyno MSLN
kD=11.70nM
Human MSLN
kD=3.87nM
Mock transfected
aMSLN 1.33HL-BiTE
median-APC
3000
2500
2000
1500
1000
500
0
0.001
0.01
0.1
1
10
100
1000
BiTE,[nM]
Cyno MSLN
kD=8.15nM
Human MSLN
kD=5.50nM
Mock transfected
aMSLN 2.69.2HL-BiTE
median-APC
2500
2000
1500
1000
500
0
0.001
0.01
0.1
1
10
100
1000
BiTE,[nM]
Cyno MSLN
kD=2.19nM
Human MSLN
kD=2.60nM
Mock transfected MSLN-BiTE molecules activate T cells and cause cytokine release.

FIG. 23

MSLN-BiTE molecules cause cytokine release.

| | Th1 type cytokines | | | | Th2 type cytokines | | | | | |
|---|---|---|---|---|---|---|---|---|---|---|
| | INFγ EC50 pM | TNFα EC50 pM | IL-1B EC50 pM | IL-2 EC50 pM | IL-6 EC50 pM | IL-4 EC50 pM | IL-5 EC50 pM | IL-10 EC50 pM | IL-12 EC50 pM | IL-13 EC50 pM |
| Cetuximab-BiTE | 10 | 40 | 9 | 10 | 0.8 | 2 | 2 | 6 | 4 | 4 |
| MSLN 2.37-BiTE | 20 | 30 | 4 | 9 | 0.4 | 3 | 1 | 2 | 3 | 1 |
| MSLN 1.78-BiTE | 50 | 70 | 5 | 10 | 0.3 | 4 | 1 | 4 | 3 | 2 |

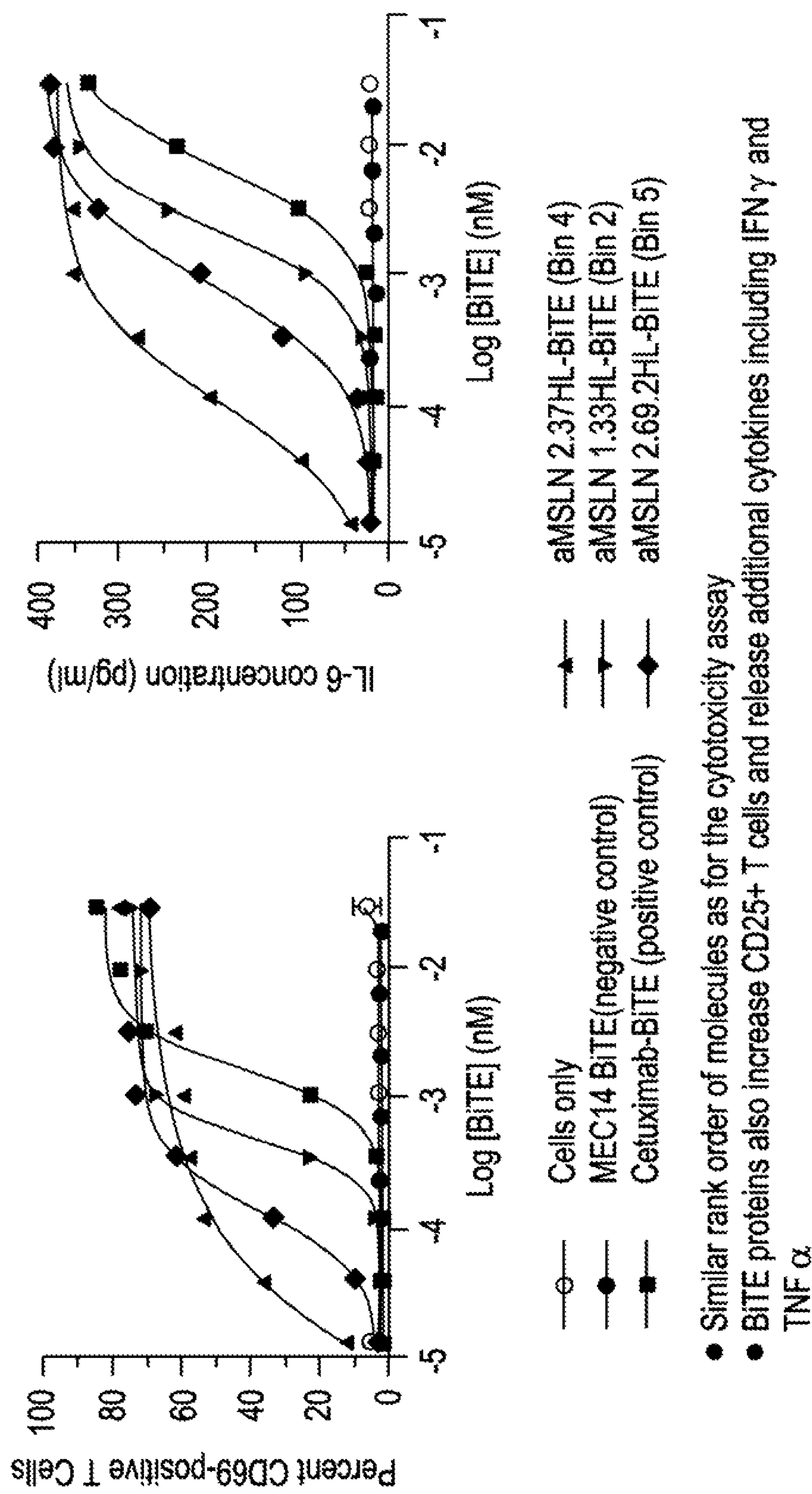
FIG. 24
MSLN-BiTE Proteins Activate T Cells and Cause Cytokine Production
OVCAR-8 cells (65,000 site/cell) and human pan-T cells 10:1
24h T cell activation assay
48h Cytokine release assay
Percent CD69-positive T Cells
100
80
60
40
20
0
-5
-4
-3
-2
-1
Log [BiTE] (nM)
IL-6 concentration (pg/ml)
400
300
200
100
0
-5
-4
-3
-2
-1
Log [BiTE] (nM)
Cells only
MEC14 BiTE(negative control)
Cetuximab-BiTE (positive control)
aMSLN 2.37HL-BiTE (Bin 4)
aMSLN 1.33HL-BiTE (Bin 2)
aMSLN 2.69.2HL-BiTE (Bin 5)
• Similar rank order of molecules as for the cytotoxicity assay
• BiTE proteins also increase CD25+ T cells and release additional cytokines including IFNγ and TNF α

MSLN-BiTE induces cytoxicity in tumor cells.

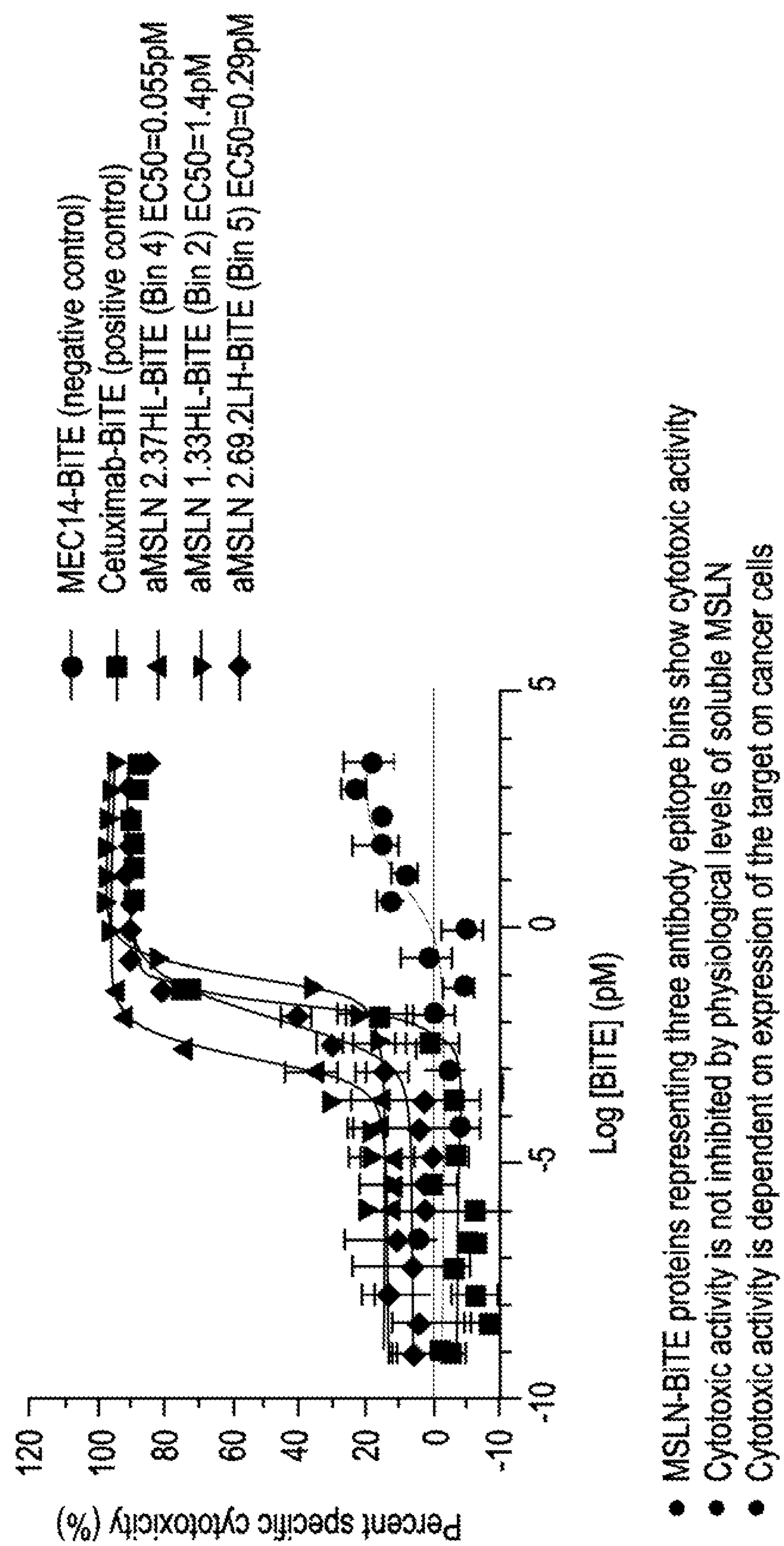
FIG. 26
MSLN-BiTE Proteins Induce Cytotoxicity of Cancer Cells
48h TDCC assay
OVCAR-8 cells (65,000 sites/cell) and human pan-T cells 10:1
Percent specific cytotoxicity (%)
120
100
80
60
40
20
0
-10
-10
-5
0
5
Log [BiTE] (pM)
MEC14-BiTE (negative control)
Cetuximab-BiTE (positive control)
aMSLN 2.37HL-BiTE (Bin 4) EC50=0.055pM
aMSLN 1.33HL-BiTE (Bin 2) EC50=1.4pM
aMSLN 2.69.2LH-BiTE (Bin 5) EC50=0.29pM
• MSLN-BiTE proteins representing three antibody epitope bins show cytotoxic activity
• Cytotoxic activity is not inhibited by physiological levels of soluble MSLN
• Cytotoxic activity is dependent on expression of the target on cancer cells Tool MSLN-BiTE (P73362) Inhibits growth of NCI-N87 Tumor Growth in an Admixture Model

• Tool MSLN-BiTE is 2.37 scFv with 8H9 CD3

Tool MSLN-BiTE (P73362) Inhibits tumor Growth in the BiTE Screen Model

| Cell line | TDCC EC50 (pM) | |
|---|---|---|
| | 2.37HL-BiTE | 1.33HL-BiTE |
| NCI-N87 | 0.35 | 1.27 |
| OVCAR-8 | 0.05 | 1.4 |
| SKOV-3 | 0.33 | 22.69 |

- Athymic nude mice implanted with 4 different luciferace labeled tumor cell lines and human pan T cells in 1:1 ratio
- Mice dosed IP once a day from Day 1 to Day 11
- Data graphed as fold change from Day 1 biolumimescence Pharmacokinetics of MSLN-BiTE is Consistent with Dose-Dependent inhibition of Tumor Growth

| IP Dose (µg/kg) | $t_{1/2,z}$ (h) | CL/F (mL/h/kg) | $C_{max}$ (ng/mL) | $AUC_{inf}$ (ng•h/mL) |
|---|---|---|---|---|
| 1.33 50 | 2.1 | 397 | 31.3 | 126 |
| 1.33 500 | 1.4 | 407 | 402 | 1230 |
| 2.37 50 | 2.0 | 522 | 25.3 | 95.8 |
| 2.37 500 | 1.6 | 598 | 317 | 837 |

SEQUENCE LISTING

```
<160> NUMBER OF SEQ ID NOS: 197

<210> SEQ ID NO 1
<211> LENGTH: 2187
<212> TYPE: DNA
<213> ORGANISM: Homo sapiens

<400> SEQUENCE: 1

tgccaggctc tccacccccca cttcccaatt gaggaaaccg aggcagagga ggctcagcgc      60

cacgcactcc tctttctgcc tggccggcca ctcccgtctg ctgtgacgcg cggacagaga     120

gctaccggtg gacccacggt gcctccctcc ctgggatcta cacagaccat ggccttgcca     180

acggctcgac ccctgttggg gtcctgtggg acccccgccc tcggcagcct cctgttcctg     240

ctcttcagcc tcggatgggt gcagccctcg aggaccctgg ctggagagac agggcaggag     300
```

```
gctgcgcccc tggacggagt cctggccaac ccacctaaca tttccagcct ctcccctcgc    360

caactccttg gcttcccgtg tgcggaggtg tccggcctga gcacggagcg tgtccgggag    420

ctggctgtgg ccttggcaca gaagaatgtc aagctctcaa cagagcagct gcgctgtctg    480

gctcaccggc tctctgagcc ccccgaggac ctggacgccc tcccattgga cctgctgcta    540

ttcctcaacc cagatgcgtt ctcggggccc caggcctgca cccgtttctt ctcccgcatc    600

acgaaggcca atgtggacct gctcccgagg ggggctcccg agcgacagcg gctgctgcct    660

gcggctctgg cctgctgggg tgtgcggggg tctctgctga gcgaggctga tgtgcgggct    720

ctgggaggcc tggcttgcga cctgcctggg cgctttgtgg ccgagtcggc cgaagtgctg    780

ctaccccggc tggtgagctg cccgggaccc ctggaccagg accagcagga ggcagccagg    840

gcggctctgc agggcggggg acccccctac ggcccccccgt cgacatggtc tgtctccacg    900

atggacgctc tgcggggcct gctgcccgtg ctgggccagc ccatcatccg cagcatcccg    960

cagggcatcg tggccgcgtg gcggcaacgc tcctctcggg acccatcctg gcggcagcct   1020

gaacggacca tcctccggcc gcggttccgg cgggaagtgg agaagacagc ctgtccttca   1080

ggcaagaagg cccgcgagat agacgagagc ctcatcttct acaagaagtg ggagctggaa   1140

gcctgcgtgg atgcggccct gctggccacc cagatggacc gcgtgaacgc catccccttc   1200

acctacgagc agctggacgt cctaaagcat aaactggatg agctctaccc acaaggttac   1260

cccgagtctg tgatccagca cctgggctac ctcttcctca agatgagccc tgaggacatt   1320

cgcaagtgga atgtgacgtc cctggagacc ctgaaggctt tgcttgaagt caacaaaggg   1380

cacgaaatga gtcctcaggt ggccaccctg atcgaccgct ttgtgaaggg aaggggccag   1440

ctagacaaag acaccctaga caccctgacc gccttctacc ctgggtacct gtgctccctc   1500

agccccgagg agctgagctc cgtgccccc agcagcatct gggcggtcag gccccaggac   1560

ctggacacgt gtgacccaag gcagctggac gtcctctatc ccaaggcccg ccttgctttc   1620

cagaacatga acgggtccga atacttcgtg aagatccagt ccttcctggg tggggccccc   1680

acggaggatt tgaaggcgct cagtcagcag aatgtgagca tggacttggc cacgttcatg   1740

aagctgcgga cggatgcggt gctgccgttg actgtggctg aggtgcagaa acttctggga   1800

ccccacgtgg agggcctgaa ggcggaggag cggcaccgcc cggtgcggga ctggatccta   1860

cggcagcggc aggacgacct ggacacgctg gggctggggc tacagggcgg catccccaac   1920

ggctacctgg tcctagacct cagcatgcaa gaggccctct cggggacgcc ctgcctccta   1980

ggacctggac ctgttctcac cgtcctggca ctgctcctag cctccaccct ggcctgaggg   2040

ccccactccc ttgctggccc cagccctgct ggggatcccc gcctggccag gagcaggcac   2100

gggtggtccc cgttccaccc caagagaact cgcgctcagt aaacgggaac atgccccctg   2160

cagacacgta aaaaaaaaaa aaaaaaa                                        2187
```

<210> SEQ ID NO 2
<211> LENGTH: 630
<212> TYPE: PRT
<213> ORGANISM: Homo sapiens

<400> SEQUENCE: 2

```
Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30
```

```
Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
```

```
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
    530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
        595                 600                 605

Pro Cys Leu Leu Gly Pro Gly Pro Val Leu Thr Val Leu Ala Leu Leu
    610                 615                 620

Leu Ala Ser Thr Leu Ala
625                 630
```

<210> SEQ ID NO 3
<211> LENGTH: 2135
<212> TYPE: DNA
<213> ORGANISM: Mus musculus

<400> SEQUENCE: 3

```
ggacagctgc tttcccaggc ccaaaagccc cttcgttgtc tccaaacagt ggtgtgggtt      60

gaggggtggg acaagtgggg acctcagagt cattgttatc cacagaccat ggccttgcca     120

acagctcgac ccctgctggg gtcctgtgga agtcccatct gcagccgaag cttcctactg     180

cttctcctta gtcttgggtg gataccacgt ctgcagaccc agactacaaa gacaagccag     240

gaggccacac tcctccatgc tgtgaacggt gccgctgact ttgccagtct ccccacaggc     300

ctctttcttg gcctcacatg tgaggaggta tctgacctga gcatggaaca agccaagggg     360

ctggctatgg ctgtaagaca gaagaacatt acactccggg gacatcagct gcgttgtctg     420

gcacgtcgcc ttcctaggca cctcaccgac gaggaactga atgctcttcc actggacctg     480

ctgctcttcc tcaacccagc catgtttcca gggcaacagg cttgtgccca cttcttctcc     540

ctcatctcta aagccaatgt ggatgtactc ccacggaggt ctctggagcg ccagaggctg     600

ctgatggagg ctctgaagtg ccagggcgtg tatggatttc aagtgagtga ggcagatgtg     660

cgggctctcg gaggcctggc ctgtgacctg cctgggaaat ttgtggccag atcttccgaa     720

gttctcctcc cctggctggc aggatgccaa ggacccctgg accagagcca ggaaaaggca     780

gtcagggagg ttctgaggag tggaagaacc caatatggcc ccccatcgaa gtggtcagtc     840

tccaccctgg atgccctgca gagcttggta gcagtgttgg atgagtccat cgtccagagc     900

atccccaagg atgtcaaagc tgaatggctg caacacatct ccagagaccc ctccaggctg     960

gggtctaagc tgaccgtcat acacccaagg ttccgacggg atgcagaaca gaaagcctgc    1020

cctccaggga aggagcccta caaggtggat gaagacctca tcttctacca gaattgggag    1080
```

```
ctggaggctt gtgtagatgg caccatgctg gccagacaaa tggaccttgt gaacgagatt   1140

cccttcacct atgagcagct cagtatcttt aagcacaaac tggacaagac ctacccacaa   1200

ggctatcctg agtccctgat ccagcagctg ggtcacttct tcagatatgt tagccctgaa   1260

gacatccacc agtggaatgt gacctcacca gacacagtga aaactctgct caaagtcagc   1320

aaaggacaaa agatgaatgc tcaggcgatt gccttggtcg cctgctatct tcggggagga   1380

ggccagctgg acgaggatat ggtaaaagcc ctgggcgaca tcccgttaag ctatctatgt   1440

gacttcagcc cccaggatct gcactcggta ccctccagtg tcatgtggct ggttgggccc   1500

caagacctgg acaagtgcag ccagaggcat ctgggtctcc tctaccagaa ggcctgctca   1560

gccttccaga atgtgagcgg cctagaatac tttgagaaaa tcaagacatt cctgggtggg   1620

gcctccgtga aggacctgcg ggccctcagc cagcacaatg tgagcatgga catagccact   1680

ttcaagaggc tgcaggtgga ttccctggtg gggctgagtg tggctgaggt acagaaactt   1740

ctggggccaa acattgtgga cctgaagacc gaggaggata aaagccctgt ccgtgactgg   1800

ctgttccggc agcatcagaa agacctagac aggctgggtt tgggacttca gggtggcatc   1860

cccaatggct acctggtcct ggacttcaat gtccgagagg ccttctccag cagagcctca   1920

ctccttgggc caggatttgt attaatatgg attccagctc tgctcccagc tttaaggctg   1980

agctgagacc accaccctgc aaggctcctg gtcccagctc tactggggcc ctcttgacca   2040

ggagtgggta ccaggggtca ttgccaaagt ttgaggactc ttgaactcaa taaacagtgg   2100

catatgctcc cttgaaaaaa aaaaaaaaaa aaaaa                              2135
```

<210> SEQ ID NO 4
<211> LENGTH: 625
<212> TYPE: PRT
<213> ORGANISM: Mus musculus

<400> SEQUENCE: 4

```
Met Ala Leu Pro Thr Ala Arg Pro Leu Leu Gly Ser Cys Gly Ser Pro
1               5                   10                  15

Ile Cys Ser Arg Ser Phe Leu Leu Leu Leu Leu Ser Leu Gly Trp Ile
            20                  25                  30

Pro Arg Leu Gln Thr Gln Thr Thr Lys Thr Ser Gln Glu Ala Thr Leu
        35                  40                  45

Leu His Ala Val Asn Gly Ala Ala Asp Phe Ala Ser Leu Pro Thr Gly
    50                  55                  60

Leu Phe Leu Gly Leu Thr Cys Glu Glu Val Ser Asp Leu Ser Met Glu
65                  70                  75                  80

Gln Ala Lys Gly Leu Ala Met Ala Val Arg Gln Lys Asn Ile Thr Leu
                85                  90                  95

Arg Gly His Gln Leu Arg Cys Leu Ala Arg Arg Leu Pro Arg His Leu
            100                 105                 110

Thr Asp Glu Glu Leu Asn Ala Leu Pro Leu Asp Leu Leu Leu Phe Leu
        115                 120                 125

Asn Pro Ala Met Phe Pro Gly Gln Gln Ala Cys Ala His Phe Phe Ser
    130                 135                 140

Leu Ile Ser Lys Ala Asn Val Asp Val Leu Pro Arg Arg Ser Leu Glu
145                 150                 155                 160

Arg Gln Arg Leu Leu Met Glu Ala Leu Lys Cys Gln Gly Val Tyr Gly
                165                 170                 175

Phe Gln Val Ser Glu Ala Asp Val Arg Ala Leu Gly Gly Leu Ala Cys
            180                 185                 190
```

```
Asp Leu Pro Gly Lys Phe Val Ala Arg Ser Ser Glu Val Leu Leu Pro
        195                 200                 205

Trp Leu Ala Gly Cys Gln Gly Pro Leu Asp Gln Ser Gln Glu Lys Ala
    210                 215                 220

Val Arg Glu Val Leu Arg Ser Gly Arg Thr Gln Tyr Gly Pro Pro Ser
225                 230                 235                 240

Lys Trp Ser Val Ser Thr Leu Asp Ala Leu Gln Ser Leu Val Ala Val
                245                 250                 255

Leu Asp Glu Ser Ile Val Gln Ser Ile Pro Lys Asp Val Lys Ala Glu
            260                 265                 270

Trp Leu Gln His Ile Ser Arg Asp Pro Ser Arg Leu Gly Ser Lys Leu
        275                 280                 285

Thr Val Ile His Pro Arg Phe Arg Arg Asp Ala Glu Gln Lys Ala Cys
    290                 295                 300

Pro Pro Gly Lys Glu Pro Tyr Lys Val Asp Glu Asp Leu Ile Phe Tyr
305                 310                 315                 320

Gln Asn Trp Glu Leu Glu Ala Cys Val Asp Gly Thr Met Leu Ala Arg
                325                 330                 335

Gln Met Asp Leu Val Asn Glu Ile Pro Phe Thr Tyr Glu Gln Leu Ser
            340                 345                 350

Ile Phe Lys His Lys Leu Asp Lys Thr Tyr Pro Gln Gly Tyr Pro Glu
        355                 360                 365

Ser Leu Ile Gln Gln Leu Gly His Phe Phe Arg Tyr Val Ser Pro Glu
    370                 375                 380

Asp Ile His Gln Trp Asn Val Thr Ser Pro Asp Thr Val Lys Thr Leu
385                 390                 395                 400

Leu Lys Val Ser Lys Gly Gln Lys Met Asn Ala Gln Ala Ile Ala Leu
                405                 410                 415

Val Ala Cys Tyr Leu Arg Gly Gly Gly Gln Leu Asp Glu Asp Met Val
            420                 425                 430

Lys Ala Leu Gly Asp Ile Pro Leu Ser Tyr Leu Cys Asp Phe Ser Pro
        435                 440                 445

Gln Asp Leu His Ser Val Pro Ser Ser Val Met Trp Leu Val Gly Pro
    450                 455                 460

Gln Asp Leu Asp Lys Cys Ser Gln Arg His Leu Gly Leu Leu Tyr Gln
465                 470                 475                 480

Lys Ala Cys Ser Ala Phe Gln Asn Val Ser Gly Leu Glu Tyr Phe Glu
                485                 490                 495

Lys Ile Lys Thr Phe Leu Gly Gly Ala Ser Val Lys Asp Leu Arg Ala
            500                 505                 510

Leu Ser Gln His Asn Val Ser Met Asp Ile Ala Thr Phe Lys Arg Leu
        515                 520                 525

Gln Val Asp Ser Leu Val Gly Leu Ser Val Ala Glu Val Gln Lys Leu
    530                 535                 540

Leu Gly Pro Asn Ile Val Asp Leu Lys Thr Glu Glu Asp Lys Ser Pro
545                 550                 555                 560

Val Arg Asp Trp Leu Phe Arg Gln His Gln Lys Asp Leu Asp Arg Leu
                565                 570                 575

Gly Leu Gly Leu Gln Gly Gly Ile Pro Asn Gly Tyr Leu Val Leu Asp
            580                 585                 590

Phe Asn Val Arg Glu Ala Phe Ser Ser Arg Ala Ser Leu Leu Gly Pro
        595                 600                 605
```

```
Gly Phe Val Leu Ile Trp Ile Pro Ala Leu Leu Pro Ala Leu Arg Leu
    610                 615                 620

Ser
625


<210> SEQ ID NO 5
<211> LENGTH: 2099
<212> TYPE: DNA
<213> ORGANISM: Rattus norvegicus

<400> SEQUENCE: 5

tgccaacagg cccctcactg tgtccaaaca gtggtgtgag ttgaggggtg ggacaggtgg     60

ggacctcaga accattgtta tccacagacc atggccttgc caacagccca accccctgctg   120

gggtcctgtg gaagccccat ctgcagccgc agctttctac tgcttctcct tagtcttggg    180

tggttgccac ttctgcagac ccagactaca aggacaagcc aggaggccgc acttctccat    240

gctgtgaccg gcaccgttga ctttgccagt cttcccacag gcctctttct tggcctcacg    300

tgtgatgagg tatctggcct aagcatggga cacgccaagg agctggctat ggctgtgaga    360

cagaagaata tcgtgctcca agtacatcag ctgcgctgtc tggcccgtcg cctccctaag    420

cacctcacca acgaggaact ggatgctctc ccactggacc tgctgctctt cctcaatcca    480

gccatgtttc cggggcaaca ggcttgtgcc cacttcttct ccctcatctc taaagccaat    540

gtaaatgtac tcccacggag atctctggag cgccagaggc tgctgaccgg ggctctgaaa    600

tgccagggtg tgtatggatt tcaagtgagt gagacggatg cacgggctct cggaggcctg    660

gcctgtgacc tgcctgggga attcgtggcc aaatcttcgg aagtcctcct cccctggctg    720

gcaagatgcg gaggacccct ggaccaaggc caggcaaagg ctgtcaggga ggttctgagg    780

agtggaagag ccccctatgg tcccccatcg acgtggtcag tctccaccct ggatgccctg    840

cagggtttgc tggtagtgtt ggatgagtcc attgtccaca gcatccctaa ggatgttatc    900

actgaatggc tgcaaggcat ctccagagag ccctccaggc tggggtctaa gtggactgtc    960

acacacccaa ggttccggcg ggacacagaa cagaaagcct gccctccagg gaaggagcct   1020

aacgtggtgg atgaaaacct catcttctac cagaattggg agctggaggc ttgtgtcgat   1080

ggtaccctgc tggccggcca gatggacctt gtgaatgaaa ttccctttac ctacgagcag   1140

ctcagcatct tcaagcacaa actggacaag acctacccac aaggctatcc cgagtccctg   1200

atcaagcagc tgggccactt cttcagatac gttagccctg aggacatccg gcagtggaat   1260

gtgacttcac cagacacagt gaatactctg cttaaagtca gcaaaggaca aaagatggat   1320

gctcaggtga ttgccttggt cgcctgctat cttcggggag gaggcaagct ggacgaggac   1380

atagtaaaag ccctggacaa catcccctta agttacctat gtgacttcag cccccaggat   1440

ctgcacgcta taccctccag tgttatgtgg ctggttgggc tccatgacct ggacaagtgc   1500

agccagaggc atctgggtat cctctatcag aaggcctgct cagccttcca gaacgtgagc   1560

gggctggaat actttgagaa aatcaggaca tttctgggtg gggcctccag ggaggacctg   1620

cgggccctca gccagcacaa tgtgagtatg gacatagcca ctttcaagaa gctgcaggtg   1680

gatgccctgg tggggctgag tgtggctgag gtacagaaac ttctagggcc acacattggg   1740

gacctgaaga ctgaggagga taaaagccct gtccgggact ggctcttccg acagcagcag   1800

aaagacctgg acagtctggg tttgggactt cagggtggca tccccaatgg ctacctgatc   1860

ctagacttca atgtccgaga ggccttctcc agtggagccc cactccttgg gccaggattt   1920

gtgtttgcat ggattccagc tctgctctca gctttaagac tgagctgaga ccaccactcc   1980
```

taaggctcct ggtcccagct ctattgtcga gccccatctt gaccaggagg ggataccagg 2040
ggtcattgcc aaagtttgag gattcttgaa cccaataaac agtggcatgt gcccccttg 2099

<210> SEQ ID NO 6
<211> LENGTH: 625
<212> TYPE: PRT
<213> ORGANISM: Rattus norvegicus

<400> SEQUENCE: 6

```
Met Ala Leu Pro Thr Ala Gln Pro Leu Leu Gly Ser Cys Gly Ser Pro
1               5                   10                  15

Ile Cys Ser Arg Ser Phe Leu Leu Leu Leu Leu Ser Leu Gly Trp Leu
            20                  25                  30

Pro Leu Leu Gln Thr Gln Thr Thr Arg Thr Ser Gln Glu Ala Ala Leu
        35                  40                  45

Leu His Ala Val Thr Gly Thr Val Asp Phe Ala Ser Leu Pro Thr Gly
    50                  55                  60

Leu Phe Leu Gly Leu Met Cys Asp Glu Val Ser Gly Leu Ser Met Gly
65                  70                  75                  80

His Ala Lys Glu Leu Ala Met Ala Val Arg Gln Lys Asn Ile Val Leu
                85                  90                  95

Gln Val His Gln Leu Arg Cys Leu Ala Arg Arg Leu Pro Lys His Leu
            100                 105                 110

Thr Asn Glu Glu Leu Asp Ala Leu Pro Leu Asp Leu Leu Leu Phe Leu
        115                 120                 125

Asn Pro Ala Met Phe Pro Gly Gln Gln Ala Cys Ala His Phe Phe Ser
    130                 135                 140

Leu Ile Ser Lys Ala Asn Val Asn Val Leu Pro Arg Arg Ser Leu Glu
145                 150                 155                 160

Arg Gln Arg Leu Leu Thr Gly Ala Leu Lys Cys Gln Gly Val Tyr Gly
                165                 170                 175

Phe Gln Val Ser Glu Thr Asp Ala Arg Ala Leu Gly Gly Leu Ala Cys
            180                 185                 190

Asp Leu Pro Gly Glu Phe Val Ala Lys Ser Ser Glu Val Leu Leu Pro
        195                 200                 205

Trp Leu Ala Arg Cys Gly Gly Pro Leu Asp Gln Gly Gln Ala Lys Ala
    210                 215                 220

Val Arg Glu Val Leu Arg Ser Gly Arg Ala Pro Tyr Gly Pro Pro Ser
225                 230                 235                 240

Thr Trp Ser Val Ser Thr Leu Asp Ala Leu Gln Gly Leu Leu Val Val
                245                 250                 255

Leu Asp Glu Ser Ile Val His Ser Ile Pro Lys Asp Val Ile Thr Glu
            260                 265                 270

Trp Leu Gln Gly Ile Ser Arg Glu Pro Ser Arg Leu Gly Ser Lys Trp
        275                 280                 285

Thr Val Thr His Pro Arg Phe Arg Arg Asp Thr Glu Gln Lys Ala Cys
    290                 295                 300

Pro Pro Gly Lys Glu Pro Asn Val Val Asp Glu Asn Leu Ile Phe Tyr
305                 310                 315                 320

Gln Asn Trp Glu Leu Glu Ala Cys Val Asp Gly Thr Leu Leu Ala Gly
                325                 330                 335

Gln Met Asp Leu Val Asn Glu Ile Pro Phe Thr Tyr Glu Gln Leu Ser
            340                 345                 350
```

```
Ile Phe Lys His Lys Leu Asp Lys Thr Tyr Pro Gln Gly Tyr Pro Glu
        355                 360                 365

Ser Leu Ile Lys Gln Leu Gly His Phe Phe Arg Tyr Val Ser Pro Glu
    370                 375                 380

Asp Ile Arg Gln Trp Asn Val Thr Ser Pro Asp Thr Val Asn Thr Leu
385                 390                 395                 400

Leu Lys Val Ser Lys Gly Gln Lys Met Asp Ala Gln Val Ile Ala Leu
                405                 410                 415

Val Ala Cys Tyr Leu Arg Gly Gly Gly Lys Leu Asp Glu Asp Ile Val
            420                 425                 430

Lys Ala Leu Asp Asn Ile Pro Leu Ser Tyr Leu Cys Asp Phe Ser Pro
        435                 440                 445

Gln Asp Leu His Ala Ile Pro Ser Ser Val Met Trp Leu Val Gly Leu
    450                 455                 460

His Asp Leu Asp Lys Cys Ser Gln Arg His Leu Gly Ile Leu Tyr Gln
465                 470                 475                 480

Lys Ala Cys Ser Ala Phe Gln Asn Val Ser Gly Leu Glu Tyr Phe Glu
                485                 490                 495

Lys Ile Arg Thr Phe Leu Gly Gly Ala Ser Arg Glu Asp Leu Arg Ala
            500                 505                 510

Leu Ser Gln His Asn Val Ser Met Asp Ile Ala Thr Phe Lys Lys Leu
        515                 520                 525

Gln Val Asp Ala Leu Val Gly Leu Ser Val Ala Glu Val Gln Lys Leu
    530                 535                 540

Leu Gly Pro His Ile Gly Asp Leu Lys Thr Glu Glu Asp Lys Ser Pro
545                 550                 555                 560

Val Arg Asp Trp Leu Phe Arg Gln Gln Gln Lys Asp Leu Asp Ser Leu
                565                 570                 575

Gly Leu Gly Leu Gln Gly Gly Ile Pro Asn Gly Tyr Leu Ile Leu Asp
            580                 585                 590

Phe Asn Val Arg Glu Ala Phe Ser Ser Gly Ala Pro Leu Leu Gly Pro
        595                 600                 605

Gly Phe Val Phe Ala Trp Ile Pro Ala Leu Leu Ser Ala Leu Arg Leu
    610                 615                 620

Ser
625


<210> SEQ ID NO 7
<211> LENGTH: 1988
<212> TYPE: DNA
<213> ORGANISM: Macaca mulatta

<400> SEQUENCE: 7

atggccttgc caatggctcg acccctgtcg gggtcctgtg ggacccccgc cctcggcagc      60

ctcctgttcc tgctcttcag cctcggatgg gtgcagccct cgagggtcct ggctggagag     120

acaaggcagg ccgcgcccct ggatggaatc ctgaccaatg cacctgacat tgccagcctc     180

tccccacgcc aactccttgg cttcacgtgt gtggaggtgt ccggcctgag cacagagctc     240

gtccaggagc tggctgtggc cttgggacag aagaatgtca agctctccgc agagcagctg     300

cgctgtctgg ctcaccagct ctctgagccc cccgaggacc tggacgccct cccgctggac     360

ctgctgctct tcctcaaccc agacgcgttc tcggggcccc aggcctgcac ccacttcttc     420

tcccgcgtcg cgaaggccaa cgtggacctg ctcccgcggg ggctcctga gagacagagg     480

ctgctgcccg gggctctgac ctgctggggt gtgcgggggt ctctgctgag cgaggctgat     540
```

```
gtacgggctc tgggaggcct ggcttgcgac ctgcctgggc gctttgtggc cgagtcggca    600

gaagtggtgc taccccggct ggtccgctgc ttgggacccc tggaccagga ccagcaggaa    660

gcagccaggg cggctctgca gagaggagga ccccccctacg gcccccgtc aacgtggtct    720

atctccaccc tggacgatct gcagagcctg ttgcctgtgc tgggccagcc cgtcatctct    780

gctcgtcctc agggcatcct ggccgcatgg cggcaacgct cctctcggga cccatcctgg    840

cagcagccgg aacagaccgt cctccggctg aggttccggc gggacgtgga gaggacaacc    900

tgtcccccag agaaagaggt ccacgagata gacgagagcc tcatcttcta caagaagcgg    960

gagctggaag cctgcgtgga cccagccctg ctggccgccc agatggaccg tgtggacgcc   1020

atccccttca cctacgagca gctggacgtc ctaaagcata aactggatga gctctaccca   1080

caaggctacc ccgagtctgt gatccggcac ctgggccacc tcttcctcaa gatgagccct   1140

gaggacattc gcaaatggaa cgtgacgtcc ctggagaccc tgaaggctct gctcaaagtc   1200

agcaaggggc atgaaatgag tgctcaggtg gccaccctga ttgaccgcgt tgtggtggga   1260

aggggccagc tagacaaaga caccgtagac acgctgactg ccttctgccc cgggtgcctg   1320

tgctccctca gccccgagag gctgagctcc gtgcccccca gcgtcatcgg ggcggtcagg   1380

ccccaggacc tggacacgtg tggcccgagg cagctggacg tcctctatcc caaggcccgc   1440

cttgctttcc agaacatgag cgggtccgaa tacttcgtga agatccggcc cttcctgggt   1500

ggggccccca cggaggatgt gaaggctctc agtcagcaga atgtgagcat ggacttggcc   1560

acgttcatga agctgcggag ggaagcggtg ctgccgttga ctgtggctga agtgcagaaa   1620

cttctgggac cccacgtgga gggcctgaag gtggaggagc agcacagccc cgtgcgggac   1680

tggatcctaa agcagcggca ggacgacctg gacacactgg ggctggggct acagggcggc   1740

atccccaacg gctacctgat cctagacctc agtgtgcgag aggccctctc ggggacgccc   1800

tgcctcctag gacctggacc tgtactcacc gtcctggctt tgctcctggc ctccaccctg   1860

gcctgaggac cctactccct tgctggcccc agccctgctg gggatccccg cctggccagg   1920

agcaggcata ggtggtccct gttccacccc aggagaactt gcgctcagta aacgcgaaca   1980

tgcccct                                                             1988
```

<210> SEQ ID NO 8
<211> LENGTH: 514
<212> TYPE: PRT
<213> ORGANISM: Macaca fascicularis

<400> SEQUENCE: 8

```
Met Ala Leu Pro Met Ala Arg Pro Leu Ser Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Val Leu Ala Gly Glu Thr Arg Gln Glu Ala Ala Pro Leu
        35                  40                  45

Asp Gly Ile Leu Thr Asn Ala Pro Asp Ile Ala Ser Leu Ser Pro Arg
    50                  55                  60

Gln Leu Leu Gly Phe Thr Cys Val Glu Val Ser Gly Leu Ser Thr Glu
65                  70                  75                  80

Leu Val Gln Glu Leu Ala Val Ala Leu Gly Gln Lys Asn Val Lys Leu
                85                  90                  95

Ser Ala Glu Gln Leu Arg Cys Leu Ala His Arg Leu Ser Glu Pro Pro
            100                 105                 110
```

-continued

```
Glu Asp Leu Asp Ala Leu Pro Leu Asp Leu Leu Leu Phe Leu Lys Gln
        115                 120                 125

Ala Ser Val Gln Gly Val Arg Gly Ser Leu Leu Ser Glu Ala Asp Val
    130                 135                 140

Arg Ala Leu Gly Gly Leu Ala Cys Asp Leu Pro Gly Arg Phe Val Ala
145                 150                 155                 160

Glu Ser Ala Glu Val Val Leu Pro Arg Leu Val Arg Cys Leu Gly Pro
                165                 170                 175

Leu Asp Gln Asp Gln Gln Glu Ala Ala Arg Ala Ala Leu Gln Arg Gly
            180                 185                 190

Gly Pro Pro Tyr Gly Pro Pro Ser Thr Trp Ser Ile Ser Thr Leu Asp
        195                 200                 205

Asp Leu Gln Ser Leu Leu Pro Val Leu Gly Gln Pro Val Ile His Ser
    210                 215                 220

Ile Pro Gln Gly Ile Leu Ala Ala Trp Arg Gln Arg Ser Ser Arg Asp
225                 230                 235                 240

Pro Ser Trp Gln Gln Pro Glu Gln Thr Val Leu Arg Pro Arg Phe Arg
                245                 250                 255

Arg Asp Val Glu Arg Thr Thr Cys Pro Pro Glu Lys Glu Val His Glu
            260                 265                 270

Ile Asp Glu Asn Leu Ile Phe Tyr Lys Lys Arg Glu Leu Glu Ala Cys
        275                 280                 285

Val Asp Ala Ala Leu Leu Ala Ala Gln Met Asp Arg Val Asp Ala Ile
    290                 295                 300

Pro Phe Thr Tyr Glu Gln Leu Asp Val Leu Lys His Lys Leu Asp Glu
305                 310                 315                 320

Leu Tyr Pro Gln Gly Tyr Pro Glu Ser Val Ile Arg His Leu Gly His
                325                 330                 335

Leu Phe Leu Lys Met Ser Pro Glu Asp Ile Arg Lys Trp Asn Val Thr
            340                 345                 350

Ser Leu Glu Thr Leu Lys Ala Leu Leu Lys Val Ser Lys Gly His Glu
        355                 360                 365

Met Ser Ala Gln Val Ala Thr Leu Ile Asp Arg Val Val Val Gly Arg
    370                 375                 380

Gly Gln Leu Asp Lys Asp Thr Ala Asp Thr Leu Thr Ala Phe Cys Pro
385                 390                 395                 400

Gly Cys Leu Cys Ser Leu Ser Pro Glu Arg Leu Arg Ser Val Pro Pro
                405                 410                 415

Ser Val Ile Gly Ala Val Arg Pro Gln Asp Leu Asp Thr Cys Gly Pro
            420                 425                 430

Arg Gln Leu Asp Val Leu Tyr Pro Lys Ala Arg Leu Ala Phe Gln Asn
        435                 440                 445

Met Ser Gly Ser Glu Tyr Phe Val Lys Ile Arg Pro Phe Leu Gly Gly
    450                 455                 460

Ala Pro Thr Glu Asp Leu Lys Ala Leu Ser Gln Gln Asn Val Ser Met
465                 470                 475                 480

Asp Leu Ala Thr Phe Met Lys Leu Arg Arg Glu Ala Val Leu Val Gly
                485                 490                 495

Arg Ala Gly Gly Gly Ala Ser Gly Gly Gly Asp Asn Arg Gly Arg Glu
            500                 505                 510

Gly Val
```

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Arg Ala Ser Gln Ser Ile Asn Asn Tyr Leu Asn
1 5 10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Ala Ala Ser Ser Leu Gln Ser
1 5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Gln Gln Thr Tyr Ser Asn Pro Thr
1 5

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Arg Ala Ser Gln Tyr Ile Gly Ser Asn Leu His
1 5 10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Tyr Ala Ser Gln Ser Phe Ser
1 5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

His Gln Ser Ser Ser Leu Pro Trp Thr
1 5

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Gln Ser Ser Leu Ser Leu Gln His Ser Asn Gly Lys Thr Tyr Leu Tyr
1 5 10 15

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Glu Val Ser Asn Arg Phe Ser
1 5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Met Gln Ser Lys Gln Leu Pro Cys Ser
1 5

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Gln Ser Ser Leu Ser Leu Gln His Ser Asn Gly Lys Thr Tyr Leu Tyr
1 5 10 15

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Glu Val Ser Asn Arg Phe Ser
1 5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

Met Gln Ser Lys Gln Leu Pro Tyr Ser
1 5

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Arg Ala Ser Gln Thr Val Ser Ser Ser Tyr Leu Ala
1 5 10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Gly Ala Ser Ile Arg Ala Thr
1 5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Gln Gln Tyr Gly Ser Ser Leu Thr
1 5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Arg Ala Ser Gln Ser Ile Gly Ser Ser Leu His
1 5 10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Tyr Ala Ser Gln Ser Phe Ser
1 5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 26

His Gln Ser Ser Ser Leu Pro Trp Thr
1 5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Arg Ser Ser Gln Ser Leu Val His Ser Asp Arg Asn Thr Tyr Leu Ser
1 5 10 15

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 28

Lys Ile Ser Asn Arg Phe Ser
1 5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Met Gln Ala Thr Gln Phe Pro Leu Thr
1 5

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Arg Ser Ser Leu Ser Leu Leu His Ser Asn Gly Tyr Asn Tyr Leu Asp
1 5 10 15

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Leu Gly Ser Asn Arg Ala Ser
1 5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 32

Met Gln Gly Leu His Thr Pro Pro Ser
1 5

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Gln Ala Ser Gln Asp Ile Ser Asn Tyr Leu Asn
1 5 10

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 34

Ala Ala Ser Ser Leu Glu Thr
1 5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 35

Gln Gln Tyr Asp Asn Leu Pro
1 5

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 36

Gln Ala Ser Gln Asp Ile Ser Asn Tyr Leu Asn
1 5 10

<210> SEQ ID NO 37
<211> LENGTH: 7
<212> TYPE: PRT

<213> ORGANISM: Artificial Sequence
<220> FEATURE:
<223> OTHER INFORMATION: Description of Artificial Sequence: Synthetic peptide

<400> SEQUENCE: 37

Ala Ala Ser Ser Leu Glu Thr
1 5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

Gln Gln Tyr Asp Asn Leu Pro
1 5

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 39

Arg Ala Ser Gln Gly Ile Arg Asn Ala Leu Gly
1 5 10

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 40

Ala Ala Ser Ser Leu Gln Ser
1 5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 41

Leu Gln His Asn Ser Tyr Pro Arg Thr
1 5

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 42

Arg Ala Ser Gln Gly Ile Arg Asn Asp Leu His
1 5 10

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

Ala Ala Ser Ser Leu Gln Ser
1 5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

Leu Gln His Tyr Ser Tyr Pro Trp Thr
1 5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

Asn Asn Asn Tyr Tyr Trp Thr
1 5

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

Tyr Ile Tyr Tyr Ser Gly Ser Thr Phe Tyr Asn Pro Ser Leu Lys Ser
1 5 10 15

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Glu Asp Thr Met Thr Gly Leu Asp Val
1 5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Ser Tyr Gly Met His
1               5

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Ala Ile Trp Tyr Asp Gly Ser Asn Lys Tyr Tyr Ala Asp Ser Val Lys
1               5                   10                  15

Gly

<210> SEQ ID NO 50
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Asp Leu Ser Ile Phe Gly Val Val Ile Leu Ser Asp Tyr
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 51

Gly Asp Gly His Phe Trp Ser
1               5

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 52

Tyr Ile Tyr Tyr Ser Gly Ser Thr Tyr Tyr Asn Pro Ser Leu Lys Ser
1               5                   10                  15

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 53

Leu Arg Gly Gly Tyr Lys Phe Asp Tyr
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 54

```
Asn Tyr Tyr Trp Ser
1               5
```

<210> SEQ ID NO 55
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 55

```
Arg Ile Phe Thr Ser Gly Ser Thr Asn Tyr Asn Pro Ser Leu Lys Ser
1               5                   10                  15
```

<210> SEQ ID NO 56
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 56

```
Glu Gly Gly His Tyr Gly Ser Ser Gly Tyr Leu Tyr Tyr Tyr Tyr Phe
1               5                   10                  15

Gly Met Asp Val
            20
```

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 57

```
Ser Tyr Gly Met His
1               5
```

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

```
Ala Ile Trp Tyr Asp Gly Ser Asn Lys Tyr Tyr Ala Asp Ser Val Lys
1               5                   10                  15

Gly
```

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Asp Leu Ser Ile Phe Gly Val Val Ile Leu Ser Asp Tyr
1 5 10

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Ser Gly Gly Tyr Tyr Trp Asn
1 5

<210> SEQ ID NO 61
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Tyr Ile Tyr Tyr Ser Gly Ser Thr Tyr Tyr Asn Pro Ser Leu Arg Gly
1 5 10 15

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Asp Gly Gly Asp Ser Tyr Gly Arg Met Asp Val
1 5 10

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Ser Asn Ser Val Ala Trp Asn
1 5

<210> SEQ ID NO 64
<211> LENGTH: 18
<212> TYPE: PRT
<213> ORGANISM: Artificial Sequence
<220> FEATURE:
<223> OTHER INFORMATION: Description of Artificial Sequence: Synthetic peptide

<400> SEQUENCE: 64

Arg Thr Tyr Tyr Arg Ser Lys Trp Tyr Asn Asp Tyr Ala Val Ser Val
1 5 10 15

Lys Ser

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Gly Ile Phe Val Val Pro Ala Val Pro Arg Phe Asp Tyr
1 5 10

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Ser His Tyr Trp Ser
1 5

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Tyr Ile Tyr Tyr Ser Gly Ser Thr Asn Tyr Asn Pro Ser Leu Lys Ser
1 5 10 15

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Asp Gly Trp Ser Ala Phe Asp Tyr
1 5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Ser Tyr Tyr Trp Ser
1 5

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Tyr Ile Tyr Tyr Ser Gly Ser Thr Asn Tyr Asn Pro Ser Leu Lys Ser
1 5 10 15

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Val Asp Tyr Lys Ala Phe Asp Ile
1 5

<210> SEQ ID NO 72
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Asn Asn Tyr
20 25 30

Leu Asn Trp Tyr Gln Gln Lys Pro Gly Lys Ala Pro Thr Leu Leu Ile
35 40 45

Tyr Ala Ala Ser Ser Leu Gln Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Ala Tyr Phe Cys Gln Gln Thr Tyr Ser Asn Pro Thr
85 90 95

Phe Gly Gln Gly Thr Lys Val Glu Val Lys
100 105

<210> SEQ ID NO 73
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

Glu Ile Val Leu Thr Gln Ser Pro Asp Phe Gln Ser Val Thr Pro Lys
1 5 10 15

Glu Lys Val Thr Ile Thr Cys Arg Ala Ser Gln Tyr Ile Gly Ser Asn
20 25 30

Leu His Trp Tyr Gln Gln Thr Pro Asp Gln Ser Pro Lys Leu Leu Ile
35 40 45

Lys Tyr Ala Ser Gln Ser Phe Ser Gly Val Pro Ser Arg Phe Ser Gly
50 55 60

Ser Gly Ser Gly Thr Asp Phe Thr Leu Thr Ile Asn Ser Leu Glu Ala
65 70 75 80

```
Glu Asp Ala Ala Thr Tyr Tyr Cys His Gln Ser Ser Ser Leu Pro Trp
                85                  90                  95

Thr Phe Gly Gln Gly Thr Lys Val Glu Ile Lys
            100                 105


<210> SEQ ID NO 74
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Ile Val Met Thr Gln Thr Pro Leu Ser Leu Ser Val Ala Pro Gly
1               5                   10                  15

Gln Pro Ala Ser Ile Ser Cys Gln Ser Ser Leu Ser Leu Gln His Ser
            20                  25                  30

Asn Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Lys Gln Leu Pro Cys Ser Phe Gly Gln Gly Thr Lys Leu Glu Ile Lys
            100                 105                 110


<210> SEQ ID NO 75
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Asp Ile Val Met Thr Gln Thr Pro Leu Ser Leu Ser Val Ala Pro Gly
1               5                   10                  15

Gln Pro Ala Ser Ile Ser Cys Gln Ser Ser Leu Ser Leu Gln His Ser
            20                  25                  30

Asn Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Lys Gln Leu Pro Tyr Ser Phe Gly Gln Gly Thr Lys Leu Glu Ile Lys
            100                 105                 110


<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 76

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys
            100                 105
```

<210> SEQ ID NO 77
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 77

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Arg Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Gly Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Trp
                85                  90                  95

Thr Phe Gly Gln Gly Thr Lys Val Glu Ile Lys
            100                 105
```

<210> SEQ ID NO 78
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 78

```
Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Arg Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
```

```
65                  70                  75                  80

Ser Arg Val Glu Ala Glu Asp Val Gly Val Tyr Tyr Cys Met Gln Ala
                85                  90                  95

Thr Gln Phe Pro Leu Thr Phe Gly Gly Gly Thr Lys Val Glu Ile Lys
            100                 105                 110


<210> SEQ ID NO 79
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Asp Ile Val Met Thr Gln Ser Pro Leu Ser Leu Ser Val Thr Pro Gly
1               5                   10                  15

Glu Pro Ala Ser Ile Ser Cys Arg Ser Ser Leu Ser Leu Leu His Ser
            20                  25                  30

Asn Gly Tyr Asn Tyr Leu Asp Trp Phe Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Asp Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu His Thr Pro Pro Ser Phe Gly Gln Gly Thr Lys Leu Glu Ile Lys
            100                 105                 110


<210> SEQ ID NO 80
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Glu Thr Gly Val Pro Ser Arg Phe Ser Gly
    50                  55                  60

Gly Gly Ser Gly Thr Asp Phe Ala Phe Thr Ile Ser Ser Leu Gln Pro
65                  70                  75                  80

Glu Asp Ile Ala Pro Tyr Tyr Cys Gln Gln Tyr Asp Asn Leu Pro Phe
                85                  90                  95

Gly Pro Gly Thr Lys Val Asp Ile Lys
            100                 105


<210> SEQ ID NO 81
<211> LENGTH: 105
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 81

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asn Leu Pro Phe
                85                  90                  95

Gly Gln Gly Thr Lys Val Asp Ile Lys
            100                 105
```

<210> SEQ ID NO 82
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Ala
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Arg Arg
            100                 105
```

<210> SEQ ID NO 83
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 83

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu His Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Tyr Ser Tyr Pro Trp
                85                  90                  95

Thr Phe Gly Gln Gly Thr Lys Val Glu Ile Lys
            100                 105


<210> SEQ ID NO 84
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 85
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Met Asp Met Arg Val Pro Ala Gln Leu Leu Gly Leu Leu Leu Leu Trp
1               5                   10                  15

Leu Arg Gly Ala Arg Cys
            20


<210> SEQ ID NO 86
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45
```

```
Trp Ile Gly Tyr Ile Tyr Tyr Ser Gly Ser Thr Phe Tyr Asn Pro Ser
    50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
            100                 105                 110

Thr Thr Val Thr Val Ser Ser
        115


<210> SEQ ID NO 87
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Ile Phe Gly Val Val Ile Leu Ser Asp Tyr Trp
            100                 105                 110

Gly Gln Gly Thr Leu Val Thr Val Ser Ser
        115                 120


<210> SEQ ID NO 88
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Gly Asp
            20                  25                  30

Gly His Phe Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

Cys Ala Arg Leu Arg Gly Gly Tyr Lys Phe Asp Tyr Trp Gly Gln Gly
100 105 110

Thr Leu Val Thr Val Ser Ser
115

<210> SEQ ID NO 89
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 89

Gln Val Gln Leu Gln Glu Ser Gly Pro Gly Leu Val Lys Pro Ser Glu
1 5 10 15

Thr Leu Ser Leu Thr Cys Thr Val Ser Gly Asp Ser Ile Asn Asn Tyr
20 25 30

Tyr Trp Ser Trp Ile Arg Gln Pro Ala Gly Lys Gly Leu Glu Trp Ile
35 40 45

Gly Arg Ile Phe Thr Ser Gly Ser Thr Asn Tyr Asn Pro Ser Leu Lys
50 55 60

Ser Arg Val Thr Met Ser Ile Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Glu Gly Gly His Tyr Gly Ser Ser Gly Tyr Leu Tyr Tyr Tyr Tyr
100 105 110

Phe Gly Met Asp Val Trp Gly Gln Gly Thr Thr Val Thr Val Ser Ser
115 120 125

<210> SEQ ID NO 90
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Ala Ile Trp Tyr Asp Gly Ser Asn Lys Tyr Tyr Ala Asp Ser Val
50 55 60

Lys Gly Arg Phe Thr Ile Ser Arg Asp Asn Ser Lys Asn Met Leu Tyr
65 70 75 80

Leu Gln Met Asn Ser Leu Arg Ala Glu Asp Thr Ala Val Tyr Tyr Cys
85 90 95

Ala Arg Asp Leu Ser Ile Phe Gly Val Val Ile Leu Ser Asp Tyr Trp
100 105 110

Gly Gln Gly Thr Leu Val Thr Val Ser Ser
115 120

<210> SEQ ID NO 91
<211> LENGTH: 121

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Arg Gly Arg Leu Ile Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Asp Gly Gly Asp Ser Tyr Gly Arg Met Asp Val Trp Gly
            100                 105                 110

Gln Gly Thr Thr Val Thr Val Ser Ala
        115                 120
```

<210> SEQ ID NO 92
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Ile Phe Val Val Pro Ala Val Pro Arg Phe
            100                 105                 110

Asp Tyr Trp Gly Gln Gly Thr Leu Val Thr Val Ser Ser
        115                 120                 125
```

<210> SEQ ID NO 93
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 93

```
Gln Val Gln Leu Gln Glu Ser Gly Pro Gly Leu Val Lys Pro Ser Glu
```

```
1               5                   10                  15

Thr Leu Ser Leu Thr Cys Thr Val Ser Gly Gly Ser Ile Ile Ser His
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Asp Gly Trp Ser Ala Phe Asp Tyr Trp Gly Gln Gly Thr Leu Val
            100                 105                 110

Thr Val Ser Ser
        115


<210> SEQ ID NO 94
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Val Asp Tyr Lys Ala Phe Asp Ile Trp Gly Gln Gly Thr Met Val
            100                 105                 110

Thr Val Ser Ser
        115


<210> SEQ ID NO 95
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Met Lys His Leu Trp Phe Phe Leu Leu Leu Val Ala Ala Pro Arg Trp
1               5                   10                  15

Val Leu Ser


<210> SEQ ID NO 96
<211> LENGTH: 330
<212> TYPE: PRT
<213> ORGANISM: Artificial Sequence
```

<220> FEATURE:
<223> OTHER INFORMATION: Description of Artificial Sequence: Synthetic polypeptide

<400> SEQUENCE: 96

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 97
<211> LENGTH: 468
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Asn Asn Asn Asn Tyr Tyr Trp Thr Trp Ile Arg Gln His Pro Gly Lys
    50                  55                  60

Gly Leu Glu Trp Ile Gly Tyr Ile Tyr Tyr Ser Gly Ser Thr Phe Tyr
65                  70                  75                  80

Asn Pro Ser Leu Lys Ser Arg Val Thr Ile Ser Val Asp Thr Ser Lys
                85                  90                  95

Thr Gln Phe Ser Leu Lys Leu Ser Ser Val Thr Ala Ala Asp Thr Ala
            100                 105                 110

Val Tyr Tyr Cys Ala Arg Glu Asp Thr Met Thr Gly Leu Asp Val Trp
        115                 120                 125

Gly Gln Gly Thr Thr Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415
```

```
Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465


<210> SEQ ID NO 98
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Asn Asn Tyr Leu Asn Trp Tyr Gln Gln Lys Pro Gly Lys
    50                  55                  60

Ala Pro Thr Leu Leu Ile Tyr Ala Ala Ser Ser Leu Gln Ser Gly Val
65                  70                  75                  80

Pro Ser Arg Phe Ser Gly Ser Arg Ser Gly Thr Asp Phe Thr Leu Thr
                85                  90                  95

Ile Ser Ser Leu Gln Pro Glu Asp Phe Ala Ala Tyr Phe Cys Gln Gln
            100                 105                 110

Thr Tyr Ser Asn Pro Thr Phe Gly Gln Gly Thr Lys Val Glu Val Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235


<210> SEQ ID NO 99
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Ile Phe Gly Val Val Ile Leu Ser Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
```

```
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 100
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Tyr Ile Gly Ser Asn
            20                  25                  30

Leu His Trp Tyr Gln Gln Thr Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 101
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Gly Asp
            20                  25                  30

Gly His Phe Trp Ser Trp Ile Arg Gln His Pro Gly Lys Gly Leu Glu
```

```
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Arg Gly Gly Tyr Lys Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 102
<211> LENGTH: 219
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

```
Asp Ile Val Met Thr Gln Thr Pro Leu Ser Leu Ser Val Ala Pro Gly
1               5                   10                  15

Gln Pro Ala Ser Ile Ser Cys Gln Ser Ser Leu Ser Leu Gln His Ser
            20                  25                  30

Asn Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Lys Gln Leu Pro Tyr Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 103
<211> LENGTH: 458
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Asn Tyr
            20                  25                  30

Tyr Trp Ser Trp Ile Arg Gln Pro Ala Gly Lys Gly Leu Glu Trp Ile
        35                  40                  45

Gly Arg Ile Phe Thr Ser Gly Ser Thr Asn Tyr Asn Pro Ser Leu Lys
    50                  55                  60

Ser Arg Val Thr Met Ser Ile Asp Thr Ser Lys Asn Gln Phe Ser Leu
65                  70                  75                  80
```

```
Lys Leu Ser Ser Val Thr Ala Ala Asp Thr Ala Val Tyr Tyr Cys Ala
                85                  90                  95

Arg Glu Gly Gly His Tyr Gly Ser Ser Gly Tyr Leu Tyr Tyr Tyr Tyr
            100                 105                 110

Phe Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Ser Ser Lys
    130                 135                 140

Ser Thr Ser Gly Gly Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Gln Thr
        195                 200                 205

Tyr Ile Cys Asn Val Asn His Lys Pro Ser Asn Thr Lys Val Asp Lys
    210                 215                 220

Lys Val Glu Pro Lys Ser Cys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Glu Glu
        355                 360                 365

Met Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```

<210> SEQ ID NO 104
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 105
<211> LENGTH: 452
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Ile Phe Gly Val Val Ile Leu Ser Asp Tyr Trp
            100                 105                 110

Gly Gln Gly Thr Leu Val Thr Val Ser Ser Ala Ser Thr Lys Gly Pro
```

```
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 106
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

```
Glu Ile Val Leu Thr Gln Ser Pro Asp Phe Gln Ser Val Thr Pro Lys
1               5                   10                  15
```

```
Glu Lys Val Thr Ile Thr Cys Arg Ala Ser Gln Ser Ile Gly Ser Ser
            20                  25                  30

Leu His Trp Tyr Arg Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Gly Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 107
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Arg Gly Arg Leu Ile Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Asp Gly Gly Asp Ser Tyr Gly Arg Met Asp Val Trp Gly
            100                 105                 110

Gln Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 108
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Arg Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
```

```
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 109
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Ile Phe Val Val Pro Ala Val Pro Arg Phe
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190
```

```
Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455


<210> SEQ ID NO 110
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Val Met Thr Gln Ser Pro Leu Ser Leu Ser Val Thr Pro Gly
1               5                   10                  15

Glu Pro Ala Ser Ile Ser Cys Arg Ser Ser Leu Ser Leu Leu His Ser
            20                  25                  30

Asn Gly Tyr Asn Tyr Leu Asp Trp Phe Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Asp Thr Asp Phe Thr Leu Lys Ile
65                  70                  75                  80

Ser Arg Val Glu Ala Glu Asp Val Gly Val Tyr Tyr Cys Met Gln Gly
                85                  90                  95
```

```
Leu His Thr Pro Pro Ser Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 111
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Asn Leu Pro Phe
                85                  90                  95

Gly Gln Gly Thr Lys Val Asp Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210
```

<210> SEQ ID NO 112
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 112

Gly Ser Ser Thr Gly Ala Val Thr Ser Gly Asn Tyr Pro Asn
1 5 10

<210> SEQ ID NO 113
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 113

Gly Thr Lys Phe Leu Ala Pro
1 5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 114

Val Leu Trp Tyr Ser Asn Arg Trp Val
1 5

<210> SEQ ID NO 115
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 115

Lys Tyr Ala Met Asn
1 5

<210> SEQ ID NO 116
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 116

Arg Ile Arg Ser Lys Tyr Asn Asn Tyr Ala Thr Tyr Tyr Ala Asp Ser
1 5 10 15

Val Lys Asp

<210> SEQ ID NO 117
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 117

His Gly Asn Phe Gly Asn Ser Tyr Ile Ser Tyr Trp Ala Tyr
1 5 10

<210> SEQ ID NO 118
<211> LENGTH: 125
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 118

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Lys Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Thr
65 70 75 80

Ala Tyr Leu Gln Met Asn Asn Leu Lys Thr Glu Asp Thr Ala Val Tyr
85 90 95

Tyr Cys Val Arg His Gly Asn Phe Gly Asn Ser Tyr Ile Ser Tyr Trp
100 105 110

Ala Tyr Trp Gly Gln Gly Thr Leu Val Thr Val Ser Ser
115 120 125

<210> SEQ ID NO 119
<211> LENGTH: 375
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 119
gaggtgcagc tggtcgagtc tggaggagga ttggtgcagc ctggagggtc attgaaactc 60
tcatgtgcag cctctggatt caccttcaat aagtacgcca tgaactgggt ccgccaggct 120
ccaggaaagg gtttggaatg ggttgctcgc ataagaagta aatataataa ttatgcaaca 180
tattatgccg attcagtgaa agacaggttc accatctcca gagatgattc aaaaaacact 240
gcctatctac aaatgaacaa cttgaaaact gaggacactg ccgtgtacta ctgtgtgaga 300
catgggaact tcggtaatag ctacatatcc tactgggctt actggggcca agggactctg 360
gtcaccgtct cctca 375

<210> SEQ ID NO 120
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 120

Gln Thr Val Val Thr Gln Glu Pro Ser Leu Thr Val Ser Pro Gly Gly
1 5 10 15

```
Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105
```

<210> SEQ ID NO 121
<211> LENGTH: 327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 121

```
cagactgttg tgactcagga accttcactc accgtatcac ctggtggaac agtcacactc     60

acttgtggct cctcgactgg ggctgttaca tctggcaact acccaaactg ggtccaacaa    120

aaaccaggtc aggcaccccg tggtctaata ggtgggacta agttcctcgc ccccggtact    180

cctgccagat tctcaggctc cctgcttgga ggcaaggctg ccctcaccct ctcaggggta    240

cagccagagg atgaggcaga atattactgt gttctatggt acagcaaccg ctgggtgttc    300

ggtggaggaa ccaaactgac tgtccta                                        327
```

<210> SEQ ID NO 122
<211> LENGTH: 249
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 122

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140
```

Thr Gln Glu Pro Ser Leu Thr Val Ser Pro Gly Gly Thr Val Thr Leu
145 150 155 160

Thr Cys Gly Ser Ser Thr Gly Ala Val Thr Ser Gly Asn Tyr Pro Asn
165 170 175

Trp Val Gln Gln Lys Pro Gly Gln Ala Pro Arg Gly Leu Ile Gly Gly
180 185 190

Thr Lys Phe Leu Ala Pro Gly Thr Pro Ala Arg Phe Ser Gly Ser Leu
195 200 205

Leu Gly Gly Lys Ala Ala Leu Thr Leu Ser Gly Val Gln Pro Glu Asp
210 215 220

Glu Ala Glu Tyr Tyr Cys Val Leu Trp Tyr Ser Asn Arg Trp Val Phe
225 230 235 240

Gly Gly Gly Thr Lys Leu Thr Val Leu
245

<210> SEQ ID NO 123
<211> LENGTH: 747
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 123
gaggtgcagc tggtcgagtc tggaggagga ttggtgcagc ctggagggtc attgaaactc 60
tcatgtgcag cctctggatt caccttcaat aagtacgcca tgaactgggt ccgccaggct 120
ccaggaaagg gtttggaatg ggttgctcgc ataagaagta aatataataa ttatgcaaca 180
tattatgccg attcagtgaa agacaggttc accatctcca gagatgattc aaaaaacact 240
gcctatctac aaatgaacaa cttgaaaact gaggacactg ccgtgtacta ctgtgtgaga 300
catgggaact tcggtaatag ctacatatcc tactgggctt actggggcca agggactctg 360
gtcaccgtct cctcaggtgg tggtggttct ggcggcggcg gctccggtgg tggtggttct 420
cagactgttg tgactcagga accttcactc accgtatcac ctggtggaac agtcacactc 480
acttgtggct cctcgactgg ggctgttaca tctggcaact acccaaactg ggtccaacaa 540
aaaccaggtc aggcaccccg tggtctaata ggtgggacta agttcctcgc ccccggtact 600
cctgccagat tctcaggctc cctgcttgga ggcaaggctg ccctcaccct ctcaggggta 660
cagccagagg atgaggcaga atattactgt gttctatggt acagcaaccg ctgggtgttc 720
ggtggaggaa ccaaactgac tgtccta 747

<210> SEQ ID NO 124
<211> LENGTH: 1578
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 124
atggggtcaa ccgccatcct tggcctcctc ctggctgtcc tgcagggagg gcgcgcccag 60
gtgcagctgc aggagtcggg cccaggactg gtgaagcctt cacagaccct gtccctcacc 120
tgcactgtct ctggtggctc catcaacaat aataattact actggacctg gatccgccag 180
cacccaggga agggcctgga gtggattggg tacatctatt acagtgggag caccttctac 240
aacccgtccc tcaagagtcg agttaccata tcagtcgaca cgtctaagac ccagttctcc 300

```
ctgaagttga gctctgtgac tgccgcggac acggccgtgt attactgtgc gagagaggat    360
acgatgacgg gcctggacgt ctggggccaa gggaccacgg tcaccgtctc ctcaggaggc    420
ggcggttcag gcggaggtgg ctctggcggt ggcggaagtg acatccagat gacccagtct    480
ccatcctccc tgtctgcatc tgtaggagac agagtcacca tcacttgccg ggctagtcag    540
agcattaaca actatttaaa ttggtatcag cagaaaccag ggaaagcccc tacgctcctg    600
atctatgctg catccagttt gcaaagtggg gtcccatcaa ggttcagtgg cagtagatct    660
gggacagatt tcactctcac catcagcagt ctgcaacctg aagattttgc agcttacttc    720
tgtcaacaga cttacagtaa cccgacgttc ggccaaggga ccaaggtgga agtcaaaggg    780
ggtggaggct cagaggtgca gctggtggag tctgggggag gcctggtcaa gcctggggtg    840
tccctgagac tctcctgtgc agcctctgga ttcaccttca gtagatatgg catgaactgg    900
gtccgccagg ctccagggaa ggggctggag tgggtctcat ccattagtag tagtggtact    960
tacataaagt acgcagactc agtgaagggc cgattcacca tctccagaga caacgccaag   1020
aactcactga atctgcaaat gaacagcctg agagccgagg acacggctgt gtattattgt   1080
gcgagagatc gggaccggta tccccttgac tactggggcc agggaaccct ggtcaccgtc   1140
tcctcaggag gcggcggttc aggcggaggt ggctctggcg gtggcggaag ttcctatgag   1200
ctgacacagc caccctcggt gtcagtgtcc ccaggacaaa cggccaggat cacctgctct   1260
ggagatgcat tgccaaaaaa atatgcttat tggtaccagc agaagtcagg ccaggcccct   1320
gtgctggtca tctatgaggc caccaaacga ccctccggga ttcctgagag attctctggc   1380
tccagctcag ggacaatggc caccttgact ctcagtgggg cccaggtgga ggatgaagct   1440
gactactact gttactcaac agacagcact aattatcatt gggtgttcgg cggagggacc   1500
aagctgaccg tcctagcggc cgcagactac aaagacgatg acgacaaggg cagttctcac   1560
catcaccatc accactaa                                                 1578
```

```
<210> SEQ ID NO 125
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Met Gly Ser Thr Ala Ile Leu Gly Leu Leu Leu Ala Val Leu Gln Gly
1               5                   10                  15

Gly Arg Ala Gln Val Gln Leu Gln Glu Ser Gly Pro Gly Leu Val Lys
            20                  25                  30

Pro Ser Gln Thr Leu Ser Leu Thr Cys Thr Val Ser Gly Gly Ser Ile
        35                  40                  45

Asn Asn Asn Asn Tyr Tyr Trp Thr Trp Ile Arg Gln His Pro Gly Lys
    50                  55                  60

Gly Leu Glu Trp Ile Gly Tyr Ile Tyr Tyr Ser Gly Ser Thr Phe Tyr
65                  70                  75                  80

Asn Pro Ser Leu Lys Ser Arg Val Thr Ile Ser Val Asp Thr Ser Lys
                85                  90                  95

Thr Gln Phe Ser Leu Lys Leu Ser Ser Val Thr Ala Ala Asp Thr Ala
            100                 105                 110

Val Tyr Tyr Cys Ala Arg Glu Asp Thr Met Thr Gly Leu Asp Val Trp
        115                 120                 125
```

```
Gly Gln Gly Thr Thr Val Thr Val Ser Ser Gly Gly Gly Gly Ser Gly
    130                 135                 140

Gly Gly Gly Ser Gly Gly Gly Gly Ser Asp Ile Gln Met Thr Gln Ser
145                 150                 155                 160

Pro Ser Ser Leu Ser Ala Ser Val Gly Asp Arg Val Thr Ile Thr Cys
                165                 170                 175

Arg Ala Ser Gln Ser Ile Asn Asn Tyr Leu Asn Trp Tyr Gln Gln Lys
            180                 185                 190

Pro Gly Lys Ala Pro Thr Leu Leu Ile Tyr Ala Ala Ser Ser Leu Gln
        195                 200                 205

Ser Gly Val Pro Ser Arg Phe Ser Gly Ser Arg Ser Gly Thr Asp Phe
    210                 215                 220

Thr Leu Thr Ile Ser Ser Leu Gln Pro Glu Asp Phe Ala Ala Tyr Phe
225                 230                 235                 240

Cys Gln Gln Thr Tyr Ser Asn Pro Thr Phe Gly Gln Gly Thr Lys Val
                245                 250                 255

Glu Val Lys Gly Gly Gly Gly Ser Glu Val Gln Leu Val Glu Ser Gly
            260                 265                 270

Gly Gly Leu Val Lys Pro Gly Val Ser Leu Arg Leu Ser Cys Ala Ala
        275                 280                 285

Ser Gly Phe Thr Phe Ser Arg Tyr Gly Met Asn Trp Val Arg Gln Ala
    290                 295                 300

Pro Gly Lys Gly Leu Glu Trp Val Ser Ser Ile Ser Ser Ser Gly Thr
305                 310                 315                 320

Tyr Ile Lys Tyr Ala Asp Ser Val Lys Gly Arg Phe Thr Ile Ser Arg
                325                 330                 335

Asp Asn Ala Lys Asn Ser Leu Asn Leu Gln Met Asn Ser Leu Arg Ala
            340                 345                 350

Glu Asp Thr Ala Val Tyr Tyr Cys Ala Arg Asp Arg Asp Arg Tyr Pro
        355                 360                 365

Leu Asp Tyr Trp Gly Gln Gly Thr Leu Val Thr Val Ser Ser Gly Gly
    370                 375                 380

Gly Gly Ser Gly Gly Gly Gly Ser Gly Gly Gly Gly Ser Ser Tyr Glu
385                 390                 395                 400

Leu Thr Gln Pro Pro Ser Val Ser Val Ser Pro Gly Gln Thr Ala Arg
                405                 410                 415

Ile Thr Cys Ser Gly Asp Ala Leu Pro Lys Lys Tyr Ala Tyr Trp Tyr
            420                 425                 430

Gln Gln Lys Ser Gly Gln Ala Pro Val Leu Val Ile Tyr Glu Ala Thr
        435                 440                 445

Lys Arg Pro Ser Gly Ile Pro Glu Arg Phe Ser Gly Ser Ser Ser Gly
    450                 455                 460

Thr Met Ala Thr Leu Thr Leu Ser Gly Ala Gln Val Glu Asp Glu Ala
465                 470                 475                 480

Asp Tyr Tyr Cys Tyr Ser Thr Asp Ser Thr Asn Tyr His Trp Val Phe
                485                 490                 495

Gly Gly Gly Thr Lys Leu Thr Val Leu Ala Ala Ala Asp Tyr Lys Asp
            500                 505                 510

Asp Asp Asp Lys Gly Ser Ser His His His His His His
        515                 520                 525
```

<210> SEQ ID NO 126
<211> LENGTH: 1509

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 126

caggtgcagc tgcaggagtc gggcccagga ctggtgaagc cttcacagac cctgtccctc     60

acctgcactg tctctggtgg ctccatcaac aataataatt actactggac ctggatccgc    120

cagcacccag ggaagggcct ggagtggatt gggtacatct attacagtgg gagcaccttc    180

tacaacccgt ccctcaagag tcgagttacc atatcagtcg acacgtctaa gacccagttc    240

tccctgaagt tgagctctgt gactgccgcg gacacggccg tgtattactg tgcgagagag    300

gatacgatga cgggcctgga cgtctggggc caagggacca cggtcaccgt ctcctcagga    360

ggcggcggtt caggcggagg tggctctggc ggtggcggaa gtgacatcca gatgacccag    420

tctccatcct ccctgtctgc atctgtagga gacagagtca ccatcacttg ccgggctagt    480

cagagcatta acaactattt aaattggtat cagcagaaac cagggaaagc ccctacgctc    540

ctgatctatg ctgcatccag tttgcaaagt ggggtcccat caaggttcag tggcagtaga    600

tctgggacag atttcactct caccatcagc agtctgcaac ctgaagattt tgcagcttac    660

ttctgtcaac agacttacag taacccgacg ttcggccaag ggaccaaggt ggaagtcaaa    720

aggtccggag gtggtggatc cgaggtgcag ctggtcgagt ctggaggagg attggtgcag    780

cctggagggt cattgaaact ctcatgtgca gcctctggat tcaccttcaa taagtacgcc    840

atgaactggg tccgccaggc tccaggaaag ggtttggaat gggttgctcg cataagaagt    900

aaatataata attatgcaac atattatgcc gattcagtga aagacaggtt caccatctcc    960

agagatgatt caaaaaacac tgcctatcta caaatgaaca acttgaagac tgaggacact   1020

gccgtgtact actgtgtgag acatgggaac ttcggtaata gctacatatc ctactgggct   1080

tactggggcc aagggactct ggtcaccgtc tcctcaggtg gtggtggttc tggcggcggc   1140

ggctccggtg gtggtggttc tcagactgtt gtgactcagg aaccttcact caccgtatca   1200

cctggtggaa cagtcacact cacttgtggc tcctcgactg gggctgttac atctggcaac   1260

tacccaaact gggtccaaca aaaaccaggt caggcacccc gtggtctaat aggtgggact   1320

aagttcctcg cccccggtac tcctgccaga ttctcaggct ccctgcttgg aggcaaggct   1380

gccctcaccc tctcaggggt acagccagag gatgaggcag aatattactg tgttctatgg   1440

tacagcaacc gctgggtgtt cggtggagga accaaactga ctgtcctaca ccaccatcac   1500

caccactaa                                                           1509


<210> SEQ ID NO 127
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45
```

```
Trp Ile Gly Tyr Ile Tyr Tyr Ser Gly Ser Thr Phe Tyr Asn Pro Ser
    50                  55                  60

Leu Lys Ser Arg Val Thr Ile Ser Val Asp Thr Ser Lys Thr Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Asn Asn Tyr Leu Asn Trp Tyr Gln Gln Lys Pro Gly Lys
                165                 170                 175

Ala Pro Thr Leu Leu Ile Tyr Ala Ala Ser Ser Leu Gln Ser Gly Val
            180                 185                 190

Pro Ser Arg Phe Ser Gly Ser Arg Ser Gly Thr Asp Phe Thr Leu Thr
        195                 200                 205

Ile Ser Ser Leu Gln Pro Glu Asp Phe Ala Ala Tyr Phe Cys Gln Gln
    210                 215                 220

Thr Tyr Ser Asn Pro Thr Phe Gly Gln Gly Thr Lys Val Glu Val Lys
225                 230                 235                 240

Arg Ser Gly Gly Gly Gly Ser Glu Val Gln Leu Val Glu Ser Gly Gly
                245                 250                 255

Gly Leu Val Gln Pro Gly Gly Ser Leu Lys Leu Ser Cys Ala Ala Ser
            260                 265                 270

Gly Phe Thr Phe Asn Lys Tyr Ala Met Asn Trp Val Arg Gln Ala Pro
        275                 280                 285

Gly Lys Gly Leu Glu Trp Val Ala Arg Ile Arg Ser Lys Tyr Asn Asn
    290                 295                 300

Tyr Ala Thr Tyr Tyr Ala Asp Ser Val Lys Asp Arg Phe Thr Ile Ser
305                 310                 315                 320

Arg Asp Asp Ser Lys Asn Thr Ala Tyr Leu Gln Met Asn Asn Leu Lys
                325                 330                 335

Thr Glu Asp Thr Ala Val Tyr Tyr Cys Val Arg His Gly Asn Phe Gly
            340                 345                 350

Asn Ser Tyr Ile Ser Tyr Trp Ala Tyr Trp Gly Gln Gly Thr Leu Val
        355                 360                 365

Thr Val Ser Ser Gly Gly Gly Gly Ser Gly Gly Gly Gly Ser Gly Gly
    370                 375                 380

Gly Gly Ser Gln Thr Val Val Thr Gln Glu Pro Ser Leu Thr Val Ser
385                 390                 395                 400

Pro Gly Gly Thr Val Thr Leu Thr Cys Gly Ser Ser Thr Gly Ala Val
                405                 410                 415

Thr Ser Gly Asn Tyr Pro Asn Trp Val Gln Gln Lys Pro Gly Gln Ala
            420                 425                 430

Pro Arg Gly Leu Ile Gly Gly Thr Lys Phe Leu Ala Pro Gly Thr Pro
        435                 440                 445

Ala Arg Phe Ser Gly Ser Leu Leu Gly Gly Lys Ala Ala Leu Thr Leu
    450                 455                 460
```

```
Ser Gly Val Gln Pro Glu Asp Glu Ala Glu Tyr Tyr Cys Val Leu Trp
465                 470                 475                 480

Tyr Ser Asn Arg Trp Val Phe Gly Gly Gly Thr Lys Leu Thr Val Leu
                485                 490                 495

His His His His His His
            500
```

<210> SEQ ID NO 128
<211> LENGTH: 1509
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 128

```
gacatccaga tgacccagtc tccatcctcc ctgtctgcat ctgtaggaga cagagtcacc     60

atcacttgcc gggctagtca gagcattaac aactatttaa attggtatca gcagaaacca    120

gggaaagccc ctacgctcct gatctatgct gcatccagtt tgcaaagtgg ggtcccatca    180

aggttcagtg gcagtagatc tgggacagat ttcactctca ccatcagcag tctgcaacct    240

gaagattttg cagcttactt ctgtcaacag acttacagta acccgacgtt cggccaaggg    300

accaaggtgg aagtcaaaag gggaggcggc ggttcaggcg gaggtggctc tggcggtggc    360

ggaagtcagg tgcagctgca ggagtcgggc ccaggactgg tgaagccttc acagaccctg    420

tccctcacct gcactgtctc tggtggctcc atcaacaata ataattacta ctggacctgg    480

atccgccagc acccagggaa gggcctggag tggattgggt acatctatta cagtgggagc    540

accttctaca acccgtccct caagagtcga gttaccatat cagtcgacac gtctaagacc    600

cagttctccc tgaagttgag ctctgtgact gccgcggaca cggccgtgta ttactgtgcg    660

agagaggata cgatgacggg cctggacgtc tggggccaag ggaccacggt caccgtctcc    720

tcatccggag gtggtggatc cgaggtgcag ctggtcgagt ctggaggagg attggtgcag    780

cctggagggt cattgaaact ctcatgtgca gcctctggat tcaccttcaa taagtacgcc    840

atgaactggg tccgccaggc tccaggaaag ggtttggaat gggttgctcg cataagaagt    900

aaatataata attatgcaac atattatgcc gattcagtga aagacaggtt caccatctcc    960

agagatgatt caaaaaacac tgcctatcta caaatgaaca acttgaagac tgaggacact   1020

gccgtgtact actgtgtgag acatgggaac ttcggtaata gctacatatc ctactgggct   1080

tactggggcc aagggactct ggtcaccgtc tcctcaggtg gtggtggttc tggcggcggc   1140

ggctccggtg gtggtggttc tcagactgtt gtgactcagg aaccttcact caccgtatca   1200

cctggtggaa cagtcacact cacttgtggc tcctcgactg gggctgttac atctggcaac   1260

tacccaaact gggtccaaca aaaaccaggt caggcacccc gtggtctaat aggtgggact   1320

aagttcctcg cccccggtac tcctgccaga ttctcaggct ccctgcttgg aggcaaggct   1380

gccctcaccc tctcaggggt acagccagag gatgaggcag aatattactg tgttctatgg   1440

tacagcaacc gctgggtgtt cggtggagga accaaactga ctgtcctaca ccaccatcac   1500

caccactaa                                                           1509
```

<210> SEQ ID NO 129
<211> LENGTH: 502
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 129

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Asn Tyr
            20                  25                  30

Leu Asn Trp Tyr Gln Gln Lys Pro Gly Lys Ala Pro Thr Leu Leu Ile
        35                  40                  45

Tyr Ala Ala Ser Ser Leu Gln Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Ala Tyr Phe Cys Gln Gln Thr Tyr Ser Asn Pro Thr
                85                  90                  95

Phe Gly Gln Gly Thr Lys Val Glu Val Lys Arg Gly Gly Gly Gly Ser
            100                 105                 110

Gly Gly Gly Gly Ser Gly Gly Gly Gly Ser Gln Val Gln Leu Gln Glu
        115                 120                 125

Ser Gly Pro Gly Leu Val Lys Pro Ser Gln Thr Leu Ser Leu Thr Cys
    130                 135                 140

Thr Val Ser Gly Gly Ser Ile Asn Asn Asn Asn Tyr Tyr Trp Thr Trp
145                 150                 155                 160

Ile Arg Gln His Pro Gly Lys Gly Leu Glu Trp Ile Gly Tyr Ile Tyr
                165                 170                 175

Tyr Ser Gly Ser Thr Phe Tyr Asn Pro Ser Leu Lys Ser Arg Val Thr
            180                 185                 190

Ile Ser Val Asp Thr Ser Lys Thr Gln Phe Ser Leu Lys Leu Ser Ser
        195                 200                 205

Val Thr Ala Ala Asp Thr Ala Val Tyr Tyr Cys Ala Arg Glu Asp Thr
    210                 215                 220

Met Thr Gly Leu Asp Val Trp Gly Gln Gly Thr Thr Val Thr Val Ser
225                 230                 235                 240

Ser Ser Gly Gly Gly Gly Ser Glu Val Gln Leu Val Glu Ser Gly Gly
                245                 250                 255

Gly Leu Val Gln Pro Gly Gly Ser Leu Lys Leu Ser Cys Ala Ala Ser
            260                 265                 270

Gly Phe Thr Phe Asn Lys Tyr Ala Met Asn Trp Val Arg Gln Ala Pro
        275                 280                 285

Gly Lys Gly Leu Glu Trp Val Ala Arg Ile Arg Ser Lys Tyr Asn Asn
    290                 295                 300

Tyr Ala Thr Tyr Tyr Ala Asp Ser Val Lys Asp Arg Phe Thr Ile Ser
305                 310                 315                 320

Arg Asp Asp Ser Lys Asn Thr Ala Tyr Leu Gln Met Asn Asn Leu Lys
                325                 330                 335

Thr Glu Asp Thr Ala Val Tyr Tyr Cys Val Arg His Gly Asn Phe Gly
            340                 345                 350

Asn Ser Tyr Ile Ser Tyr Trp Ala Tyr Trp Gly Gln Gly Thr Leu Val
        355                 360                 365

Thr Val Ser Ser Gly Gly Gly Gly Ser Gly Gly Gly Gly Ser Gly Gly
    370                 375                 380

Gly Gly Ser Gln Thr Val Val Thr Gln Glu Pro Ser Leu Thr Val Ser
385                 390                 395                 400
```

```
Pro Gly Gly Thr Val Thr Leu Thr Cys Gly Ser Ser Thr Gly Ala Val
                405                 410                 415

Thr Ser Gly Asn Tyr Pro Asn Trp Val Gln Gln Lys Pro Gly Gln Ala
            420                 425                 430

Pro Arg Gly Leu Ile Gly Gly Thr Lys Phe Leu Ala Pro Gly Thr Pro
        435                 440                 445

Ala Arg Phe Ser Gly Ser Leu Leu Gly Gly Lys Ala Ala Leu Thr Leu
    450                 455                 460

Ser Gly Val Gln Pro Glu Asp Glu Ala Glu Tyr Tyr Cys Val Leu Trp
465                 470                 475                 480

Tyr Ser Asn Arg Trp Val Phe Gly Gly Gly Thr Lys Leu Thr Val Leu
                485                 490                 495

His His His His His His
            500
```

<210> SEQ ID NO 130
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 130

```
caggtgcagc tgcaggagtc ggggccagga ctggtgaagc cttcggagac cctgtccctc     60

acctgcactg tctctggtgg ctccatcata agtcactact ggagctggat ccggcagccc    120

ccagggaagg gactggagtg gattggatat atctattaca gtgggagcac caactacaac    180

ccctccctca agagtcgagt caccatatca gtagacacgt ccaagaacca gttctccctg    240

aagctgacct ctgtgaccgc tgcggacacg gccgtgtatt actgtgcgag agacggctgg    300

agcgcctttg actactgggg ccagggaacc ctggtcaccg tctcctcagg aggcggcggt    360

tcaggcggag gtggctctgg cggtggcgga agtgacatcc agatgaccca gtctccatcc    420

tccctgtctg catctgtagg agacagagtc accatcactt gccgggcaag tcagggcatt    480

agaaatgctt taggctggta tcagcagaaa ccagggaaag cccctaagcg cctgatctat    540

gctgcatcca gtttgcaaag tggggtccca tcaaggttca gcggcagtgg atctgggaca    600

gaattcactc tcacaatcag cagcctgcag cctgaagatt ttgcaactta ttactgtcta    660

cagcataata gttaccctcg gacgttcggc caagggacca aggtggaaat cagaagg       717
```

<210> SEQ ID NO 131
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 131

```
gacatccaga tgacccagtc tccatcctcc ctgtctgcat ctgtaggaga cagagtcacc     60

atcacttgcc gggcaagtca gggcattaga aatgctttag gctggtatca gcagaaacca    120

gggaaagccc ctaagcgcct gatctatgct gcatccagtt tgcaaagtgg ggtcccatca    180

aggttcagcg gcagtggatc tgggacagaa ttcactctca caatcagcag cctgcagcct    240

gaagattttg caacttatta ctgtctacag cataatagtt accctcggac gttcggccaa    300

gggaccaagg tggaaatcag aaggggaggc ggcggttcag gcggaggtgg ctctggcggt    360
```

```
ggcggaagtc aggtgcagct gcaggagtcg gggccaggac tggtgaagcc ttcggagacc    420

ctgtccctca cctgcactgt ctctggtggc tccatcataa gtcactactg gagctggatc    480

cggcagcccc cagggaaggg actggagtgg attggatata tctattacag tgggagcacc    540

aactacaacc cctccctcaa gagtcgagtc accatatcag tagacacgtc caagaaccag    600

ttctccctga agctgacctc tgtgaccgct gcggacacgg ccgtgtatta ctgtgcgaga    660

gacggctgga gcgcctttga ctactggggc cagggaaccc tggtcaccgt ctcctca       717
```

<210> SEQ ID NO 132
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 132

```
caggtgcagc tgcaggagtc gggcccagga ctggtgaagc cttcacagac cctgtccctc     60

acctgcactg tctctggtgg ctccatcaac aataataatt actactggac ctggatccgc    120

cagcacccag ggaagggcct ggagtggatt gggtacatct attacagtgg gagcaccttc    180

tacaacccgt ccctcaagag tcgagttacc atatcagtcg acacgtctaa gacccagttc    240

tccctgaagt tgagctctgt gactgccgcg gacacggccg tgtattactg tgcgagagag    300

gatacgatga cgggcctgga cgtctggggc caagggacca cggtcaccgt ctcctcagga    360

ggcggcggtt caggcggagg tggctctggc ggtggcggaa gtgacatcca gatgacccag    420

tctccatcct ccctgtctgc atctgtagga gacagagtca ccatcacttg ccgggctagt    480

cagagcatta acaactattt aaattggtat cagcagaaac cagggaaagc ccctacgctc    540

ctgatctatg ctgcatccag tttgcaaagt ggggtcccat caaggttcag tggcagtaga    600

tctgggacag atttcactct caccatcagc agtctgcaac ctgaagattt tgcagcttac    660

ttctgtcaac agacttacag taacccgacg ttcggccaag ggaccaaggt ggaagtcaaa    720

agg                                                                  723
```

<210> SEQ ID NO 133
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133

```
gacatccaga tgacccagtc tccatcctcc ctgtctgcat ctgtaggaga cagagtcacc     60

atcacttgcc gggctagtca gagcattaac aactatttaa attggtatca gcagaaacca    120

gggaaagccc ctacgctcct gatctatgct gcatccagtt tgcaaagtgg ggtcccatca    180

aggttcagtg gcagtagatc tgggacagat ttcactctca ccatcagcag tctgcaacct    240

gaagattttg cagcttactt ctgtcaacag acttacagta acccgacgtt cggccaaggg    300

accaaggtgg aagtcaaaag gggaggcggc ggttcaggcg gaggtggctc tggcggtggc    360

ggaagtcagg tgcagctgca ggagtcgggc ccaggactgg tgaagccttc acagaccctg    420

tccctcacct gcactgtctc tggtggctcc atcaacaata ataattacta ctggacctgg    480

atccgccagc acccagggaa gggcctggag tggattgggt acatctatta cagtgggagc    540

accttctaca acccgtccct caagagtcga gttaccatat cagtcgacac gtctaagacc    600
```

```
cagttctccc tgaagttgag ctctgtgact gccgcggaca cggccgtgta ttactgtgcg    660

agagaggata cgatgacggg cctggacgtc tggggccaag ggaccacggt caccgtctcc    720

tca                                                                  723
```

<210> SEQ ID NO 134
<211> LENGTH: 741
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 134

```
caggtgcagc tgcaggagtc gggcccagga ctggtgaagc cttcacagac cctgtccctc     60

acctgcactg tctctggcgg ctccatcagc ggtgatggtc acttctggag ctggatccgc    120

cagcacccag ggaagggcct ggagtggatt gggtacatct attacagtgg gagcacctac    180

tacaacccgt ccctcaagag tcgagttacc atatcagttg acacgtctaa gaaccagttc    240

tccctgaagc tgagctctgt gactgccgcg gacacggccg tgtattactg tgcgagatta    300

agaggtggct acaaatttga ctactggggc cagggaaccc tggtcaccgt ctcctcagga    360

ggcggcggtt caggcggagg tggctctggc ggtggcggaa gtgatattgt gatgacccag    420

actccactct ctctgtccgt cgcccctgga cagccggcct ccatctcctg ccagtctagt    480

ctgagcctcc agcatagtaa tggaaagacc tatttgtatt ggtacctgca gaagccaggc    540

cagcctccac aactcctgat ctatgaagtt tccaaccggt tctctggagt gccagatagg    600

ttcagtggca gcgggtcagg gacagatttc acgctgaaaa tcagccgggt ggaggctgag    660

gatgttggga tttattactg catgcaaagt aaacagcttc cgtacagttt tggccagggg    720

accaagctgg agatcaaacg a                                              741
```

<210> SEQ ID NO 135
<211> LENGTH: 741
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 135

```
gatattgtga tgacccagac tccactctct ctgtccgtcg cccctggaca gccggcctcc     60

atctcctgcc agtctagtct gagcctccag catagtaatg gaaagaccta tttgtattgg    120

tacctgcaga agccaggcca gcctccacaa ctcctgatct atgaagtttc caaccggttc    180

tctggagtgc cagataggtt cagtggcagc gggtcaggga cagatttcac gctgaaaatc    240

agccgggtgg aggctgagga tgttgggatt tattactgca tgcaaagtaa acagcttccg    300

tacagttttg gccaggggac caagctggag atcaaacgag gaggcggcgg ttcaggcgga    360

ggtggctctg gcggtggcgg aagtcaggtg cagctgcagg agtcgggccc aggactggtg    420

aagccttcac agaccctgtc cctcacctgc actgtctctg gcggctccat cagcggtgat    480

ggtcacttct ggagctggat ccgccagcac ccagggaagg gcctggagtg gattgggtac    540

atctattaca gtgggagcac ctactacaac ccgtccctca agagtcgagt taccatatca    600

gttgacacgt ctaagaacca gttctccctg aagctgagct ctgtgactgc cgcggacacg    660

gccgtgtatt actgtgcgag attaagaggt ggctacaaat ttgactactg gggccaggga    720
```

accctggtca ccgtctcctc a 741

<210> SEQ ID NO 136
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 136
caggtgcagc tgcaggagtc gggcccagga ctggtgaagc cttcggagac cctgtccctc 60
acctgcactg tctctggtgg ctccatcagt agttactact ggagctggat ccggcagccc 120
ccagggaagg gactggagtg gattgggtat atctattaca gtgggagcac caactacaac 180
ccctccctca agagtcgagt caccatatca gtagacacgt ccaagaacca gttctccctg 240
aagctgagct ctgtgaccgc tgcggacacg gccgtgtatt actgtgcgag agttgactac 300
aaggcttttg atatctgggg ccaagggaca atggtcaccg tctcttcagg aggcggcggt 360
tcaggcggag gtggctctgg cggtggcgga agtgacatcc agatgaccca gtctccatcc 420
tccctgtctg catctgtagg agacagagtc accatcactt gccgggcaag tcagggcatt 480
agaaatgatt tacactggta tcagcagaaa ccagggaaag cccctaagcg cctgatctat 540
gctgcatcca gtttgcaaag tggggtccca tcaaggttca gcggcagtgg atctgggaca 600
gaattcactc tcacaatcag cagcctgcag cctgaagatt ttgcaactta ttactgtcta 660
cagcattata gttacccgtg gacgttcggc caagggacca aggtggaaat caaacga 717

<210> SEQ ID NO 137
<211> LENGTH: 717
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 137
gacatccaga tgacccagtc tccatcctcc ctgtctgcat ctgtaggaga cagagtcacc 60
atcacttgcc gggcaagtca gggcattaga aatgatttac actggtatca gcagaaacca 120
gggaaagccc ctaagcgcct gatctatgct gcatccagtt tgcaaagtgg ggtcccatca 180
aggttcagcg gcagtggatc tgggacagaa ttcactctca caatcagcag cctgcagcct 240
gaagattttg caacttatta ctgtctacag cattatagtt acccgtggac gttcggccaa 300
gggaccaagg tggaaatcaa acgaggaggc ggcggttcag gcggaggtgg ctctggcggt 360
ggcggaagtc aggtgcagct gcaggagtcg ggcccaggac tggtgaagcc ttcggagacc 420
ctgtccctca cctgcactgt ctctggtggc tccatcagta gttactactg gagctggatc 480
cggcagcccc cagggaaggg actggagtgg attgggtata tctattacag tgggagcacc 540
aactacaacc cctccctcaa gagtcgagtc accatatcag tagacacgtc caagaaccag 600
ttctccctga agctgagctc tgtgaccgct gcggacacgg ccgtgtatta ctgtgcgaga 660
gttgactaca aggcttttga tatctggggc caagggacaa tggtcaccgt ctcttca 717

<210> SEQ ID NO 138
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 138
caggtgcagc tggtggagtc tgggggaggc gtggtccagc ctgggaggtc cctgagactc 60
tcctgtgcag cgtctggatt caccttcagt agctatggca tgcactgggt ccgccaggct 120
ccaggcaagg ggctggagtg ggtggcagct atatggtatg atggaagtaa taaatactat 180
gcagactccg tgaagggccg attcaccatc tccagagaca attccaagaa tatgttgtat 240
ctgcaaatga acagcctgag agccgaggac acggctgtgt attactgtgc gagagatctt 300
tcgatttttg gagtggttat tctttctgac tactggggcc agggaaccct ggtcaccgtc 360
tcctcaggag gcggcggttc aggcggaggt ggctctggcg gtggcggaag tgaaattgtg 420
ctgactcagt ctccagactt tcagtctgtg actccaaagg agaaagtcac catcacctgc 480
cgggccagtc agagcattgg tagtagctta cactggtacc ggcagaaacc agatcagtct 540
ccaaagctcc tcatcaagta tgcttcccag tccttctcag gggtcccctc gaggttcagt 600
ggcggtggtt ctgggacaga tttcaccctc accatcaata gcctggaagc tgaagatgct 660
gcaacgtatt actgtcatca gagtagtagt ttaccgtgga cgttcggcca agggaccaag 720
gtggaaatca aacga 735

<210> SEQ ID NO 139
<211> LENGTH: 735
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 139
gaaattgtgc tgactcagtc tccagacttt cagtctgtga ctccaaagga gaaagtcacc 60
atcacctgcc gggccagtca gagcattggt agtagcttac actggtaccg gcagaaacca 120
gatcagtctc caaagctcct catcaagtat gcttcccagt ccttctcagg ggtcccctcg 180
aggttcagtg gcggtggttc tgggacagat ttcaccctca ccatcaatag cctggaagct 240
gaagatgctg caacgtatta ctgtcatcag agtagtagtt taccgtggac gttcggccaa 300
gggaccaagg tggaaatcaa acgaggaggc ggcggttcag gcggaggtgg ctctggcggt 360
ggcggaagtc aggtgcagct ggtggagtct gggggaggcg tggtccagcc tgggaggtcc 420
ctgagactct cctgtgcagc gtctggattc accttcagta gctatggcat gcactgggtc 480
cgccaggctc caggcaaggg gctggagtgg gtggcagcta tatggtatga tggaagtaat 540
aaatactatg cagactccgt gaagggccga ttcaccatct ccagagacaa ttccaagaat 600
atgttgtatc tgcaaatgaa cagcctgaga gccgaggaca cggctgtgta ttactgtgcg 660
agagatcttt cgatttttgg agtggttatt ctttctgact actggggcca gggaaccctg 720
gtcaccgtct cctca 735

<210> SEQ ID NO 140
<211> LENGTH: 747
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 140
caggtgcagc tgcaggagtc gggcccagga ctggtgaagc cttcacagac cctgtccctc 60
acctgcactg tctctggtgg ctccatcagc agtggtggtt actactggaa ctggatccgc 120
cagcacccag ggaagggcct ggagtggatt gggtacatct attacagtgg gagcacctac 180
tacaacccgt ccctcagggg tcgacttata atatcagtcg acacgtctaa gaaccagttc 240
tccctgaggc tgagctctgt gactgccgcg gacacggccg tgtattactg tgcgagagat 300
ggtggagaca gctatgggcg tatggacgtc tggggccaag ggaccacggt caccgtctcc 360
tcaggaggcg gcggttcagg cggaggtggc tctggcggtg gcggaagtga tattgtcatg 420
acccagactc cactctcctc acctgtcacc cttggacagc cggcctccat ctcctgcagg 480
tctagtcaaa gcctcgtaca cagtgataga aacacctact tgagttggct tcagcagagg 540
ccaggccagc ctccaagact cctaatttat aagatttcta accggttctc tggggtccca 600
gacagattca gtggcagtgg ggcagggaca gatttcacac tgaaaatcag cagggtggaa 660
gctgaggatg tcggggttta ttactgcatg caagctacac aatttcctct cactttcggc 720
ggagggacca aggtggagat caagcga 747

<210> SEQ ID NO 141
<211> LENGTH: 747
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 141
gatattgtca tgacccagac tccactctcc tcacctgtca cccttggaca gccggcctcc 60
atctcctgca ggtctagtca aagcctcgta cacagtgata gaaacaccta cttgagttgg 120
cttcagcaga ggccaggcca gcctccaaga ctcctaattt ataagatttc taaccggttc 180
tctggggtcc cagacagatt cagtggcagt ggggcaggga cagatttcac actgaaaatc 240
agcagggtgg aagctgagga tgtcggggtt tattactgca tgcaagctac acaatttcct 300
ctcactttcg gcggagggac caaggtggag atcaagcgag gaggcggcgg ttcaggcgga 360
ggtggctctg gcggtggcgg aagtcaggtg cagctgcagg agtcgggccc aggactggtg 420
aagccttcac agaccctgtc cctcacctgc actgtctctg gtggctccat cagcagtggt 480
ggttactact ggaactggat ccgccagcac ccagggaagg gcctggagtg gattgggtac 540
atctattaca gtgggagcac ctactacaac ccgtccctca ggggtcgact tataatatca 600
gtcgacacgt ctaagaacca gttctccctg aggctgagct ctgtgactgc cgcggacacg 660
gccgtgtatt actgtgcgag agatggtgga gacagctatg ggcgtatgga cgtctggggc 720
caagggacca cggtcaccgt ctcctca 747

<210> SEQ ID NO 142
<211> LENGTH: 753
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 142
caggtgcagc tgcaggagtc gggcccagga ctggtgaagc cttcggagac cctgtccctc 60
acctgcactg tctctggtga ctccatcaat aattactact ggagctggat ccggcagccc 120
gccgggaagg gactggagtg gattgggcgt atctttacca gtgggagcac caactacaac 180

```
ccctccctca agagtcgagt caccatgtca atagacacgt ccaagaacca gttctccctg    240

aagctgagct ctgtgaccgc cgcggacacg gccgtgtatt actgtgcgag agaggggga    300

cactatggta gtagtggtta tctatactat tactatttcg gtatggacgt ctggggccaa    360

gggaccacgg tcaccgtctc ctcaggaggc ggcggttcag gcggaggtgg ctctggcggt    420

ggcggaagtg aaattgtgtt gacgcagtct ccaggcaccc tgtctttgtc tccaggggaa    480

agagccaccc tctcctgcag ggccagtcag actgttagca gcagctactt agcctggtac    540

cagcagaaac ctggccaggc tcccaggctc ctcatctatg gtgcatccat cagggccact    600

ggcatcccag acaggttcag tggcagtggg tctgggacag acttcactct caccatcagc    660

agactggagc ctgaagattt tgcagtgtat tactgtcagc agtatggtag ctcactcact    720

ttcggcggag ggaccaaggt ggagatcaaa cga                                 753
```

<210> SEQ ID NO 143
<211> LENGTH: 753
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 143

```
gaaattgtgt tgacgcagtc tccaggcacc ctgtctttgt ctccagggga aagagccacc     60

ctctcctgca gggccagtca gactgttagc agcagctact tagcctggta ccagcagaaa    120

cctggccagg ctcccaggct cctcatctat ggtgcatcca tcagggccac tggcatccca    180

gacaggttca gtggcagtgg gtctgggaca gacttcactc tcaccatcag cagactggag    240

cctgaagatt ttgcagtgta ttactgtcag cagtatggta gctcactcac tttcggcgga    300

gggaccaagg tggagatcaa acgaggaggc ggcggttcag gcggaggtgg ctctggcggt    360

ggcggaagtc aggtgcagct gcaggagtcg ggcccaggac tggtgaagcc ttcggagacc    420

ctgtccctca cctgcactgt ctctggtgac tccatcaata attactactg gagctggatc    480

cggcagcccg ccgggaaggg actggagtgg attgggcgta tctttaccag tgggagcacc    540

aactacaacc cctccctcaa gagtcgagtc accatgtcaa tagacacgtc caagaaccag    600

ttctccctga agctgagctc tgtgaccgcc gcggacacgg ccgtgtatta ctgtgcgaga    660

gaggggggac actatggtag tagtggttat ctatactatt actatttcgg tatggacgtc    720

tggggccaag ggaccacggt caccgtctcc tca                                 753
```

<210> SEQ ID NO 144
<211> LENGTH: 759
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 144

```
caggtacagc tgcagcagtc aggtccagga ctggtgaagc cctcgcagac cctctcactc     60

acctgtgcca tctccgggga cagtgtctct agcaacagtg ttgcttggaa ctggatcagg    120

cagtccccat cgagaggcct tgagtggctg ggaaggacat actacaggtc caagtggtat    180

aatgattatg cagtatctgt gaaaagtcga ataaccatca acccagacac atccaagaac    240

cagttctccc tgcagctgaa ctctgtgact cccgaggaca cggctgtgta ttactgtgca    300

agaggtattt tcgtagtgcc agctgttcct aggtttgact actggggcca gggaaccctg    360
```

```
gtcaccgtct cctcaggagg cggcggttca ggcggaggtg gctctggcgg tggcggaagt    420

gatattgtga tgactcagtc tccactctct ctgtccgtca cccctggaga gccggcctcc    480

atctcctgca ggtctagtct gagcctcctg catagtaatg gatacaacta tttggattgg    540

ttcctgcaga agccagggca gtctccacag ctcctgatct atttgggttc taatcgggcc    600

tccggggtcc ctgacaggtt cagtggcagt gggtcagaca cagattttac gctgaaaatc    660

agcagagtgg aggctgagga tgttggggtt tattactgca tgcaaggtct acatactcct    720

cctagttttg gccaggggac caagctggag atcaaacga                           759
```

```
<210> SEQ ID NO 145
<211> LENGTH: 759
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145

gatattgtga tgactcagtc tccactctct ctgtccgtca cccctggaga gccggcctcc     60

atctcctgca ggtctagtct gagcctcctg catagtaatg gatacaacta tttggattgg    120

ttcctgcaga agccagggca gtctccacag ctcctgatct atttgggttc taatcgggcc    180

tccggggtcc ctgacaggtt cagtggcagt gggtcagaca cagattttac gctgaaaatc    240

agcagagtgg aggctgagga tgttggggtt tattactgca tgcaaggtct acatactcct    300

cctagttttg gccaggggac caagctggag atcaaacgag gaggcggcgg ttcaggcgga    360

ggtggctctg gcggtggcgg aagtcaggta cagctgcagc agtcaggtcc aggactggtg    420

aagccctcgc agaccctctc actcacctgt gccatctccg ggacagtgt ctctagcaac    480

agtgttgctt ggaactggat caggcagtcc ccatcgagag gccttgagtg gctgggaagg    540

acatactaca ggtccaagtg gtataatgat tatgcagtat ctgtgaaaag tcgaataacc    600

atcaacccag acacatccaa gaaccagttc tccctgcagc tgaactctgt gactcccgag    660

gacacggctg tgtattactg tgcaagaggt attttcgtag tgccagctgt tcctaggttt    720

gactactggg gccagggaac cctggtcacc gtctcctca                           759
```

```
<210> SEQ ID NO 146
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 146

caagtgcagc ttgtggaaag cggaggcggg gtcgtgcaac ccggacgctc actgcgcctg     60

agctgtgccg cctctgggtt caccttctcc taccacgggc tgcattgggt gagacaagca    120

cccggaaaag gcctggaatg ggtcgccgtg atctggtatg acggtaataa caagaattac    180

gctgatagcg tgaagggtcg gtttactatc tcacgcgaca attccaagaa caccctgttt    240

ctccaaatga actctctgag ggccgaggac accgccgtgt actactgcgc tcggaaggga    300

tctggcaaag gatgcatgga tgtgtgggga caggggacca ccgtgactgt cagctctggt    360

ggaggagggt ccgggggagg tgggagcggc ggagggggaa gcgaaattgt cctgactcaa    420

tcacctggca ccctgagcct ttcaccagga gagagggcaa ccctcagctg tcgggcttca    480
```

cagagcgtgt ccttcagcta tctggcttgg tatcagcaaa agcctggaca ggcccccaga 540
cttctcatct acggagcctc ttcacgggcc accggcatcc ctgaccgctt ctctggtagc 600
gggtcaggaa ccgacttcac cctcaccatt tcacgccttg agccagagga cttcgcagtc 660
tactattgcc agcattacga tgggtctatt acttttggac cggggactaa ggtggacatt 720
gaaaga 726

<210> SEQ ID NO 147
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 147
gaaattgtcc tgactcaatc acctggcacc ctgagccttt caccaggaga gagggcaacc 60
ctcagctgtc gggcttcaca gagcgtgtcc ttcagctatc tggcttggta tcagcaaaag 120
cctggacagg cccccagact tctcatctac ggagcctctt cacgggccac cggcatccct 180
gaccgcttct ctggtagcgg gtcaggaacc gacttcaccc tcaccatttc acgccttgag 240
ccagaggact tcgcagtcta ctattgccag cattacgatg ggtctattac ttttggaccg 300
gggactaagg tggacattga aagaggtgga ggagggtccg ggggaggtgg gagcggcgga 360
gggggaagcc aagtgcagct tgtggaaagc ggaggcgggg tcgtgcaacc cggacgctca 420
ctgcgcctga gctgtgccgc ctctgggttc accttctcct accacgggct gcattgggtg 480
agacaagcac ccggaaaagg cctggaatgg gtcgccgtga tctggtatga cggtaataac 540
aagaattacg ctgatagcgt gaagggtcgg tttactatct cacgcgacaa ttccaagaac 600
accctgtttc tccaaatgaa ctctctgagg gccgaggaca ccgccgtgta ctactgcgct 660
cggaagggat ctggcaaagg atgcatggat gtgtggggac aggggaccac cgtgactgtc 720
agctca 726

<210> SEQ ID NO 148
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 148
caagtccagc tcgaacaatc agggggaggg gtggtccaac ccggcagatc actgaggctc 60
tcatgtgctg catcagggtt taccttctca tcttatggta tgcattgggt cagacaggct 120
ccagggaagg ggcttgagtg ggtggccgtg atttggtacg acggaaacaa taaggactac 180
cgggacagcg tgactggtcg gttcaccatc tcacgggata acagcaagaa taccctctac 240
cttcaaatgt catcacttcg cgctgaagat accgccgtgt attactgcgc caggaaggga 300
tctggtaaag gttgcatgga cgtgtggggt cggggaacta ccgtgaccgt gtcatctggt 360
ggaggcggct ccgggggtgg aggaagcggc ggaggagggt ccgagattgt cctcacccag 420
tctcccggaa ctctttccct gagccctggt gacagagcaa ccctgtcatg ccgcgcttct 480
cagtccgtgt cttttagctt tctggcctgg tatcagcaga ccccagggca ggcaccccgc 540
cttctgatct acggagccta ctctagggct accggcattc ccgacaggtt ctctggtagc 600
ggcagcggca ccgacttcgc cctcactatt tcacgccttg agccggaaga tttcgcagtg 660

```
tactactgcc agcattatgg aacctctatc accttcggtc ctggcactaa ggtggacctt    720

aaaagg                                                               726


<210> SEQ ID NO 149
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 149

gagattgtcc tcacccagtc tcccggaact ctttccctga gccctggtga cagagcaacc     60

ctgtcatgcc gcgcttctca gtccgtgtct tttagctttc tggcctggta tcagcagacc    120

ccagggcagg caccccgcct tctgatctac ggagcctact ctagggctac cggcattccc    180

gacaggttct ctggtagcgg cagcggcacc gacttcgccc tcactatttc acgccttgag    240

ccggaagatt tcgcagtgta ctactgccag cattatggaa cctctatcac cttcggtcct    300

ggcactaagg tggaccttaa aaggggtgga ggcggctccg gggtggagg aagcggcgga    360

ggagggtccc aagtccagct cgaacaatca gggggagggg tggtccaacc cggcagatca    420

ctgaggctct catgtgctgc atcagggttt accttctcat cttatggtat gcattgggtc    480

agacaggctc cagggaaggg gcttgagtgg gtggccgtga tttggtacga cggaaacaat    540

aaggactacc gggacagcgt gactggtcgg ttcaccatct cacgggataa cagcaagaat    600

accctctacc ttcaaatgtc atcacttcgc gctgaagata ccgccgtgta ttactgcgcc    660

aggaagggat ctggtaaagg ttgcatggac gtgtggggtc ggggaactac cgtgaccgtg    720

tcatct                                                               726


<210> SEQ ID NO 150
<211> LENGTH: 726
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 150

caagtgcaac tcgtcgagtc aggaggggt gtggtccagc ctggacgctc actcagactt     60

tcatgcgctg catctgggtt cactttttcc agctacggga tgcattgggt gcggcaggct    120

ccgggaaaag gtctggaatg ggtgactgtg atttggtacg acgggaataa caaagactat    180

gccgattccg tgaagggaag attcaccatt agcagggact cctcaaagaa cacccctttat    240

ctccaaatga atagccttcg cgctgaggac accgccgtct actattgtgc caggaagggg    300

tcaggaaagg ggtgcatgga tgtgtgggga caggggacta ccgtcactgt ctcatcaggc    360

ggaggcggat ctggcggtgg agggtctggt gggggaggct cagaaatcgt gctgacccag    420

agcccaggca ccctcagcct gtcacccgga gagcgggcca ccctgtcatg tcgggccagc    480

cagtcagtct cttactcttt cctcgcttgg tatcagcaga agcctggtca agcccctcgc    540

ctcctgatct acgccgcctc atcacgggct actggtatcc cagatcggtt ttctggtagc    600

ggcagcggaa ccgacttcac cctgaccatt tcccgcctgg aacccgagga ctttgctgtg    660

tactactgcc aacattacgg atcttctatc accttcggtc cgggcaccaa ggtggacatt    720

aagagg                                                               726
```

<210> SEQ ID NO 151
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 151
gaaatcgtgc tgacccagag cccaggcacc ctcagcctgt cacccggaga gcgggccacc 60
ctgtcatgtc gggccagcca gtcagtctct tactctttcc tcgcttggta tcagcagaag 120
cctggtcaag cccctcgcct cctgatctac gccgcctcat cacgggctac tggtatccca 180
gatcggtttt ctggtagcgg cagcggaacc gacttcaccc tgaccatttc ccgcctggaa 240
cccgaggact ttgctgtgta ctactgccaa cattacggat cttctatcac cttcggtccg 300
ggcaccaagg tggacattaa gaggggcgga ggcggatctg gcggtggagg gtctggtggg 360
ggaggctcac aagtgcaact cgtcgagtca ggagggggtg tggtccagcc tggacgctca 420
ctcagacttt catgcgctgc atctgggttc actttttcca gctacgggat gcattgggtg 480
cggcaggctc cgggaaaagg tctggaatgg gtgactgtga tttggtacga cgggaataac 540
aaagactatg ccgattccgt gaagggaaga ttcaccatta gcagggactc ctcaaagaac 600
accctttatc tccaaatgaa tagccttcgc gctgaggaca ccgccgtcta ctattgtgcc 660
aggaaggggt caggaaaggg gtgcatggat gtgtggggac aggggactac cgtcactgtc 720
tcatct 726

<210> SEQ ID NO 152
<211> LENGTH: 738
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 152
gaagtccagc ttgaacagag cggtggaggg ctcgtgcaac caggtgggag ccttcgcctg 60
agctgcgccg catcagggtt caccttctca tcatacgata tgcattgggt ccgccaggcc 120
accgggaagg gcctggaatg ggtgagcgtg attggcaccg ctggcgacac ttattacccc 180
gactccgtga agggacgctt taccatttca agggagaacg ccaaaaactc tctttacctc 240
caaatgaact cccttcgggc tggggatact gccgtctatt actgcgtccg gggaggtgga 300
tggaattatg gatactacta ttacggaatg gacgtgtggg gacagtggac caccgtgact 360
gtgtcaagcg gaggaggggg ttcaggcggt gggggcagcg gggggaggcgg atcagacatc 420 caaatgaccc agagcccctc atcactgtca gcctctgtgg gagacagagt gactatcact 480
tgtcgggcct cagagtcaat caggcgctat ctgaattggt atcaagaaaa gccaggaaaa 540
gctcctaagc tgctgatcta cgcagcttcc agcagccaaa gcggggtgcc atcacggttc 600
tctggtagcg gatctggaac tgacttcacc ctgaccatct ctagcctcca gccggaggat 660
ttcgccactt actactgcca gcagtcctac attaatccgc ccacctttgg acagggaacc 720
aaggtcgaga ttaagaga 738

<210> SEQ ID NO 153
<211> LENGTH: 738
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 153

```
gacatccaaa tgacccagag cccctcatca ctgtcagcct ctgtgggaga cagagtgact     60

atcacttgtc gggcctcaga gtcaatcagg cgctatctga attggtatca agaaaagcca    120

ggaaaagctc ctaagctgct gatctacgca gcttccagca gccaaagcgg ggtgccatca    180

cggttctctg gtagcggatc tggaactgac ttcaccctga ccatctctag cctccagccg    240

gaggatttcg ccacttacta ctgccagcag tcctacatta atccgcccac ctttggacag    300

ggaaccaagg tcgagattaa gagaggagga gggggttcag gcggtggggg cagcggggga    360

ggcggatcag aagtccagct tgaacagagc ggtggagggc tcgtgcaacc aggtgggagc    420

cttcgcctga gctgcgccgc atcagggttc accttctcat catacgatat gcattgggtc    480

cgccaggcca ccgggaaggg cctggaatgg gtgagcgtga ttggcaccgc tggcgacact    540

tattaccccg actccgtgaa gggacgcttt accatttcaa gggagaacgc caaaaactct    600

ctttacctcc aaatgaactc ccttcgggct ggggatactg ccgtctatta ctgcgtccgg    660

ggaggtggat ggaattatgg atactactat tacggaatgg acgtgtgggg acagtggacc    720

accgtgactg tgtcaagc                                                  738
```

<210> SEQ ID NO 154
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 154

```
caagtccagc tcgaacagtc tggcccaggg cttgtgaagc cctcccagac cctcagcctg     60

acttgcactg tgtcaggagg ttccattagc tccggcggat attactggtc atggatcagg    120

cagcatcccg gaaagggcct ggaatggatt ggatacatct acttcagcgg gaacactaat    180

tacaatccct ctctgaaatc tcgggtcact atcagcgtgg ataccagcaa gaaccagttc    240

tccctgaagc tcagctcagt gaccgctgct gacaccgccg tctactactg tgctagagaa    300

tactgcgacg atgactgcta tggcttcgac tactggggtc agggaaccct tgtgaccgtc    360

agctctggag gagggggttc tggcggtgga ggctcagggg gaggcggatc agacattcaa    420

gtgactcaat ctcctagctc tctgtcagcc tcagtgggcg accgcgtcac catcacctgt    480

cgggcatccc agggaatccg caatgacctc gggtggtatc aacagaaacc aggaaaggcc    540

ccgaagagac ttatctacgc agcctcctct ctccaaagcg gtgtgccatc tcgcttttct    600

ggctctggca gcggaaccga gttcaccctg actatttcat ctctgcagcc ggaggacttc    660

gcaacctatt actgcctgca atattcaatc tacccacgca cctttgggca ggggaccaag    720

gtcgagatta agcgg                                                     735
```

<210> SEQ ID NO 155
<211> LENGTH: 734
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 155
gacattcaag tgactcaatc tcctagctct ctgtcagcct cagtgggcga ccgcgtcacc 60
atcacctgtc gggcatccca gggaatccgc aatgacctcg ggtggtatca acagaaacca 120
ggaaaggccc cgaagagact tatctacgca gcctcctctc tccaaagcgg tgtgccatct 180
cgcttttctg gctctggcag cggaaccgag ttcaccctga ctatttcatc tctgcagccg 240
gaggacttcg caacctatta ctgcctgcaa tattcaatct acccacgcac ctttgggcag 300
gggaccaagg tcgagattaa gcggggagga gggggttctg gcggtggagg ctcaggggga 360
ggcggatcac aagtccagct cgaacagtct ggcccagggc ttgtgaagcc ctcccagacc 420
ctcagcctga cttgcactgt gtcaggaggt tccattagct ccggcggata ttactggtca 480
tggatcaggc agcatcccgg aaagggcctg gaatggattg gatacatcta cttcagcggg 540
aacactaatt acaatccctc tctgaaatct cgggtcacta tcagcgtgga taccagcaag 600
aaccagttct ccctgaagct cagctcagtg accgctgctg acaccgccgt ctactactgt 660
gctagagaat actgcgacga tgactgctat ggcttcgact actggggtca gggaaccctt 720
gtgaccgtca gctc 734

<210> SEQ ID NO 156
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 156
caagtccagc ttgtcgagag cggtgggggc gtggtccagc ccggacgctc acttaggctg 60
tcatgcgccg caagcggttt caccttttca tcatacggca tgcactgggt ccggcaggcc 120
ccagggaagg gcctggaatg ggtggccgtg atctggtacg atgggtcaaa taagtactat 180
gcagattcag tgaagggtcg gtttaccatc tctagggaca atagcaaaaa caccctctac 240
ctccaaatga acagcctcag agccgaggac accgccgtgt attactgtgc ccgcgacctg 300
tcaattttcg gggtcgtggt gctgtctgac tactggggtc aaggtactct cgtgaccgtg 360
tctagcgggg gaggaggaag cggagggggt gggtcaggcg gaggcgggtc tgaaattgtg 420
ctgactcaat cacccgactt ccaatccgtc accectaagg agaaagtgac tattacctgt 480
cgggcctccc agtacatcgg gtctaatctc cattggtatc agcagacccc cgaccagtca 540
cctaagctcc tgattaagta cgcctctcag tcttttagcg gagtcccatc tcgcttctct 600
ggatcaggat ctggaactga tttcactctg accatcaact cacttgaagc tgaggacgct 660
gctacctact actgccatca atcatcatca cttccgtgga ccttcggaca gggcaccaag 720
gtggaaatca agaga 735

<210> SEQ ID NO 157
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 157
gaaattgtgc tgactcaatc acccgacttc caatccgtca cccctaagga gaaagtgact 60
attacctgtc gggcctccca gtacatcggg tctaatctcc attggtatca gcagaccccc 120

```
gaccagtcac ctaagctcct gattaagtac gcctctcagt cttttagcgg agtcccatct    180

cgcttctctg gatcaggatc tggaactgat ttcactctga ccatcaactc acttgaagct    240

gaggacgctg ctacctacta ctgccatcaa tcatcatcac ttccgtggac cttcggacag    300

ggcaccaagg tggaaatcaa gagaggggga ggaggaagcg gagggggtgg gtcaggcgga    360

ggcgggtctc aagtccagct tgtcgagagc ggtgggggcg tggtccagcc cggacgctca    420

cttaggctgt catgcgccgc aagcggtttc accttttcat catacggcat gcactgggtc    480

cggcaggccc cagggaaggg cctggaatgg gtggccgtga tctggtacga tgggtcaaat    540

aagtactatg cagattcagt gaagggtcgg tttaccatct ctagggacaa tagcaaaaac    600

accctctacc tccaaatgaa cagcctcaga gccgaggaca ccgccgtgta ttactgtgcc    660

cgcgacctgt caattttcgg ggtcgtggtg ctgtctgact actggggtca aggtactctc    720

gtgaccgtgt cttca                                                      735


<210> SEQ ID NO 158
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 158

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ile Ser His
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Asp Gly Trp Ser Ala Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Asp Ile Gln Met Thr Gln Ser Pro Ser Ser Leu Ser Ala
    130                 135                 140

Ser Val Gly Asp Arg Val Thr Ile Thr Cys Arg Ala Ser Gln Gly Ile
145                 150                 155                 160

Arg Asn Ala Leu Gly Trp Tyr Gln Gln Lys Pro Gly Lys Ala Pro Lys
                165                 170                 175

Arg Leu Ile Tyr Ala Ala Ser Ser Leu Gln Ser Gly Val Pro Ser Arg
            180                 185                 190

Phe Ser Gly Ser Gly Ser Gly Thr Glu Phe Thr Leu Thr Ile Ser Ser
        195                 200                 205

Leu Gln Pro Glu Asp Phe Ala Thr Tyr Tyr Cys Leu Gln His Asn Ser
    210                 215                 220

Tyr Pro Arg Thr Phe Gly Gln Gly Thr Lys Val Glu Ile Arg Arg
225                 230                 235
```

<210> SEQ ID NO 159
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 159

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Ala
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Arg
                85                  90                  95

Thr Phe Gly Gln Gly Thr Lys Val Glu Ile Arg Arg Gly Gly Gly Gly
            100                 105                 110

Ser Gly Gly Gly Gly Ser Gly Gly Gly Gly Ser Gln Val Gln Leu Gln
        115                 120                 125

Glu Ser Gly Pro Gly Leu Val Lys Pro Ser Glu Thr Leu Ser Leu Thr
    130                 135                 140

Cys Thr Val Ser Gly Gly Ser Ile Ile Ser His Tyr Trp Ser Trp Ile
145                 150                 155                 160

Arg Gln Pro Pro Gly Lys Gly Leu Glu Trp Ile Gly Tyr Ile Tyr Tyr
                165                 170                 175

Ser Gly Ser Thr Asn Tyr Asn Pro Ser Leu Lys Ser Arg Val Thr Ile
            180                 185                 190

Ser Val Asp Thr Ser Lys Asn Gln Phe Ser Leu Lys Leu Thr Ser Val
        195                 200                 205

Thr Ala Ala Asp Thr Ala Val Tyr Tyr Cys Ala Arg Asp Gly Trp Ser
    210                 215                 220

Ala Phe Asp Tyr Trp Gly Gln Gly Thr Leu Val Thr Val Ser Ser
225                 230                 235
```

<210> SEQ ID NO 160
<211> LENGTH: 241
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 160

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Asn Asn
            20                  25                  30

Asn Tyr Tyr Trp Thr Trp Ile Arg Gln His Pro Gly Lys Gly Leu Glu
        35                  40                  45

Trp Ile Gly Tyr Ile Tyr Tyr Ser Gly Ser Thr Phe Tyr Asn Pro Ser
    50                  55                  60

Leu Lys Ser Arg Val Thr Ile Ser Val Asp Thr Ser Lys Thr Gln Phe
```

```
65                  70                  75                  80

Ser Leu Lys Leu Ser Ser Val Thr Ala Ala Asp Thr Ala Val Tyr Tyr
                85                  90                  95

Cys Ala Arg Glu Asp Thr Met Thr Gly Leu Asp Val Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Asn Asn Tyr Leu Asn Trp Tyr Gln Gln Lys Pro Gly Lys
                165                 170                 175

Ala Pro Thr Leu Leu Ile Tyr Ala Ala Ser Ser Leu Gln Ser Gly Val
            180                 185                 190

Pro Ser Arg Phe Ser Gly Ser Arg Ser Gly Thr Asp Phe Thr Leu Thr
        195                 200                 205

Ile Ser Ser Leu Gln Pro Glu Asp Phe Ala Ala Tyr Phe Cys Gln Gln
    210                 215                 220

Thr Tyr Ser Asn Pro Thr Phe Gly Gln Gly Thr Lys Val Glu Val Lys
225                 230                 235                 240

Arg


<210> SEQ ID NO 161
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Ser Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Asn Asn
            20                  25                  30

Tyr Leu Asn Trp Tyr Gln Gln Lys Pro Gly Lys Ala Pro Thr Leu Leu
        35                  40                  45

Ile Tyr Ala Ala Ser Ser Leu Gln Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Ala Tyr Phe Cys Gln Gln Thr Tyr Ser Asn Pro
                85                  90                  95

Thr Phe Gly Gln Gly Thr Lys Val Glu Val Lys Arg Gly Gly Gly Gly
            100                 105                 110

Ser Gly Gly Gly Gly Ser Gly Gly Gly Gly Ser Gln Val Gln Leu Gln
        115                 120                 125

Glu Ser Gly Pro Gly Leu Val Lys Pro Ser Gln Thr Leu Ser Leu Thr
    130                 135                 140

Cys Thr Val Ser Gly Gly Ser Ile Asn Asn Asn Asn Tyr Tyr Trp Thr
145                 150                 155                 160

Trp Ile Arg Gln His Pro Gly Lys Gly Leu Glu Trp Ile Gly Tyr Ile
                165                 170                 175

Tyr Tyr Ser Gly Ser Thr Phe Tyr Asn Pro Ser Leu Lys Ser Arg Val
```

```
            180                 185                 190

Thr Ile Ser Val Asp Thr Ser Lys Thr Gln Phe Ser Leu Lys Leu Ser
        195                 200                 205

Ser Val Thr Ala Ala Asp Thr Ala Val Tyr Tyr Cys Ala Arg Glu Asp
    210                 215                 220

Thr Met Thr Gly Leu Asp Val Trp Gly Gln Gly Thr Thr Val Thr Val
225                 230                 235                 240

Ser Ser


<210> SEQ ID NO 162
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Gly Asp
            20                  25                  30

Gly His Phe Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Arg Gly Gly Tyr Lys Phe Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Val Met Thr Gln Thr Pro Leu Ser
    130                 135                 140

Leu Ser Val Ala Pro Gly Gln Pro Ala Ser Ile Ser Cys Gln Ser Ser
145                 150                 155                 160

Leu Ser Leu Gln His Ser Asn Gly Lys Thr Tyr Leu Tyr Trp Tyr Leu
                165                 170                 175

Gln Lys Pro Gly Gln Pro Pro Gln Leu Leu Ile Tyr Glu Val Ser Asn
            180                 185                 190

Arg Phe Ser Gly Val Pro Asp Arg Phe Ser Gly Ser Gly Ser Gly Thr
        195                 200                 205

Asp Phe Thr Leu Lys Ile Ser Arg Val Glu Ala Glu Asp Val Gly Ile
    210                 215                 220

Tyr Tyr Cys Met Gln Ser Lys Gln Leu Pro Tyr Ser Phe Gly Gln Gly
225                 230                 235                 240

Thr Lys Leu Glu Ile Lys Arg
                245


<210> SEQ ID NO 163
<211> LENGTH: 247
<212> TYPE: PRT
<213> ORGANISM: Artificial Sequence
<220> FEATURE:
<223> OTHER INFORMATION: Description of Artificial Sequence: Synthetic
```

polypeptide

<400> SEQUENCE: 163

```
Asp Ile Val Met Thr Gln Thr Pro Leu Ser Leu Ser Val Ala Pro Gly
1               5                   10                  15

Gln Pro Ala Ser Ile Ser Cys Gln Ser Ser Leu Ser Leu Gln His Ser
            20                  25                  30

Asn Gly Lys Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ser
                85                  90                  95

Lys Gln Leu Pro Tyr Ser Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Gln Leu Gln Glu Ser Gly Pro Gly Leu Val Lys Pro Ser Gln
    130                 135                 140

Thr Leu Ser Leu Thr Cys Thr Val Ser Gly Gly Ser Ile Ser Gly Asp
145                 150                 155                 160

Gly His Phe Trp Ser Trp Ile Arg Gln His Pro Gly Lys Gly Leu Glu
                165                 170                 175

Trp Ile Gly Tyr Ile Tyr Tyr Ser Gly Ser Thr Tyr Tyr Asn Pro Ser
            180                 185                 190

Leu Lys Ser Arg Val Thr Ile Ser Val Asp Thr Ser Lys Asn Gln Phe
        195                 200                 205

Ser Leu Lys Leu Ser Ser Val Thr Ala Ala Asp Thr Ala Val Tyr Tyr
    210                 215                 220

Cys Ala Arg Leu Arg Gly Gly Tyr Lys Phe Asp Tyr Trp Gly Gln Gly
225                 230                 235                 240

Thr Leu Val Thr Val Ser Ser
                245
```

<210> SEQ ID NO 164
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 164

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

```
                85                  90                  95

Arg Val Asp Tyr Lys Ala Phe Asp Ile Trp Gly Gln Gly Thr Met Val
            100                 105                 110

Thr Val Ser Ser Gly Gly Gly Gly Ser Gly Gly Gly Gly Ser Gly Gly
        115                 120                 125

Gly Gly Ser Asp Ile Gln Met Thr Gln Ser Pro Ser Ser Leu Ser Ala
    130                 135                 140

Ser Val Gly Asp Arg Val Thr Ile Thr Cys Arg Ala Ser Gln Gly Ile
145                 150                 155                 160

Arg Asn Asp Leu His Trp Tyr Gln Gln Lys Pro Gly Lys Ala Pro Lys
                165                 170                 175

Arg Leu Ile Tyr Ala Ala Ser Ser Leu Gln Ser Gly Val Pro Ser Arg
            180                 185                 190

Phe Ser Gly Ser Gly Ser Gly Thr Glu Phe Thr Leu Thr Ile Ser Ser
        195                 200                 205

Leu Gln Pro Glu Asp Phe Ala Thr Tyr Tyr Cys Leu Gln His Tyr Ser
    210                 215                 220

Tyr Pro Trp Thr Phe Gly Gln Gly Thr Lys Val Glu Ile Lys Arg
225                 230                 235


<210> SEQ ID NO 165
<211> LENGTH: 239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu His Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Tyr Ser Tyr Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Gln
        115                 120                 125

Glu Ser Gly Pro Gly Leu Val Lys Pro Ser Glu Thr Leu Ser Leu Thr
    130                 135                 140

Cys Thr Val Ser Gly Gly Ser Ile Ser Ser Tyr Tyr Trp Ser Trp Ile
145                 150                 155                 160

Arg Gln Pro Pro Gly Lys Gly Leu Glu Trp Ile Gly Tyr Ile Tyr Tyr
                165                 170                 175

Ser Gly Ser Thr Asn Tyr Asn Pro Ser Leu Lys Ser Arg Val Thr Ile
            180                 185                 190

Ser Val Asp Thr Ser Lys Asn Gln Phe Ser Leu Lys Leu Ser Ser Val
        195                 200                 205
```

```
Thr Ala Ala Asp Thr Ala Val Tyr Tyr Cys Ala Arg Val Asp Tyr Lys
    210                 215                 220

Ala Phe Asp Ile Trp Gly Gln Gly Thr Met Val Thr Val Ser Ser
225                 230                 235


<210> SEQ ID NO 166
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Ala Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Ile Phe Gly Val Val Ile Leu Ser Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Glu Ile Val Leu Thr Gln Ser
    130                 135                 140

Pro Asp Phe Gln Ser Val Thr Pro Lys Glu Lys Val Thr Ile Thr Cys
145                 150                 155                 160

Arg Ala Ser Gln Ser Ile Gly Ser Ser Leu His Trp Tyr Arg Gln Lys
                165                 170                 175

Pro Asp Gln Ser Pro Lys Leu Leu Ile Lys Tyr Ala Ser Gln Ser Phe
            180                 185                 190

Ser Gly Val Pro Ser Arg Phe Ser Gly Gly Gly Ser Gly Thr Asp Phe
        195                 200                 205

Thr Leu Thr Ile Asn Ser Leu Glu Ala Glu Asp Ala Ala Thr Tyr Tyr
    210                 215                 220

Cys His Gln Ser Ser Ser Leu Pro Trp Thr Phe Gly Gln Gly Thr Lys
225                 230                 235                 240

Val Glu Ile Lys Arg
                245


<210> SEQ ID NO 167
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Glu Ile Val Leu Thr Gln Ser Pro Asp Phe Gln Ser Val Thr Pro Lys
1               5                   10                  15
```

```
Glu Lys Val Thr Ile Thr Cys Arg Ala Ser Gln Ser Ile Gly Ser Ser
            20                  25                  30

Leu His Trp Tyr Arg Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Gly Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Glu Ser Gly Gly Gly Val Val Gln Pro Gly Arg Ser Leu Arg Leu Ser
    130                 135                 140

Cys Ala Ala Ser Gly Phe Thr Phe Ser Ser Tyr Gly Met His Trp Val
145                 150                 155                 160

Arg Gln Ala Pro Gly Lys Gly Leu Glu Trp Val Ala Ala Ile Trp Tyr
                165                 170                 175

Asp Gly Ser Asn Lys Tyr Tyr Ala Asp Ser Val Lys Gly Arg Phe Thr
            180                 185                 190

Ile Ser Arg Asp Asn Ser Lys Asn Met Leu Tyr Leu Gln Met Asn Ser
        195                 200                 205

Leu Arg Ala Glu Asp Thr Ala Val Tyr Tyr Cys Ala Arg Asp Leu Ser
    210                 215                 220

Ile Phe Gly Val Val Ile Leu Ser Asp Tyr Trp Gly Gln Gly Thr Leu
225                 230                 235                 240

Val Thr Val Ser Ser
                245


<210> SEQ ID NO 168
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Asn Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Arg Gly Arg Leu Ile Ile Ser Val Asp Thr Ser Lys Asn Gln Phe
65                  70                  75                  80

Ser Leu Arg Leu Ser Ser Val Thr Ala Ala Asp Thr Ala Val Tyr Tyr
                85                  90                  95

Cys Ala Arg Asp Gly Gly Asp Ser Tyr Gly Arg Met Asp Val Trp Gly
            100                 105                 110

Gln Gly Thr Thr Val Thr Val Ser Ser Gly Gly Gly Gly Ser Gly Gly
        115                 120                 125
```

```
Gly Gly Ser Gly Gly Gly Gly Ser Asp Ile Val Met Thr Gln Thr Pro
    130                 135                 140

Leu Ser Ser Pro Val Thr Leu Gly Gln Pro Ala Ser Ile Ser Cys Arg
145                 150                 155                 160

Ser Ser Gln Ser Leu Val His Ser Asp Arg Asn Thr Tyr Leu Ser Trp
                165                 170                 175

Leu Gln Gln Arg Pro Gly Gln Pro Pro Arg Leu Leu Ile Tyr Lys Ile
            180                 185                 190

Ser Asn Arg Phe Ser Gly Val Pro Asp Arg Phe Ser Gly Ser Gly Ala
        195                 200                 205

Gly Thr Asp Phe Thr Leu Lys Ile Ser Arg Val Glu Ala Glu Asp Val
    210                 215                 220

Gly Val Tyr Tyr Cys Met Gln Ala Thr Gln Phe Pro Leu Thr Phe Gly
225                 230                 235                 240

Gly Gly Thr Lys Val Glu Ile Lys Arg
                245


<210> SEQ ID NO 169
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Arg Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Thr Gln Phe Pro Leu Thr Phe Gly Gly Gly Thr Lys Val Glu Ile Lys
            100                 105                 110

Arg Gly Gly Gly Gly Ser Gly Gly Gly Gly Ser Gly Gly Gly Gly Ser
        115                 120                 125

Gln Val Gln Leu Gln Glu Ser Gly Pro Gly Leu Val Lys Pro Ser Gln
    130                 135                 140

Thr Leu Ser Leu Thr Cys Thr Val Ser Gly Gly Ser Ile Ser Ser Gly
145                 150                 155                 160

Gly Tyr Tyr Trp Asn Trp Ile Arg Gln His Pro Gly Lys Gly Leu Glu
                165                 170                 175

Trp Ile Gly Tyr Ile Tyr Tyr Ser Gly Ser Thr Tyr Tyr Asn Pro Ser
            180                 185                 190

Leu Arg Gly Arg Leu Ile Ile Ser Val Asp Thr Ser Lys Asn Gln Phe
        195                 200                 205

Ser Leu Arg Leu Ser Ser Val Thr Ala Ala Asp Thr Ala Val Tyr Tyr
    210                 215                 220

Cys Ala Arg Asp Gly Gly Asp Ser Tyr Gly Arg Met Asp Val Trp Gly
```

```
225                 230                 235                 240

Gln Gly Thr Thr Val Thr Val Ser Ser
                245
```

```
<210> SEQ ID NO 170
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Val Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Asn Asn Tyr
            20                  25                  30

Tyr Trp Ser Trp Ile Arg Gln Pro Ala Gly Lys Gly Leu Glu Trp Ile
        35                  40                  45

Gly Arg Ile Phe Thr Ser Gly Ser Thr Asn Tyr Asn Pro Ser Leu Lys
    50                  55                  60

Ser Arg Val Thr Met Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Gly His Tyr Gly Ser Ser Gly Tyr Leu Tyr Tyr Tyr Tyr
            100                 105                 110

Phe Gly Met Asp Val Trp Gly Gln Gly Thr Thr Val Thr Val Ser Ser
        115                 120                 125

Gly Gly Gly Gly Ser Gly Gly Gly Gly Ser Gly Gly Gly Gly Ser Glu
    130                 135                 140

Ile Val Leu Thr Gln Ser Pro Gly Thr Leu Ser Leu Ser Pro Gly Glu
145                 150                 155                 160

Arg Ala Thr Leu Ser Cys Arg Ala Ser Gln Thr Val Ser Ser Ser Tyr
                165                 170                 175

Leu Ala Trp Tyr Gln Gln Lys Pro Gly Gln Ala Pro Arg Leu Leu Ile
            180                 185                 190

Tyr Gly Ala Ser Ile Arg Ala Thr Gly Ile Pro Asp Arg Phe Ser Gly
        195                 200                 205

Ser Gly Ser Gly Thr Asp Phe Thr Leu Thr Ile Ser Arg Leu Glu Pro
    210                 215                 220

Glu Asp Phe Ala Val Tyr Tyr Cys Gln Gln Tyr Gly Ser Ser Leu Thr
225                 230                 235                 240

Phe Gly Gly Gly Thr Lys Val Glu Ile Lys Arg
                245                 250
```

```
<210> SEQ ID NO 171
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Ser Ser Ser
```

```
            20                  25                  30

Tyr Leu Ala Trp Tyr Gln Gln Lys Pro Gly Gln Ala Pro Arg Leu Leu
        35                  40                  45

Ile Tyr Gly Ala Ser Ile Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gly Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Gln
        115                 120                 125

Glu Ser Gly Pro Gly Leu Val Lys Pro Ser Glu Thr Leu Ser Leu Thr
    130                 135                 140

Cys Thr Val Ser Gly Asp Ser Ile Asn Asn Tyr Tyr Trp Ser Trp Ile
145                 150                 155                 160

Arg Gln Pro Ala Gly Lys Gly Leu Glu Trp Ile Gly Arg Ile Phe Thr
                165                 170                 175

Ser Gly Ser Thr Asn Tyr Asn Pro Ser Leu Lys Ser Arg Val Thr Met
            180                 185                 190

Ser Ile Asp Thr Ser Lys Asn Gln Phe Ser Leu Lys Leu Ser Ser Val
        195                 200                 205

Thr Ala Ala Asp Thr Ala Val Tyr Tyr Cys Ala Arg Glu Gly Gly His
    210                 215                 220

Tyr Gly Ser Ser Gly Tyr Leu Tyr Tyr Tyr Tyr Phe Gly Met Asp Val
225                 230                 235                 240

Trp Gly Gln Gly Thr Thr Val Thr Val Ser Ser
                245                 250
```

<210> SEQ ID NO 172
<211> LENGTH: 253
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Val Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Ile Phe Val Val Pro Ala Val Pro Arg Phe
            100                 105                 110

Asp Tyr Trp Gly Gln Gly Thr Leu Val Thr Val Ser Ser Gly Gly Gly
        115                 120                 125
```

```
Gly Ser Gly Gly Gly Gly Ser Gly Gly Gly Gly Ser Asp Ile Val Met
    130                 135                 140

Thr Gln Ser Pro Leu Ser Leu Ser Val Thr Pro Gly Glu Pro Ala Ser
145                 150                 155                 160

Ile Ser Cys Arg Ser Ser Leu Ser Leu Leu His Ser Asn Gly Tyr Asn
                165                 170                 175

Tyr Leu Asp Trp Phe Leu Gln Lys Pro Gly Gln Ser Pro Gln Leu Leu
            180                 185                 190

Ile Tyr Leu Gly Ser Asn Arg Ala Ser Gly Val Pro Asp Arg Phe Ser
        195                 200                 205

Gly Ser Gly Ser Asp Thr Asp Phe Thr Leu Lys Ile Ser Arg Val Glu
    210                 215                 220

Ala Glu Asp Val Gly Val Tyr Tyr Cys Met Gln Gly Leu His Thr Pro
225                 230                 235                 240

Pro Ser Phe Gly Gln Gly Thr Lys Leu Glu Ile Lys Arg
                245                 250


<210> SEQ ID NO 173
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Asp Ile Val Met Thr Gln Ser Pro Leu Ser Leu Ser Val Thr Pro Gly
1               5                   10                  15

Glu Pro Ala Ser Ile Ser Cys Arg Ser Ser Leu Ser Leu Leu His Ser
            20                  25                  30

Asn Gly Tyr Asn Tyr Leu Asp Trp Phe Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Asp Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu His Thr Pro Pro Ser Phe Gly Gln Gly Thr Lys Leu Glu Ile Lys
            100                 105                 110

Arg Gly Gly Gly Gly Ser Gly Gly Gly Gly Ser Gly Gly Gly Gly Ser
        115                 120                 125

Gln Val Gln Leu Gln Gln Ser Gly Pro Gly Leu Val Lys Pro Ser Gln
    130                 135                 140

Thr Leu Ser Leu Thr Cys Ala Ile Ser Gly Asp Ser Val Ser Ser Asn
145                 150                 155                 160

Ser Val Ala Trp Asn Trp Ile Arg Gln Ser Pro Ser Arg Gly Leu Glu
                165                 170                 175

Trp Leu Gly Arg Thr Tyr Tyr Arg Ser Lys Trp Tyr Asn Asp Tyr Ala
            180                 185                 190

Val Ser Val Lys Ser Arg Ile Thr Ile Asn Pro Asp Thr Ser Lys Asn
        195                 200                 205

Gln Phe Ser Leu Gln Leu Asn Ser Val Thr Pro Glu Asp Thr Ala Val
    210                 215                 220

Tyr Tyr Cys Ala Arg Gly Ile Phe Val Val Pro Ala Val Pro Arg Phe
225                 230                 235                 240
```

```
Asp Tyr Trp Gly Gln Gly Thr Leu Val Thr Val Ser Ser
                245                 250


<210> SEQ ID NO 174
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr His
            20                  25                  30

Gly Leu His Trp Val Arg Gln Ala Pro Gly Lys Gly Leu Glu Trp Val
        35                  40                  45

Ala Val Ile Trp Tyr Asp Gly Asn Asn Lys Asn Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Lys Gly Ser Gly Lys Gly Cys Met Asp Val Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Glu Ile Val Leu Thr Gln Ser Pro Gly Thr
    130                 135                 140

Leu Ser Leu Ser Pro Gly Glu Arg Ala Thr Leu Ser Cys Arg Ala Ser
145                 150                 155                 160

Gln Ser Val Ser Phe Ser Tyr Leu Ala Trp Tyr Gln Gln Lys Pro Gly
                165                 170                 175

Gln Ala Pro Arg Leu Leu Ile Tyr Gly Ala Ser Ser Arg Ala Thr Gly
            180                 185                 190

Ile Pro Asp Arg Phe Ser Gly Ser Gly Ser Gly Thr Asp Phe Thr Leu
        195                 200                 205

Thr Ile Ser Arg Leu Glu Pro Glu Asp Phe Ala Val Tyr Tyr Cys Gln
    210                 215                 220

His Tyr Asp Gly Ser Ile Thr Phe Gly Pro Gly Thr Lys Val Asp Ile
225                 230                 235                 240

Glu Arg


<210> SEQ ID NO 175
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Phe Ser
            20                  25                  30
```

```
Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Asp Gly Ser Ile
                85                  90                  95

Thr Phe Gly Pro Gly Thr Lys Val Asp Ile Glu Arg Gly Gly Gly Gly
            100                 105                 110

Ser Gly Gly Gly Gly Ser Gly Gly Gly Gly Ser Gln Val Gln Leu Val
        115                 120                 125

Glu Ser Gly Gly Gly Val Val Gln Pro Gly Arg Ser Leu Arg Leu Ser
    130                 135                 140

Cys Ala Ala Ser Gly Phe Thr Phe Ser Tyr His Gly Leu His Trp Val
145                 150                 155                 160

Arg Gln Ala Pro Gly Lys Gly Leu Glu Trp Val Ala Val Ile Trp Tyr
                165                 170                 175

Asp Gly Asn Asn Lys Asn Tyr Ala Asp Ser Val Lys Gly Arg Phe Thr
            180                 185                 190

Ile Ser Arg Asp Asn Ser Lys Asn Thr Leu Phe Leu Gln Met Asn Ser
        195                 200                 205

Leu Arg Ala Glu Asp Thr Ala Val Tyr Tyr Cys Ala Arg Lys Gly Ser
    210                 215                 220

Gly Lys Gly Cys Met Asp Val Trp Gly Gln Gly Thr Thr Val Thr Val
225                 230                 235                 240

Ser Ser
```

<210> SEQ ID NO 176
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 176

```
Gln Val Gln Leu Glu Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Asn Asn Lys Asp Tyr Arg Asp Ser Val
    50                  55                  60

Thr Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Lys Gly Ser Gly Lys Gly Cys Met Asp Val Trp Gly Arg Gly
            100                 105                 110

Thr Thr Val Thr Val Ser Ser Gly Gly Gly Gly Ser Gly Gly Gly Gly
        115                 120                 125

Ser Gly Gly Gly Gly Ser Glu Ile Val Leu Thr Gln Ser Pro Gly Thr
    130                 135                 140
```

```
Leu Ser Leu Ser Pro Gly Asp Arg Ala Thr Leu Ser Cys Arg Ala Ser
145                 150                 155                 160

Gln Ser Val Ser Phe Ser Phe Leu Ala Trp Tyr Gln Gln Thr Pro Gly
                165                 170                 175

Gln Ala Pro Arg Leu Leu Ile Tyr Gly Ala Tyr Ser Arg Ala Thr Gly
            180                 185                 190

Ile Pro Asp Arg Phe Ser Gly Ser Gly Ser Gly Thr Asp Phe Ala Leu
        195                 200                 205

Thr Ile Ser Arg Leu Glu Pro Glu Asp Phe Ala Val Tyr Tyr Cys Gln
    210                 215                 220

His Tyr Gly Thr Ser Ile Thr Phe Gly Pro Gly Thr Lys Val Asp Leu
225                 230                 235                 240

Lys Arg


<210> SEQ ID NO 177
<211> LENGTH: 242
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Ile Val Leu Thr Gln Ser Pro Gly Thr Leu Ser Leu Ser Pro Gly
1               5                   10                  15

Asp Arg Ala Thr Leu Ser Cys Arg Ala Ser Gln Ser Val Ser Phe Ser
            20                  25                  30

Phe Leu Ala Trp Tyr Gln Gln Thr Pro Gly Gln Ala Pro Arg Leu Leu
        35                  40                  45

Ile Tyr Gly Ala Tyr Ser Arg Ala Thr Gly Ile Pro Asp Arg Phe Ser
    50                  55                  60

Gly Ser Gly Ser Gly Thr Asp Phe Ala Leu Thr Ile Ser Arg Leu Glu
65                  70                  75                  80

Pro Glu Asp Phe Ala Val Tyr Tyr Cys Gln His Tyr Gly Thr Ser Ile
                85                  90                  95

Thr Phe Gly Pro Gly Thr Lys Val Asp Leu Lys Arg Gly Gly Gly Gly
            100                 105                 110

Ser Gly Gly Gly Gly Ser Gly Gly Gly Gly Ser Gln Val Gln Leu Glu
        115                 120                 125

Gln Ser Gly Gly Gly Val Val Gln Pro Gly Arg Ser Leu Arg Leu Ser
    130                 135                 140

Cys Ala Ala Ser Gly Phe Thr Phe Ser Ser Tyr Gly Met His Trp Val
145                 150                 155                 160

Arg Gln Ala Pro Gly Lys Gly Leu Glu Trp Val Ala Val Ile Trp Tyr
                165                 170                 175

Asp Gly Asn Asn Lys Asp Tyr Arg Asp Ser Val Thr Gly Arg Phe Thr
            180                 185                 190

Ile Ser Arg Asp Asn Ser Lys Asn Thr Leu Tyr Leu Gln Met Ser Ser
        195                 200                 205

Leu Arg Ala Glu Asp Thr Ala Val Tyr Tyr Cys Ala Arg Lys Gly Ser
    210                 215                 220

Gly Lys Gly Cys Met Asp Val Trp Gly Arg Gly Thr Thr Val Thr Val
225                 230                 235                 240

Ser Ser
```

<210> SEQ ID NO 178
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 178

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Thr Val Ile Trp Tyr Asp Gly Asn Asn Lys Asp Tyr Ala Asp Ser Val
50 55 60

Lys Gly Arg Phe Thr Ile Ser Arg Asp Ser Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Lys Gly Ser Gly Lys Gly Cys Met Asp Val Trp Gly Gln Gly
100 105 110

Thr Thr Val Thr Val Ser Ser Gly Gly Gly Gly Ser Gly Gly Gly Gly
115 120 125

Ser Gly Gly Gly Gly Ser Glu Ile Val Leu Thr Gln Ser Pro Gly Thr
130 135 140

Leu Ser Leu Ser Pro Gly Glu Arg Ala Thr Leu Ser Cys Arg Ala Ser
145 150 155 160

Gln Ser Val Ser Tyr Ser Phe Leu Ala Trp Tyr Gln Gln Lys Pro Gly
165 170 175

Gln Ala Pro Arg Leu Leu Ile Tyr Ala Ala Ser Ser Arg Ala Thr Gly
180 185 190

Ile Pro Asp Arg Phe Ser Gly Ser Gly Ser Gly Thr Asp Phe Thr Leu
195 200 205

Thr Ile Ser Arg Leu Glu Pro Glu Asp Phe Ala Val Tyr Tyr Cys Gln
210 215 220

His Tyr Gly Ser Ser Ile Thr Phe Gly Pro Gly Thr Lys Val Asp Ile
225 230 235 240

Lys Arg

<210> SEQ ID NO 179
<211> LENGTH: 242
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 179

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Tyr Ser
20 25 30

Phe Leu Ala Trp Tyr Gln Gln Lys Pro Gly Gln Ala Pro Arg Leu Leu
35 40 45

Ile Tyr Ala Ala Ser Ser Arg Ala Thr Gly Ile Pro Asp Arg Phe Ser
50 55 60

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Ile
                85                  90                  95

Thr Phe Gly Pro Gly Thr Lys Val Asp Ile Lys Arg Gly Gly Gly Gly
            100                 105                 110

Ser Gly Gly Gly Gly Ser Gly Gly Gly Gly Ser Gln Val Gln Leu Val
        115                 120                 125

Glu Ser Gly Gly Gly Val Val Gln Pro Gly Arg Ser Leu Arg Leu Ser
    130                 135                 140

Cys Ala Ala Ser Gly Phe Thr Phe Ser Ser Tyr Gly Met His Trp Val
145                 150                 155                 160

Arg Gln Ala Pro Gly Lys Gly Leu Glu Trp Val Thr Val Ile Trp Tyr
                165                 170                 175

Asp Gly Asn Asn Lys Asp Tyr Ala Asp Ser Val Lys Gly Arg Phe Thr
            180                 185                 190

Ile Ser Arg Asp Ser Ser Lys Asn Thr Leu Tyr Leu Gln Met Asn Ser
        195                 200                 205

Leu Arg Ala Glu Asp Thr Ala Val Tyr Tyr Cys Ala Arg Lys Gly Ser
    210                 215                 220

Gly Lys Gly Cys Met Asp Val Trp Gly Gln Gly Thr Thr Val Thr Val
225                 230                 235                 240

Ser Ser


<210> SEQ ID NO 180
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val Gln Leu Glu Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45

Ser Val Ile Gly Thr Ala Gly Asp Thr Tyr Tyr Pro Asp Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Val
                85                  90                  95

Arg Gly Gly Gly Trp Asn Tyr Gly Tyr Tyr Tyr Tyr Gly Met Asp Val
            100                 105                 110

Trp Gly Gln Trp Thr Thr Val Thr Val Ser Ser Gly Gly Gly Gly Ser
        115                 120                 125

Gly Gly Gly Gly Ser Gly Gly Gly Gly Ser Asp Ile Gln Met Thr Gln
    130                 135                 140

Ser Pro Ser Ser Leu Ser Ala Ser Val Gly Asp Arg Val Thr Ile Thr
145                 150                 155                 160

Cys Arg Ala Ser Glu Ser Ile Arg Arg Tyr Leu Asn Trp Tyr Gln Glu
                165                 170                 175
```

```
Lys Pro Gly Lys Ala Pro Lys Leu Leu Ile Tyr Ala Ala Ser Ser Ser
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Ser Tyr Ile Asn Pro Pro Thr Phe Gly Gln Gly Thr
225                 230                 235                 240

Lys Val Glu Ile Lys Arg
                245


<210> SEQ ID NO 181
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Arg Arg Tyr
            20                  25                  30

Leu Asn Trp Tyr Gln Glu Lys Pro Gly Lys Ala Pro Lys Leu Leu Ile
        35                  40                  45

Tyr Ala Ala Ser Ser Ser Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Asn Pro Pro
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Glu Val Gln Leu Glu
        115                 120                 125

Gln Ser Gly Gly Gly Leu Val Gln Pro Gly Gly Ser Leu Arg Leu Ser
    130                 135                 140

Cys Ala Ala Ser Gly Phe Thr Phe Ser Ser Tyr Asp Met His Trp Val
145                 150                 155                 160

Arg Gln Ala Thr Gly Lys Gly Leu Glu Trp Val Ser Val Ile Gly Thr
                165                 170                 175

Ala Gly Asp Thr Tyr Tyr Pro Asp Ser Val Lys Gly Arg Phe Thr Ile
            180                 185                 190

Ser Arg Glu Asn Ala Lys Asn Ser Leu Tyr Leu Gln Met Asn Ser Leu
        195                 200                 205

Arg Ala Gly Asp Thr Ala Val Tyr Tyr Cys Val Arg Gly Gly Gly Trp
    210                 215                 220

Asn Tyr Gly Tyr Tyr Tyr Tyr Gly Met Asp Val Trp Gly Gln Trp Thr
225                 230                 235                 240

Thr Val Thr Val Ser Ser
                245


<210> SEQ ID NO 182
<211> LENGTH: 245
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 182

Gln Val Gln Leu Glu Gln Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Phe Ser Gly Asn Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Tyr Cys Asp Asp Asp Cys Tyr Gly Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Ile Gln Val Thr Gln Ser
    130                 135                 140

Pro Ser Ser Leu Ser Ala Ser Val Gly Asp Arg Val Thr Ile Thr Cys
145                 150                 155                 160

Arg Ala Ser Gln Gly Ile Arg Asn Asp Leu Gly Trp Tyr Gln Gln Lys
                165                 170                 175

Pro Gly Lys Ala Pro Lys Arg Leu Ile Tyr Ala Ala Ser Ser Leu Gln
            180                 185                 190

Ser Gly Val Pro Ser Arg Phe Ser Gly Ser Gly Ser Gly Thr Glu Phe
        195                 200                 205

Thr Leu Thr Ile Ser Ser Leu Gln Pro Glu Asp Phe Ala Thr Tyr Tyr
    210                 215                 220

Cys Leu Gln Tyr Ser Ile Tyr Pro Arg Thr Phe Gly Gln Gly Thr Lys
225                 230                 235                 240

Val Glu Ile Lys Arg
                245

<210> SEQ ID NO 183
<211> LENGTH: 245
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 183

Asp Ile Gln Val Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro

```
65                  70                  75                  80

Glu Asp Phe Ala Thr Tyr Tyr Cys Leu Gln Tyr Ser Ile Tyr Pro Arg
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Glu
        115                 120                 125

Gln Ser Gly Pro Gly Leu Val Lys Pro Ser Gln Thr Leu Ser Leu Thr
    130                 135                 140

Cys Thr Val Ser Gly Gly Ser Ile Ser Ser Gly Gly Tyr Tyr Trp Ser
145                 150                 155                 160

Trp Ile Arg Gln His Pro Gly Lys Gly Leu Glu Trp Ile Gly Tyr Ile
                165                 170                 175

Tyr Phe Ser Gly Asn Thr Asn Tyr Asn Pro Ser Leu Lys Ser Arg Val
            180                 185                 190

Thr Ile Ser Val Asp Thr Ser Lys Asn Gln Phe Ser Leu Lys Leu Ser
        195                 200                 205

Ser Val Thr Ala Ala Asp Thr Ala Val Tyr Tyr Cys Ala Arg Glu Tyr
    210                 215                 220

Cys Asp Asp Asp Cys Tyr Gly Phe Asp Tyr Trp Gly Gln Gly Thr Leu
225                 230                 235                 240

Val Thr Val Ser Ser
                245
```

<210> SEQ ID NO 184
<211> LENGTH: 245
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 184

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Ile Phe Gly Val Val Val Leu Ser Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Glu Ile Val Leu Thr Gln Ser
    130                 135                 140

Pro Asp Phe Gln Ser Val Thr Pro Lys Glu Lys Val Thr Ile Thr Cys
145                 150                 155                 160

Arg Ala Ser Gln Tyr Ile Gly Ser Asn Leu His Trp Tyr Gln Gln Thr
                165                 170                 175
```

```
Pro Asp Gln Ser Pro Lys Leu Leu Ile Lys Tyr Ala Ser Gln Ser Phe
            180                 185                 190

Ser Gly Val Pro Ser Arg Phe Ser Gly Ser Gly Ser Gly Thr Asp Phe
        195                 200                 205

Thr Leu Thr Ile Asn Ser Leu Glu Ala Glu Asp Ala Ala Thr Tyr Tyr
    210                 215                 220

Cys His Gln Ser Ser Ser Leu Pro Trp Thr Phe Gly Gln Gly Thr Lys
225                 230                 235                 240

Val Glu Ile Lys Arg
                245


<210> SEQ ID NO 185
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Tyr Ile Gly Ser Asn
            20                  25                  30

Leu His Trp Tyr Gln Gln Thr Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Trp
                85                  90                  95

Thr Phe Gly Gln Gly Thr Lys Val Glu Ile Lys Arg Gly Gly Gly Gly
            100                 105                 110

Ser Gly Gly Gly Gly Ser Gly Gly Gly Gly Ser Gln Val Gln Leu Val
        115                 120                 125

Glu Ser Gly Gly Gly Val Val Gln Pro Gly Arg Ser Leu Arg Leu Ser
    130                 135                 140

Cys Ala Ala Ser Gly Phe Thr Phe Ser Ser Tyr Gly Met His Trp Val
145                 150                 155                 160

Arg Gln Ala Pro Gly Lys Gly Leu Glu Trp Val Ala Val Ile Trp Tyr
                165                 170                 175

Asp Gly Ser Asn Lys Tyr Tyr Ala Asp Ser Val Lys Gly Arg Phe Thr
            180                 185                 190

Ile Ser Arg Asp Asn Ser Lys Asn Thr Leu Tyr Leu Gln Met Asn Ser
        195                 200                 205

Leu Arg Ala Glu Asp Thr Ala Val Tyr Tyr Cys Ala Arg Asp Leu Ser
    210                 215                 220

Ile Phe Gly Val Val Val Leu Ser Asp Tyr Trp Gly Gln Gly Thr Leu
225                 230                 235                 240

Val Thr Val Ser Ser
                245


<210> SEQ ID NO 186
<211> LENGTH: 981
<212> TYPE: DNA
<213> ORGANISM: Artificial Sequence
```

<220> FEATURE:
<223> OTHER INFORMATION: Description of Artificial Sequence: Synthetic polynucleotide

<400> SEQUENCE: 186

```
gctagcacca agggcccatc ggtcttcccc ctggcgccct gctccaggag cacctccgag     60

agcacagcgg ccctgggctg cctggtcaag gactacttcc ccgaaccggt gacggtgtcg    120

tggaactcag gcgctctgac cagcggcgtg cacaccttcc cagctgtcct acagtcctca    180

ggactctact ccctcagcag cgtggtgacc gtgccctcca gcaacttcgg cacccagacc    240

tacacctgca acgtagatca caagcccagc aacaccaagg tggacaagac agttgagcgc    300

aaatgttgtg tcgagtgccc accgtgccca gcaccacctg tggcaggacc gtcagtcttc    360

ctcttccccc caaaacccaa ggacaccctc atgatctccc ggacccctga ggtcacgtgc    420

gtggtggtgg acgtgagcca cgaagacccc gaggtccagt tcaactggta cgtggacggc    480

gtggaggtgc ataatgccaa gacaaagcca cgggaggagc agttcaacag cacgttccgt    540

gtggtcagcg tcctcaccgt tgtgcaccag gactggctga acggcaagga gtacaagtgc    600

aaggtctcca acaaaggcct cccagccccc atcgagaaaa ccatctccaa aaccaaaggg    660

cagccccgag aaccacaggt gtacaccctg cccccatccc gggaggagat gaccaagaac    720

caggtcagcc tgacctgcct ggtcaaaggc ttctacccca gcgacatcgc cgtggagtgg    780

gagagcaatg ggcagccgga gaacaactac aagaccacac ctcccatgct ggactccgac    840

ggctccttct tcctctacag caagctcacc gtggacaaga gcaggtggca gcaggggaac    900

gtcttctcat gctccgtgat gcatgaggct ctgcacaacc actacacgca gaagagcctc    960

tccctgtctc cgggtaaatg a                                              981
```

<210> SEQ ID NO 187
<211> LENGTH: 326
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
```

```
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 188
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 188

cgtacggtgg ctgcaccatc tgtcttcatc ttcccgccat ctgatgagca gttgaaatct      60

ggaactgcct ctgttgtgtg cctgctgaat aacttctatc ccagagaggc caaagtacag     120

tggaaggtgg ataacgccct ccaatcgggt aactcccagg agagtgtcac agagcaggac     180

agcaaggaca gcacctacag cctcagcagc accctgacgc tgagcaaagc agactacgag     240

aaacacaaag tctacgcctg cgaagtcacc catcagggcc tgagctcgcc cgtcacaaag     300

agcttcaaca ggggagagtg ttag                                            324


<210> SEQ ID NO 189
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
```

```
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 190
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 190

ggccaaccga aagcggcgcc ctcggtcact ctgttcccgc cctcctctga ggagcttcaa      60

gccaacaagg ccacactggt gtgtctcata agtgacttct acccgggagc cgtgacagtg     120

gcctggaagg cagatagcag ccccgtcaag gcgggagtgg agaccaccac accctccaaa     180

caaagcaaca acaagtacgc ggccagcagc tatctgagcc tgacgcctga gcagtggaag     240

tcccacagaa gctacagctg ccaggtcacg catgaaggga gcaccgtgga gaagacagtg     300

gcccctacag aatgttcata g                                                321


<210> SEQ ID NO 191
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 192
<211> LENGTH: 330
<212> TYPE: PRT
<213> ORGANISM: Homo sapiens

<400> SEQUENCE: 192

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 193
<211> LENGTH: 326
<212> TYPE: PRT
<213> ORGANISM: Homo sapiens

<400> SEQUENCE: 193

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
```

```
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 194
<211> LENGTH: 377
<212> TYPE: PRT
<213> ORGANISM: Homo sapiens

<400> SEQUENCE: 194

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110
```

```
Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375


<210> SEQ ID NO 195
<211> LENGTH: 327
<212> TYPE: PRT
<213> ORGANISM: Homo sapiens

<400> SEQUENCE: 195

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110
```

```
Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 196
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (27)..(27)
<223> OTHER INFORMATION: Phe, Gly or Asp
<220> FEATURE:
<221> NAME/KEY: MOD_RES
<222> LOCATION: (32)..(32)
<223> OTHER INFORMATION: Gly, Asp, Asn or not present
<220> FEATURE:
<221> NAME/KEY: MOD_RES
<222> LOCATION: (33)..(33)
<223> OTHER INFORMATION: Gly, Asn, Ser or not present
<220> FEATURE:
<221> NAME/KEY: MOD_RES
<222> LOCATION: (37)..(37)
<223> OTHER INFORMATION: His, Asn, Ser or Thr
<220> FEATURE:
<221> NAME/KEY: MOD_RES
<222> LOCATION: (52)..(52)
<223> OTHER INFORMATION: Val, Tyr, Arg or Ala
<220> FEATURE:
<221> NAME/KEY: MOD_RES
<222> LOCATION: (61)..(61)
<223> OTHER INFORMATION: May or may not be present
<220> FEATURE:
<221> NAME/KEY: MOD_RES
<222> LOCATION: (62)..(62)
<223> OTHER INFORMATION: Tyr, Asp or not present
```

<220> FEATURE:
<221> NAME/KEY: MOD_RES
<222> LOCATION: (103)..(103)
<223> OTHER INFORMATION: Leu, Gly, Ile or not present
<220> FEATURE:
<221> NAME/KEY: MOD_RES
<222> LOCATION: (104)..(110)
<223> OTHER INFORMATION: May or may not be present
<220> FEATURE:
<221> NAME/KEY: MOD_RES
<222> LOCATION: (111)..(111)
<223> OTHER INFORMATION: Ser, Tyr, Phe or not present
<220> FEATURE:
<221> NAME/KEY: MOD_RES
<222> LOCATION: (113)..(113)
<223> OTHER INFORMATION: Phe, Lys, Gly, Leu, Tyr, Glu or Val
<220> FEATURE:
<221> NAME/KEY: MOD_RES
<222> LOCATION: (114)..(114)
<223> OTHER INFORMATION: Gly, Asp, Arg, Tyr or Pro
<220> FEATURE:
<221> NAME/KEY: MOD_RES
<222> LOCATION: (115)..(115)
<223> OTHER INFORMATION: Val, Ser, Gly, Tyr, Val Thr, Ala or not present
<220> FEATURE:
<221> NAME/KEY: MOD_RES
<222> LOCATION: (117)..(117)
<223> OTHER INFORMATION: Val, Gly, Tyr, Phe, Ile, Thr, Pro or not present
<220> FEATURE:
<221> NAME/KEY: MOD_RES
<222> LOCATION: (118)..(118)
<223> OTHER INFORMATION: Leu, Cys, Arg, Lys or Gly
<220> FEATURE:
<221> NAME/KEY: MOD_RES
<222> LOCATION: (156)..(156)
<223> OTHER INFORMATION: Asp, Gly, Leu or Ser
<220> FEATURE:
<221> NAME/KEY: MOD_RES
<222> LOCATION: (177)..(177)
<223> OTHER INFORMATION: Gly, Ser, Val, Gln, Asn or Leu
<220> FEATURE:
<221> NAME/KEY: MOD_RES
<222> LOCATION: (178)..(178)
<223> OTHER INFORMATION: Phe, His, Ser, Asn or not present
<220> FEATURE:
<221> NAME/KEY: MOD_RES
<222> LOCATION: (180)..(180)
<223> OTHER INFORMATION: Asp, Asn or not present
<220> FEATURE:
<221> NAME/KEY: MOD_RES
<222> LOCATION: (181)..(181)
<223> OTHER INFORMATION: Arg, Gly or not present
<220> FEATURE:
<221> NAME/KEY: MOD_RES
<222> LOCATION: (182)..(182)
<223> OTHER INFORMATION: Asn, Lys, Tyr or not present
<220> FEATURE:
<221> NAME/KEY: MOD_RES
<222> LOCATION: (186)..(186)
<223> OTHER INFORMATION: His, Ala, Ser, Tyr, Asn or Asp
<220> FEATURE:
<221> NAME/KEY: MOD_RES
<222> LOCATION: (202)..(202)
<223> OTHER INFORMATION: Tyr, Gly, Lys, Glu, Ala or Leu
<220> FEATURE:
<221> NAME/KEY: MOD_RES
<222> LOCATION: (235)..(235)
<223> OTHER INFORMATION: Ala, Phe or Val
<220> FEATURE:
<221> NAME/KEY: MOD_RES
<222> LOCATION: (241)..(241)
<223> OTHER INFORMATION: His, Gln or Met
<220> FEATURE:
<221> NAME/KEY: MOD_RES
<222> LOCATION: (244)..(244)
<223> OTHER INFORMATION: Ser, Gly, Thr, Lys, Leu or not present
<220> FEATURE:
<221> NAME/KEY: MOD_RES

```
<222> LOCATION: (245)..(245)
<223> OTHER INFORMATION: Ser, Gln, Gly, Tyr, His or not present
<220> FEATURE:
<221> NAME/KEY: MOD_RES
<222> LOCATION: (248)..(248)
<223> OTHER INFORMATION: Trp, Ile, Leu, Tyr or Pro

<400> SEQUENCE: 196

Gln Val Gln Leu Gln Glu Ser Gly Pro Gly Leu Val Lys Pro Ser Gln
1               5                   10                  15

Thr Leu Ser Leu Thr Cys Thr Val Ser Gly Xaa Ser Ile Ser Ser Xaa
            20                  25                  30

Xaa Tyr Tyr Trp Xaa Trp Ile Arg Gln Ala Pro Gly Lys Gly Leu Glu
        35                  40                  45

Trp Ile Gly Xaa Ile Tyr Tyr Ser Gly Ser Thr Tyr Asn Xaa Tyr Asn
    50                  55                  60

Pro Ser Leu Lys Ser Arg Val Thr Ile Ser Val Asp Thr Ser Lys Asn
65                  70                  75                  80

Gln Phe Ser Leu Gln Leu Ser Ser Val Thr Ala Glu Asp Thr Ala Val
                85                  90                  95

Tyr Tyr Cys Ala Arg Asp Xaa Gly His Tyr Gly Ser Ser Gly Xaa Ile
            100                 105                 110

Xaa Xaa Xaa Val Xaa Xaa Met Asp Tyr Trp Gly Gln Gly Thr Thr Val
        115                 120                 125

Thr Val Ser Ser Gly Gly Gly Gly Ser Gly Gly Gly Gly Ser Gly Gly
    130                 135                 140

Gly Gly Ser Asp Ile Val Leu Thr Gln Ser Pro Xaa Ser Leu Ser Val
145                 150                 155                 160

Thr Pro Gly Glu Arg Ala Thr Ile Ser Cys Arg Ala Ser Gln Ser Ile
                165                 170                 175

Xaa Xaa Ser Xaa Xaa Xaa Ser Tyr Leu Xaa Trp Tyr Gln Gln Lys Pro
            180                 185                 190

Gly Gln Ala Pro Arg Leu Leu Ile Tyr Xaa Ala Ser Asn Arg Phe Ser
        195                 200                 205

Gly Val Pro Asp Arg Phe Ser Gly Ser Gly Ser Gly Thr Asp Phe Thr
    210                 215                 220

Leu Thr Ile Ser Arg Leu Glu Ala Glu Asp Xaa Ala Val Tyr Tyr Cys
225                 230                 235                 240

Xaa Gln Ser Xaa Xaa Ser Pro Xaa Thr Phe Gly Gln Gly Thr Lys Val
                245                 250                 255

Glu Ile Lys Arg
            260


<210> SEQ ID NO 197
<211> LENGTH: 226
<212> TYPE: PRT
<213> ORGANISM: Artificial Sequence
<220> FEATURE:
<223> OTHER INFORMATION: Consensus sequence

<400> SEQUENCE: 197

Gln Val Gln Leu Gln Glu Ser Gly Pro Gly Leu Val Lys Pro Ser Gln
1               5                   10                  15

Thr Leu Ser Leu Thr Cys Thr Val Ser Gly Ser Ile Ser Ser Tyr Tyr
            20                  25                  30

Trp Trp Ile Arg Gln Ala Pro Gly Lys Gly Leu Glu Trp Ile Gly Ile
        35                  40                  45
```

-continued

```
Tyr Tyr Ser Gly Ser Thr Tyr Tyr Asn Pro Ser Leu Lys Ser Arg Val
    50                  55                  60

Thr Ile Ser Val Asp Thr Ser Lys Asn Gln Phe Ser Leu Gln Leu Ser
65                  70                  75                  80

Ser Val Thr Ala Glu Asp Thr Ala Val Tyr Tyr Cys Ala Arg Asp Ile
                85                  90                  95

Val Met Asp Tyr Trp Gly Gln Gly Thr Thr Val Thr Val Ser Ser Gly
            100                 105                 110

Gly Gly Gly Ser Gly Gly Gly Gly Ser Gly Gly Gly Gly Ser Asp Ile
        115                 120                 125

Val Leu Thr Gln Ser Pro Ser Leu Ser Val Thr Pro Gly Glu Arg Ala
    130                 135                 140

Thr Ile Ser Cys Arg Ala Ser Gln Ser Ile Ser Ser Tyr Leu Trp Tyr
145                 150                 155                 160

Gln Gln Lys Pro Gly Gln Ala Pro Arg Leu Leu Ile Tyr Ala Ser Asn
                165                 170                 175

Arg Phe Ser Gly Val Pro Asp Arg Phe Ser Gly Ser Gly Ser Gly Thr
            180                 185                 190

Asp Phe Thr Leu Thr Ile Ser Arg Leu Glu Ala Glu Asp Ala Val Tyr
        195                 200                 205

Tyr Cys Gln Ser Ser Pro Thr Phe Gly Gln Gly Thr Lys Val Glu Ile
    210                 215                 220

Lys Arg
225
```

ANTI-MESOTHELIN BINDING PROTEINS

This application is a division of U.S. application Ser. No. 16/123,827, filed Sep. 6, 2018, now U.S. Pat. No. 10,919,975, which is a continuation of U.S. application Ser. No. 15/141,463, filed Apr. 28, 2016, now U.S. Pat. No. 10,100,121, which was a continuation of U.S. application Ser. No. 13/926,847, filed Jun. 25, 2013, now abandoned, which claims the benefit of U.S. Provisional Application No. 61/789,678 filed Mar. 15, 2013 and U.S. Provisional Application No. 61/665,139 filed Jun. 27, 2012, both of which are incorporated by reference in their entirety.

REFERENCE TO THE SEQUENCE LISTING

The present application is being filed along with a Sequence Listing in electronic format. The Sequence Listing is provided as a file entitled 50129C SeqListing.xml; Size: 316,576 bytes: Created: Jul. 26, 2023. The information in the electronic format of the Sequence Listing is incorporated herein by reference in its entirety.

FIELD OF THE INVENTION

The field of this invention relates to compositions and methods related to anti-mesothelin binding proteins.

BACKGROUND OF THE INVENTION

Mesothelin is a glycoprotein present on the surface of cells of the mesothelial lining of the peritoneal, pleural and pericardial body cavities. Mesothelin (MSLN) was identified in 1992 with the mAb K1 that was generated by the immunization of mice with human ovarian carcinoma (OVCAR-3) cells (Chang, et al., Int J. Cancer. (1992) 50:373-81). It was purified from the human pancreatic cancer cell line HPC-Y5 and was shown to have megakaryocyte potentiating ability and hence named megakaryocyte potentiating factor (MPF) (Yamaguchi et al. (1994) J. Biol. Chem. 269:805-808). The mesothelin gene (MSLN) encodes a 71-kilodalton (kDa) precursor protein that is processed to a 40-kDa protein termed mesothelin, which is a glycosyl-phosphatidylinositol-anchored glycoprotein present on the cell surface (Chang, et al, Proc Natl Acad Sci USA (1996) 93:136-40). The mesothelin cDNA was cloned from a library prepared from the HPC-Y5 cell line (Kojima et al. (1995) J. Biol. Chem. 270:21984-21990). The cDNA also was cloned using the monoclonal antibody K1, which recognizes mesotheliomas (Chang and Pastan (1996) Proc. Natl. Acad. Sci. USA 93:136-40).

Mesothelin is a differentiation antigen whose expression in normal human tissues is limited to mesothelial cells lining the body cavity, such as the pleura, pericardium and peritoneum. Mesothelin is also highly expressed in several different human cancers, including mesotheliomas, pancreatic adenocarcinomas, ovarian cancers, stomach and lung adenocarcinomas. (Hassan, et al., Eur J Cancer (2008) 44:46-53) (Ordonez, Am J Surg Pathol (2003) 27:1418-28; Ho, et al., Clin Cancer Res (2007) 13:1571-5).

Mesothelin is also shed from tumor cells as a soluble form of the protein, as compared to the native membrane bound version (Hellstrom, et al, Cancer Epidemiol Biomarkers Prev (2006) 15:1014-20; Ho, et al., Cancer Epidemiol Biomarkers Prev (2006) 15:1751). Structurally, mesothelin is expressed on the cell surface as a 60 kDa precursor polypeptide, which is proteolytically processed into a 31 kDa shed component (corresponding to MPF) and a 40 kDa membrane bound component (Hassan et al. (2004) Clin. Cancer. Res. 10:3937-3942). Shed serum mesothelin has been approved by the US Food and Drug Administration as a diagnostic biomarker in malignant mesothelioma.

The biological function of mesothelin is still not clear. Knockout mice have been prepared in which the mesothelin gene was disrupted by homologous recombination (Bera, T. K. and Pastan, I. (2000) Mol. Cell. Biol. 20:2902-2906). No anatomical, hematologic or reproductive abnormalities were detected, indicating that mesothelin function is not essential for growth or reproduction, at least in those mice.

Mesothelin does specifically interact with CA125 (also known as MUC-16), a mucin-like glycoprotein present on the surface of tumor cells that previously had been identified as an ovarian cancer antigen. Further, binding of CA125 to membrane-bound mesothelin mediates heterotypic cell adhesion and CA125 and mesothelin are co-expressed in advanced grade ovarian adenocarcinoma (Rump, A. et al. (2004) J. Biol. Chem. 279:9190-9198). Expression of mesothelin in the lining of the peritoneum correlates with the preferred site of metastasis formation of ovarian cancer and mesothelin-CA125 binding is thought to facilitate peritoneal metastasis of ovarian tumors (Gubbels, J. A. et al. (2006) Mol. Cancer. 5:50).

Mesothelin can also be used a marker for diagnosis and prognosis of certain types of cancer because trace amounts of mesothelin can be detected in the blood of some patients with mesothelin-positive cancers (Cristaudo et al., Clin. Cancer Res. 13:5076-5081, 2007). It has been reported that mesothelin may be released into serum through deletion at its carboxyl terminus or by proteolytic cleavage from its membrane bound form (Hassan et al., Clin. Cancer Res. 10:3937-3942, 2004). An increase in the soluble form of mesothelin was detectable several years before malignant mesotheliomas occurred among workers exposed to asbestos (Creaney and Robinson, Hematol. Oncol. Clin. North Am. 19:1025-1040, 2005). Furthermore, patients with ovarian, pancreatic, and lung cancers also have elevated soluble mesothelin in serum (Cristaudo et al., Clin. Cancer Res. 13:5076-5081, 2007; Hassan et al., Clin. Cancer Res. 12:447-453, 2006; Croso et al., Cancer Detect. Prev. 30:180-187, 2006). Accordingly, mesothelin is an appropriate target for methods of disease prevention or treatment and there is a need for effective antibodies specific for mesothelin.

SUMMARY OF THE INVENTION

In one embodiment, the invention provides an isolated anti-mesothelin human antibody or fragment thereof, wherein said antibody has at least one of the following properties: binds to a different epitope than the MORAb-009 antibody; competes for binding with Ab237; specifically binds to human, cyno, rat and murine mesothelin; does not internalize upon binding to mesothelin; when bound to mesothelin, does not inhibit CA125 interaction with mesothelin; has a binding affinity KD of at least 5.0 pM against human mesothelin; has enhanced effector function; binds to membrane-bound mesothelin preferentially over soluble mesothelin; reduces the growth of mesothelin expressing tumor cells in vivo.

In another embodiment, the invention provides a method of inhibiting or reducing the growth of mesothelin expressing tumor cells in an animal, comprising administering to said animal a therapeutically effective dose of the antibodies of the invention.

In a further embodiment, the invention provides a method of determining if a subject has mesothelin expressing tumor cells, comprising: contacting a tumor sample from the subject with an antibody of the invention; and detecting binding of the antibody to the sample, wherein an increase in binding of the antibody to the sample as compared to binding of the antibody to a control sample identifies the subject as having mesothelin expressing tumor cells.

In another embodiment, the invention provides an isolated antibody or antigen binding protein or fragment thereof, wherein the antibody or antigen binding protein or fragment thereof specifically binds to mesothelin and comprises 3 heavy chain CDRs and 3 light chain CDRs with sequences selected from the group consisting of: SEQ ID NOs: 45, 46, 47 of the heavy chain and SEQ ID NOs: 9, 10, 11 of the light chain; SEQ ID NOs: 48, 49, 50 of the heavy chain and SEQ ID NOs: 12, 13, 14 of the light chain; SEQ ID NOs: 51, 52, 53 of the heavy chain and SEQ ID NOs: 15, 16, 17 of the light chain; SEQ ID NOs: 51, 52, 53 of the heavy chain and SEQ ID NOs: 18, 19, 20 of the light chain; SEQ ID NOs: 54, 55, 56 of the heavy chain and SEQ ID NOs: 21, 22, 23 of the light chain; SEQ ID NOs: 57, 58, 59 of the heavy chain and SEQ ID NOs: 24, 25, 26 of the light chain; SEQ ID NOs: 60, 61, 62 of the heavy chain and SEQ ID NOs: 27, 28, 29 of the light chain; SEQ ID NOs: 63, 64, 65 of the heavy chain and SEQ ID NOs: 30, 31, 32 of the light chain; SEQ ID NOs: 63, 64, 65 of the heavy chain and SEQ ID NOs: 33, 34, 35 of the light chain; and SEQ ID NOs: 63, 64, 65 of the heavy chain and SEQ ID NOs: 36, 37, 38 of the light chain, wherein each of said CDRs are identical to or comprise 1, 2, or 3 amino acid residue substitutions relative to their specified sequence.

In another embodiment, the invention provides an isolated antibody or antigen binding protein or fragment thereof, wherein the antibody or antigen binding protein or fragment thereof specifically binds mesothelin and comprises a heavy chain variable domain and a light chain variable domain selected from the group consisting of: a heavy chain variable domain comprising SEQ ID NO: 86 and a light chain variable domain comprising SEQ ID NO: 72; a heavy chain variable domain comprising SEQ ID NO: 87 and a light chain variable domain comprising SEQ ID NO: 73; a heavy chain variable domain comprising SEQ ID NO: 88 and a light chain variable domain comprising SEQ ID NO: 74; a heavy chain variable domain comprising SEQ ID NO: 88 and a light chain variable domain comprising SEQ ID NO: 75; a heavy chain variable domain comprising SEQ ID NO: 89 and a light chain variable domain comprising SEQ ID NO: 76; a heavy chain variable domain comprising SEQ ID NO: 90 and a light chain variable domain comprising SEQ ID NO: 77; a heavy chain variable domain comprising SEQ ID NO: 91 and a light chain variable domain comprising SEQ ID NO: 78; a heavy chain variable domain comprising SEQ ID NO: 92 and a light chain variable domain comprising SEQ ID NO: 79; a heavy chain variable domain comprising SEQ ID NO: 92 and a light chain variable domain comprising SEQ ID NO: 80; a heavy chain variable domain comprising SEQ ID NO: 92 and a light chain variable domain comprising SEQ ID NO: 81; a heavy chain variable domain comprising SEQ ID NO: 93 and a light chain variable domain comprising SEQ ID NO: 82; a heavy chain variable domain comprising SEQ ID NO: 94 and a light chain variable domain comprising SEQ ID NO: 83, wherein each of said heavy chain variable domain and light chain variable domain have at least 90%, 95% or 100% identity relative to their specified sequence.

In a further embodiment, the invention provides an antibody or antigen binding protein or fragment thereof is a bispecific antibody and binds an additional target other than MSLN. In one embodiment, the additional target is CD3. In a further embodiment, the CD3 is human and/or cynomolgus CD3. In yet a further embodiment, the CD3 is human and/or mouse and/or rat and/or cynomolgus CD3.

In another embodiment, the invention provides a bispecific single chain antibody, said bispecific single chain antibody comprising binding domains specific for CD3 and MSLN, wherein the corresponding variable heavy chain regions ($V_H$) and the corresponding variable light chain regions ($V_L$) regions are arranged, from N-terminus to C-terminus, in the order, $V_H$(MSLN)-$V_L$(MSLN)-$V_H$(CD3)-$V_L$(CD3), or $V_H$(CD3)-$V_L$(CD3)-$V_H$(MSLN)-$V_L$(MSLN), or $V_L$(MSLN)-$V_H$(MSLN)-$V_H$(CD3)-$V_L$(CD3), or $V_H$(CD3)-$V_L$(CD3)-$V_L$(MSLN)-$V_H$(MSLN), or $V_L$(MSLN)-$V_H$(MSLN)-$V_L$(CD3)-$V_H$(CD3), or $V_L$(CD3)-$V_H$(CD3)-$V_L$(MSLN)-$V_H$(MSLN), or $V_H$(MSLN)-$V_L$(MSLN)-$V_L$(CD3)-$V_H$(CD3), or $V_L$(CD3)-$V_H$(CD3)-$V_H$(MSLN)-$V_L$(MSLN).

In one embodiment, the invention provides a bispecific single chain antibody that comprises a first VH as set forth in SEQ ID NO: 86, a first VL as set forth in SEQ ID NO: 72, a second VH as set forth in SEQ ID NO: 118, and a second VL as set forth in SEQ ID NO: 120.

In another embodiment, the invention provides a bispecific single chain antibody that comprises: a first VH CDR1 having an amino acid sequence identical to or comprising 1, 2, or 3 amino acid residue substitutions relative to SEQ ID NO: 45; a first VH CDR2 having an amino acid sequence identical to or comprising 1, 2, or 3 amino acid residue substitutions relative to SEQ ID NO: 46; a first VH CDR3 having an amino acid sequence identical to or comprising 1, 2, or 3 amino acid residue substitutions relative to SEQ ID NO: 47; a first VL CDR1 having an amino acid sequence identical to or comprising 1, 2, or 3 amino acid residue substitutions relative to SEQ ID NO: 9; a first VL CDR2 having an amino acid sequence identical to or comprising 1, 2, or 3 amino acid residue substitutions relative to SEQ ID NO: 10; and a first VL CDR3 having an amino acid sequence identical to or comprising 1, 2, or 3 amino acid residue substitutions relative to SEQ ID NO: 11; a second VH CDR1 having an amino acid sequence identical to or comprising 1, 2, or 3 amino acid residue substitutions relative to SEQ ID NO: 115; a second VH CDR2 having an amino acid sequence identical to or comprising 1, 2, or 3 amino acid residue substitutions relative to SEQ ID NO: 116; a second VH CDR3 having an amino acid sequence identical to or comprising 1, 2, or 3 amino acid residue substitutions relative to SEQ ID NO: 117; a second VL CDR1 having an amino acid sequence identical to or comprising 1, 2, or 3 amino acid residue substitutions relative to SEQ ID NO: 112; a second VL CDR2 having an amino acid sequence identical to or comprising 1, 2, or 3 amino acid residue substitutions relative to SEQ ID NO: 113; and a second VL CDR3 having an amino acid sequence identical to or comprising 1, 2, or 3 amino acid residue substitutions relative to SEQ ID NO: 114.

In another embodiment, the invention provides a bispecific single chain antibody having the sequence is set forth in SEQ ID NO: 127 or SEQ ID NO: 129. In another embodiment, the invention provides a bispecific single chain antibody comprising any of SEQ ID NOs: 158-185 and further comprising SEQ ID NO: 122.

BRIEF DESCRIPTION OF THE FIGURES

FIG. 3 summarizes the estimated new cases and deaths attributed to cancers expressing MSLN, and the % incidence of MSLN expression.

FIG. 4 summarizes binding and biochemical characteristics of the anti-MSLN antibodies, including Kd and species (cynomolgus, rat, mouse) cross-reactivity.

FIGS. 5 and 6 summarize antibody binning data of the anti-MSLN antibodies.

FIG. 13 provides a photographic summary of results of ADCP assays using anti-MSLN antibodies.

FIGS. 15-17 summarize in vivo results of anti-tumor activity of the anti-MSLN antibodies.

FIGS. 20 and 21 summarize in vitro assays performed with several anti-MSLN/anti-CD3 BiTE molecules (different VH/VL orientations of the same BiTE) as compared to control, demonstrating binding to both human MSLN and human CD3 expressed on tumor cells; experiments were also performed that demonstrate binding to both cynomolgus MSLN and cynomolgus CD3 (data not shown).

FIGS. 23-24 summarize in vitro assays performed with several anti-MSLN/anti-CD3 BiTE molecules as compared to control BiTE molecules, demonstrating cytokine release when the anti-MSLN/anti-CD3 BiTE molecules are incubated with MSLN expressing tumor cells in the presence of unstimulated T-cells.

FIGS. 25 and 26 summarize in vitro cytotoxicity assays performed with several anti-MSLN/anti-CD3 BiTE molecules as compared to control BiTE molecules, demonstrating specific T-cell mediated lysis of MSLN-expressing ovarian tumor cells.

DETAILED DESCRIPTION OF THE INVENTION

Figure 1:
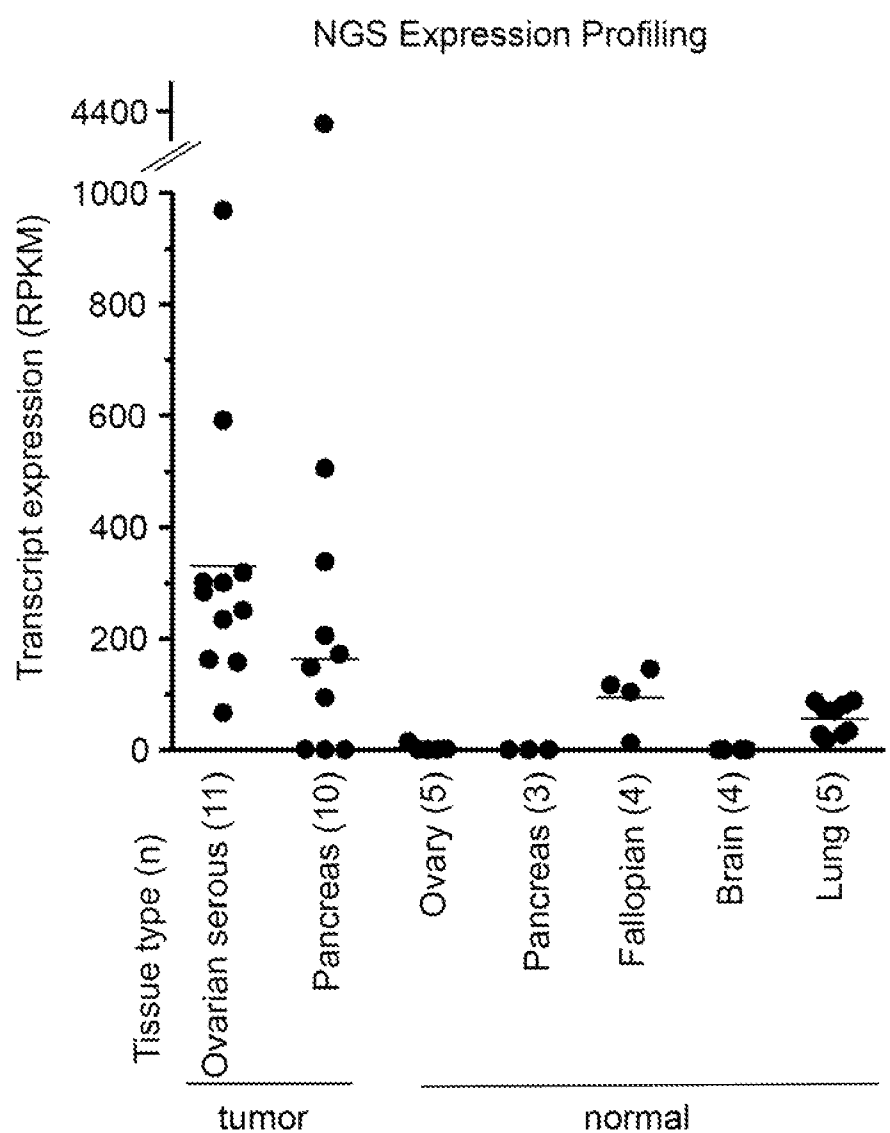
FIG. 1 provides a summary of MSLN expression data from ovarian and pancreatic tumor and normal cells.
Figure 2:
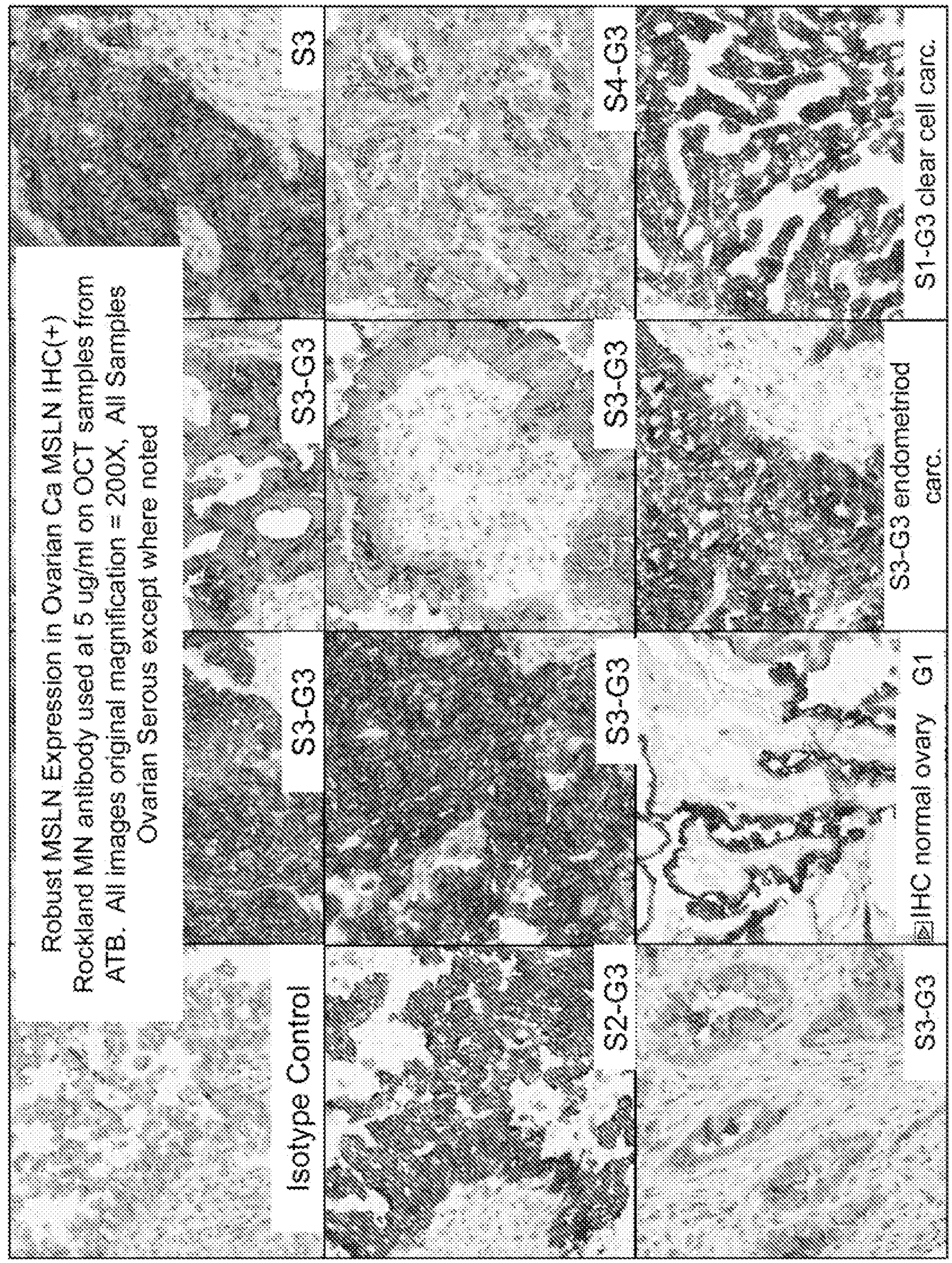
FIG. 2 provides images of MSLN expression from primary ovarian tumor samples.

The present invention relates to antigen binding proteins such as antibodies that specifically bind to mesothelin. In one embodiment, the mesothelin is human mesothelin. In another embodiment, the mesothelin is cynomologous mesothelin. In another embodiment, the mesothelin is murine mesothelin. In another embodiment, the mesothelin is rat mesothelin. In one embodiment, the antibodies of the invention specifically bind to human, cynomologous, murine and rat mesothelin, and as such, the term mesothelin as used herein refers to all of these species of mesothelin. The antigen binding proteins are useful for treating cancer and related diseases.

The present invention further provides compositions, kits, and methods relating to antigen binding proteins that specifically bind to mesothelin. Also provided are nucleic acid molecules, and derivatives and fragments thereof, comprising a sequence of polynucleotides that encode all or a portion of a polypeptide that binds to mesothelin, such as a nucleic acid encoding all or part of an anti-mesothelin antibody, antibody fragment, or antibody derivative. The present invention further provides vectors and plasmids comprising such nucleic acids, and cells or cell lines comprising such nucleic acids and/or vectors and plasmids. The provided methods include, for example, methods of making, identifying, or isolating antigen binding proteins that bind to human mesothelin, such as anti-mesothelin antibodies, methods of determining whether an antigen binding protein binds to mesothelin, methods of making compositions, such as pharmaceutical compositions, comprising an antigen binding protein that binds to human mesothelin, and methods for administering an antigen binding protein that binds mesothelin to a subject, for example, methods for treating cancer that comprises tumor cells that express mesothelin.

Definitions

Polynucleotide and polypeptide sequences are indicated using standard one- or three-letter abbreviations. Unless otherwise indicated, polypeptide sequences have their amino termini at the left and their carboxy termini at the right, and single-stranded nucleic acid sequences, and the top strand of double-stranded nucleic acid sequences, have their 5' termini at the left and their 3' termini at the right. A particular section of a polypeptide can be designated by amino acid residue number such as amino acids 1 to 50, or by the actual residue at that site such as asparagine to proline. A particular polypeptide or polynucleotide sequence also can be described by explaining how it differs from a reference sequence.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings: The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature. Thus, a molecule that is chemically synthesized, or expressed in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "peptide" "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence).

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified, e.g., via conjugation to another chemical moiety such as, for example, polyethylene glycol, albumin (e.g., human serum albumin), phosphorylation, and glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129 (2003); Roque et al., Biotechnol. Prog. 20:639-654 (2004). In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in Sequences of Proteins of Immunological Interest, 5' Ed., US Dept. of Health and Human Services, PHS, NIH, NIH Publication no. 91-3242, 1991.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', $F(ab')_2$, Fv, domain antibodies (dAbs), fragments including complementarity determining regions (CDRs), single-chain antibodies (scFv), chimeric antibodies, diabodies, triabodies, tetrabodies, bispecific single chain antibodies (e.g., bispecific T-cell engagers or BiTEs), and other bispecific antibodies, and polypeptides that contain at least a portion of an immunoglobulin that is sufficient to confer specific antigen binding to the polypeptide.

The term "bispecific single chain antibody" relates to a construct comprising a first domain consisting of variable regions (or parts thereof) capable of specifically interacting with or binding to human CD3, and comprising a second domain consisting of variable regions (or parts thereof), capable of specifically interacting with or binding to human mesothelin.

A Fab fragment is a monovalent fragment having the $V_L$, $V_H$, $C_L$ and $C_H1$ domains; a $F(ab')_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546 (1989)).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., Science 242:423-26 (1988) and Huston et al., 1988, Proc. Natl. Acad. Sci. USA 85:5879-83 (1988)). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48 (1993), and Poljak et al., Structure 2:1121-23 (1994)). If the two polypeptide chains of a diabody are identical, then a diabody resulting from their pairing will have two identical antigen binding sites. Polypeptide chains having different sequences can be used to make a diabody with two different antigen binding sites. Similarly, tribodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. in Sequences of Proteins of Immunological Interest, 5th Ed., US Dept. of Health and Human Services, PHS, NIH, NIH Publication no. 91-3242, 1991. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways known in the art, nonlimiting examples of which are described herein, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies. In one embodiment, one or more of the CDRs are derived from a human anti-mesothelin antibody. In another embodiment, all of the CDRs are derived from a human anti-mesothelin antibody. In another embodiment, the CDRs from more than one human anti-mesothelin antibodies are mixed and matched in a chimeric antibody. For instance, a chimeric antibody may comprise a CDR1 from the light chain of a first human anti-mesothelin antibody, a CDR2 and a CDR3 from the light chain of a second human anti-mesothelin antibody, and the CDRs from the heavy chain from a third anti-mesothelin antibody. Further, the framework regions may be derived from one of the same anti-mesothelin antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody or antibodies from another species or belonging to another antibody class or subclass. Also included are fragments of such antibodies that exhibit the desired biological activity (i.e., the ability to specifically bind the human mesothelin).

A "neutralizing antibody" or "inhibitory antibody" refers to an antibody that inhibits the binding of ligand to the receptor, and/or inhibits or reduces receptor signalling. The inhibition need not be complete and may be, in one embodiment, reduced binding or signalling by at least 20%. In further embodiments, the reduction in binding or signalling is at least 30%, 40%, 50%, 60%, 70%, 80%, 85%, 90%, 95%, 97%, 99% and 99.9%.

Fragments or analogs of antibodies can be readily prepared by those of ordinary skill in the art following the teachings of this specification and using techniques well-known in the art. Preferred amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., Science 253:164 (1991).

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein including an antibody "specifically binds" to an antigen, such as human mesothelin if it binds to the antigen with a high binding affinity as determined by a dissociation constant (Kd, or corresponding Kb, as defined below) value of $10^{-7}$ M or less. An antigen binding protein that specifically binds to human mesothelin may be able to bind to mesothelin from other species as well with the same or different affinities.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, CA)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, CA and Baron et al., 1995, Nucleic Acids Res. 23:3605-06.

A "host cell" is a cell that can be used to express a nucleic acid, e.g., a nucleic acid of the invention. A host cell can be a prokaryote, for example, *E. coli*, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to, e.g., mutation or environmental influence, such progeny may not, in fact, be identical to the parent cell, but are still included within the scope of the term as used herein.

As used herein, a "non-chimpanzee primate" or "non-chimp primate" or grammatical variants thereof refers to any primate other than chimpanzee, i.e. other than an animal of belonging to the genus *Pan*, and including the species *Pan paniscus* and *Pan troglodytes*, also known as *Anthropopithecus troglodytes* or *Simia satyrus*. Most preferred is *Macaca fascicularis* (also known as Cynomolgus monkey and, therefore, throughout the application alternatively referred to as "Cynomolgus") and *Macaca mulatta* (rhesus monkey, or "rhesus").

In one embodiment, the antigen binding proteins of the present invention may be selected to bind to membrane-bound mesothelin as expressed on cells. In certain embodiments, the antigen binding proteins of the present invention preferentially bind membrane-bound mesothelin over soluble mesothelin. In one embodiment, the antigen binding proteins bind membrane-bound mesothelin at least 5 fold, 10 fold, 15 fold, 20 fold, 25 fold, 30 fold, 40 fold, 50 fold, 100 fold, 500 fold, or 1000 fold greater than soluble mesothelin. In one embodiment, the antigen binding proteins of the present invention preferentially bind membrane-bound mesothelin 30 fold greater than soluble mesothelin.

In one embodiment, the antigen binding proteins of the present invention specifically bind to human mesothelin. In a further embodiment, the antigen binding proteins binding to human mesothelin may also bind to mesothelin of other species. In one embodiment, the antigen binding proteins of the present invention bind to human, cynomologous and murine mesothelin.

The polynucleotide and polypeptide sequences for several species of mesothelin are known. Table 1 presents nonlimiting, representative examples of sequences for human, mouse, rat, and nonhuman primate (e.g., cynomolgus). Additional examples are readily found in publicly available databases (e.g., NCBI).

TABLE 1

| Mesothelin Sequences |
|---|
| Human (*Homo sapiens*) polynucleotides (SEQ ID NO: 1) |
| NCBI Reference Sequence: NM_005823.5 (Variant 1) |
| TGCCAGGCTCTCCACCCCCACTTCCCAATTGAGGAAACCGAGGCAGAGGAGGCTCAGCGCCACGCACTCC |
| TCTTTCTGCCTGGCCGGCCACTCCCGTCTGCTGTGACGCGCGGACAGAGAGCTACCGGTGGACCCACGGT |
| GCCTCCCTCCCTGGGATCTACACAGACCATGGCCTTGCCAACGGCTCGACCCCTGTTGGGGTCCTGTGGG |
| ACCCCCGCCCTCGGCAGCCTCCTGTTCCTGCTCTTCAGCCTCGGATGGGTGCAGCCCTCGAGGACCCTGG |
| CTGGAGAGACAGGGCAGGAGGCTGCGCCCCTGGACGGAGTCCTGGCCAACCCACCTAACATTTCCAGCCT |
| CTCCCCTCGCCAACTCCTTGGCTTCCCGTGTGCGGAGGTGTCCGGCCTGAGCACGGAGCGTGTCCGGGAG |
| CTGGCTGTGGCCTTGGCACAGAAGAATGTCAAGCTCTCAACAGAGCAGCTGCGCTGTCTGGCTCACCGGC |
| TCTCTGAGCCCCCCGAGGACCTGGACGCCCTCCCATTGGACCTGCTGCTATTCCTCAACCCAGATGCGTT |
| CTCGGGGCCCCAGGCCTGCACCCGTTTCTTCTCCCGCATCACGAAGGCCAATGTGGACCTGCTCCCGAGG |
| GGGGCTCCCGAGCGACAGCGGCTGCTGCCTGCGGCTCTGGCCTGCTGGGGTGTGCGGGGGTCTCTGCTGA |
| GCGAGGCTGATGTGCGGGCTCTGGGAGGCCTGGCTTGCGACCTGCCTGGGCGCTTTGTGGCCGAGTCGGC |
| CGAAGTGCTGCTACCCCGGCTGGTGAGCTGCCCGGGACCCCTGGACCAGGACCAGCAGGAGGCAGCCAGG |
| GCGGCTCTGCAGGGCGGGGGACCCCCCTACGGCCCCCCGTCGACATGGTCTGTCTCCACGATGGACGCTC |
| TGCGGGGCCTGCTGCCCGTGCTGGGCCAGCCCATCATCCGCAGCATCCCGCAGGGCATCGTGGCCGCGTG |
| GCGGCAACGCTCCTCTCGGGACCCATCCTGGCGGCAGCCTGAACGGACCATCCTCCGGCCGCGGTTCCGG |
| CGGGAAGTGGAGAAGACAGCCTGTCCTTCAGGCAAGAAGGCCCGCGAGATAGACGAGAGCCTCATCTTCT |
| ACAAGAAGTGGGAGCTGGAAGCCTGCGTGGATGCGGCCCTGCTGGCCACCCAGATGGACCGCGTGAACGC |
| CATCCCCTTCACCTACGAGCAGCTGGACGTCCTAAAGCATAAACTGGATGAGCTCTACCCACAAGGTTAC |
| CCCGAGTCTGTGATCCAGCACCTGGGCTACCTCTTCCTCAAGATGAGCCCTGAGGACATTCGCAAGTGGA |
| ATGTGACGTCCCTGGAGACCCTGAAGGCTTTGCTTGAAGTCAACAAAGGGCACGAAATGAGTCCTCAGGT |
| GGCCACCCTGATCGACCGCTTTGTGAAGGGAAGGGGCCAGCTAGACAAAGACACCCTAGACACCCTGACC |
| GCCTTCTACCCTGGGTACCTGTGCTCCCTCAGCCCCGAGGAGCTGAGCTCCGTGCCCCCCAGCAGCATCT |
| GGGCGGTCAGGCCCCAGGACCTGGACACGTGTGACCCAAGGCAGCTGGACGTCCTCTATCCCAAGGCCCG |
| CCTTGCTTTCCAGAACATGAACGGGTCCGAATACTTCGTGAAGATCCAGTCCTTCCTGGGTGGGGCCCCC |
| ACGGAGGATTTGAACGCGCTCAGTCAGCAGAATGTCAGCATGGACTTGGCCACGTTCATGAAGCTCCGCA |
| CGGATGCGGTGCTGCCGTTGACTGTGGCTGAGGTGCAGAAACTTCTGGGACCCCACGTGGAGGGCCTGAA |
| GGCGGAGGAGCGGCACCGCCCGGTGCGGGACTGGATCCTACGGCAGCGGCAGGACGACCTGGACACGCTG |
| GGGCTGGGGCTACAGGGCGGCATCCCCAACGGCTACCTGGTCCTAGACCTCAGCATGCAAGAGGCCCTCT |
| CGGGGACGCCCTGCCTCCTAGGACCTGGACCTGTTCTCACCGTCCTGGCACTGCTCCTAGCCTCCACCCT |
| GGCCTGAGGGCCCCACTCCCTTGCTGGCCCCAGCCCTGCTGGGGATCCCCGCCTGGCCAGGAGCAGGCAC |
| GGGTGGTCCCCGTTCCACCCCAAGAGAACTCGCGCTCAGTAAACGGGAACATGCCCCCTGCAGACACGTA |
| AAAAAAAAAAAAAAAAA |

TABLE 1-continued

Mesothelin Sequences

Human (Homo sapiens) amino acid (SEQ ID NO: 2)
GenBank: BAA08419.1; GenBank: AAH09272.1
MALPTARPLLGSCGTPALGSLLFLLFSLGWVQPSRTLAGETGQEAAPLDGVLANPPNISS
LSPRQLLGFPCAEVSGLSTERVRELAVALAQKNVKLSTEQLRCLAHRLSEPPEDLDALPL
DLLLFLNPDAFSGPQACTRFFSRITKANVDLLPRGAPERQRLLPAALACWGVRGSLLSEA
DVRALGGLACDLPGRFVAESAEVLLPRLVSCPGPLDQDQQEAARAALQGGGPPYGPPSTW
SVSTMDALRGLLPVLGQPIIRSIPQGIVAAWRQRSSRDPSWRQPERTILRPRFRREVEKT
ACPSGKKAREIDESLIFYKKWELEACVDAALLATQMDRVNAIPFTYEQLDVLKHKLDELY
PQGYPESVIQHLGYLFLKMSPEDLRKWNVTSLETLKALLEVNKGHEMSPQAPRRPLPQVA
TLIDRFVKGRGQLDKDTLDTLTAFYPGYLCSLSPEELSSVPPSSIWAVRPQDLDTCDPRQ
LDVLYPKARLAFQNMNGSEYFVKLQSFLGGAPTEDLKALSQQNVSMDLATFMKLRTDAVL
PLTVAEVQKLLGPHVEGLKAEERHRPVRDWILRQRQDDLDTLGLGLQGGIPNGYLVLDLS
MQEALSGTPCLLGPGPVLTVLALLLASTLA Mouse (*Mus musculus*) polynucleotide (SEQ ID NO: 3)
NCBI Reference Sequence: NM_018857.1
GGACAGCTGCTTTCCCAGGCCCAAAAGCCCCTTCGTTGTCTCCAAACAGTGGTGTGGGTTGAGGGGTGGG
ACAAGTGGGGACCTCAGAGTCATTGTTATCCACAGACCATGGCCTTGCCAACAGCTCGACCCCTGCTGGG
GTCCTGTGGAAGTCCCATCTGCAGCCGAAGCTTCCTACTGCTTCTCCTTAGTCTTGGGTGGATACCACGT
CTGCAGACCCAGACTACAAAGACAAGCCAGGAGGCCACACTCCTCCATGCTGTGAACGGTGCCGCTGACT
TTGCCAGTCTCCCCACAGGCCTCTTTCTTGGCCTCACATGTGAGGAGGTATCTGACCTGAGCATGGAACA
AGCCAAGGGGCTGGCTATGGCTGTAAGACAGAAGAACATTACACTCCGGGGACATCAGCTGCGTTGTCTG
GCACGTCGCCTTCCTAGGCACCTCACCGACGAGGAACTGAATGCTCTTCCACTGGACCTGCTGCTCTTCC
TCAACCCAGCCATGTTTCCAGGGCAACAGGCTTGTGCCCACTTCTTCTCCCTCATCTCTAAAGCCAATGT
GGATGTACTCCCACGGAGGTCTCTGGAGCGCCAGAGGCTGCTGATGGAGGCTCTGAAGTGCCAGGGCGTG
TATGGATTTCAAGTGAGTGAGGCAGATGTGCGGGCTCTCGGAGGCCTGGCCTGTGACCTGCCTGGGAAAT
TTGTGGCCAGATCTTCCGAAGTTCTCCTCCCCTGGCTGGCAGGATGCCAAGGACCCCTGGACCAGAGCCA
GGAAAAGGCAGTCAGGGAGGTTCTGAGGAGTGGAAGAACCCAATATGGCCCCCCATCGAAGTGGTCAGTC
TCCACCCTGGATGCCCTGCAGAGCTTGGTAGCAGTGTTGGATGAGTCCATCGTCCAGAGCATCCCCAAGG
ATGTCAAAGCTGAATGGCTGCAACACATCTCCAGAGACCCCTCCAGGCTGGGGTCTAAGCTGACCGTCAT
ACACCCAAGGTTCCGACGGGATGCAGAACAGAAAGCCTGCCCTCCAGGGAAGGAGCCCTACAAGGTGGAT
GAAGACCTCATCTTCTACCAGAATTGGGAGCTGGAGGCTTGTGTAGATGGCACCATGCTGGCCAGACAAA
TGGACCTTGTGAACGAGATTCCCTTCACCTATGAGCAGCTCAGTATCTTTAAGCACAAACTGGACAAGAC
CTACCCACAAGGCTATCCTGAGTCCCTGATCCAGCAGCTGGGTCACTTCTTCAGATATGTTAGCCCTGAA
GACATCCACCAGTGGAATGTGACCTCACCAGACACAGTGAAAACTCTGCTCAAAGTCAGCAAAGGACAAA
AGATGAATGCTCAGGCGATTGCCTTGGTCGCCTGCTATCTTCGGGGAGGAGGCCAGCTGGACGAGGATAT
GGTAAAAGCCCTGGGCGACATCCCGTTAAGCTATCTATGTGACTTCAGCCCCCAGGATCTGCACTCGGTA
CCCTCCAGTGTCATGTGGCTGGTTGGGCCCCAAGACCTGGACAAGTGCAGCCAGAGGCATCTGGGTCTCC
TCTACCAGAAGGCCTGCTCAGCCTTCCAGAATGTGAGCGGCCTAGAATACTTTGAGAAAATCAAGACATT
CCTGGGTGGGGCCTCCGTGAAGGACCTGCGGGCCCTCAGCCAGCACAATGTGAGCATGGACATAGCCACT
TTCAAGAGGCTGCAGGTGGATTCCCTGGTGGGGCTGAGTGTGGCTGAGGTACAGAAACTTCTGGGGCCAA
ACATTGTGGACCTGAAGACCGAGGAGGATAAAAGCCCTGTCCGTGACTGGCTGTTCCGGCAGCATCAGAA
AGACCTAGACAGGCTGGGTTTGGGACTTCAGGGTGGCATCCCCAATGGCTACCTGGTCCTGGACTTCAAT
GTCCGAGAGGCCTTCTCCAGCAGAGCCTCACTCCTTGGGCCAGGATTTGTATTAATATGGATTCCAGCTC
TGCTCCCAGCTTTAAGGCTGAGCTGAGACCACCACCCTGCAAGGCTCCTGGTCCCAGCTCTACTGGGGCC
CTCTTGACCAGGAGTGGGTACCAGGGGTCATTGCCAAAGTTTGAGGACTCTTGAACTCAATAAACAGTGG
CATATGCTCCCTTGAAAAAAAAAAAAAAAAAAAAA Mouse (*Mus musculus*) amino acid (SEQ ID NO: 4)
GenBank: EDL22444.1
MALPTARPLLGSCGSPICSRSFLLLLLSLGWIPRLQTQTTKTSQEATLLHAVNGAADFASLPTGLFLGLT
CEEVSDLSMEQAKGLAMAVRQKNITLRGHQLRCLARRLPRHLTDEELNALPLDLLLFLNPAMFPGQQACA
HFFSLISKANVDVLPRRSLERQRLLMEALKCQGVYGFQVSEADVRALGGLACDLPGKFVARSSEVLLPWL
AGCQGPLDQSQEKAVREVLRSGRTQYGPPSKWSVSTLDALQSLVAVLDESIVQSIPKDVKAEWLQHISRD
PSRLGSKLTVIHPRFRRDAEQKACPPGKEPYKVDEDLIFYQNWELEACVDGTMLARQMDLVNEIPFTYEQ
LSIFKHKLDKTYPQGYPESLIQQLGHFFRYVSPEDIHQWNVTSPDTVKTLLKVSKGQKMNAQAIALVACY
LRGGGQLDEDMVKALGDIPLSYLCDFSPQDLHSVPSSVMWLVGPQDLDKCSQRHLGLLYQKACSAFQNVS
GLEYFEKIKTFLGGASVKDLRALSQHNVSMDIATFKRLQVDSLVGLSVAEVQKLLGPNIVDLKTEEDKSP
VRDWLFRQHQKDLDRLGLGLQGGIPNGYLVLDFNVREAFSSRASLLGPGFVLIWIPALLPALRLS Rat (*Rattus norvegicus*) polynucleotide (SEQ ID NO: 5)
GenBank: D87351.1
TGCCAACAGGCCCCTCACTGTGTCCAAACAGTGGTGTGAGTTGAGGGGTGGGACAGGTGGGGACCTCAGA
ACCATTGTTATCCACAGACCATGGCCTTGCCAACAGCCCAACCCCTGCTGGGGTCCTGTGGAAGCCCCAT
CTGCAGCCGCAGCTTTCTACTGCTTCTCCTTAGTCTTGGGTGGTTGCCACTTCTGCAGACCCAGACTACA
AGGACAAGCCAGGAGGCCGCACTTCTCCATGCTGTGACCGGCACCGTTGACTTTGCCAGTCTTCCCACAG
GCCTCTTTCTTGGCCTCACGTGTGATGAGGTATCTGGCCTAAGCATGGGACACGCCAAGGAGCTGGCTAT
GGCTGTGAGACAGAAGAATATCGTGCTCCAAGTACATCAGCTGCGCTGTCTGGCCCGTCGCCTCCCTAAG
CACCTCACCAACGAGGAACTGGATGCTCTCCCACTGGACCTGCTGCTCTTCCTCAATCCAGCCATGTTTC
CGGGGCAACAGGCTTGTGCCCACTTCTTCTCCCTCATCTCTAAAGCCAATGTAAATGTACTCCCACGGAG
ATCTCTGGAGCGCCAGAGGCTGCTGACCGGGGCTCTGAAATGCCAGGGTGTGTATGGATTTCAAGTGAGT
GAGACGGATGCACGGGCTCTCGGAGGCCTGGCCTGTGACCTGCCTGGGGAATTCGTGGCCAAATCTTCGG
AAGTCCTCCTCCCCTGGCTGGCAAGATGCGGAGGACCCCTGGACCAAGGCCAGGCAAAGGCTGTCAGGGA
GGTTCTGAGGAGTGGAAGAGCCCCCTATGGTCCCCCATCGACGTGGTCAGTCTCCACCCTGGATGCCCTG
CAGGGTTTGCTGGTAGTGTTGGATGAGTCCATTGTCCACAGCATCCCTAAGGATGTTATCACTGAATGGC
TGCAAGGCATCTCCAGAGAGCCCTCCAGGCTGGGGTCTAAGTGGACTGTCACACACCCAAGGTTCCGGCG
GGACACAGAACAGAAAGCCTGCCCTCCAGGGAAGGAGCCTAACGTGGTGGATGAAAACCTCATCTTCTAC
CAGAATTGGGAGCTGGAGGCTTGTGTCGATGGTACCCTGCTGGCCGGCCAGATGGACCTTGTGAATGAAA TABLE 1-continued Mesothelin Sequences TTCCCTTTACCTACGAGCAGCTCAGCATCTTCAAGCACAAACTGGACAAGACCTACCCACAAGGCTATCC
CGAGTCCCTGATCAAGCAGCTGGGCCACTTCTTCAGATACGTTAGCCCTGAGGACATCCGGCAGTGGAAT
GTGACTTCACCAGACACAGTGAATACTCTGCTTAAAGTCAGCAAAGGACAAAAGATGGATGCTCAGGTGA
TTGCCTTGGTCGCCTGCTATCTTCGGGGAGGAGGCAAGCTGGACGAGGACATAGTAAAAGCCCTGGACAA
CATCCCCTTAAGTTACCTATGTGACTTCAGCCCCCAGGATCTGCACGCTATACCCTCCAGTGTTATGTGG
CTGGTTGGGCTCCATGACCTGGACAAGTGCAGCCAGAGGCATCTGGGTATCCTCTATCAGAAGGCCTGCT
CAGCCTTCCAGAACGTGAGCGGGCTGGAATACTTTGAGAAAATCAGGACATTTCTGGGTGGGGCCTCCAG
GGAGGACCTGCGGGCCCTCAGCCAGCACAATGTGAGTATGGACATAGCCACTTTCAAGAAGCTGCAGGTG
GATGCCCTGGTGGGGCTGAGTGTGGCTGAGGTACAGAAACTTCTAGGGCCACACATTGGGGACCTGAAGA
CTGAGGAGGATAAAAGCCCTGTCCGGGACTGGCTCTTCCGACAGCAGCAGAAAGACCTGGACAGTCTGGG
TTTGGGACTTCAGGGTGGCATCCCCAATGGCTACCTGATCCTAGACTTCAATGTCCGAGAGGCCTTCTCC
AGTGGAGCCCCACTCCTTGGGCCAGGATTTGTGTTTGCATGGATTCCAGCTCTGCTCTCAGCTTTAAGAC
TGAGCTGAGACCACCACTCCTAAGGCTCCTGGTCCCAGCTCTATTGTCGAGCCCCATCTTGACCAGGAGG
GGATACCAGGGGTCATTGCCAAAGTTTGAGGATTCTTGAACCCAATAAACAGTGGCATGTGCCCCCTTG Rat (Rattus norvegicus) amino acid (SEQ ID NO: 6)
GenBank: EDM03949.1
MALPTAQPLLGSCGSPICSRSFLLLLLSLGWLPLLQTQTTRTSQEAALLHAVTGTVDFASLPTGLFLGLM
CDEVSGLSMGHAKELAMAVRQKNIVLQVHQLRCLARRLPKHLTNEELDALPLDLLLFLNPAMFPGQQACA
HFFSLISKANVNVLPRRSLERQRLLTGALKCQGVYGFQVSETDARALGGLACDLPGEFVAKSSEVLLPWL
ARCGGPLDQGQAKAVREVLRSGRAPYGPPSTWSVSTLDALQGLLVVLDESIVHSIPKDVITEWLQGISRE
PSRLGSKWTVTHPRFRRDTEQKACPPGKEPNVVDENLIFYQNWELEACVDGTLLAGQMDLVNEIPFTYEQ
LSIFKHKLDKTYPQGYPESLIKQLGHFFRYVSPEDIRQWNVTSPDTVNTLLKVSKGQKMDAQVIALVACY
LRGGGKLDEDIVKALDNIPLSYLCDFSPQDLHAIPSSVMWLVGLHDLDKCSQRHLGILYQKACSAFQNVS
GLEYFEKIRTFLGGASREDLRALSQHNVSMDIATFKKLQVDALVGLSVAEVQKLLGPHIGDLKTEEDKSP
VRDWLFRQQQKDLDSLGLGLQGGIPNGYLILDFNVREAFSSGAPLLGPGFVFAWIPALLSALRLS Cynomolgus (*Macaca mulatta*) polynucleotides (SEQ ID NO: 7)
NCBI Reference Sequence: XM_001087333.2 (predicted)
ATGGCCTTGCCAATGGCTCGACCCCTGTCGGGGTCCTGTGGACCCCCGCCCTCGGCAGCCTCCTGTTCC
TGCTCTTCAGCCTCGGATGGGTGCAGCCCTCGAGGGTCCTGGCTGGAGAGACAAGGCAGGCCGCGCCCCT
GGATGGAATCCTGACCAATGCACCTGACATTGCCAGCCTCTCCCCACGCCAACTCCTTGGCTTCACGTGT
GTGGAGGTGTCCGGCCTGAGCACAGAGCTCGTCCAGGAGCTGGCTGTGGCCTTGGGACAGAAGAATGTCA
AGCTCTCCGCAGAGCAGCTGCGCTGTCTGGCTCACCAGCTCTCTGAGCCCCCCGAGGACCTGGACGCCCT
CCCGCTGGACCTGCTGCTCTTCCTCAACCCAGACGCGTTCTCGGGGCCCCAGGCCTGCACCCACTTCTTC
TCCCGCGTCGCGAAGGCCAACGTGGACCTGCTCCCGCGGGGGGCTCCTGAGAGACAGAGGCTGCTGCCCG
GGGCTCTGACCTGCTGGGGTGTGCGGGGGTCTCTGCTGAGCGAGGCTGATGTACGGGCTCTGGGAGGCCT
GGCTTGCGACCTGCCTGGGCGCTTTGTGGCCGAGTCGGCAGAAGTGGTGCTACCCCGGCTGGTCCGCTGC
TTGGGACCCCTGGACCAGGACCAGCAGGAAGCAGCCAGGGCGGCTCTGCAGAGAGGAGGACCCCCCTACG
GCCCCCCGTCAACGTGGTCTATCTCCACCCTGGACGATCTGCAGAGCCTGTTGCCTGTGCTGGGCCAGCC
CGTCATCTCTGCTCGTCCTCAGGGCATCCTGGCCGCATGGCGGCAACGCTCCTCTCGGGACCCATCCTGG
CAGCAGCCGGAACAGACCGTCCTCCGGCTGAGGTTCCGGCGGGACGTGGAGAGGACAACCTGTCCCCCAG
AGAAAGAGGTCCACGAGATAGACGAGAGCCTCATCTTCTACAAGAAGCGGGAGCTGGAAGCCTGCGTGGA
CCCAGCCCTGCTGGCCGCCCAGATGGACCGTGTGGACGCCATCCCCTTCACCTACGAGCAGCTGGACGTC
CTAAAGCATAAACTGGATGAGCTCTACCCACAAGGCTACCCCGAGTCTGTGATCCGGCACCTGGGCCACC
TCTTCCTCAAGATGAGCCCTGAGGACATTCGCAAATGGAACGTGACGTCCCTGGAGACCCTGAAGGCTCT
GCTCAAAGTCAGCAAGGGGCATGAAATGAGTGCTCAGGTGGCCACCCTGATTGACCGCGTTGTGGTGGGA
AGGGGCCAGCTAGACAAAGACACCGTAGACACGCTGACTGCCTTCTGCCCCGGGTGCCTGTGCTCCCTCA
GCCCCGAGAGGCTGAGCTCCGTGCCCCCCAGCGTCATCGGGGCGGTCAGGCCCCAGGACCTGGACACGTG
TGGCCCGAGGCAGCTGGACGTCCTCTATCCCAAGGCCCGCCTTGCTTTCCAGAACATGAGCGGGTCCGAA
TACTTCGTGAAGATCCGGCCCTTCCTGGGTGGGGCCCCCACGGAGGATGTGAAGGCTCTCAGTCAGCAGA
ATGTGAGCATGGACTTGGCCACGTTCATGAAGCTGCGGAGGGAAGCGGTGCTGCCGTTGACTGTGGCTGA
AGTGCAGAAACTTCTGGGACCCCACGTGGAGGGCCTGAAGGTGGAGGAGCAGCACAGCCCCGTGCGGGAC
TGGATCCTAAAGCAGCGGCAGGACGACCTGGACACACTGGGGCTGGGGCTACAGGGCGGCATCCCCAACG
GCTACCTGATCCTAGACCTCAGTGTGCGAGAGGCCCTCTCGGGGACGCCCTGCCTCCTAGGACCTGGACC
TGTACTCACCGTCCTGGCTTTGCTCCTGGCCTCCACCCTGGCCTGAGGACCCTACTCCCTTGCTGGCCCC
AGCCCTGCTGGGGATCCCCGCCTGGCCAGGAGCAGGCATAGGTGGTCCCTGTTCCACCCCAGGAGAACTT
GCGCTCAGTAAACGCGAACATGCCCCCT Cynomolgus (Macaca fascicularis) amino acid (SEQ ID NO: 8) (partial hypothetical) GenBank: EHH60027.1
MALPMARPLSGSCGTPALGSLLFLLFSLGWVQPSRVLAGETRQEAAPLDGILTNAPDIASLSPRQLLGFT
CVEVSGLSTELVQELAVALGQKNVKLSAEQLRCLAHRLSEPPEDLDALPLDLLLFLKQASVQGVRGSLLS
EADVRALGGLACDLPGREVAESAEVVLPRLVRCLGPLDQDQQEAARAALQRGGPPYGPPSTWSISTLDDL
QSLLPVLGQPVIHSIPQGILAAWRQRSSRDPSWQQPEQTVLRPRFRRDVERTTCPPEKEVHEIDENLIFY
KKRELEACVDAALLAAQMDRVDAIPFTYEQLDVLKHKLDELYPQGYPESVIRHLGHLFLKMSPEDIRKWN
VTSLETLKALLKVSKGHEMSAQVATLIDRVVVGRGQLDKDTADTLTAFCPGCLCSLSPERLRSVPPSVIG
AVRPQDLDTCGPRQLDVLYPKARLAFQNMSGSEYFVKIRPFLGGAPTEDLKALSQQNVSMDLATFMKLRR
EAVLVGRAGGGASGGGDNRGREGV Antigen Binding Proteins In referring to the different antigen binding proteins of the invention, arbitrary designations have been given to identify the different antigen binding proteins (e.g., "ab237"). In some instances, the designation may have variations for the same antigen binding proteins (e.g., "ab237" "237", or "2.37" all refer to the same antigen binding protein).

In one aspect, the present invention provides antigen binding proteins (e.g., antibodies, antibody fragments, antibody derivatives, antibody muteins, and antibody variants), that specifically bind to human mesothelin. In one embodiment the antigen binding protein is a human antibody.

In one embodiment, the antigen binding protein (e.g., antibody) comprises sequences that each independently differ by 5, 4, 3, 2, 1, or 0 single amino acid additions, substitutions, and/or deletions from a CDR sequence of those listed in Table 2 below. As used herein, a CDR sequence that differs by no more than a total of, for example, four amino acid additions, substitutions and/or deletions from a CDR sequence shown in Table 2 below refers to a sequence with 4, 3, 2, 1 or 0 single amino acid additions, substitutions, and/or deletions compared with the sequences shown in Table 2.

The amino acid sequences of light chain CDRs of exemplary antigen binding proteins (antibodies) and the heavy chain CDRs of exemplary antigen binding proteins (antibodies) are shown below in Table 2.

TABLE 2

| LIGHT CHAIN CDR AMINO ACID SEQUENCES | | | |
|---|---|---|---|
| Ab | CDR 1 | CDR 2 | CDR 3 |
| Ab237 AA | RASQSINNYLN (SEQ ID NO: 9) | AASSLQS (SEQ ID NO: 10) | QQTYSNPT (SEQ ID NO: 11) |
| Ab1.1.2 AA | RASQYIGSNLH (SEQ ID NO: 12) | YASQSFS (SEQ ID NO: 13) | HQSSSLPWT (SEQ ID NO: 14) |
| Ab1.33.1 AA | QSSLSLQHSNGKTYLY (SEQ ID NO: 15) | EVSNRFS (SEQ ID NO: 16) | MQSKQLPCS (SEQ ID NO: 17) |
| Ab1.33.1y AA | QSSLSLQHSNGKTYLY (SEQ ID NO: 18) | EVSNRFS (SEQ ID NO: 19) | MQSKQLPYS (SEQ ID NO: 20) |
| Ab1.68.1 AA | RASQTVSSSYLA (SEQ ID NO: 21) | GASIRAT (SEQ ID NO: 22) | QQYGSSLT (SEQ ID NO: 23) |
| Ab1.78.1 AA | RASQSIGSSLH (SEQ ID NO: 24) | YASQSFS (SEQ ID NO: 25) | HQSSSLPWT (SEQ ID NO: 26) |
| Ab1.119.1 AA | RSSQSLVHSDRNTYLS (SEQ ID NO: 27) | KISNRFS (SEQ ID NO: 28) | MQATQFPLT (SEQ ID NO: 29) |
| Ab2.69.2 AA | RSSLSLLHSNGYNYLD (SEQ ID NO: 30) | LGSNRAS (SEQ ID NO: 31) | MQGLHTPPS (SEQ ID NO: 32) |
| Ab2.69.2-cv AA | QASQDISNYLN (SEQ ID NO: 33) | AASSLET (SEQ ID NO: 34) | QQYDNLP (SEQ ID NO: 35) |
| Ab2.69.2-s AA | QASQDISNYLN (SEQ ID NO: 36) | AASSLET (SEQ ID NO: 37) | QQYDNLP (SEQ ID NO: 38) |
| Ab1.58 | RASQGIRNALG (SEQ ID NO: 39) | AASSLQS (SEQ ID NO: 40) | LQHNSYPRT (SEQ ID NO: 41) |
| Ab1.51 | RASQGIRNDLH (SEQ ID NO: 42) | AASSLQS (SEQ ID NO: 43) | LQHYSYPWT (SEQ ID NO: 44) |

| HEAVY CHAINS CDR AMINO ACID SEQUENCES | | | |
|---|---|---|---|
| Ab | CDR 1 | CDR 2 | CDR 3 |
| Ab237 AA | NNNYYWT (SEQ ID NO: 45) | YIYYSGSTFYNPSLKS (SEQ ID NO: 46) | EDTMTGLDV (SEQ ID NO: 47) |
| Ab1.1.2 AA | SYGMH (SEQ ID NO: 48) | AIWYDGSNKYYADSVKG (SEQ ID NO: 49) | DLSIFGVVILSDY (SEQ ID NO: 50) |
| Ab1.33.1 AA | GDGHFWS (SEQ ID NO: 51) | YIYYSGSTYYNPSLKS (SEQ ID NO: 52) | LRGGYKFDY (SEQ ID NO: 53) |
| Ab1.68.1 AA | NYYWS (SEQ ID NO: 54) | RIFTSGSTNYNPSLKS (SEQ ID NO: 55) | EGGHYGSSGYLYYYYFGMDV (SEQ ID NO: 56) |
| Ab1.78.1 AA | SYGMH (SEQ ID NO: 57) | AIWYDGSNKYYADSVKG (SEQ ID NO: 58) | DLSIFGVVILSDY (SEQ ID NO: 59) |
| Ab1.119.1 AA | SGGYYWN (SEQ ID NO: 60) | YIYYSGSTYYNPSLRG (SEQ ID NO: 61) | DGGDSYGRMDV (SEQ ID NO: 62) |

TABLE 2-continued

| | | | |
|---|---|---|---|
| Ab2.69.2 AA | SNSVAWN (SEQ ID NO: 63) | RTYYRSKWYNDYAVSVKS (SEQ ID NO: 64) | GIFVVPAVPRFDY (SEQ ID NO: 65) |
| Ab1.58 | SHYWS (SEQ ID NO: 66) | YIYYSGSTNYNPSLKS (SEQ ID NO: 67) | DGWSAFDY (SEQ ID NO: 68) |
| Ab1.51 | SYYWS (SEQ ID NO: 69) | YIYYSGSTNYNPSLKS (SEQ ID NO: 70) | VDYKAFDI (SEQ ID NO: 71) |

Table 3 below also provides the amino acid sequences of the variable light and variable heavy domains for exemplary anti-mesothelin antibodies.

TABLE 3

| Anti-Mesothelin Variable Region Amino Acid Sequences |
|---|
| Light Chain Variable Region Polynucleotide and Amino acid sequences |
| Ab237<br>DIQMTQSPSSLSASVGDRVTITCRASQSINNYLNWYQQKPGKAPTLLIYA<br>ASSLQSGVPSRFSGSRSGTDFTLTISSLQPEDFAAYFCQQTYSNPTFGQG<br>TKVEVK<br>(SEQ ID NO: 72) |
| Ab1.1.2<br>EIVLTQSPDFQSVTPKEKVTITCRASQYIGSNLHWYQQTPDQSPKLLIKY<br>ASQSFSGVPSRFSGSGSGTDFTLTINSLEAEDAATYYCHQSSSLPWTFGQ<br>GTKVEIK<br>(SEQ ID NO: 73) |
| Ab1.33.1<br>DIVMTQTPLSLSVAPGQPASISCQSSLSLQHSNGKTYLYWYLQKPGQPPQ<br>LLIYEVSNRFSGVPDRFSGSGSGTDFTLKISRVEAEDVGIYYCMQSKQLP<br>CSFGQGTKLEIK<br>(SEQ ID NO: 74) |
| Ab1.33.1-y<br>DIVMTQTPLSLSVAPGQPASISCQSSLSLQHSNGKTYLYWYLQKPGQPPQ<br>LLIYEVSNRFSGVPDRFSGSGSGTDFTLKISRVEAEDVGIYYCMQSKQLP<br>YSFGQGTKLEIK<br>(SEQ ID NO: 75) |
| Ab1.68.1<br>EIVLTQSPGTLSLSPGERATLSCRASQTVSSSYLAWYQQKPGQAPRLLIY<br>GASIRATGIPDRFSGSGSGTDFTLTISRLEPEDFAVYYCQQYGSSLTFGG<br>GTKVEIK<br>(SEQ ID NO: 76) |
| Ab1.78.1<br>EIVLTQSPDFQSVTPKEKVTITCRASQSIGSSLHWYRQKPDQSPKLLIKY<br>ASQSFSGVPSRFSGGGSGTDFTLTINSLEAEDAATYYCHQSSSLPWTFGQ<br>GTKVEIK<br>(SEQ ID NO: 77) |
| Ab1.119.1<br>DIVMTQTPLSSPVTLGQPASISCRSSQSLVHSDRNTYLSWLQQRPGQPPR<br>LLIYKISNRFSGVPDRFSGSGAGTDFTLKISRVEAEDVGVYYCMQATQFP<br>LTFGGGTKVEIK<br>(SEQ ID NO: 78) |
| Ab2.69.2<br>DIVMTQSPLSLSVTPGEPASISCRSSLSLLHSNGYNYLDWFLQKPGQSPQ<br>LLIYLGSNRASGVPDRFSGSGSDTDFTLKISRVEAEDVGVYYCMQGLHTP<br>PSFGQGTKLEIK<br>(SEQ ID NO: 79) |
| Ab2.69.2-s<br>DIQMTQSPSSLSASVGDRVTITCQASQDISNYLNWYQQKPGKAPNLLIYA<br>ASSLETGVPSRFSGGGSGTDFAFTISSLQPEDIAPYYCQQYDNLPFGPGT<br>KVDIK<br>(SEQ ID NO: 80) |

TABLE 3-continued

| Anti-Mesothelin Variable Region Amino Acid Sequences |
| --- |
| Ab2.69.2-cv<br>DIQMTQSPSSLSASVGDRVTITCQASQDISNYLNWYQQKPGKAPKLLIYA<br>ASSLETGVPSRFSGSGSGTDFTLTISSLQPEDFATYYCQQYDNLPFGQGT<br>KVDIK<br>(SEQ ID NO: 81) |
| Ab1.58<br>DIQMTQSPSSLSASVGDRVTITCRASQGIRNALGWYQQKPGKAPKRLIYA<br>ASSLQSGVPSRFSGSGSGTEFTLTISSLQPEDFATYYCLQHNSYPRTFGQ<br>GTKVEIRR (SEQ ID NO: 82) |
| Ab1.51<br>DIQMTQSPSSLSASVGDRVTITCRASQGIRNDLHWYQQKPGKAPKRLIYA<br>ASSLQSGVPSRFSGSGSGTEFTLTISSLQPEDFATYYCLQHYSYPWTFGQ<br>GTKVEIK (SEQ ID NO: 83) |
| Light Chain Constant Domain<br>Optionally, a light chain constant domain is provided.<br>An exemplary sequence is:<br>RTVAAPSVFIFPPSDEQLKSGTASVVCLLNNFYPREAKVQWKVD<br>NALQSGNSQESVTEQDSKDSTYSLSSTLTLSKADYEKHKVYACEVTHQGL<br>SSPVTKSFNRGEC (SEQ ID NO: 84) |
| Leader Sequence<br>Optionally, a leader sequence is included to facilitate expression<br>of the light chains in cell culture. An exemplary sequence is:<br>MDMRVPAQLLGLLLLWLRGARC (SEQ ID NO: 85) |
| **Heavy Chain Variable Region Amino acid Sequences** |
| Ab237<br>QVQLQESGPGLVKPSQTLSLTCTVSGGSINNNNYYWTWIRQHPGKGLEWI<br>GYIYYSGSTFYNPSLKSRVTISVDTSKTQFSLKLSSVTAADTAVYYCARE<br>DTMTGLDVWGQGTTVTVSS (SEQ ID NO: 86) |
| Ab1.1.2<br>QVQLVESGGGVVQPGRSLRLSCAASGFTFSSYGMHWVRQAPGKGLEWVAA<br>IWYDGSNKYYADSVKGRFTISRDNSKNMLYLQMNSLRAEDTAVYYCARDL<br>SIFGVVILSDYWGQGTLVTVSS (SEQ ID NO: 87) |
| Ab1.33.1<br>QVQLQESGPGLVKPSQTLSLTCTVSGGSISGDGHFWSWIRQHPGKGLEWI<br>GYIYYSGSTYYNPSLKSRVTISVDTSKNQFSLKLSSVTAADTAVYYCARL<br>RGGYKFDYWGQGTLVTVSS (SEQ ID NO: 88) |
| Ab1.68.1<br>QVQLQESGPGLVKPSETLSLTCTVSGDSINNYYWSWIRQPAGKGLEWIGR<br>IFTSGSTNYNPSLKSRVTMSIDTSKNQFSLKLSSVTAADTAVYYCAREGG<br>HYGSSGYLYYYYFGMDVWGQGTTVTVSS (SEQ ID NO: 89) |
| Ab1.78.1<br>QVQLVESGGGVVQPGRSLRLSCAASGFTFSSYGMHWVRQAPGKGLEWVAA<br>IWYDGSNKYYADSVKGRFTISRDNSKNMLYLQMNSLRAEDTAVYYCARDL<br>SIFGVVILSDYWGQGTLVTVSS (SEQ ID NO: 90) |
| Ab1.119.1<br>QVQLQESGPGLVKPSQTLSLTCTVSGGSISSGGYYWNWIRQHPGKGLEWI<br>GYIYYSGSTYYNPSLRGRLIISVDTSKNQFSLRLSSVTAADTAVYYCARD<br>GGDSYGRMDVWGQGTTVTVSA (SEQ ID NO: 91) |
| Ab2.69.2<br>QVQLQQSGPGLVKPSQTLSLTCAISGDSVSSNSVAWNWIRQSPSRGLEWL<br>GRTYYRSKWYNDYAVSVKSRITINPDTSKNQFSLQLNSVTPEDTAVYYCA<br>RGIFVVPAVPRFDYWGQGTLVTVSS (SEQ ID NO: 92) |
| Ab1.58<br>QVQLQESGPGLVKPSETLSLTCTVSGGSIISHYWSWIRQPPGKGLEWIGY<br>IYYSGSTNYNPSLKSRVTISVDTSKNQFSLKLTSVTAADTAVYYCARDGW<br>SAFDYWGQGTLVTVSS (SEQ ID NO: 93) |
| Ab1.51<br>QVQLQESGPGLVKPSETLSLTCTVSGGSISSYYWSWIRQPPGKGLEWIGY<br>IYYSGSTNYNPSLKSRVTISVDTSKNQFSLKLSSVTAADTAVYYCARVDY<br>KAFDIWGQGTMVTVSS (SEQ ID NO: 94) |

TABLE 3-continued

| Anti-Mesothelin Variable Region Amino Acid Sequences |
|---|
| Leader Sequence<br>Optionally, a leader sequence is included to facilitate expression of the heavy chains in cell culture. An exemplary sequence is:<br>MKHLWFFLLLVAAPRWVLS (SEQ ID NO: 95) |
| Heavy Chain Constant Domain<br>Optionally, a heavy chain constant domain is provided. In certain embodiment, this sequence consists of the heavy chain constant domain sequence from an IgG1, IgG2, IgG3, IgG4 or IgM. An exemplary sequence is:<br>ASTKGPSVFPLAPSSKSTSGGTAALGCLVKDYFPEPVTVSWNSGALTSGVHTFPAVLQSSGL<br>YSLSSVVTVPSSSLGTQTYICNVNHKPSNTKVDKKVEPKSCDKTHTCPPCPAPELLGGPSVF<br>LFPPKPKDTLMISRTPEVTCVVVDVSHEDPEVKFNWYVDGVEVHNAKTKPREEQYNSTYRVV<br>SVLTVLHQDWLNGKEYKCKVSNKALPAPIEKTISKAKGQPREPQVYTLPPSREEMTKNQVSL<br>TCLVKGFYPSDIAVEWESNGQPENNYKTTPPVLDSDGSFFLYSKLTVDKSRWQQGNVFSCSV<br>MHEALHNHYTQKSLSLSPGK (SEQ ID NO: 96) |

Particular embodiments of antigen binding proteins of the present invention comprise one or more amino acid sequences that are identical to the amino acid sequences of one or more of the CDRs and/or FRs (framework regions) illustrated above. In one embodiment, the antigen binding protein comprises a light chain CDR1 sequence illustrated above. In another embodiment, the antigen binding protein comprises a light chain CDR2 sequence illustrated above. In another embodiment, the antigen binding protein comprises a light chain CDR3 sequence illustrated in above. In another embodiment, the antigen binding protein comprises a heavy chain CDR1 sequence illustrated above. In another embodiment, the antigen binding protein comprises a heavy chain CDR2 sequence illustrated above. In another embodiment, the antigen binding protein comprises a heavy chain CDR3 sequence illustrated above. In another embodiment, the antigen binding protein comprises a light chain FR1 sequence illustrated above. In another embodiment, the antigen binding protein comprises a light chain FR2 sequence illustrated above. In another embodiment, the antigen binding protein comprises a light chain FR3 sequence illustrated above. In another embodiment, the antigen binding protein comprises a light chain FR4 sequence illustrated above. In another embodiment, the antigen binding protein comprises a heavy chain FR1 sequence illustrated above. In another embodiment, the antigen binding protein comprises a heavy chain FR2 sequence illustrated above. In another embodiment, the antigen binding protein comprises a heavy chain FR3 sequence illustrated above. In another embodiment, the antigen binding protein comprises a heavy chain FR4 sequence illustrated above.

In another embodiment, at least one of the antigen binding protein's CDR3 sequences differs by no more than 6, 5, 4, 3, 2, 1 or 0 single amino acid addition, substitution, and/or deletion from a CDR3 sequence from the sequences as shown in Tables 2 and 3 above. In another embodiment, the antigen binding protein's light chain CDR3 sequence differs by no more than 6, 5, 4, 3, 2, 1 or 0 single amino acid addition, substitution, and/or deletion from a light chain CDR3 sequence from the sequences as shown above and the antigen binding protein's heavy chain CDR3 sequence differs by no more than 6, 5, 4, 3, 2, 1 or 0 single amino acid addition, substitution, and/or deletion from a heavy chain CDR3 sequence from the sequences as shown above. In another embodiment, the antigen binding protein further comprises 1, 2, 3, 4, or 5 CDR sequences that each independently differs by 6, 5, 4, 3, 2, 1, or 0 single amino acid additions, substitutions, and/or deletions from a CDR sequence of the sequences shown above. In another embodiment, the antigen binding protein comprises the CDRs of the light chain variable region and the CDRs of the heavy chain variable region set forth above. In a further embodiment, the antigen binding protein comprises the CDRs of any one of the antibodies listed above. In one embodiment, the antigen binding protein is a human antibody. In another embodiment, the antigen binding protein is a humanized antibody.

In one embodiment, the antigen binding protein (such as an antibody or antibody fragment) comprises a light chain variable domain comprising a sequence of amino acids that differs from the sequence of a light chain variable domain listed above only at 15, 14, 13, 12, 11, 10, 9, 8, 7, 6, 5, 4, 3, 2, 1 or 0 residues, wherein each such sequence difference is independently either a deletion, insertion, or substitution of one amino acid residue. In another embodiment, the light-chain variable domain comprises a sequence of amino acids that is at least 70%, 75%, 80%, 85%, 90%, 95%, 97%, or 99% identical to the sequence of a light chain variable domain listed above. In another embodiment, the light chain variable domain comprises a sequence of amino acids that is encoded by a nucleotide sequence that is at least 70%, 75%, 80%, 85%, 90%, 95%, 97%, or 99% identical to the polynucleotide sequence listed above. In another embodiment, the light chain variable domain comprises a sequence of amino acids that is encoded by a polynucleotide that hybridizes under moderately stringent conditions to the complement of a polynucleotide that encodes a light chain variable domain selected from the sequences listed above. In another embodiment, the light chain variable domain comprises a sequence of amino acids that is encoded by a polynucleotide that hybridizes under stringent conditions to the complement of a polynucleotide that encodes a light chain variable domain selected from the group consisting of the sequences listed above.

In another embodiment, the present invention provides an antigen binding protein comprising a heavy chain variable domain comprising a sequence of amino acids that differs from the sequence of a heavy chain variable domain selected from the sequences listed above only at 15, 14, 13, 12, 11, 10, 9, 8, 7, 6, 5, 4, 3, 2, 1 or 0 residue(s), wherein each such sequence difference is independently either a deletion, insertion, or substitution of one amino acid residue. In another embodiment, the heavy chain variable domain comprises a sequence of amino acids that is at least 70%, 75%, 80%, 85%, 90%, 95%, 97%, or 99% identical to the sequence of a heavy chain variable domain selected from the sequences listed above. In another embodiment, the heavy chain variable domain comprises a sequence of amino acids that is encoded by a nucleotide sequence that is at least 70%, 75%, 80%, 85%, 90%, 95%, 97%, or 99% identical to a nucleotide sequence that encodes a heavy chain variable domain selected from the sequences listed above. In another embodiment, the heavy chain variable domain comprises a sequence of amino acids that is encoded by a polynucleotide that hybridizes under moderately stringent conditions to the complement of a polynucleotide that encodes a heavy chain variable domain selected from the sequences listed above. In another embodiment, the heavy chain variable domain comprises a sequence of amino acids that is encoded by a polynucleotide that hybridizes under stringent conditions to the complement of a polynucleotide that encodes a heavy chain variable domain selected from the sequences listed above.

Antigen binding proteins (e.g., antibodies, antibody fragments, and antibody derivatives) of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

The nucleic acid (DNA) encoding constant heavy and constant light chain domains, and the amino acids sequences of heavy and light chain domains are provided herein below.

Lambda variable domains can be fused to lambda constant domains and kappa variable domains can be fused to kappa constant domains.

IgG2 Heavy Constant domain DNA (SEQ ID NO: 186):
gctagcaccaagggcccatcggtcttccccctggcgccctgctccagga
gcacctccgagagcacagcggccctgggctgcctggtcaaggactactt
ccccgaaccggtgacggtgtcgtggaactcaggcgctctgaccagcggc
gtgcacaccttcccagctgtcctacagtcctcaggactctactccctca
gcagcgtggtgaccgtgccctccagcaacttcggcacccagacctacac
ctgcaacgtagatcacaagcccagcaacaccaaggtggacaagacagtt
gagcgcaaatgttgtgtcgagtgcccaccgtgcccagcaccacctgtgg
caggaccgtcagtcttcctcttccccccaaaacccaaggacaccctcat
gatctcccggacccctgaggtcacgtgcgtggtggtggacgtgagccac
gaagaccccgaggtccagttcaactggtacgtggacggcgtggaggtgc
ataatgccaagacaaagccacgggaggagcagttcaacagcacgttccg
tgtggtcagcgtcctcaccgttgtgcaccaggactggctgaacggcaag
gagtacaagtgcaaggtctccaacaaaggcctcccagcccccatcgaga
aaaccatctccaaaaccaaagggcagccccgagaaccacaggtgtacac
cctgcccccatcccgggaggagatgaccaagaaccaggtcagcctgacc
tgcctggtcaaaggcttctaccccagcgacatcgccgtggagtgggaga
gcaatgggcagccggagaacaactacaagaccacacctcccatgctgga
ctccgacggctccttcttcctctacagcaagctcaccgtggacaagagc -continued aggtggcagcaggggaacgtcttctcatgctccgtgatgcatgaggctc
tgcacaaccactacacgcagaagagcctctccctgtctccgggtaaatg
a IgG2 Heavy Constant domain Protein (SEQ ID NO: 187):
ASTKGPSVFPLAPCSRSTSESTAALGCLVKDYFPEPVTVSWNSGALTSG
VHTFPAVLQSSGLYSLSSVVTVPSSNFGTQTYTCNVDHKPSNTKVDKTV
ERKCCVECPPCPAPPVAGPSVFLFPPKPKDTLMISRTPEVTCVVVDVSH
EDPEVQFNWYVDGVEVHNAKTKPREEQFNSTFRVVSVLTVVHQDWLNGK
EYKCKVSNKGLPAPIEKTISKTKGQPREPQVYTLPPSREEMTKNQVSLT
CLVKGFYPSDIAVEWESNGQPENNYKTTPPMLDSDGSFFLYSKLTVDKS
RWQQGNVFSCSVMHEALHNHYTQKSLSLSPGK Kappa Light Constant domain DNA (SEQ ID NO: 188):
cgtacggtggctgcaccatctgtcttcatcttcccgccatctgatgagca
gttgaaatctggaactgcctctgttgtgtgcctgctgaataacttctatc
ccagagaggccaaagtacagtggaaggtggataacgccctccaatcgggt
aactcccaggagagtgtcacagagcaggacagcaaggacagcacctacag
cctcagcagcaccctgacgctgagcaaagcagactacgagaaacacaaag
tctacgcctgcgaagtcacccatcagggcctgagctcgcccgtcacaaag
agcttcaacaggggagagtgttag Kappa Light Constant domain Protein (SEQ ID NO: 189):
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC Lambda Light Constant domain DNA (SEQ ID NO: 190):
ggccaaccgaaagcggcgccctcggtcactctgttcccgccctcctctga
ggagcttcaagccaacaaggccacactggtgtgtctcataagtgacttct
acccgggagccgtgacagtggcctggaaggcagatagcagccccgtcaag
gcgggagtggagaccaccacaccctccaaacaaagcaacaacaagtacgc
ggccagcagctatctgagcctgacgcctgagcagtggaagtcccacagaa
gctacagctgccaggtcacgcatgaagggagcaccgtggagaagacagtg
gcccctacagaatgttcatag Lambda Light Constant domain Protein (SEQ ID NO: 191):
GQPKAAPSVTLFPPSSEELQANKATLVCLISDFYPGAVTVAWKADSSPVK
AGVETTTPSKQSNNKYAASSYLSLTPEQWKSHRSYSCQVTHEGSTVEKTV
APTECS The specific binding agents of the present invention, such as the antibodies, antibody fragments, and antibody derivatives of the invention include those comprising, for example, the variable domain combinations provided herein having a desired isotype (for example, IgA, IgG1, IgG2, IgG3, IgG4, IgM, IgE, and IgD) as well as Fab or F(ab')2 fragments thereof. Moreover, if an IgG4 is desired, it may also be desired to introduce a point mutation in the hinge region as described in Bloom et al., 1997, Protein Science 6:407 (incorporated by reference herein) to alleviate a tendency to form intra-H chain disulfide bonds that can lead to heterogeneity in the IgG4 antibodies.

Additional Useful Sequence Information

The following sequences of the IgG1, IgG2, IgG3, and IgG4 isotypes are used in combination with the variable heavy chain sequences of the antibodies of the present invention to make a specific desired isotype of said antibody:

```
Human IgG1
                                    (SEQ ID NO: 192)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Human IgG2
                                    (SEQ ID NO: 193)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK

Human IgG3
                                    (SEQ ID NO: 194)
ASTKGPSVFPLAPCSRSTSGGTAALGCLVKDYFPEPVTVSWNSGALTSGV

HTFPAVLQSSGLYSLSSVVTVPSSSLGTQTYTCNVNHKPSNTKVDKRVEL

KTPLGDTTHTCPRCPEPKSCDTPPPCPRCPEPKSCDTPPPCPRCPEPKSC

DTPPPCPRCPAPELLGGPSVFLFPPKPKDTLMISRTPEVTCVVVDVSHED

PEVQFKWYVDGVEVHNAKTKPREEQYNSTFRVVSVLTVLHQDWLNGKEYK

CKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQG

NIFSCSVMHEALHNRFTQKSLSLSPGK

Human IgG4
                                    (SEQ ID NO: 195)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFEGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK
```

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lanitto et al., Methods Mol. Biol. 178:303-16 (2002).

In one embodiment, an antigen binding protein of the invention further comprises the constant light chain kappa or lambda domains or a fragment of these. Sequences of the light chain constant regions and polynucleotides encoding them are well known in the art. In another embodiment, an antigen binding protein of the invention further comprises a heavy chain constant domain, or a fragment thereof, such as the IgG1 or IgG2 heavy chain constant region, the sequences of which are well known in the art.

The antigen binding proteins (for example, antibodies) of the present invention include those having a desired isotype (for example, IgA, IgG1, IgG2, IgG3, IgG4, IgM, IgE, and IgD) as well as Fab or $F(ab')_2$ fragments thereof. Moreover, if an IgG4 is desired, it may also be desired to introduce a point mutation in the hinge region as described in Bloom et al., 1997, Protein Science 6:407, (incorporated by reference herein) to alleviate a tendency to form intra-H chain disulfide bonds that can lead to heterogeneity in the IgG4 antibodies.

Antibodies and Antibody Fragments

In one embodiment the antigen binding proteins are antibodies. The term "antibody" refers to an intact antibody, or an antigen binding fragment thereof, as described extensively in the definition section. An antibody may comprise a complete antibody molecule (including polyclonal, monoclonal, chimeric, humanized, or human versions having full length heavy and/or light chains), or comprise an antigen binding fragment thereof. Antibody fragments include $F(ab')_2$, Fab, Fab', Fv, Fc, and Fd fragments, and can be incorporated into single domain antibodies, single-chain antibodies, maxibodies, minibodies, intrabodies, diabodies, triabodies, tetrabodies, v-NAR and bis-scFv (see e.g., Hollinger and Hudson, 2005, Nature Biotechnology, 23, 9, 1126-1136). Also included are antibody polypeptides such as those disclosed in U.S. Pat. No. 6,703,199, including fibronectin polypeptide monobodies. Other antibody polypeptides are disclosed in U.S. Patent Publication 2005/0238646, which are single-chain polypeptides. In one embodiment, the antibodies of the present invention comprise at least one CDR set forth in Table 2 above. In another aspect, the present invention provides hybridomas capable of producing the antibodies of the invention, and methods of producing antibodies from hybridomas, as described further below.

Chimeric antibodies and humanized antibodies are defined in the definition section and may be prepared by known techniques. In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody. Techniques for humanizing antibodies are discussed in, e.g., U.S. Pat. Nos. 5,869,619; 5,225,539; 5,821,337; 5,859,205; 6,881,557, Padlan et al., 1995, FASEB J. 9:133-39, Tamura et al., 2000, J. Immunol. 164:1432-41, Zhang, W., et al., Molecular Immunology. 42(12):1445-1451, 2005; Hwang W. et al., Methods. 36(1): 35-42, 2005; Dall'Acqua W F, et al., Methods 36(1):43-60, 2005; and Clark, M., Immunology Today. 21(8):397-402, 2000.

An antibody of the present invention may also be a fully human monoclonal antibody. Fully human monoclonal antibodies may be generated by any number of techniques with which those having ordinary skill in the art will be familiar. Such methods include, but are not limited to, Epstein Barr Virus (EBV) transformation of human peripheral blood cells (e.g., containing B lymphocytes), in vitro immunization of human B-cells, fusion of spleen cells from immunized transgenic mice carrying inserted human immunoglobulin genes, isolation from human immunoglobulin V region phage libraries, or other procedures as known in the art and based on the disclosure herein.

Procedures have been developed for generating human monoclonal antibodies in non-human animals. For example, mice in which one or more endogenous immunoglobulin genes have been inactivated by various means have been prepared. Human immunoglobulin genes have been introduced into the mice to replace the inactivated mouse genes. In this technique, elements of the human heavy and light chain locus are introduced into strains of mice derived from embryonic stem cell lines that contain targeted disruptions of the endogenous heavy chain and light chain loci (see also Bruggemann et al., Curr. Opin. Biotechnol. 8:455-58 (1997)). For example, human immunoglobulin transgenes may be mini-gene constructs, or transloci on yeast artificial chromosomes, which undergo B-cell-specific DNA rearrangement and hypermutation in the mouse lymphoid tissue.

Antibodies produced in the animal incorporate human immunoglobulin polypeptide chains encoded by the human genetic material introduced into the animal. In one embodiment, a non-human animal, such as a transgenic mouse, is immunized with a suitable mesothelin immunogen.

Examples of techniques for production and use of transgenic animals for the production of human or partially human antibodies are described in U.S. Pat. Nos. 5,814,318, 5,569,825, and 5,545,806, Davis et al., Production of human antibodies from transgenic mice in Lo, ed. Antibody Engineering: Methods and Protocols, Humana Press, NJ:191-200 (2003), Kellermann et al., 2002, Curr Opin Biotechnol. 13:593-97, Russel et al., 2000, Infect Immun. 68:1820-26, Gallo et al., 2000, Eur J Immun. 30:534-40, Davis et al., 1999, Cancer Metastasis Rev. 18:421-25, Green, 1999, J Immunol Methods. 231:11-23, Jakobovits, 1998, Advanced Drug Delivery Reviews 31:33-42, Green et al., 1998, J Exp Med. 188:483-95, Jakobovits A, 1998, Exp. Opin. Invest. Drugs. 7:607-14, Tsuda et al., 1997, Genomics. 42:413-21, Mendez et al., 1997, Nat Genet. 15:146-56, Jakobovits, 1994, Curr Biol. 4:761-63, Arbones et al., 1994, Immunity. 1:247-60, Green et al., 1994, Nat Genet. 7:13-21, Jakobovits et al., 1993, Nature. 362:255-58, Jakobovits et al., 1993, Proc Natl Acad Sci USA. 90:2551-55. Chen, J., M. Trounstine, F. W. Alt, F. Young, C. Kurahara, J. Loring, D. Huszar. "Immunoglobulin gene rearrangement in B-cell deficient mice generated by targeted deletion of the JH locus." International Immunology 5 (1993): 647-656, Choi et al., 1993, Nature Genetics 4: 117-23, Fishwild et al., 1996, Nature Biotechnology 14: 845-51, Harding et al., 1995, Annals of the New York Academy of Sciences, Lonberg et al., 1994, Nature 368: 856-59, Lonberg, 1994, Transgenic Approaches to Human Monoclonal Antibodies in Handbook of Experimental Pharmacology 113: 49-101, Lonberg et al., 1995, Internal Review of Immunology 13: 65-93, Neuberger, 1996, Nature Biotechnology 14: 826, Taylor et al., 1992, Nucleic Acids Research 20: 6287-95, Taylor et al., 1994, International Immunology 6: 579-91, Tomizuka et al., 1997, Nature Genetics 16: 133-43, Tomizuka et al., 2000, Proceedings of the National Academy of Sciences USA 97: 722-27, Tuaillon et al., 1993, Proceedings of the National Academy of Sciences USA 90: 3720-24, and Tuaillon et al., 1994, Journal of Immunology 152: 2912-20; Lonberg et al., Nature 368:856, 1994; Taylor et al., Int. Immun. 6:579, 1994; U.S. Pat. No. 5,877,397; Bruggemann et al., 1997 Curr. Opin. Biotechnol. 8:455-58; Jakobovits et al., 1995 Ann. N. Y. Acad. Sci. 764:525-35. In addition, protocols involving the XenoMouse® (Abgenix, now Amgen, Inc.) are described, for example in U.S. Ser. No. 05/011,8643 and WO 05/694879, WO 98/24838, WO 00/76310, and U.S. Pat. No. 7,064,244.

Lymphoid cells from the immunized transgenic mice are fused with myeloma cells for example to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in such fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

The lymphoid (e.g., spleen) cells and the myeloma cells may be combined for a few minutes with a membrane fusion-promoting agent, such as polyethylene glycol or a nonionic detergent, and then plated at low density on a selective medium that supports the growth of hybridoma cells but not unfused myeloma cells. One selection media is HAT (hypoxanthine, aminopterin, thymidine). After a sufficient time, usually about one to two weeks, colonies of cells are observed. Single colonies are isolated, and antibodies produced by the cells may be tested for binding activity to mesothelin using any one of a variety of immunoassays known in the art and described herein. The hybridomas are cloned (e.g., by limited dilution cloning or by soft agar plaque isolation) and positive clones that produce an antibody specific to mesothelin are selected and cultured. The monoclonal antibodies from the hybridoma cultures may be isolated from the supernatants of hybridoma cultures. Thus the present invention provides hybridomas that comprise polynucleotides encoding the antigen binding proteins of the invention in the chromosomes of the cell. These hybridomas can be cultured according to methods described herein and known in the art.

Another method for generating human antibodies of the invention includes immortalizing human peripheral blood cells by EBV transformation. See, e.g., U.S. Pat. No. 4,464,456. Such an immortalized B-cell line (or lymphoblastoid cell line) producing a monoclonal antibody that specifically binds to mesothelin can be identified by immunodetection methods as provided herein, for example, an ELISA, and then isolated by standard cloning techniques. The stability of the lymphoblastoid cell line producing an anti-mesothelin antibody may be improved by fusing the transformed cell line with a murine myeloma to produce a mouse-human hybrid cell line according to methods known in the art (see, e.g., Glasky et al., Hybridoma 8:377-89 (1989)). Still another method to generate human monoclonal antibodies is in vitro immunization, which includes priming human splenic B-cells with human mesothelin, followed by fusion of primed B-cells with a heterohybrid fusion partner. See, e.g., Boerner et al., 1991 J. Immunol. 147:86-95.

In certain embodiments, a B-cell that is producing an anti-human mesothelin antibody is selected and the light chain and heavy chain variable regions are cloned from the B-cell according to molecular biology techniques known in the art (WO 92/02551; U.S. Pat. No. 5,627,052; Babcook et al., Proc. Natl. Acad. Sci. USA 93:7843-48 (1996)) and described herein. B-cells from an immunized animal may be isolated from the spleen, lymph node, or peripheral blood sample by selecting a cell that is producing an antibody that specifically binds to mesothelin. B-cells may also be isolated from humans, for example, from a peripheral blood sample. Methods for detecting single B-cells that are producing an antibody with the desired specificity are well known in the art, for example, by plaque formation, fluorescence-activated cell sorting, in vitro stimulation followed by detection of specific antibody, and the like. Methods for selection of specific antibody-producing B-cells include, for example, preparing a single cell suspension of B-cells in soft agar that contains human mesothelin. Binding of the specific antibody produced by the B-cell to the antigen results in the formation of a complex, which may be visible as an immunoprecipitate. After the B-cells producing the desired antibody are selected, the specific antibody genes may be cloned by isolating and amplifying DNA or mRNA according to methods known in the art and described herein.

An additional method for obtaining antibodies of the invention is by phage display. See, e.g., Winter et al., 1994 Annu. Rev. Immunol. 12:433-55; Burton et al., 1994 Adv. Immunol. 57:191-280. Human or murine immunoglobulin variable region gene combinatorial libraries may be created in phage vectors that can be screened to select Ig fragments (Fab, Fv, sFv, or multimers thereof) that bind specifically to TGF-beta binding protein or variant or fragment thereof. See, e.g., U.S. Pat. No. 5,223,409; Huse et al., 1989 Science 246:1275-81; Sastry et al., Proc. Natl. Acad. Sci. USA 86:5728-32 (1989); Alting-Mees et al., Strategies in Molecular Biology 3:1-9 (1990); Kang et al., 1991 Proc. Natl. Acad. Sci. USA 88:4363-66; Hoogenboom et al., 1992 J. Molec. Biol. 227:381-388; Schlebusch et al., 1997 Hybridoma 16:47-52 and references cited therein. For example, a library containing a plurality of polynucleotide sequences encoding Ig variable region fragments may be inserted into the genome of a filamentous bacteriophage, such as M13 or a variant thereof, in frame with the sequence encoding a phage coat protein. A fusion protein may be a fusion of the coat protein with the light chain variable region domain and/or with the heavy chain variable region domain. According to certain embodiments, immunoglobulin Fab fragments may also be displayed on a phage particle (see, e.g., U.S. Pat. No. 5,698,426).

Heavy and light chain immunoglobulin cDNA expression libraries may also be prepared in lambda phage, for example, using λImmunoZap™ (H) and λImmunoZap™ (L) vectors (Stratagene, La Jolla, CA). Briefly, mRNA is isolated from a B-cell population, and used to create heavy and light chain immunoglobulin cDNA expression libraries in the λImmunoZap(H) and λImmunoZap(L) vectors. These vectors may be screened individually or co-expressed to form Fab fragments or antibodies (see Huse et al., supra; see also Sastry et al., supra). Positive plaques may subsequently be converted to a non-lytic plasmid that allows high level expression of monoclonal antibody fragments from *E. coli*.

In one embodiment, in a hybridoma the variable regions of a gene expressing a monoclonal antibody of interest are amplified using nucleotide primers. These primers may be synthesized by one of ordinary skill in the art, or may be purchased from commercially available sources. (See, e.g., Stratagene (La Jolla, California), which sells primers for mouse and human variable regions including, among others, primers for $V_{Ha}$, $V_{Hb}$, $V_{Hc}$, $V_{Hd}$, $C_{H1}$, $V_L$ and $C_L$ regions.) These primers may be used to amplify heavy or light chain variable regions, which may then be inserted into vectors such as ImmunoZAP™ H or ImmunoZAP™ L (Stratagene), respectively. These vectors may then be introduced into *E. coli*, yeast, or mammalian-based systems for expression. Large amounts of a single-chain protein containing a fusion of the $V_H$ and $V_L$ domains may be produced using these methods (see Bird et al., Science 242:423-426, 1988).

Once cells producing antibodies according to the invention have been obtained using any of the above-described immunization and other techniques, the specific antibody genes may be cloned by isolating and amplifying DNA or mRNA therefrom according to standard procedures as described herein. The antibodies produced therefrom may be sequenced and the CDRs identified and the DNA coding for the CDRs may be manipulated as described previously to generate other antibodies according to the invention.

In certain embodiments, antibodies are generated by first identifying antibodies that bind to cells expressing mesothelin and/or compete for binding with the antibodies described in this application.

It will be understood by one skilled in the art that some proteins, such as antibodies, may undergo a variety of posttranslational modifications. The type and extent of these modifications often depends on the host cell line used to express the protein as well as the culture conditions. Such modifications may include variations in glycosylation, methionine oxidation, diketopiperizine formation, aspartate isomerization and asparagine deamidation. A frequent modification is the loss of a carboxy-terminal basic residue (such as lysine or arginine) due to the action of carboxypeptidases (as described in Harris, R. J. Journal of Chromatography 705:129-134, 1995).

An alternative method for production of a murine monoclonal antibody is to inject the hybridoma cells into the peritoneal cavity of a syngeneic mouse, for example, a mouse that has been treated (e.g., pristane-primed) to promote formation of ascites fluid containing the monoclonal antibody. Monoclonal antibodies can be isolated and purified by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in Methods in Molecular Biology, Vol. 10, pages 79-104 (The Humana Press, Inc. 1992)). Monoclonal antibodies may be purified by affinity chromatography using an appropriate ligand selected based on particular properties of the antibody (e.g., heavy or light chain isotype, binding specificity, etc.). Examples of a suitable ligand, immobilized on a solid support, include Protein A, Protein G, an anticonstant region (light chain or heavy chain) antibody, an anti-idiotype antibody, and a TGF-beta binding protein, or fragment or variant thereof.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, J. Mol. Biol. 263:551. Accordingly, such techniques are useful in preparing antibodies to mesothelin.

Antigen binding proteins directed against mesothelin can be used, for example, in assays to detect the presence of mesothelin, either in vitro or in vivo.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (for example, monkey such as cynomolgous or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antibodies also may be prepared by any of a number of conventional techniques. For example, they may be purified from cells that naturally express them (e.g., an antibody can be purified from a hybridoma that produces it), or produced in recombinant expression systems, using any technique known in the art. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, NY, (1988). This is discussed in the nucleic acid section below.

Where it is desired to improve the affinity of antibodies according to the invention containing one or more of the above-mentioned CDRs can be obtained by a number of affinity maturation protocols including maintaining the CDRs (Yang et al., J. Mol. Biol., 254, 392-403, 1995), chain shuffling (Marks et al., Bio/Technology, 10, 779-783, 1992), use of mutation strains of *E. coli*. (Low et al., J. Mol. Biol., 250, 350-368, 1996), DNA shuffling (Patten et al., Curr. Opin. Biotechnol., 8, 724-733, 1997), phage display (Thompson et al., J. Mol. Biol., 256, 7-88, 1996) and additional PCR techniques (Crameri, et al., Nature, 391, 288-291, 1998). All of these methods of affinity maturation are discussed by Vaughan et al. (Nature Biotechnology, 16, 535-539, 1998).

Antibody Fragments

In another aspect, the present invention provides fragments of an anti-mesothelin antibody of the invention. Such fragments can consist entirely of antibody-derived sequences or can comprise additional sequences. Examples of antigen-binding fragments include Fab, F(ab')2, single chain antibodies, diabodies, triabodies, tetrabodies, and domain antibodies. Other examples are provided in Lunde et al., 2002, Biochem. Soc. Trans. 30:500-06.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87. Single chain antibodies derived from antibodies provided herein include, but are not limited to, scFvs comprising the variable domain combinations L1H1, L2H2, L3H3, L4H4, L5H5, L6H6, L7H7, L8H8, L9H9, and L10H10 are encompassed by the present invention.

Antigen binding fragments derived from an antibody can also be obtained, for example, by proteolytic hydrolysis of the antibody, for example, pepsin or papain digestion of whole antibodies according to conventional methods. By way of example, antibody fragments can be produced by enzymatic cleavage of antibodies with pepsin to provide a 5S fragment termed $F(ab')_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using papain produces two monovalent Fab fragments and an Fc fragment directly. These methods are described, for example, by Goldenberg, U.S. Pat. No. 4,331,647, Nisonoff et al., Arch. Biochem. Biophys. 89:230, 1960; Porter, Biochem. J. 73:119, 1959; Edelman et al., in Methods in Enzymology 1:422 (Academic Press 1967); and by Andrews, S. M. and Titus, J. A. in Current Protocols in Immunology (Coligan J. E., et al., eds), John Wiley & Sons, New York (2003), pages 2.8.1-2.8.10 and 2.10A.1-2.10A.5. Other methods for cleaving antibodies, such as separating heavy chains to form monovalent light-heavy chain fragments (Fd), further cleaving of fragments, or other enzymatic, chemical, or genetic techniques may also be used, so long as the fragments bind to the antigen that is recognized by the intact antibody.

Another form of an antibody fragment is a peptide comprising one or more complementarity determining regions (CDRs) of an antibody. CDRs can be obtained by constructing polynucleotides that encode the CDR of interest. Such polynucleotides are prepared, for example, by using the polymerase chain reaction to synthesize the variable region using mRNA of antibody-producing cells as a template (see, for example, Larrick et al., Methods: A Companion to Methods in Enzymology 2:106, 1991; Courtenay-Luck, "Genetic Manipulation of Monoclonal Antibodies," in Monoclonal Antibodies: Production, Engineering and Clinical Application, Ritter et al. (eds.), page 166 (Cambridge University Press 1995); and Ward et al., "Genetic Manipulation and Expression of Antibodies," in Monoclonal Antibodies: Principles and Applications, Birch et al., (eds.), page 137 (Wiley-Liss, Inc. 1995)). The antibody fragment further may comprise at least one variable region domain of an antibody described herein. Thus, for example, the V region domain may be monomeric and be a $V_H$ or $V_L$ domain, which is capable of independently binding mesothelin with an affinity at least equal to $10^{-7}$ M or less as described below.

The variable region domain may be any naturally occurring variable domain or an engineered version thereof. By engineered version is meant a variable region domain that has been created using recombinant DNA engineering techniques. Such engineered versions include those created, for example, from a specific antibody variable region by insertions, deletions, or changes in or to the amino acid sequences of the specific antibody. Particular examples include engineered variable region domains containing at least one CDR and optionally one or more framework amino acids from a first antibody and the remainder of the variable region domain from a second antibody.

The variable region domain may be covalently attached at a C-terminal amino acid to at least one other antibody domain or a fragment thereof. Thus, for example, a VH domain that is present in the variable region domain may be linked to an immunoglobulin CH1 domain, or a fragment thereof. Similarly a $V_L$ domain may be linked to a $C_K$ domain or a fragment thereof. In this way, for example, the antibody may be a Fab fragment wherein the antigen binding domain contains associated $V_H$ and $V_L$ domains covalently linked at their C-termini to a CH1 and $C_K$ domain, respectively. The CH1 domain may be extended with further amino acids, for example to provide a hinge region or a portion of a hinge region domain as found in a Fab' fragment, or to provide further domains, such as antibody CH2 and CH3 domains.

Bispecific Single Chain Antibodies (e.g., Bispecific T-Cell Engagers or BiTEs)

In one embodiment, the invention provides bispecific single chain antibodies, such as, but not limited to, bispecific T-cell engaging molecules (BiTEs). In certain embodiments, the contemplated bispecific single chain antibodies utilize at least two Fv regions to direct binding to target molecules of choice. It is contemplated that two different Fv regions are used, although it is further contemplated that a single Fv region can be used at least twice in a single bispecific single chain antibody. It is contemplated that at least two different target molecules are targeted by the bispecific single chain antibodies of the invention, although it is further contemplated that the same target molecule can be targeted by the at least two Fv regions of the bispecific single chain antibodies.

As is well known, Fv, the minimum antibody fragment which contains a complete antigen recognition and binding site, consists of a dimer of one heavy and one light chain variable domain (VH and VL) in non-covalent association. In this configuration corresponding to the one found in native antibodies, the three CDRs of each variable domain interact to define an antigen binding site on the surface of the VH-VL dimer. Collectively, the six CDRs confer antigen binding specificity to the antibody. Frameworks (FRs) flanking the CDRs have a tertiary structure which is essentially conserved in native immunoglobulins of species as diverse as human and mouse. These FRs serve to hold the CDRs in their appropriate orientation. The constant domains are not required for binding function, but may aid in stabilizing VH-VL interaction.

As used herein, CD3 epsilon denotes a molecule expressed as part of the T cell receptor and has the meaning as typically ascribed to it in the prior art. In human, it encompasses in individual or independently combined form all known CD3 subunits, for example CD3 epsilon, CD3 delta, CD3 gamma, CD3 zeta, CD3 alpha and CD3 beta. The non-chimpanzee primate CD3 antigens as referred to herein are, for example, *Macaca fascicularis* CD3 and *Macaca mulatta* CD3. In *Macaca fascicularis*, it encompasses CD3 epsilon FN-18 negative and CD3 epsilon FN-18 positive, CD3 gamma and CD3 delta. In *Macaca mulatta*, it encompasses CD3 epsilon, CD3 gamma and CD3 delta. Preferably, said CD3 as used herein is CD3 epsilon. Additional examples of non-chimpanzee primate CD3 molecules are contemplated, for example, cynomolgus CD3.

The human CD3 epsilon is indicated in GenBank Accession No. NM-000733. The human CD3 gamma is indicated in GenBank Accession NO. NM-000073. The human CD3 delta is indicated in GenBank Accession No. NM-000732.

It is also envisaged in the context of the present invention that the bispecific antibody constructs provided in the pharmaceutical composition of the invention are further modified. In particular, it is envisaged that the bispecific single chain antibody construct in the format $V_H$(MSLN)-$V_L$(MSLN)-$V_H$(CD3)-$V_L$(CD3), $V_H$(CD3)-$V_L$(CD3)-$V_H$(MSLN)-$V_L$(MSLN) or $V_H$(CD3)-$V_L$(CD3)-$V_L$(MSLN)-$V_H$(MSLN) as defined herein are deimmunized. In certain embodiments, at least the CD3-binding portion is deimmunized. Deimmunization entails carrying out substitutions of amino acids within potential T cell epitopes.

In certain embodiments, the bispecific single chain antibodies comprise at least one CDR-3 of a VH-region of an antibody directed against human CD3, at least one CDR-3 of a VL-region of an antibody directed against human CD3, at least one CDR-3 of a VH-region of an antibody directed against human MSLN and at least one CDR-3 of a VL-region of an antibody directed against human MSLN. In further embodiments, the bispecific single chain antibodies comprise VH and VL regions which comprise not only CDR-3 but also CDR1 and/or CDR2 regions. In particular, CDR-regions (e.g., CDRs 1-3 of the VH and VL) may be employed to generate further bispecific single chain constructs. In further embodiments, the bispecific single chain antibodies are derived from the parental antibodies as disclosed herein and share, as disclosed above, at least the CDR-3 domain of the VH-region and the CDR-3 domain of the VL-region with said parental antibodies, and in certain embodiments share CDRs 1-3 of the VH and VL regions of said parental antibodies. It is also envisaged that the bispecific single chain antibodies further comprise modified CDR regions. It is, e.g., envisaged that in particular CDR2 and/or CDR1 regions (or frameworks or linkers between CDRs) are deimmunized. For further disclosure relating to bispecific single chain antibodies, see, for example, U.S. Pat. Nos. 6,723,538; 7,112,324; 7,227,002; 7,235,641; 7,323,440; 7,332,168; 7,635,472; 7,820,166; 7,919,089; 8,017,748; 8,076,459; 8,101,722; 8,236,308; and 8,247,194. See also, for example, U.S. Patent Publication Nos. 20090241202, 20090291072, 20100150918 (WO 2008/119567), 20110262439, 20110293619, 20120034228, and 20120244162.

In one embodiment, the VH and VL regions of said CD3 specific domain are derived from a CD3 specific antibody selected from the group consisting of X35-3, VIT3, BMA030 (BW264/56), CLB-T3/3, CRIS7, YTH12.5, F111-409, CLB-T3.4.2, WT31, WT32, SPv-T3b, 11D8, XIII-141, XIII-46, XIII-87, 12F6, T3/RW2-8C8, T3/RW2-4B6, OKT3D, M-T301, SMC2 and F101.01. These CD3-specific antibodies are well known in the art and described in Tunnacliffe (1989), Int. Immunol. 1, 546-550. In another embodiment, said VH and VL regions of said CD3 specific domain are derived from OKT3 (as described above). In a further embodiment, said VH and VL regions are or are derived from an antibody/antibody derivative specifically directed against CD3 described by Traunecker (1991), EMBO J. 10, 3655-3659. In a further embodiment, said VH and VL regions are or are derived from an antibody/antibody derivative specifically directed against CD3 described in U.S. Patent Publication No. 20100150918 (WO 2008/119567). In a specific embodiment, said VH and VL regions are or are derived from an antibody/antibody I2C as described in U.S. Patent Publication No. 20100150918 (WO 2008/119567).

In accordance with this invention, said VH and VL regions are derived from antibodies/antibody derivatives and the like which are capable of specifically recognizing human CD3 epsilon in the context of other TCR subunits, e.g. in mouse T cells transgenic for human CD3 epsilon. These transgenic mouse cells express human CD3 epsilon in a native or near native conformation. Accordingly, the VH and VL regions derived from a CD3-epsilon-specific antibody are envisioned as further embodiments in accordance with this invention and said (parental) antibodies should be capable of specifically binding epitopes reflecting the native or near native structure or a conformational epitope of human CD3 presented in context of the TCR complex. Such antibodies have been classified by Tunnacliffe (1989) as "group II" antibodies.

Further classifications in Tunnacliffe (1989) comprise the definition of "group I" and "group III" antibodies directed against CD3. "Group I" antibodies, like UCHT1, recognize CD3 epsilon both expressed as recombinant protein as well as part of the TCR on the cell surface. Therefore, "group I" antibodies are highly specific for CD3 epsilon. In contrast, the herein preferred "group II" antibodies recognize CD3 epsilon only in the native TCR complex in association with other TCR subunits. Without being bound by theory, it is speculated in context of this invention that in "group II" antibodies, the TCR context is required for recognition of CD3 epsilon. CD3 gamma and/or delta, being associated with epsilon, are also involved in binding of "group II" antibodies. All three subunits express immuno-tyrosine activation motifs (ITAMs) which can be tyrosine phosphorylated by protein tyrosine kinases. For this reason "group II" antibodies induce T cell signaling via CD3 epsilon, gamma and delta, leading to a stronger signal compared to "group I" antibodies selectively inducing T cell signaling via CD3 epsilon. Yet, since for therapeutic applications induction of a strong T cell signaling is desired, the VH (CD3)/VL (CD3)-regions (or parts thereof) to be employed in the bispecific single chain constructs comprised in the inventive pharmaceutical composition, are derived from antibodies directed against human CD3 and classified as "group II" by Tunnacliffe (1989).

Derivatives and Variants of Antigen Binding Proteins

The nucleotide sequences of the antibodies of the present invention, encoding the corresponding amino acid sequences of the antibodies of the present invention, can be altered, for example, by random mutagenesis or by site-directed mutagenesis (e.g., oligonucleotide-directed site-specific mutagenesis) to create an altered polynucleotide comprising one or more particular nucleotide substitutions, deletions, or insertions as compared to the non-mutated polynucleotide. Examples of techniques for making such alterations are described in Walder et al., 1986, Gene 42:133; Bauer et al. 1985, Gene 37:73; Craik, BioTechniques, January 1985, 12-19; Smith et al., 1981, Genetic Engineering: Principles and Methods, Plenum Press; and U.S. Pat. Nos. 4,518,584 and 4,737,462. These and other methods can be used to make, for example, derivatives of anti-mesothelin antibodies that have a desired property, for example, increased affinity, avidity, or specificity for mesothelin increased activity or stability in vivo or in vitro, or reduced in vivo side-effects as compared to the underivatized antibody.

Other derivatives of anti-mesothelin antibodies within the scope of this invention include covalent or aggregative conjugates of anti-mesothelin antibodies, or fragments thereof, with other proteins or polypeptides, such as by expression of recombinant fusion proteins comprising heterologous polypeptides fused to the N-terminus or C-terminus of an anti-mesothelin antibody polypeptide. For example, the conjugated peptide may be a heterologous signal (or leader) polypeptide, e.g., the yeast alpha-factor leader, or a peptide such as an epitope tag. Antigen binding protein-containing fusion proteins can comprise peptides added to facilitate purification or identification of antigen binding protein (e.g., poly-His). An antigen binding protein also can be linked to the FLAG peptide as described in Hopp et al., Bio/Technology 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, MO).

In another embodiment, oligomers that contain one or more antigen binding proteins may be employed as mesothelin antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have mesothelin binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in Current Protocols in Immunology, Suppl. 4, pages 10.19.1-10.19.11. One embodiment of the present invention is directed to a dimer comprising two fusion proteins created by fusing a mesothelin binding fragment of an anti-mesothelin antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. In other embodiments, the variable portion of the heavy and/or light chains of an anti-mesothelin antibody may be substituted for the variable portion of an antibody heavy and/or light chain.

Alternatively, the oligomer is a fusion protein comprising multiple antigen binding proteins, with or without peptide linkers (spacer peptides). Among the suitable peptide linkers are those described in U.S. Pat. Nos. 4,751,180 and 4,935,233.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-mesothelin antibody fragment or derivative fused to a leucine zipper peptide are expressed in suitable host cells, and the soluble oligomeric anti-mesothelin antibody fragments or derivatives that form are recovered from the culture supernatant.

In another embodiment, the antibody derivatives can comprise at least one of the CDRs disclosed herein. For example, one or more CDR may be incorporated into known antibody framework regions (IgG1, IgG2, etc.), or conjugated to a suitable vehicle to enhance the half-life thereof. Suitable vehicles include, but are not limited to Fc, albumin, transferrin, and the like. These and other suitable vehicles are known in the art. Such conjugated CDR peptides may be in monomeric, dimeric, tetrameric, or other form. In one embodiment, one or more water-soluble polymer is bonded at one or more specific position, for example at the amino terminus, of a binding agent. In an example, an antibody derivative comprises one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative comprises one or more of monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers. In certain embodiments, one or more water-soluble polymer is randomly attached to one or more side chains. In certain embodiments, PEG can act to improve the therapeutic capacity for a binding agent, such as an antibody. Certain such methods are discussed, for example, in U.S. Pat. No. 6,133,426, which is hereby incorporated by reference for any purpose.

It will be appreciated that an antigen binding protein or antibody of the present invention may have at least one amino acid substitution, providing that the antigen binding protein or antibody retains binding specificity. Therefore, modifications to the antigen binding protein or antibody structures are encompassed within the scope of the invention. These may include amino acid substitutions, which may be conservative or non-conservative, that do not destroy the mesothelin binding capability of an antigen binding protein or antibody. Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties. A conservative amino acid substitution may also involve a substitution of a native amino acid residue with a normative residue such that there is little or no effect on the polarity or charge of the amino acid residue at that position. Non-conservative substitutions may involve the exchange of a member of one class of amino acids or amino acid mimetics for a member from another class with different physical properties (e.g. size, polarity, hydrophobicity, charge). For example, such substituted residues may be introduced into regions of the human antibody that are homologous with non-human antibodies, or into the non-homologous regions of the molecule.

In certain embodiments, an amino acid substitution is made to improve protein expression, or to improve upon protein stability. For example, but not limited to, in one embodiment, the glutamine (Gln, Q) at the amino terminus of a variable heavy and/or a variable light chain of a binding protein is substituted with glutamic acid (Glu, E).

Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

A skilled artisan will be able to determine suitable variants of the polypeptide as set forth herein using well-known techniques. In certain embodiments, one skilled in the art may identify suitable areas of the molecule that may be changed without destroying activity by targeting regions not believed to be important for activity. In certain embodiments, one can identify residues and portions of the molecules that are conserved among similar polypeptides. In certain embodiments, even areas that may be important for biological activity or for structure may be subject to conservative amino acid substitutions without destroying the biological activity or without adversely affecting the polypeptide structure. Additionally, one skilled in the art can review structure-function studies identifying residues in similar polypeptides that are important for activity or structure. In view of such a comparison, one can predict the importance of amino acid residues in a protein that correspond to amino acid residues which are important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art may predict the alignment of amino acid residues of an antibody with respect to its three dimensional structure. In certain embodiments, one skilled in the art may choose not to make radical changes to amino acid residues predicted to be on the surface of the protein, since such residues may be involved in important interactions with other molecules. A number of scientific publications have been devoted to the prediction of secondary structure. See Moult J., Curr. Op. in Biotech., 7(4):422-427 (1996), Chou et al., Biochemistry, 13(2):222-245 (1974); Chou et al., Biochemistry, 113(2):211-222 (1974); Chou et al., Adv. Enzymol. Relat. Areas Mol. Biol., 47:45-148 (1978); Chou et al., Ann. Rev. Biochem., 47:251-276 and Chou et al., Biophys. J., 26:367-384 (1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural database (PDB) has provided enhanced predictability of secondary structure, including the potential number of folds within a polypeptide's or protein's structure. See Holm et al., Nucl. Acid. Res., 27(1):244-247 (1999). It has been suggested (Brenner et al., Curr. Op. Struct. Biol., 7(3):369-376 (1997)) that there are a limited number of folds in a given polypeptide or protein and that once a critical number of structures have been resolved, structural prediction will become dramatically more accurate.

Additional methods of predicting secondary structure include "threading" (Jones, D., Curr. Opin. Struct. Biol., 7(3):377-87 (1997); Sippl et al., Structure, 4(1):15-19 (1996)), "profile analysis" (Bowie et al., Science, 253:164-170 (1991); Gribskov et al., Meth. Enzym., 183:146-159 (1990); Gribskov et al., Proc. Nat. Acad. Sci., 84(13):4355-4358 (1987)), and "evolutionary linkage" (See Holm, supra (1999), and Brenner, supra (1997)). In certain embodiments, variants of antibodies include glycosylation variants wherein the number and/or type of glycosylation site has been altered compared to the amino acid sequences of a parent polypeptide. In certain embodiments, variants comprise a greater or a lesser number of N-linked glycosylation sites than the native protein. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional antibody variants include cysteine variants wherein one or more cysteine residues are deleted from or substituted for another amino acid (e.g., serine) as compared to the parent amino acid sequence. Cysteine variants may be useful when antibodies must be refolded into a biologically active conformation such as after the isolation of insoluble inclusion bodies. Cysteine variants generally have fewer cysteine residues than the native protein, and typically have an even number to minimize interactions resulting from unpaired cysteines.

Desired amino acid substitutions (whether conservative or non-conservative) can be determined by those skilled in the art at the time such substitutions are desired. In certain embodiments, amino acid substitutions can be used to identify important residues of antibodies to mesothelin, or to increase or decrease the affinity of the antibodies to mesothelin described herein.

According to certain embodiments, preferred amino acid substitutions are those which: (1) reduce susceptibility to proteolysis, (2) reduce susceptibility to oxidation, (3) alter binding affinity for forming protein complexes, (4) alter binding affinities, and/or (4) confer or modify other physiochemical or functional properties on such polypeptides. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts). In certain embodiments, a conservative amino acid substitution typically may not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

In certain embodiments, antibodies of the invention may be chemically bonded with polymers, lipids, or other moieties.

The antigen binding proteins may comprise at least one of the CDRs described herein incorporated into a biocompatible framework structure. In one example, the biocompatible framework structure comprises a polypeptide or portion thereof that is sufficient to form a conformationally stable structural support, or framework, or scaffold, which is able to display one or more sequences of amino acids that bind to an antigen (e.g., CDRs, a variable region, etc.) in a localized surface region. Such structures can be a naturally occurring polypeptide or polypeptide "fold" (a structural motif), or can have one or more modifications, such as additions, deletions or substitutions of amino acids, relative to a naturally occurring polypeptide or fold. These scaffolds can be derived from a polypeptide of any species (or of more than one species), such as a human, other mammal, other vertebrate, invertebrate, plant, bacteria or virus.

Typically the biocompatible framework structures are based on protein scaffolds or skeletons other than immunoglobulin domains. For example, those based on fibronectin, ankyrin, lipocalin, neocarzinostain, cytochrome b, CP1 zinc finger, PST1, coiled coil, LACI-D1, Z domain and tendamistat domains may be used (See e.g., Nygren and Uhlen, 1997, Current Opinion in Structural Biology, 7, 463-469).

Additionally, one skilled in the art will recognize that suitable binding agents include portions of these antibodies, such as one or more of heavy chain CDR1, CDR2, CDR3, light chain CDR1, CDR2 and CDR3 as specifically disclosed herein. At least one of the regions of heavy chain CDR1, CDR2, CDR3, CDR1, CDR2 and CDR3 may have at least one amino acid substitution, provided that the antibody or antigen binding protein retains the binding specificity of the non-substituted CDR. The non-CDR portion of the antibody or antigen binding protein may be a non-protein molecule. The non-CDR portion of the antibody or antigen binding protein may be composed of amino acids, wherein the antibody or antigen binding protein is a recombinant binding protein or a synthetic peptide.

Nucleic Acids

In one aspect, the present invention provides isolated nucleic acid molecules that encode the antigen binding proteins of the present invention. In addition, provided are vectors comprising the nucleic acids, cell comprising the nucleic acids, and methods of making the antigen binding proteins of the invention. The nucleic acids comprise, for example, polynucleotides that encode all or part of an antigen binding protein, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) may be isolated from B-cells of mice that have been immunized with mesothelin antigen. The nucleic acid may be isolated by conventional procedures such as polymerase chain reaction (PCR).

Nucleic acid sequences encoding the variable regions of the heavy and light chain variable regions are shown above. The skilled artisan will appreciate that, due to the degeneracy of the genetic code, each of the polypeptide sequences disclosed herein is encoded by a large number of other nucleic acid sequences. The present invention provides each degenerate nucleotide sequence encoding each antigen binding protein of the invention.

The invention further provides nucleic acids that hybridize to other nucleic acids (e.g., nucleic acids comprising a nucleotide sequence of any of A1-A14) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, for example, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA. Changes can be introduced by mutation into a nucleic acid, thereby leading to changes in the amino acid sequence of a polypeptide (e.g., an antigen binding protein) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property.

Mutations can be introduced into a nucleic acid without significantly altering the biological activity of a polypeptide that it encodes. For example, one can make nucleotide substitutions leading to amino acid substitutions at non-essential amino acid residues. In one embodiment, a nucleotide sequence provided herein for of the antibodies of the present invention, or a desired fragment, variant, or derivative thereof, is mutated such that it encodes an amino acid sequence comprising one or more deletions or substitutions of amino acid residues that are shown herein for the light chains of the antibodies of the present invention or the heavy chains of the antibodies of the present invention to be residues where two or more sequences differ. In another embodiment, the mutagenesis inserts an amino acid adjacent to one or more amino acid residues shown herein for the light chains of the antibodies of the present invention or the heavy chains of the antibodies of the present invention to be residues where two or more sequences differ. Alternatively, one or more mutations can be introduced into a nucleic acid that selectively change the biological activity. (e.g., binding to mesothelin) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antigen binding protein.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., a mesothelin binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell or eukaryotic cell. Prokaryotic host cells include gram negative or gram positive organisms, for example *E. coli* or bacilli. Higher eukaryotic cells include insect cells, yeast cells, and established cell lines of mammalian origin. Examples of suitable mammalian host cell lines include Chinese hamster ovary (CHO) cells or their derivatives such as Veggie CHO and related cell lines which grow in serum-free media (see Rasmussen et al., 1998, Cytotechnology 28:31) or CHO strain DXB-11, which is deficient in DHFR (see Urlaub et al., 1980, Proc. Natl. Acad. Sci. USA 77:4216-20). Additional CHO cell lines include CHO-K1 (ATCC #CCL-61), EM9 (ATCC #CRL-1861), and UV20 (ATCC #CRL-1862). Additional host cells include the COS-7 line of monkey kidney cells (ATCC CRL 1651) (see Gluzman et al., 1981, Cell 23:175), L cells, C127 cells, 3T3 cells (ATCC CCL 163), AM-1/D cells (described in U.S. Pat. No. 6,210,924), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Appropriate cloning and expression vectors for use with bacterial, fungal, yeast, and mammalian cellular hosts are described by Pouwels et al. (Cloning Vectors: A Laboratory Manual, Elsevier, New York, 1985).

Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Additional selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

The transformed cells can be cultured under conditions that promote expression of the polypeptide, and the polypeptide recovered by conventional protein purification procedures. Polypeptides contemplated for use herein include substantially homogeneous recombinant mammalian anti-mesothelin antibody or antigen binding polypeptides substantially free of contaminating endogenous materials.

Cells containing the nucleic acid encoding the antigen binding proteins of the present invention also include hybridomas. The production and culturing of hybridomas are discussed in the antibody section above.

Antigen Binding Protein and Antibody Production

The antigen binding proteins and antibodies of the invention can be produced by any method known in the art for the synthesis of antibodies, in particular, by chemical synthesis or preferably, by recombinant expression techniques.

Recombinant expression of an antigen binding protein or antibody of the invention, or fragment, derivative or analog thereof, (e.g., a heavy or light chain of an antibody of the invention or a single chain antibody of the invention), requires construction of an expression vector containing a polynucleotide that encodes the antigen binding protein or antibody or a fragment of the antibody or antigen binding protein. Once a polynucleotide encoding an antibody or antigen binding protein has been obtained, the vector for the production of the antibody or antigen binding protein may be produced by recombinant DNA technology. An expression vector is constructed containing antibody or antigen binding protein coding sequences and appropriate transcriptional and translational control signals. These methods include, for example, in vitro recombinant DNA techniques, synthetic techniques, and in vivo genetic recombination.

The expression vector is transferred to a host cell by conventional techniques and the transfected cells are then cultured by conventional techniques to produce an antibody or antigen binding protein of the invention. In one aspect of the invention, vectors encoding both the heavy and light chains may be co-expressed in the host cell for expression of the entire immunoglobulin molecule, as detailed below.

A variety of host-expression vector systems may be utilized to express the antibody or antigen binding protein of the invention as described above. Such host-expression systems represent vehicles by which the coding sequences of interest may be produced and subsequently purified, but also represent cells which may, when transformed or transfected with the appropriate nucleotide coding sequences, express an antibody or antigen binding protein of the invention in situ. Bacterial cells such as *E. coli*, and eukaryotic cells are commonly used for the expression of a recombinant antibody or antigen binding protein, especially for the expression of whole recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, COS, 293, 3T3, or myeloma cells.

For long-term, high-yield production of recombinant proteins, stable expression is preferred. For example, cell lines which stably express the antibody or antigen binding protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody or antigen binding protein. Such engineered cell lines may be particularly useful in screening and evaluation of compounds that interact directly or indirectly with the antibody or antigen binding protein.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk, hgprt or aprt-cells, respectively. Also, antimetabolite resistance can be used as the basis of selection for the following genes: dhfr, which confers resistance to methotrexate (Wigler et al., Proc. Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Wu and Wu, Biotherapy 3:87-95 (1991)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds), Current Protocols in Human Genetics, John Wiley & Sons, N Y (1994); Colberre-Garapin et al., J. Mol. Biol. 150:1 (1981), which are incorporated by reference herein in their entireties.

The expression levels of an antibody or antigen binding protein can be increased by vector amplification (for a review, see Bebbington and Hentschel, "The use of vectors based on gene amplification for the expression of cloned genes in mammalian cells" (DNA Cloning, Vol. 3. Academic Press, New York, 1987)). When a marker in the vector system expressing antibody or antigen binding protein is amplifiable, increase in the level of inhibitor present in culture of host cell will increase the number of copies of the marker gene. Since the amplified region is associated with the antibody gene, production of the antibody or antigen binding protein will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody or antigen binding protein of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and size-exclusion chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide. Fused or conjugated antibodies of the present invention may be used for ease in purification. See e.g., Harbor et al., supra, and PCT publication WO 93/21232; EP 439,095; Naramura et al., Immunol. Lett. 39:91-99 (1994); U.S. Pat. No. 5,474,981; Gillies et al., Proc. Natl. Acad. Sci. 89:1428-1432 (1992); Fell et al., J. Immunol. 146:2446-2452 (1991).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

Binding to Mesothelin

In one embodiment, the present invention provides antigen binding proteins that compete for binding with a reference antibody or antigen binding protein, wherein the reference antibody or antigen binding protein comprises a combination of light chain and heavy chain variable domain sequences selected from the sequences provided herein. In another embodiment, the present invention provides human antibodies or antigen binding proteins that cross-compete for binding with a reference antibody, wherein the reference antibody is Ab237, Ab1.1.2, Ab1.33.1, Ab1.68.1, Ab1.78.1, Ab1.119.1, or Ab2.69.2. The ability to cross-compete with an antibody can be determined using any suitable assay, with nonlimiting examples further described below.

Epitope

As described herein, an epitope is the portion of a molecule that is bound by an antigen binding protein (e.g., an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antibody or antigen binding protein). Further, an epitope can comprise or consist of simply a linear, contiguous polypeptide sequence. In determining binding of an antigen binding protein to a target molecule, one skilled in the art can, for example, determine if the antigen binding protein competes for the same epitope as compared to another antigen binding protein or, e.g., the known ligand or receptor of the target molecule.

The term "compete" or "cross-compete" when used in the context of antigen binding proteins (e.g., neutralizing antigen binding proteins or neutralizing antigen binding proteins or non-neutralizing antigen binding proteins) that compete for the same epitope means competition between antigen binding proteins as determined by an assay in which the antigen binding protein (e.g., antibody or immunologically functional fragment thereof) being tested prevents or inhibits (e.g., reduces) specific binding of a reference antigen binding protein (e.g., a ligand, or a reference antibody) to a common antigen (e.g., PCSK9 or a fragment thereof).

Numerous competition assays are well known in the art, with nonlimiting examples being competition ELISA, use of the BiaCore® platform, the Kinexa® platform, or the like. Further examples include: solid phase direct or indirect radioimmunoassay (MA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antigen binding protein and a labeled reference antigen binding protein. Competitive inhibition is measured by determining the amount of label bound to the solid surface or cells in the presence of the test antigen binding protein. Usually the test antigen binding protein is present in excess. Antigen binding proteins identified by competition assay (competing antigen binding proteins) include antigen binding proteins binding to the same epitope as the reference antigen binding proteins and antigen binding proteins binding to an adjacent epitope sufficiently proximal to the epitope bound by the reference antigen binding protein for steric hindrance to occur. Usually, when a competing antigen binding protein is present in excess, it will inhibit (e.g., reduce) specific binding of a reference antigen binding protein to a target antigen by at least 40-45%, 45-50%, 50-55%, 55-60%, 60-65%, 65-70%, 70-75% or 75% or more. In some embodiments, binding is inhibited by at least 40%, 45%, 50%, 55%, 60%, 65%, 70%, 75%, 80%, 85%, 90%, or 95%. In some embodiments, binding is inhibited by at least 80-85%, 85-90%, 90-95%, 95-97%, or 97% or more.

Accordingly, the invention provides anti-human mesothelin antibodies that compete for binding with the antibodies of the invention. In one embodiment, the invention provides for antibodies that compete for binding with Ab237. In one embodiment, the invention provides for antibodies that compete for binding with Ab1.1.2. In one embodiment, the invention provides for antibodies that compete for binding with Ab1.33.1. In one embodiment, the invention provides for antibodies that compete for binding with Ab1.33.1y. In one embodiment, the invention provides for antibodies that compete for binding with Ab1.68.1. In one embodiment, the invention provides for antibodies that compete for binding with Ab1.78.1. In one embodiment, the invention provides for antibodies that compete for binding with Ab1.119.1. In one embodiment, the invention provides for antibodies that compete for binding with Ab2.69.2. In one embodiment, the invention provides for antibodies that compete for binding with Ab2.69.2cv. In one embodiment, the invention provides for antibodies that compete for binding with Ab2.69.2s. In one embodiment, the invention provides for antibodies that compete for binding with Ab1.58. In one embodiment, the invention provides for antibodies that compete for binding with Ab1.51.

Activity of Antigen Binding Proteins

In certain embodiments, the present invention provides antigen binding proteins, in particular human, humanized, or chimeric antibodies, that specifically bind to human mesothelin. In another embodiment, the present invention provides antigen binding proteins that specifically bind to cynomologous mesothelin. In another embodiment, the present invention provides antigen binding proteins that specifically bind to murine mesothelin. In another embodiment, the present invention provides antigen binding proteins that specifically bind to rat mesothelin. In another embodiment, the present invention provides antigen binding proteins that specifically bind to human, cynomologous, murine and rat mesothelin. In another embodiment, the present invention provides antigen binding proteins that specifically bind to human, cynomologous and murine mesothelin. In another embodiment, the present invention provides antigen binding proteins that specifically bind to human and cynomologous mesothelin. In another embodiment, the present invention provides antigen binding proteins that specifically bind to human and murine mesothelin. In another embodiment, the present invention provides antigen binding proteins that specifically bind to human and rat mesothelin. Such antibodies include antagonizing or neutralizing antibodies.

In certain embodiments, the antigen binding proteins of the invention, such as the human antibodies of the present invention have an IC50 value of 90 nM or less, in another embodiment, an IC50 value of 80 nM or less, in another embodiment, 70 nM or less, in another embodiment, 60 nM or less, in another embodiment, 50 nM or less, in another embodiment, 40 nM or less, in another embodiment, 30 nM or less, in another embodiment 25 nM or less.

In certain embodiments, the antigen binding proteins of the invention do not interernalize into the cell that expresses MSLN upon binding to MSLN. This is an advantageous and unexpected property, as in certain embodiments it is desirable to keep the antigen binding protein exposed at the cell surface. For example, for effector cell mediated killing of the cell expressing MSLN (e.g., ADCC), it is desirable to maintain the antigen binding protein at the cell surface so that effector cells can bind to, e.g., the Fc region of an antigen binding protein. In another nonlimiting example such as a bispecific single chain antibody that binds to MSLN and CD3, it is desirable to maintain this antibody at the cell surface so that the CD3 expressing effector cells can efficiently be brought into proximity of the MSLN expressing target cell. Determining whether an antigen binding protein of the invention internalizes or not can be readily determined using assays well known in the art.

In certain embodiments, the antigen binding proteins of the invention do not inhibit or interfere with the MSLN/CA125 interaction. Although the significance of the MSLN and CA125 interaction has not been fully elucidated, as described herein, it is known that this interaction plays a role in cell adhesion and may also play a role in tumor metastasis. Analysis of the MSLN/CA125 interaction can be readily determined using assays well known in the art. Nonlimiting examples include using competition assays described herein. In some embodiments the antigen binding proteins of the invention inhibit or interfere with the MSLN/CA125 interaction by less than about 1%, 2%, 3%, 4%, 5%, 10%, 15%, or 20%. In some embodiments, the antigen binding proteins of the invention inhibit or interfere with the MSLN/CA125 interaction by less than about 0.1% to about 1%, less than about 1% to about 5%, less than about 1% to about 10%, less than about 1% to about 15% or less than about 1% to about 20%.

In certain embodiments, the antibody or antigen binding proteins of the invention specifically bind to MSLN have a dissociation constant or $K_d$ ($k_{of}/k_{on}$) of less than $10^{-2}$M, less than 5e$10^{-2}$M, less than $10^{-3}$M, less than 5e$10^{-3}$M, less than $10^{-4}$ M, less than 5e$10^{-4}$ M, less than $10^{-5}$M, less than 5e$10^{-5}$M, less than $10^{-6}$M, less than 5e$10^{-6}$M, less than $10^{-7}$M, less than 5e$10^{-7}$M, less than $10^{-8}$ M, less than 5e$10^{-9}$ M, less than $10^{-9}$M, less than 5e$10^{-9}$M, less than $10^{-10}$M, less than 5e$10^{-10}$M, less than $10^{-11}$ M, less than 5e$10^{-11}$ M, less than $10^{-12}$M, less than 5e$10^{-12}$ M, less than $10^{-13}$M, less than 5e$10^{-3}$M, less than $10^{-14}$M, less than 5e$10^{-14}$M, less than $10^{-5}$M, or less than 5e$10^{-15}$M. In a further embodiment, an ADC that specifically binds to least on Eph receptor has a dissociation constant or K.sub.d (k.sub.off/k.sub.on) of less than about $10^{-2}$M, less than about 5e$10^{-2}$M, less than about $10^{-3}$M, less than about 5e$10^{-3}$M, less than about $10^{-4}$M, less than about 5e$10^{-4}$ M, less than about $10^{-5}$M, less than about 5e$10^{-5}$M, less than about $10^{-6}$M, less than about 5e$10^{-6}$M, less than about $10^{-7}$M, less than about 5e$10^{-7}$M, less than about $10^{-8}$ M, less than about 5e$10^{-8}$ M, less than about $10^{-9}$M, less than about 5e$10^{-9}$M, less than about $10^{-10}$M, less than about 5e$10^{-10}$M, less than about $10^{-11}$ M, less than about 5e$10^{-11}$ M, less than about $10^{-12}$ M, less than about 5e$10^{-12}$ M, less than about $10^{-13}$M, less than about 5e$10^{-13}$M, less than about $10^{-14}$M, less than about 5e$10^{-14}$M, less than about $10^{-15}$M, or less than about 5e$10^{-15}$M.

In another embodiment, an antibody or antigen binding protein that specifically binds to MSLN has a $K_d$ of greater than $10^{-9}$ M, greater than 5e$10^{-9}$ M, greater than $10^{-10}$ M, greater than 5e$10^{-10}$ M, greater than $10^{-11}$ M, greater than 5e$10^{-11}$ M, greater than $10^{-12}$ M, greater than 5e$10^{-12}$ M, greater than $10^{-13}$ M, greater than 5e$10^{-3}$ M, greater than $10^{-14}$ M, greater than 5e$10^{-14}$ M or greater than $10^{-14}$ M. In another embodiment, an antibody or antigen binding protein that specifically binds to MSLN has a $K_d$ of greater than about $10^{-9}$ M, greater than about 5e$10^{-9}$ M, greater than about $10^{-10}$ M, greater than about 5e$10^{-11}$ M, greater than about $10^{-11}$ M, greater than about 5e$10^{-11}$ M, greater than about $10^{-12}$ M, greater than about 5e$10^{-12}$ M, greater than about $10^{-13}$ M, greater than about 5e$10^{-13}$ M, greater than about $10^{-14}$ M, greater than about 5e$10^{-14}$ M or greater than about $10^{-14}$ M.

In a further embodiment, an antibody or antigen binding protein that specifically binds to MSLN has a $K_d$ of between about $10^{-9}$ M and about $10^{-14}$ M, between about $10^{-9}$ M and about $10^{-13}$ M, between about $10^{-9}$ M and about $10^{-12}$ M, between about $10^{-9}$ M and about $10^{-11}$ M, or between about $10^{-9}$ M and about $10^{-10}$ M. In a further embodiment, an antibody or antigen binding protein that specifically binds to MSLN has a $K_d$ of between about $10^{-9}$ M and about $10^{-14}$ M, between about $10^{-10}$ M and about $10^{-14}$ M, between about $10^{-11}$ M and about $10^{-14}$ M, between about $10^{-12}$ M and about $10^{-14}$ M, or between about $10^{-13}$ M and about $10^{-14}$ M. In a further embodiment, an antibody or antigen binding protein that specifically binds to MSLN has a $K_d$ of between $10^{-9}$ M and $10^{-14}$ M, between $10^{-9}$ M and $10^{-13}$ M, between $10^{-9}$ M and $10^{-12}$ M, between $10^{-9}$ M and $10^{-11}$ M, or between $10^{-9}$ M and $10^{-10}$ M. In a further embodiment, an antibody or antigen binding protein that specifically binds to MSLN has a $K_d$ of between $10^{-9}$ M and $10^{-14}$ M, between $10^{-10}$ M and $10^{-14}$ M, between $10^{-11}$ M and $10^{-14}$ M, between $10^{-12}$ M and $10^{-14}$ M, or between $10^{-13}$ M and $10^{-14}$ M.

$K_d$ for the antigen binding proteins of the invention can be readily determined by assays well known in the art. Nonlimiting examples include the BIAcore® platform or the Kinexa® platform as described herein.

In certain embodiments, the antigen binding proteins of the invention preferentially bind membrane bound MSLN over soluble MSLN. Membrane bound MSLN refers to the presence of MSLN in or on the cell membrane surface of a cell that expresses MSLN. Soluble MSLN refers to MSLN that is no longer on in or on the cell membrane surface of a cell that expresses or expressed MSLN. In certain instances, the soluble MSLN is present in the blood and/or lymphatic circulation in a subject. In one embodiment, the antigen binding proteins bind membrane-bound mesothelin at least 5 fold, 10 fold, 15 fold, 20 fold, 25 fold, 30 fold, 40 fold, 50 fold, 100 fold, 500 fold, or 1000 fold greater than soluble mesothelin. In one embodiment, the antigen binding proteins of the present invention preferentially bind membrane-bound mesothelin 30 fold greater than soluble mesothelin. Determining the preferential binding of an antigen binding protein to membrane bound MSLN over soluble MSLN can be readily determined using assays well known in the art. Nonlimiting examples are competition assays as described herein.

In certain embodiments, the antigen binding molecules of the invention reduces the growth of tumor cells in vivo when administered to a subject who has tumor cells that express MSLN. Measurement of the reduction of the growth of tumor cells can be determined by multiple different methodologies well known in the art. Nonlimiting examples include direct measurement of tumor dimension, measurement of excised tumor mass and comparison to control subjects, measurement via imaging techniques (e.g. CT or MRI) that may or may not use isotopes or luminescent molecules (e.g. luciferase) for enhanced analysis, and the like. In specific embodiments, administration of the antigen binding agents of the invention results in a reduction of in vivo growth of tumor cells as compared to a control antigen binding agent by at least about 10%, 20%, 30%, 40%, 50%, 60%, 70%, 80%, 90% or 100%, with an about 100% reduction in tumor growth indicating a complete response and disappearance of the tumor. In further embodiments, administration of the antigen binding agents of the invention results in a reduction of in vivo growth of tumor cells as compared to a control antigen binding agent by about 50-100%, about 75-100% or about 90-100%. In further embodiments, administration of the antigen binding agents of the invention results in a reduction of in vivo growth of tumor cells as compared to a control antigen binding agent by about 50-60%, about 60-70%, about 70-80%, about 80-90%, or about 90-100%. Dosing can readily be determined by one skilled in the art and is discussed further herein.

Antibody or Antigen Binding Protein Effector Function

The present invention provides anti-mesothelin binding molecules with increased effector function. Nonlimiting examples of methods for increasing effector function can be found in U.S. Pat. Nos. 5,624,821, 6,602,684, 7,029,872, U.S. Patent Application Publication Nos. 2006/0067930A1, 2005/0272128A1, 2005/0079605A1, 2005/0123546A1, 2004/0072290A1, 2006/0257399A1, 2004/0261148A1, 2007/0092521, 2006/0040325A1, and 2006/0039904A1, and International Patent Application Publication Nos. WO 04/029207, WO03011878, WO05044859, WO 06071856, and WO 06071280.

Methods of engineering Fc regions of antibodies so as to alter effector functions are known in the art (e.g., U.S. Patent Publication No. 20040185045 and PCT Publication No. WO 2004/016750, both to Koenig et al., which describe altering the Fc region to enhance the binding affinity for Fc gamma RIIB as compared with the binding affinity for FC gamma RIIA; see, also, PCT Publication Nos. WO 99/58572 to Armour et al., WO 99/51642 to Idusogie et al., and U.S. Pat. No. 6,395,272 to Deo et al.). Methods of modifying the Fc region to decrease binding affinity to Fc gamma RIIB are also known in the art (e.g., U.S. Patent Publication No. 20010036459 and PCT Publication No. WO 01/79299, both to Ravetch et al.). Modified antibodies having variant Fc regions with enhanced binding affinity for Fc gamma RIIIA and/or Fc gamma RIIA as compared with a wildtype Fc region have also been described (e.g., PCT Publication Nos. WO 2004/063351, to Stavenhagen et al., the disclosure of which is incorporated herein in its entirety). Throughout the specification, and in particular the examples, the terms "2X" and "3X" in reference to the anti-MSLN antibodies are used. These terms refer to substitutions in the Fc region that result in enhanced ADCC through increased binding affinity to the Fc receptor as described above. In one embodiment, the "2X" molecule has the following substitutions: S239D/I332E and the "3X" molecule has the following mutations: S239D/I332E/A330L.

Antibody or antigen binding protein effector function may also be modified through the generation of antibodies with altered glycosylation patterns. In the present invention, such antibodies may be referred to as "low fucose" antibodies. For example, an antibody or antigen binding protein can be made that has an altered type of glycosylation, such as an afucosylated/hypofucosylated antibody or antigen binding protein having reduced amounts of fucosyl residues or an antibody or antigen binding protein having increased bisecting GlcNac structures. Such altered glycosylation patterns have been demonstrated to increase the ADCC ability of antibodies. Such carbohydrate modifications can be accomplished by, for example, expressing the antibody or antigen binding protein in a host cell with altered glycosylation machinery. Cells with altered glycosylation machinery have been described in the art and can be used as host cells in which to express recombinant antibodies of the invention to thereby produce an antibody or antigen binding protein with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180). PCT Publication WO 2009009086 by Collingwood et al. describes the use of zinc finger constructs to inactivate the FUT8 gene in cells.

Methods for generating antibodies with altered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003; J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); and GlycoMAb™ glycosylation engineering technology (GLYCART biotechnology AG, Zurich, Switzerland). See, e.g., WO 00061739; EA01229125; US 20030115614; Okazaki et al., 2004, JMB, 336: 1239-49. It is contemplated that antibodies with altered fucosylation pattern may also be prepared by post-translational removal of fucose (e.g. with a fucosidase enzyme).

Half-Life

The present invention provides for antibodies or antigen binding protein or fragments thereof that specifically bind to mesothelin which have an extended half-life in vivo. In particular, the present invention provides antibodies or antigen binding protein or fragments thereof which have a half-life in a mammal (for example, but not limited to, a human), of greater than 3 days, greater than 7 days, greater than 10 days, greater than 15 days, greater than 25 days, greater than 30 days, greater than 35 days, greater than 40 days, greater than 45 days, greater than 2 months, greater than 3 months, greater than 4 months, or greater than 5 months.

To prolong the serum circulation of antibodies (for example, but not limited to, monoclonal antibodies and single chain antibodies) or antigen binding protein or fragments thereof (for example, but not limited to, Fab fragments) in vivo, for example, inert polymer molecules such as high molecular weight polyethyleneglycol (PEG) can be attached to the antibodies or antigen binding proteins (including fragments thereof) with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody—or antigen binding proteins—PEG conjugates by size-exclusion or by ion-exchange chromatography. PEG-derivatized antibodies or antigen binding proteins (including fragments thereof) can be tested for binding activity as well as for in vivo efficacy using methods known to those of skill in the art, for example, by immunoassays described herein.

Antibodies having an increased half-life in vivo can also be generated by introducing one or more amino acid modifications (i.e., substitutions, insertions or deletions) into an IgG constant domain, or FcRn binding fragment thereof (e.g., Fc or hinge Fc domain fragment). See, e.g., International Publication No. WO 98/23289; International Publication No. WO 97/34631; and U.S. Pat. No. 6,277,375, each of which is incorporated herein by reference in its entirety.

Conjugates

According to certain aspects of the invention, therapeutic agents or toxins can be conjugated to chimerized, human, or humanized anti-mesothelin antibodies for use in the compositions and methods of the invention. In certain embodiments, these conjugates can be generated as fusion proteins. Examples of therapeutic agents and toxins include, but are not limited to, members of the enediyne family of molecules, such as calicheamicin and esperamicin. Chemical toxins can also be taken from the group consisting of duocarmycin (see, e.g., U.S. Pat. Nos. 5,703,080 and 4,923,990), methotrexate, doxorubicin, melphalan, chlorambucil, ARA-C, vindesine, mitomycin C, cis-platinum, etoposide, bleomycin and 5-fluorouracil. Examples of chemotherapeutic agents also include Adriamycin, Doxorubicin, 5-Fluorouracil, Cytosine arabinoside (Ara-C), Cyclophosphamide, Thiotepa, Taxotere (docetaxel), Busulfan, Cytoxin, Taxol, Methotrexate, Cisplatin, Melphalan, Vinblastine, Bleomycin, Etoposide, Ifosfamide, Mitomycin C, Mitoxantrone, Vincreistine, Vinorelbine, Carboplatin, Teniposide, Daunomycin, Caminomycin, Aminopterin, Dactinomycin, Mitomycins, Esperamicins (see, U.S. Pat. No. 4,675,187), Melphalan, and other related nitrogen mustards.

Other toxins that can be used in the immunoconjugates of the invention include poisonous lectins, plant toxins such as ricin, abrin, modeccin, botulina, and diphtheria toxins. Combinations of the various toxins could also be coupled to one antibody or antigen binding protein thereby accommodating variable cytotoxicity. Nonlimiting examples of toxins which are suitably employed in the combination therapies of the invention are ricin, abrin, ribonuclease, DNase I, Staphylococcal enterotoxin-A, pokeweed anti-viral protein, gelonin, diphtherin toxin, *Pseudomonas* exotoxin, and *Pseudomonas* endotoxin. See, for example, Pastan et al., Cell, 47:641 (1986), and Goldenberg et al., Cancer Journal for Clinicians, 44:43 (1994). Enzymatically active toxins and fragments thereof which can be used include diphtheria A chain, non-binding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin and the tricothecenes. See, for example, WO 93/21232 published Oct. 28, 1993. Suitable toxins and chemotherapeutic agents are described in Remington's Pharmaceutical Sciences, 19th Ed. (Mack Publishing Co. 1995), and in Goodman And Gilman's The Pharmacological Basis of Therapeutics, 7th Ed. (MacMillan Publishing Co. 1985). Other suitable toxins and/or chemotherapeutic agents are known to those of skill in the art.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as beta-galactosidase and neuraminidase useful for converting glycosylated prodrugs into free drugs; beta-lactamase useful for converting drugs derivatized with alpha-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes," can be used to convert the prodrugs of the invention into free active drugs (see, e.g., Massey, Nature 328:457-458 (1987)). Antibody-abzyme conjugates can be prepared as described herein for delivery of the abzyme as desired to portions of a human affected by a B cell malignancy.

The enzymes can be covalently bound to the antibodies of the present invention by techniques well-known in the art such as the use of the heterobifunctional crosslinking reagents discussed above. Alternatively, fusion proteins comprising at least the antigen-binding region of an antibody of the invention linked to at least a functionally active portion of an enzyme of the invention can be constructed using recombinant DNA techniques well-known in the art (see, e.g., Neuberger et al., Nature, 312:604-608 (1984)).

Covalent modifications of the anti-mesothelin antibody or antigen binding proteins of the invention are included within the scope of this invention. They may be made by chemical synthesis or by enzymatic or chemical cleavage of the antibody or antigen binding proteins, if applicable. Other types of covalent modifications of the anti-mesothelin antibody or antigen binding proteins are introduced into the molecule by reacting targeted amino acid residues of the antibody or antigen binding proteins with an organic derivatizing agent that is capable of reacting with selected side chains or the N- or C-terminal residues.

Cysteinyl residues most commonly are reacted with alpha-haloacetates (and corresponding amines), such as chloroacetic acid or chloroacetamide, to give carboxymethyl or carboxyamidomethyl derivatives. Similarly, iodo-reagents may also be used. Cysteinyl residues also are derivatized by reaction with bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysyl and amino-terminal residues are reacted with succinic or other carboxylic acid anhydrides. Derivatization with these agents has the effect of reversing the charge of the lysinyl residues. Other suitable reagents for derivatizing .alpha.-amino-containing residues and/or e-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginyl residues generally requires that the reaction be performed in alkaline conditions because of the high pKa of the guanidine functional group. Furthermore, these reagents may react with the epsilon-amino groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $I^{125}$ or $I^{131}$ to prepare labeled proteins for use in radioimmunoassay.

Carboxyl side groups (aspartyl or glutamyl) are selectively modified by reaction with carbodiimides (R—N═C═N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the .alpha.-amino groups of lysine, arginine, and histidine side chains (T. E. Creighton, Proteins: Structure and Molecular Properties, W.H. Freeman & Co., San Francisco, pp. 79-86 (1983)), acetylation of the N-terminal amine, and amidation of any C-terminal carboxyl group.

Another type of covalent modification involves chemically or enzymatically coupling glycosides to the antibody or antigen binding proteins. These procedures are advantageous in that they do not require production of the antibody or antigen binding proteins in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, CRC Crit. Rev. Biochem., pp. 259-306 (1981).

Methods of Treatment

In another aspect, a method of treating a subject, comprising administering a therapeutic dosage of the antigen binding proteins of the present invention is provided. In one embodiment, the antigen binding proteins are human antibodies. As used herein the term "subject" refers to a mammal, including humans, and is used interchangeably with the term "patient". The human antibodies, can be used to treat, control or prevent a disorder or condition characterized by cells expressing or overexpressing mesothelin in a subject. These disorders include cancer and other hyperproliferative disorders characterized by expression or overexpression of mesothelin.

Cancers and related disorders that can be treated, prevented, or managed by methods and compositions of the present invention include but are not limited to cancers of an epithelial cell origin. Examples of such cancers include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

Accordingly, the methods and compositions of the invention are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the skin, lung, colon, breast, prostate, bladder, kidney, pancreas, ovary, or uterus. In other specific embodiments, sarcoma, melanoma, or leukemia is treated or prevented.

In some embodiments, the cancer is malignant and overexpresses mesothelin. In other embodiments, the disorder to be treated is a pre-cancerous condition associated with cells that overexpress mesothelin.

The term "treatment" encompasses alleviation or prevention of at least one symptom or other aspect of a disorder, or reduction of disease severity, and the like. An antigen binding protein, in particular a human antibody according to the present invention, need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an antigen binding protein such as a human antibody in an amount and for a time sufficient to induce a sustained improvement over baseline of an indicator that reflects the severity of the particular disorder.

As is understood in the pertinent field, pharmaceutical compositions comprising the antigen binding proteins of the invention are administered to a subject in a manner appropriate to the indication and the composition. In one embodiment, pharmaceutical compositions comprise the human antibodies of the present invention. Pharmaceutical compositions may be administered by any suitable technique, including but not limited to parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Delivery by inhalation includes, for example, nasal or oral inhalation, use of a nebulizer, inhalation of the antigen binding protein in aerosol form, and the like. Other alternatives include oral preparations including pills, syrups, or lozenges.

Advantageously, the antigen binding proteins of the invention, are administered in the form of a composition comprising one or more additional components such as a physiologically acceptable carrier, excipient or diluent. Optionally, the composition additionally comprises one or more physiologically active agents, for example, as described below. In various particular embodiments, the composition comprises one, two, three, four, five, or six physiologically active agents in addition to one or more antigen binding proteins (e.g, human antibodies) of the present invention.

In one embodiment, the pharmaceutical composition comprises a human antibody or antigen binding protein of the invention together with one or more substances selected from the group consisting of a buffer suitable for antibodies at a suitable pH, an antioxidant such as ascorbic acid, a low molecular weight polypeptide (such as those having fewer than 10 amino acids), a protein, an amino acid, a carbohydrate such as dextrin, a chelating agent such as EDTA, glutathione, a stabilizer, and an excipient. In accordance with appropriate industry standards, preservatives may also be added. The composition may be formulated as a lyophilizate using appropriate excipient solutions as diluents. Suitable components are nontoxic to recipients at the dosages and concentrations employed. Further examples of components that may be employed in pharmaceutical formulations are presented in Remington's Pharmaceutical Sciences, 16 Ed. (1980) and 20$^{th}$ Ed. (2000), Mack Publishing Company, Easton, PA.

Kits for use by medical practitioners are provided including one or more antigen binding proteins of the invention and a label or other instructions for use in treating any of the conditions discussed herein. In one embodiment, the kit includes a sterile preparation of one or more human antibodies, which may be in the form of a composition as disclosed above, and may be in one or more vials.

Dosages and the frequency of administration may vary according to such factors as the route of administration, the particular antibodies employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

An antigen binding protein, in particular, the human antibodies, of the invention may be administered, for example, once or more than once, e.g., at regular intervals over a period of time. In particular embodiments, a human antibody or antigen binding protein is administered over a period of at least once a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the human antibody or antigen binding protein is administered until the patient manifests a medically relevant degree of improvement over baseline for the chosen indicator or indicators.

One example of therapeutic regimens provided herein comprise subcutaneous injection of an antigen binding protein such as a human antibody or antigen binding protein once a week, or once every two weeks, at an appropriate dosage, to treat a condition in which it is desired to target cells expressing mesothelin. Weekly or monthly administration of antigen binding protein would be continued until a desired result is achieved, e.g., the subject's symptoms subside. Treatment may resume as needed, or, alternatively, maintenance doses may be administered. Alternatively, various other routes of administration, such as intravenous, intraperitoneal, or intramuscular injection can be employed.

For the treatment of the disease, the appropriate dosage of the agent of the present invention depends on the type of disease to be treated, the severity and course of the disease, the responsiveness of the disease, whether the agent is administered for therapeutic or preventative purposes, previous therapy, patient's clinical history, and so on all at the discretion of the treating physician. The agent can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody or antigen binding protein or agent. The administering physician can readily determine optimum dosages, dosing methodologies and repetition rates. In certain embodiments, dosage is from 0.01 μg to 100 mg per kg of body weight, and can be given once or more daily, weekly, monthly or yearly. In certain embodiments, the agent is given once every two weeks or once every three weeks. In certain embodiments, the dosage of the agent is from about 0.1 mg to about 20 mg per kg of body weight. The treating physician can estimate repetition rates for dosing based on measured residence times and concentrations of the drug in bodily fluids or tissues.

Combination Therapies

Particular embodiments of methods and compositions of the invention involve the use of an antigen binding protein such as an anti-mesothelin antibody or antigen binding proteins of the present invention and one or more cancer therapeutics, for example. In one embodiment, antigen binding proteins of the present invention are administered alone or in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which an antigen binding protein is administered at least once during a course of treatment that involves administering at least one other therapeutic agent to the patient.

In another aspect, the present invention provides a method of treating a subject with cancer or a hyperproliferative disorder associated with the expression or overexpression of mesothelin with a therapeutic antigen binding protein of the present invention, such as the fully human therapeutic antibodies described herein, together with one or more other treatments. In one embodiment, such a combination therapy achieves a synergistic effect. The antigen binding proteins may be in combination with one or more of the following treatments currently available. Nonlimiting examples of anti-cancer agents that can be used in the various embodiments of the invention, including pharmaceutical compositions and dosage forms and kits of the invention, include: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-nl interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other examples of anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In a specific embodiment, the anti-mesothelin antibodies of the present invention are used in combination with gemcitabine.

Diagnostic Uses

In one aspect, anti-mesothelin antibodies of the invention are useful for detecting the presence of mesothelin in a biological sample. The term "detecting" as used herein encompasses quantitative or qualitative detection. In certain embodiments, a biological sample comprises a cell or tissue. In certain embodiments, such tissues include normal and/or cancerous tissues that express mesothelin at higher levels relative to other tissues.

In one aspect, the invention provides a method of detecting the presence of mesothelin in a biological sample. In certain embodiments, the method comprises contacting the biological sample with an anti-mesothelin antibody or antigen binding proteins under conditions permissive for binding of the anti-mesothelin antibody or antigen binding protein to mesothelin, and detecting whether a complex is formed between the anti-mesothelin antibody or antigen binding protein and mesothelin.

In one aspect, the invention provides a method of diagnosing a disorder associated with increased expression of mesothelin. In certain embodiments, the method comprises contacting a test cell with an anti-mesothelin antibody; determining the level of expression (either quantitatively or qualitatively) of mesothelin by the test cell by detecting binding of the anti-mesothelin antibody to mesothelin; and comparing the level of expression of mesothelin by the test cell with the level of expression of mesothelin by a control cell (e.g., a normal cell of the same tissue origin as the test cell or a cell that expresses mesothelin at levels comparable to such a normal cell), wherein a higher level of expression of mesothelin by the test cell as compared to the control cell indicates the presence of a disorder associated with increased expression of mesothelin. In certain embodiments, the test cell is obtained from an individual suspected of having a disorder associated with increased expression of mesothelin. In certain embodiments, the disorder is a cell proliferative disorder, such as a cancer or a tumor.

In certain embodiments, a method of diagnosis or detection, such as those described above, comprises detecting binding of an anti-mesothelin antibody to mesothelin expressed on the surface of a cell or in a membrane preparation obtained from a cell expressing mesothelin on its surface. In certain embodiments, the method comprises contacting a cell with an anti-mesothelin antibody under conditions permissive for binding of the anti-mesothelin antibody to mesothelin, and detecting whether a complex is formed between the anti-mesothelin antibody and mesothelin on the cell surface. An exemplary assay for detecting binding of an anti-mesothelin antibody to mesothelin expressed mesothelin on the surface of a cell is a "FACS" assay.

Certain other methods can be used to detect binding of anti-mesothelin antibodies to mesothelin. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-mesothelin antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and$^{131}$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, anti-mesothelin antibodies are immobilized on an insoluble matrix. Immobilization entails separating the anti-mesothelin antibody or antigen binding protein from any mesothelin that remains free in solution. This conventionally is accomplished by either insolubilizing the anti-mesothelin antibody or antigen binding protein before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-mesothelin antibody or antigen binding protein after formation of a complex between the anti-mesothelin antibody or antigen binding protein and mesothelin, e.g., by immunoprecipitation.

The invention having been described, the following examples are offered by way of illustration, and not limitation.

EXAMPLES

Example 1-Generation of Anti-Mesothelin Antibodies

Immunization

Fully human antibodies to human MSLN were generated by immunizing XenoMouse™ transgenic mice (Mendez et al., 1997; Kellerman and Green, 2002). Mice were immunized using routine methods. The full length mesothelin cDNA was cloned into an expression vector in frame with His and V5 antigen tags. The entire protein was expressed, but the cells subsequently cleaved the 30 kDa MPF fragment. The protein sequence comprising a.a. 1-293 of mesothelin, representing the membrane attached 40 kDa fragment, was injected into the mice.

The initial immunization was with 10 μg antigen admixed 1:1 v/v with TiterMax Gold. Subsequent boosts were made with 5 or 10 μg antigen admixed 1:1 v/v with 100 g alum gel in pyrogen-free D-PBS and sometimes with 50% TiterMax Gold, followed by three injections with 10 μg antigen admixed 1:1 v/v with 10 μg mesothelin antigen in alum gel, and then a final boost of 10 μg antigen in PBS. In particular, each mouse was immunized in the footpad by subcutaneous injection. The animals were immunized on days 0, 4, 7, 10, 14, 17, 21, 32, and 45. The animals were bled on days 13 and 20 to obtain sera for harvest selection.

Anti-mesothelin antibody titers were determined by indirect ELISA. The titer value is the reciprocal of the greatest dilution of sera with an OD reading two-fold that of background. Briefly, mesothelin (84mer; 1 μg/mL) was coated onto Costar Labcoat Universal Binding Polystyrene 96 well plates overnight at four degrees. The solution containing unbound mesothelin was removed and the plates were treated with UV light (365 nm) for 4 minutes (4000 microjoules). The plates were washed five times with dH2O. Xenomouse™ mice sera from the mesothelin immunized animals, or naïve Xenomouse™ animals, were titrated in 2% milk/PBS at 1:2 dilutions in duplicate from a 1:100 initial dilution. The last well was left blank. The plates were washed five times with dH2O. A goat anti-human IgG Fc-specific HRP-conjugated antibody was added at a final concentration of 1 ug/mL for 1 hour at room temperature. The plates were washed five times with dH2O. The plates were developed with the addition of TMB for 30 minutes and the ELISA was stopped by the addition of 1 M phosphoric acid. The specific titer of individual Xenomouse™ animals was determined from the optical density at 450 nm. Lymph nodes from all immunized Xenomouse™ animals were harvested for fusion.

Immunized mice were sacrificed by carbon dioxide asphyxiation, and the lymph nodes harvested and pooled from each cohort. The lymphoid cells were dissociated by grinding in DMEM to release the cells from the tissues and the cells were suspended in DMEM. The cells were counted, and 0.9 ml DMEM per 100 million lymphocytes added to the cell pellet to resuspend the cells gently but completely. Using 100 μl of CD90+ magnetic beads per 100 million cells, the cells were labeled by incubating the cells with the magnetic beads at 40° C. for 15 minutes. The magnetically labeled cell suspension containing up to 108 positive cells (or up to $2\times10^9$ total cells) was loaded onto a LS+ column and the column washed with DMEM. The total effluent was collected as the CD90-negative fraction (most of these cells are B cells).

P3 myeloma cells and B cell-enriched lymph node cells were combined in a ratio of 1:1 (myeloma:lymph nodes) into a 50 ml conical tube in DMEM. The combined cells were centrifuged at 800×g (2000 rpm) for 5-7 min. and the supernatant immediately removed from the resulting pellet. Two to four ml of Pronase solution (CalBiochem, Cat. #53702; 0.5 mg/ml in PBS) was added to the cells to resuspend the cell pellet gently. The enzyme treatment was allowed to proceed for no more than two minutes and the reaction stopped by the addition of 3-5 ml of FBS. Enough ECF solution was added to bring the total volume to 40 ml and the mixture was centrifuged at 800×g (2000 rpm) for 5-7 min. The supernatant was removed and the cell pellet gently resuspended with a small volume of ECF solution, followed by enough ECF solution to make a total volume of 40 ml. The cells were mixed well and counted, then centrifuged at 800×g (2000 rpm) for 5-7 min. The supernatant was removed and the cells resuspended in a small volume of ECF solution. Enough additional ECF solution was added to adjust the concentration to $2\times10^6$ cells/ml.

The cells were then placed in an Electro-Cell-Fusion (ECF) generator (Model ECM2001, Genetronic, Inc., San Diego, CA) and fused according to the manufacturer's instructions. After ECF, the cell suspensions were carefully removed from the fusion chamber under sterile conditions and transferred into a sterile tube containing the same volume of Hybridoma Medium in DMEM. The cells were incubated for 15-30 minutes at 37° C., then centrifuged at 400×g (1000 rpm) for five minutes. The cells were gently resuspended in a small volume of ½ HA medium (1 bottle of 50× HA from Sigma, Cat. #A9666 and 1 liter of Hybridoma Medium) and the volume adjusted appropriately with more ½ HA medium (based on $5\times10^6$ B cells per 96-well plate and 200 μl per well). The cells were mixed well and pipetted into 96-well plates and allowed to grow. On day 7 or 10, one-half the medium was removed, and the cells re-fed with ½ HA medium.

Screening Antibodies

1. Selection of Candidate Antibodies for ELISA.

After 14 days of culture, hybridoma supernatants were screened for mesothelin-specific monoclonal antibodies. The ELISA plates (Fisher, Cat. No. 12 565 136) were coated with 50 μl/well of mesothelin (2 μg/ml) in Coating Buffer (0.1 M Carbonate Buffer, pH 9.6, $NaHCO_3$8.4 g/L), then incubated at 4° C. overnight. After incubation, the plates were washed with Washing Buffer (0.05% Tween 20 in PBS) 3 times. 200 μl/well Blocking Buffer (0.5% BSA, 0.1% Tween 20, 0.01% Thimerosal in 1×PBS) were added and the plates incubated at room temperature for 1 hour. After incubation, the plates were washed with Washing Buffer three times. Fifty (50) μl/well of hybridoma supernatants, and positive and negative controls were added and the plates incubated at room temperature for 2 hours. The positive control used throughout was XMG2 mesothelin Group 1, fp N160-7 and the negative control was XMG2 KLH Group 1, fp L627-6. After incubation, the plates were washed three times with Washing Buffer. One hundred (100) μl/well of detection antibody goat anti-huIgGfc-HRP (Caltag, Cat. #H10507), [and goat anti-hIgK-HRP (Southern Biotechnology, Cat. #2060-05) and goat anti-hIg, (Southern Biotechnology, Cat. #2070-05) in secondary screening] were added and the plates incubated at room temperature for 1 hour. In the secondary screen, three sets of samples (positives in first screening) were screened, one set for hIgG detection, one set for hKappa detection and one set for hLambda detection. After incubation, the plates were washed three times with Washing Buffer. One hundred (100) ul/well of TMB (BioFX Lab. Cat. #TMSK-0100-01) were added and the plates allowed to develop for about 10 minutes (until negative control wells barely started to show color), then 50 ul/well stop solution (TMB Stop Solution (BioFX Lab. Cat. #STPR-0100-01) were added and the plates read on an ELISA plate reader at wavelength 450 nm.

2. FACS Analysis

To ascertain that the antibodies recognizing soluble mesothelin protein also recognized the antigen when bound to the cell surface, FACS analysis was performed on cells that express mesothelin, OvCar 8, and cells that do not express the antigen, 786-0.

Example 2—Binding Affinity of Anti-Mesothelin Antibodies

Binding affinity of the anti-MSLN antibodies of the invention was tested using assays well known in the art (Biacore® and Kinexa®) using general procedures outlined by the manufacturers. The data is summarized in FIG. 4.

The following describes binding activity as assessed by surface plasmon resonance using a BIAcore® biosensor device. Briefly, anti-human Fc (or anti-murine Fc) is covalently coupled to biosensor chips (i.e., a CM5 chip) using a standard amine coupling procedure and reagents according to the manufacturer's instructions. Test antibody or a control antibody is injected over the immobilized anti-Fc, and varying amounts of MSLN (e.g., human, murine, rat, or cyno) are independently passed over an irrelevant antibody-coupled chip (negative control) as well as an anti-MSLN-coated chip using running buffer (e.g. 0.005% P20 surfactant). Regeneration of the chip may be accomplished with one 10-microliter pulse of 100 mM phosphoric acid at 10 microliters/minute. All binding is performed in HBS (10 mM HEPES, 0.15 M NaCl, 3.4 mM EDTA, 0.02% NaN3, 0.005% surfactant P20, pH 7.4) or equivalent. Binding curves were compared qualitatively for binding signal intensity, as well as for dissociation rates. Antibody binding kinetic parameters (dissociation rate constant "kd") were determined, e.g., by using software provided by the manufacturer (e.g., BIA evaluation 3.0) that allows for global fitting calculations. The lower the dissociation equilibrium constants (expressed in pM), the greater the affinity of the antibody for MSLN.

Example 3—Mesothelin Species Cross-Reactivity of Anti-Mesothelin Antibodies

Reactivity of the antibodies of the invention against several species of mesothelin (cyno, rat, mouse) was tested using assays well known in the art. The data is summarized in FIG. 4.

FACS binding assays were performed to evaluate the binding of the anti-Mesothlelin antibodies to murine, rat and cynomologous monkey mesothelin orthologues, using recombinant forms of the various receptors transiently expressed on 293T cells. FACs assays were performed by incubating hybridoma supernatants with 10,000 to 25,000 cells in PBS/2% Fetal bovine serum/2 mM Calcium Chloride at 4° C. for one hour followed by two washes with PBS/2% Fetal bovine serum/2 mM Calcium Chloride. Cells were then treated with florochrome-labeled secondary antibodies at 4° C. followed by one wash. The cells were resuspended in 50 μl of PBS/2% FBS and antibody binding was analyzed using a FACSCalibur™ instrument.

Example 4—ELISA Cross-Competition and Binning of Anti-Mesothelin Antibodies

Cross-competition ELISA assays were performed to evaluate different "bins" of antibodies. The assays utilized techniques well known in the art. The data is summarized in FIGS. 5 and 6 and indicate that several antibodies bind to a MSLN epitope distinct from MORAb-009; and that Ab237 does not interfere with CA-125 binding while MORAb-009 does.

Certain antibodies, described herein were binned generally in accordance with the protocol described in U.S. Patent Application Publication No. 20030157730. Mouse anti-hIgG conjugated beads are prepared for coupling to primary antibody. The volume of supernatant needed is calculated using the following formula: (n+10)×50 uL (where n=total number of samples on plate). Where the concentration is known, 0.5 g/mL is used. Bead stock is gently vortexed, then diluted in supernatant to a concentration of 2500 of each bead per well or 0.5×105/mL and incubated on a shaker in the dark at RT overnight, or 2 hours if at a known concentration of 0.5 g/mL. Following aspiration, 50 μL of each bead is added to each well of filter plate, then washed once by adding 100 μL/well wash buffer and aspirating. Antigen and controls are added to filter plate 50 uL/well then covered and allowed to incubate in the dark for 1 hour on shaker. Following a wash step, a secondary unknown antibody is added at 50 μL using the same dilution (or concentration if known) as is used for the primary antibody. The plates are then incubated in the dark for 2 hours at RT on shaker followed by a wash step. Next, 50 μL/well biotinylated mouse anti-hIgG diluted 1:500 is added and allowed to incubate in the dark for one hour on shaker at RT. Following a wash step, 80 μL/well Streptavidin-PE is added at 1:1000 and allowed to incubate in the dark for 15 minutes on shaker at RT. Following a wash step, each well is resuspended in 80 μL blocking buffer and read using Luminex. Results show that the monoclonal antibodies belong to distinct bins. Competitive binding by antibodies from different bins supports antibody specificity for similar or adjacent epitopes. Non competitive binding supports antibody specificity for unique epitopes. Data is summarized in FIG. 5.

Functional Antibody Cross-Competition

In this antibody binning type set of experiments anti MSLN antibodies were tested for their ability to detect recombinant soluble human MSLN in a solid phase binding assay in which one antibody was used to capture soluble human MSLN in solution and the other antibody was employed to detect bound human MSLN. The ability of the antibodies to detect MSLN in this format indicated that they bound to distinct portions of MSLN (different non-overlapping epitopes) while the inability of a particular antibody pair to detect MSLN showed that they bound so a similar epitope or overlapping epitopes.

Capture antibodies (or CA125) listed across the top of the table were immobilized on Nalge Nunc Maxisorb 96-well clear Elisa plates in PBS at a concentration of 4 ug/ml overnight at 2-8 C. After washing in PBS-Tween 20 0.05% (PBS-T) 3 times, recombinant soluble MSLN was added in binding medium (PBS, 1% BSA, 10% NGS) to the starting well for titration 100 ng/ml in 100 ul. The soluble MSLN was then tritrated 8-12 well using a two-fold dilution and allowed to incubate with the capture antibody for 1 hour at 25° C. (room temperature). Unbound MSLN was removed by washing wells 3 times employing PBS. The various detection antibodies (listed in the left hand column of the table) were then added to the wells at a concentration of 1 ug/ml and the wells allowed to incubate at room temperature for 1 hour. To measure binding of bound detection antibodies—mouse anti human MSLN antibodies (MN, MB, OV569, 4H3), the wells were washed 3 times with PBS and then gt anti mouse IgG-HRP (Southern Biotech) was added to the wells for 30 minutes at room temperature. The wells were then washed again 3 times with PBS and the HRP-signal developed by adding 100u of TMB substrate (K&P). The plate development was stopped by adding 1N sulfuric acid and reading the plate on a dual wave-length optical plate reader (450 nm-572 nm). In the case where the detection antibody was fully human(237, 158, 151) the antibody was added in along with MN or MB and detection of MN or MB was measured.

The results are summarized in FIG. 6. The results are reported as (+)-detection of soluble MSLN is not altered (≤2 fold reduction MSLN binding signal) in presence of competitor or EC50 for binding/detection is ≤1 ng/ml with the binding pair being assessed. Results reported as (−) indicates that soluble MSLN is not detected and that significant cross-competition for binding is observed.

Example 5—ADCC Activity of Anti-Mesothelin Antibodies

Throughout the specification, and in particular the examples, the terms "2X" and "3X" in reference to the anti-MSLN antibodies are used. These terms refer to substitutions in the Fc region that result in enhanced ADCC through increased binding affinity to the Fc receptor. The "2X" molecule has the following substitutions: S239D/I332E and the "3X" molecule has the following mutations: S239D/I332E/A330L.

1. Objectives

Determine the ability of Fc engineered fully human anti-MSLN antibodies to mediate ADCC as compared to the same unmodified, parental fully human anti-MSLN antibody.

2. Materials and Methods 2.1 Materials

Effectors: normal in-house donors were leukophoresed, and NK cells isolated from the leukopack by the Cell Purification Group using the Milteni AutoMacs Pro negative selection system. NK cells were held overnight at 4° C. on a rocker, then washed, counted and resuspended at $4\times10^6$ cells/mL in complete RPMI for use in the ADCC assay.

Targets: Tumor cell targets were selected based on MSLN expression. Targets were washed and counted. $6\times10^6$ targets are resuspended in complete RPMI and labeled in a final concentration of 10 μM calcein (Sigma #C1359-00UL CALCEIN AM 4 MM IN ANHYDROUS DMSO) for 40 minutes at 37 degrees, 5% CO2. Cells were washed twice in PBS, resuspended in complete RPMI and incubated at 37 degrees, 5% CO2 for 2 hrs. After labeling, target cells are washed, recounted and resuspended at 0.2×106 cells/mL in complete RPMI for use in the ADCC assay 2.2 Methods Assay was performed in a 96 well round bottom tissue culture plate (Corning 3799). Antibodies were titrated from 20 μg/mL to 0.0002 μg/mL by carrying 10 μL in 100 μL of complete RPMI containing 10% FCS (a 1:10 dilution). Calcein labeled targets were added, 50 μL to contain 10,000 cells. Target cells and various concentrations of antibody were incubated for 40 minutes at 4° C., then NK cell effectors added, 50 μL to contain 100,000 cells (10:1 E:T ratio). Cultures were incubated for 4 hrs at 37° C. then supernatants pulled and assayed for calcein release by measuring fluorescence at 485-535 nm on a Wallac Victor II 1420 Multilable HTS counter. 100% lysis values were determined by lysing six wells of labeled targets with Igepal 630 detergent (3 μL per well) and spontaneous lysis values determined by measuring the fluorescence in supernatants from targets alone.

2.3 Statistical Analysis

Percent (%) specific lysis was defined as (sample fluorescence)−(spontaneous lysis fluorescence)/(100% lysis−spontaneous lysis fluorescence). Spontaneous lysis was determined by wells containing only targets and 100% lysis was determined by wells where targets had been lysed with IGEPAL CA 630 detergent. Raw data was entered in an Excel spreadsheet with embedded formulae to calculate % specific lysis and resultant values transferred to graphic program (GraphPad Prism) where the data was transformed in a curve fit graph Subsequent analyses (linear regression calculations) were done in GraphPad to generate EC50 values.

3. Results and Discussion

Effector NK cells in wells incubated with control hIgG1 antibody were unable to mediate killing of the calcein-labeled target cells while effectors in wells with certain fully human anti-MSLN antibodies were, as measured by specific Lytic activity (% specific lysis) able to mediate antibody dependent cellular cytotoxicity.

4. Conclusions

Both ADCC enhanced anti-MSLN and WT anti-MSLN antibodies were able to induce NK mediated killing of target tumor cells expressing MSLN. ADCC enhanced anti-MSLN antibodies mediate a significantly higher level of killing than the parent unmodified anti-MSLN antibodies.

Example 6-CDC Activity of Anti-Mesothelin Antibodies

1. Study Title: Anti-MSLN Antibodies Mediate Complement Dependent Cytotoxicity of Mesothelin Expressing Tumor Cells 2. List of Abbreviations and Definition of Terms Abbreviation or Term Definition/Explanation FBS Fetal Bovine Serum
CDC Complement Dependent Cytotoxicity (assay)
CO2 Carbon Dioxide
mL milliliter
μL microliter
n number
SEM Standard error of the mean
° C. Degrees Celsius
PI Propidium Iodide
Ab Antibody
IgG1 immunoglobulin class Gi
HuIgG1 Human immunoglobulin class Gi
237 WT Hu-anti-huMesothelin-2.37-IgG1, WT
237 3× Hu-anti-huMesothelin-237-IgG1, 3×
237 low fucose Hu-anti-huMesothelin-237-IgG1, clone 6F11
cBU69 WT Chimeric anti-human CD27L IgG1, WT
cBU69 3× Chimeric anti-human CD27L IgG1, 3×

3. Objectives

The objective was to determine the ability of Fc-enhanced anti-human mesothelin 237 3× or 237 low fucose to mediate CDC as compared to the wild type anti-Mesothelin antibody 237 WT.

4. Materials and Methods 4.1 Materials
4.1.1 Test Materials

| Antibody Drug Conjugates | Source | Formulation |
|---|---|---|
| Human $IgG_1$ Kappa from human plasma | Sigma, St. Louis, MO | 20 nM tris buffered saline, pH 8.0. |
| 237 WT | Amgen Inc., Seattle, WA | 20 nM tris buffered saline, pH 8.0. |
| 237 3x | Amgen Inc., Seattle, WA | |
| 237 low fucose | Amgen Inc., Seattle, WA | |
| cBU69 WT | Amgen Inc., Seattle, WA | |
| cBU69 3x | Amgen Inc., Seattle, WA | |

4.1.2 Reagents

Target cells: Ovcar 8, Ovarian Carcinoma cells express Mesothelin (65,000 MSLN/site) and CD27L. Growth medium contained 1 L of DMEM+L-glutamine+10% FBS+10 ml MEM non-essential Amino Acids+10 ml HEPES+1 ml beta-mer captoethanol+5 ml Pen/strep+10 ml sodium pyruvate (=cDMEM)

Baby rabbit complement (Rt C') (Cederlane, Burlington, Ontario, Canada. Catalog #CL-3441-S. Lot #75540805.)

Heat inactivated (HI) complement was generated by incubating complement at 56° C. in a water bath for 30 minutes and then returning immediately to 4° C. The heat inactivated complement was used within 1 hr of heat inactivation.

Assay medium: DMEM (basal medium) with 1% heat inactivated FBS.

Propidium iodide (PI), (Roche Diagnostics Corporation, Indianapolis, IN Catalog #11348639001, lot #93352020).

Hoechst 33342, (Molecular Probes, Inc. Eugene, OR Catalog #H21492. Lot #24982W).

4.2 Methods 4.2.1 Preparation of Tumor Cells

Ovcar 8 cells were washed once with assay medium (DMEM plus 1% FBS) and resuspended in assay medium. Cells were seeded in a 96-well tissue culture plate at 100 μL per well with the cell density at $0.5\times10^4$ cells per well. Cells were incubated at 37° C., 5% CO2 overnight.

4.2.2 Treatment of Cells with Complement and Control Antibody

Two times concentrated complement was prepared in assay medium as outlined in the table below. Medium in cell in 96-well plate was removed with plate washer. Then 2× rabbit complement was added to cells in plates at 50 μL per well.

Table for preparation of 2× concentrated rabbit complements in assay medium

| 2x complements | Complement (ml) | Assay Medium (ml) | Total volume (ml) |
|---|---|---|---|
| 20% HI rabbit C' (inactive) | 0.5 | 2 | 2.5 |
| 20% no HI rabbit C' (active) | 1.5 | 6 | 7.5 |

Two times concentrated antibodies were added to cells at 50 μL per well as shown in the Experimental Design below to get a final concentration at 10 μg/mL. The total volume in each well at the start of culture was 100 μL. Cells were continuously incubated at 37° C., 5% CO2 for five hours.

Experimental Design: plate map for a 96-well plate. Antibodies were in duplicate wells for each sample with a total volume at 100 μl/well.

Note: Data obtained from NB 105783. Rt C' is referred to as baby rabbit complement; Inactive C' is referred to as heat inactivated complement.

4.2.3 Measurement of Cytotoxicity with ArrayScan Plate Reader

After 5-hour incubation, 150 μL of warm 2% FBS in PBS were added to each well. The plates were centrifuged at 1000 rpm for 5 min. The medium were discarded with plate washer where its needles were set to a height that allowed 50 μL of medium left in each well.

The cocktail of Hoechst 33342 and propidium iodide (PI) which was prepared at 1:1000 dilution in PBS solution containing 2% FBS was added into cells at 100 μL per well.

Samples were analyzed on an ArrayScan VTI HCS reader (version 6, Cellomics, Thermo Fisher Scientific, Pittsburgh, PA) with BioApplication “Target Activation” employing a 20× objective. The filter setting was indicated in table below. At least 200 cells were counted in each well.

| Channel | Target | Label | Fluor | Filter |
|---|---|---|---|---|
| 1 | Nucleic acid for all cells | Hoechst 33342 | UV/460 nm | DAPI |
| 2 | Nucleic acid for dead cells | Propidium iodide | 488/>575 nm | TRITC |

4.3 Statistical Analysis

Statistical analysis was performed using Prism 4.01 (GraphPad, San Diego, CA). A plot shows % cytotoxicity vs. the log of Ab concentration in pg/mL. The % cytotoxicity in Y axis is represented with % selected objects from output feature of ArrayScan reader and expressed as the mean+/− standard error of the mean (SEM) for duplicate measurements (n=2) except control antibodies measured in single wells.

5. Supporting Data 5.1 Figures

All WT, 3× and Low Fucose of Mesothelin HuG1, Clone 237 did not show any complement-dependent cytotoxicity (CDC) mediated killing with 10% rabbit complement against Ovcar 8 after 5 h incubation.

Figure 7:
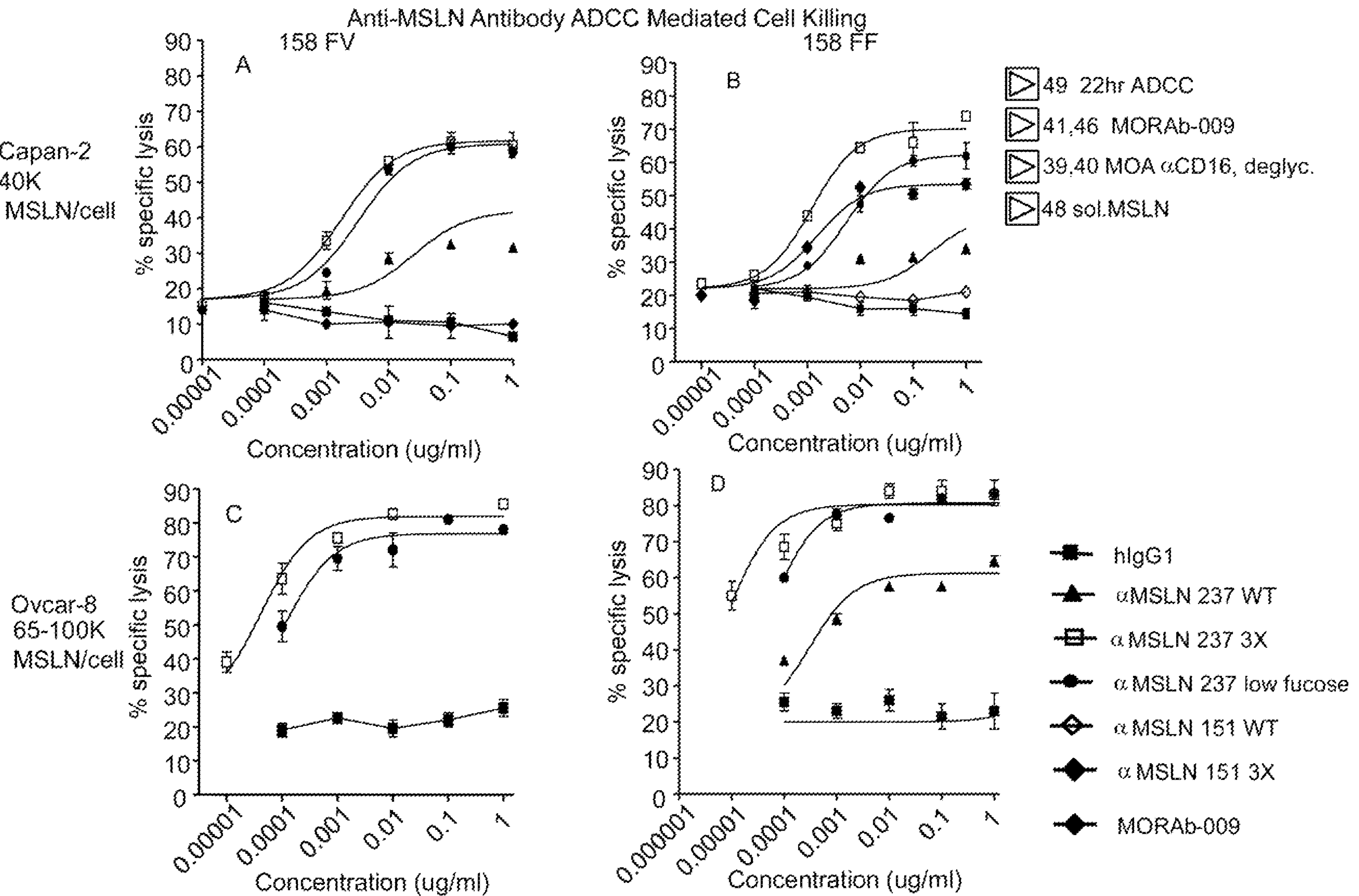
FIGS. 7A-7D and 8-9 summarize anti-MSLN antibody ADCC mediated cell killing data for several different tumor lines.
Figure 8:
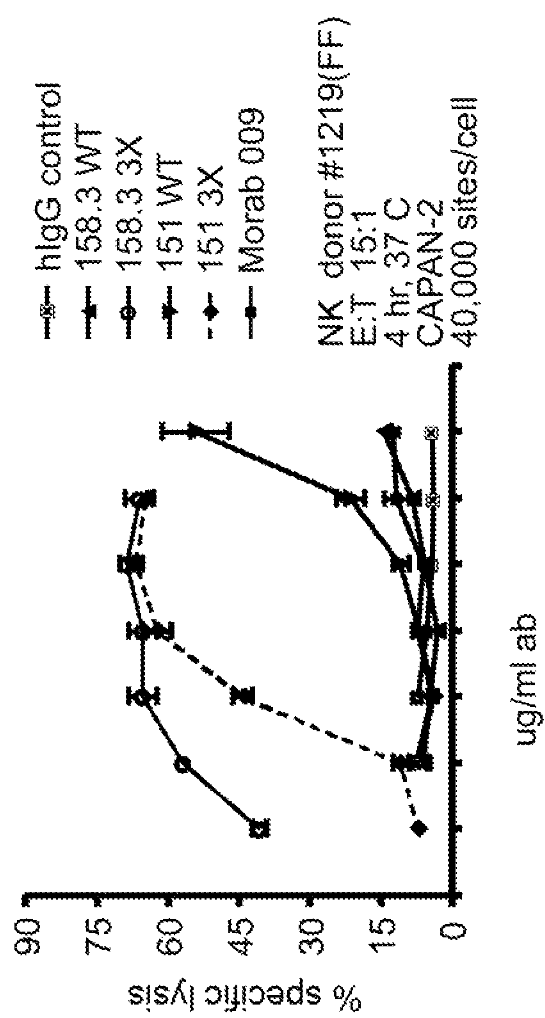
Figure 9:
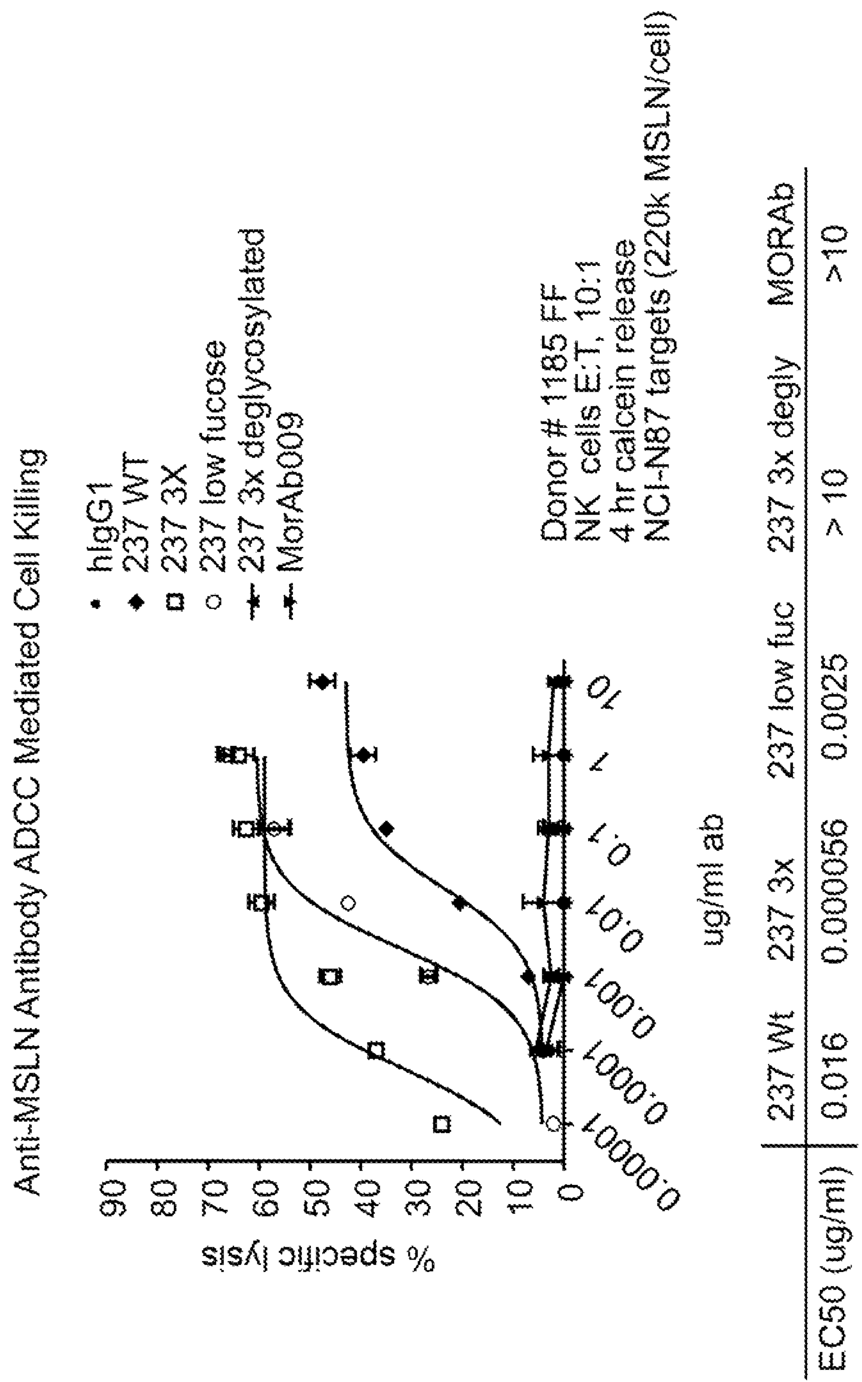

Ovcar8 cells were exposed to doses of anti-Mesothelin WT or Fc-enhanced antibodies or its negative control, huGI and positive controls cBu69 and cBU69 3× starting at 10 μg/mL (up panel). Then cells were treated with active or inactive (56° C., 30') rabbit complement (Rt C') at final concentration of 10% (up and low panel). After incubation at 37° C., 5% CO2 for 5 hrs, CDC mediated killing was measured from output feature of ArrayScan reader "% selected objects" to detect % of PI positive vs. Hoechst for % Cytotoxicity. Data are expressed as the mean and standard error of the mean (SEM) for duplicate measurements (n=2) except single wells for controls. The results of this study are summarized in FIGS. 7-9 and indicate that none of the anti-MSLN antibodies demonstrated CDC mediated cell killing.

Example 7—ADCP Activity of Anti-Mesothelin Antibodies

Anti-MSLN Antibodies Mediate Antibody Dependent Cellular Phagocytosis of Mesothelin Expressing Tumor Cells 1. List of Abbreviations and Definition of Terms

| Abbreviation or Term | Definition/Explanation |
|---|---|
| FBS | Fetal Bovine Serum |
| RPMI | Roswell Park Memorial Institute |
| CO2 | Carbon Dioxide |
| mL | milliliter |
| μL | microliter |
| n | number |
| NA | Not applicable |
| SEM | Standard error of the mean |
| ° C. | Degrees Celsius |
| ATCC | American Type Culture Collection |
| RT | Room temperature |
| Ab | Antibody |
| IgG1 | immunoglobulin class G1 |
| HuIgG1 | Human immunoglobulin class G1 |
| ADCP | Antibody Dependent Cellular Phagocytosis (assay) |
| 237 WT | Hu-anti-huMesothelin-2.37-HuIgG1, WT |
| 237 3x | Hu-anti-huMesothelin-237-HuIgG1, 3x |
| 237 low fucose | Hu-anti-huMesothelin-237-HuIgG1, clone 6F11 |
| EC50 | Half maximal effect concentration |

2. Objectives

Determine the ability of anti-MSLN antibodies to mediate ADCP.

3. Materials and Methods 3.1 Materials 3.1.1 Test Materials

Antibody Drug Conjugates

237 WT 237 3×

237 low fucose

Human IgG1 Kappa from human plasma (Cat. #I5154 1 mg; Sigma, St. Louis, MO)

20 nM tris buffered saline, pH 8.0

3.1.2 Reagents

Target cells: Ovcar 8, Ovarian Carcinoma cells express Mesothelin (65,000 MSLN/site) and CD27L. Growth medium contained 1 L of DMEM+L-glutamine+10% FBS+10 ml MEM non-essential Amino Acids+10 ml HEPES+1 ml beta-mer captoethanol+5 ml Pen/strep+10 ml sodium pyruvate (=cDMEM)

Effectors: normal in-house donor #1193 was monocytes isolated from the human peripheral blood by the Cell Purification Group (Amgen Inc., Seattle, WA) using the Milteni AutoMacs Pro negative selection system. Cells were held overnight at 4° C. on a rocker, then washed, counted and resuspended in complete RPMI for use in the ADCP assay.

PKH67 green fluorescent cell linker kit for general cell labeling (Sigma-Aldrich Corporation, St. Louis, MO Catalog #PKH67-GL, lot #076K0463).

CD11b-Biotin: mouse anti-human CD11b/Mac-1 monoclonal antibody, clone ICRF44, IgG1, Kappa. (eBioscience, San Diego, CA Catalog #13-0118-82, lot #E026682).

Streptavidin, Alexa 568 conjpgate (Molecular Probes, Inc. Eugene, OR Catalog #S-11226. Lot #34757A).

Hu M-CSF: recombinant human M-CSF (R&D Systems, Minneapolis, MN Catalog #216-MC-025, lot #MVND 16061).

3.2 Methods

Day 0: differentiation of human macrophage cells from purified monocytes

Monocytes were negative selected from human peripheral blood and stored in 4° C. cold room over night with medium RPMI 1640 containing 10% FBS. Then monocytes were seeded to a 48-well tissue culture plate at 200,000 cells per well with 200 μL of macrophage growth medium (RPMI 1640 containing 10% FBS and 40 ng/ml Hu M-CSF) and incubated at 37° C., 5% CO2 for 5-7 days to let monocytes differentiate to macrophages.

Day 6: performance of ADCP assay

1. Labeling target cells with PKH67 green dye at final concentrations of $2\times10^{-6}$ M PKH67 dye Tumor cells were collected and washed once with PBS by centrifuging the cells (400' g) for 5 minutes.

After centrifuging cells, the supernatant was carefully aspirated, but leaving no more than 25 mL of supernatant.

Four µL of the PKH67 ethanolic dye solution at stock concentration of $4\times10^{-6}$ M was added to 1 ml of Diluent C from kit in polypropylene tube and mixed well.

Cell pellets were re-suspended into 1 mL of Diluent C at a density of $20\times10^{6}$ in polypropylene tube.

Cells were rapidly transferred to dye work solution with gently pipetting to insure complete dispersion.

The mixture was incubated at room temperature for 4 minutes with mixing periodically.

Two mL of whole activated FBS was added into cells to stop the staining and incubated at room temp for 1 minute to allow binding of excess dye.

Forty mL of RPMI containing 10% FBS was added into cells and washed once by centrifuging the cells (400' g) for 10 minutes.

Cell pellets were suspended with 40 mL of medium again and transferred to a new tube.

Cells were washed again three times with medium RPMI+10% FBS and 1× with macrophage growth medium (RPMI 1640 containing 10% FBS and 40 ng/ml Hu M-CSF).

Cells were counted and suspended with macrophage growth medium at $1\times10^{6}$ cells per mL for T:E at 1:2 ratio. 2. Treatment of tumor cells with antibodies for antibody dependent cellular phagocytosis (ADCP)

Antibody dilutions were prepared in macrophage growth medium. These dilutions were concentrated at four times higher than final concentrations.

To preincubate PKH67 green labeled target cells with antibodies, 300 µl of 4× concentrated antibodies was mixed with 300 ul of green labeled tumor cells and incubated at 4° C. for 30 minutes.

The mixture of green labeled tumor cells with anti-tumor antibodies was added to macrophage cells in 48-well plate at 200 µl for each well as indicated in the Experiment Design table below. The final volume is 0.4 ml per well. The ratio of target cells to effect cells (macrophages) is 1:2.

Cells were incubated at 37° C., 5% CO2 for one hour.

Experimental design: plate map for 48-well plate. Duplicate for each treatment

3. Counterstaining macrophages with macrophage marker

Target cells and macrophages in 48-well plate were detached with Trypsin-Versene mixture.

Cells were transferred into a 96-well block with 2.2-ml volume per well and washed once with pre-warmed FASC wash solution by spinning the blocks at 400'g for 5 minutes and then discarding supernatant.

Macrophages were stained with their marker, CD11b-Biotin at 1:200 dilution in block solution with 100 µl per well for 10 min on ice.

After washing cells once, macrophages were detected with streptavidin Alexa 568 at 1:1000 dilutions for 10 minute on ice.

After washing cells 1× with PBS, cells were fixed with 4% formaldehyde in PBS at room temperature for 20 minutes. Then cells were washed 1× with dH2O.

Cell pellets were resuspended with water at 200 µl per well and transferred to a 96-well plate at 100 µl per well. Plate can be sealed and stored at 4° C. overnight if needed.

4. Quantitative measurement of phagocytosis activity on an ArrayScan VTI HCS reader (version 6, Cellomics Inc. Thermo Fisher Scientific, Pittsburgh, PA) with Target Activation BioApplication employing a 20× objective. The filter setting was indicated in table below. At least 200 cells were counted in each well.

Filter setting for ADCP:

| Channel | Target | Label | Fluor |
|---|---|---|---|
| 1 | macrophages | Ms-anti-Hu CD11b Biotinαstreptavidin Alexa 568 | red |
| 2 | Tumor cells | PHK67 | green |

3.3 Statistical Analysis

Statistical analysis was performed using Prism 4.01 (GraphPad, San Diego, CA). A plot shows % tumor cell phagocytosis vs. the log of antibody concentration in ng/ml. The percentage of tumor cell phagocytosis is represented with percentage of tumor cells that were overlapped with macrophages vs. total macrophages in the selected fields and obtained from output feature of ArrayScan reader "% ObjectCounts". The % values were expressed as the mean+/−standard error of the mean (SEM) for duplicate measurements (n=2). The EC50 was determined by using nonlinear regression analysis (Sigmoidal dose response curve fit). Data were normalized to the maximum and minimum signal and fit to a sigmoidal dose-response curve.

Figure 10:
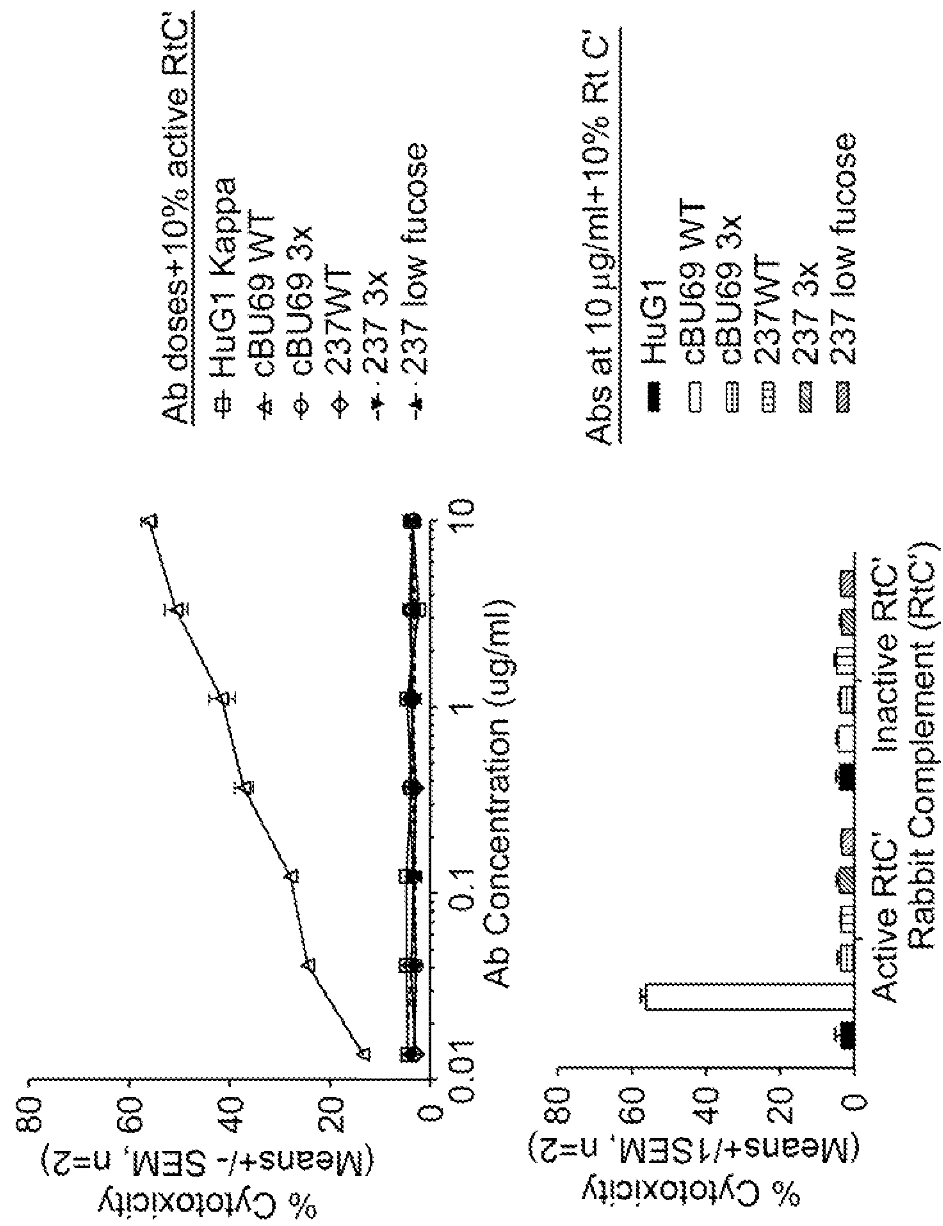
FIGS. 10-12 summarize anti-MSLN antibody CDC mediated cell killing data.

4. Supporting Data 4.1 Anti-MSLN Antibodies Induce Human Macrophages to Phagocytose Ovcar 8 Cells Anti-MSLN antibodies mediate ADCP activity against Ovcar 8 cells. Phagocytosis images were captured using ArrayScan VTI plate reader at 20× magnification. Green dye labeled tumor cells were exposed to anti-MSLN antibodies (237 Low Fucose MSLN) or its negative control, HuG1. Then cells were mixed with human macrophages at a ratio of 2:1 (effectors:tumor). After incubation at 37° C., 5% CO2 for 1 hr, macrophages were detected with the marker CD11b-Biotin plus anti-streptavidin ((aSA) Alexa 568 (red). FIG. 10 contains photographic images of these experimental results.

Figure 11:
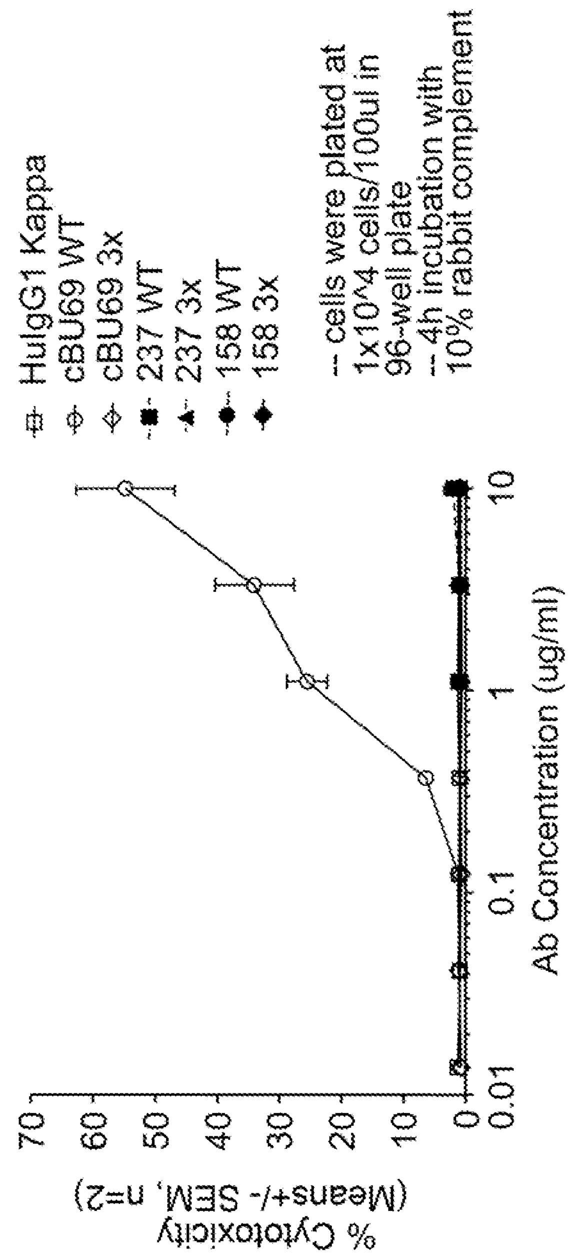
Figure 12:
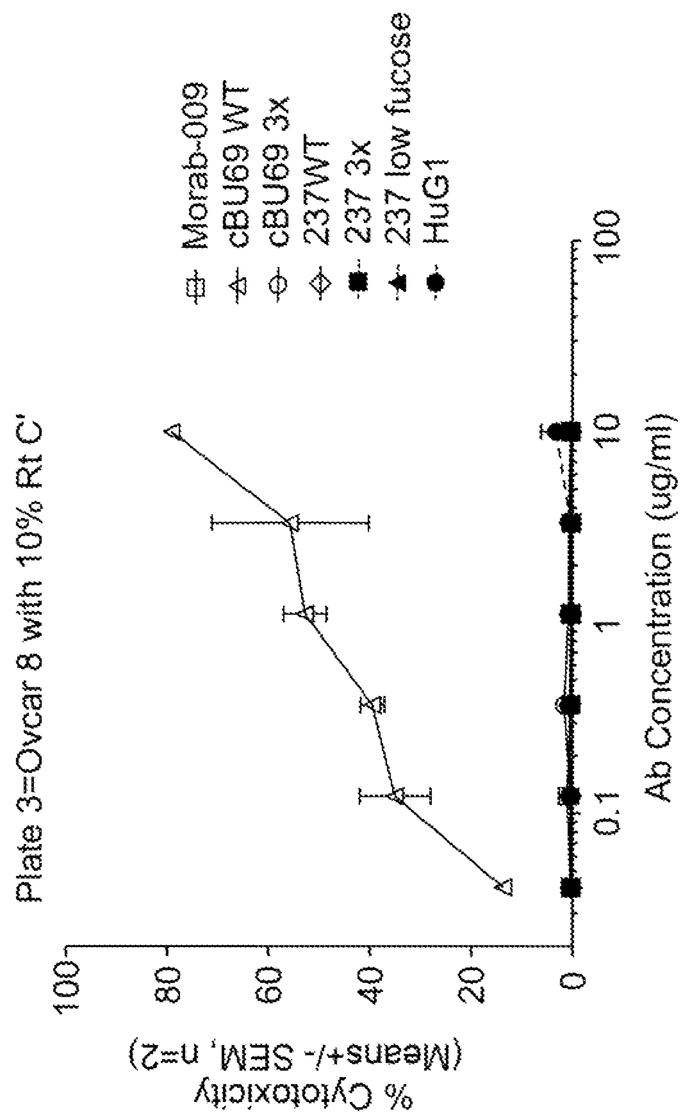
Figure 14:
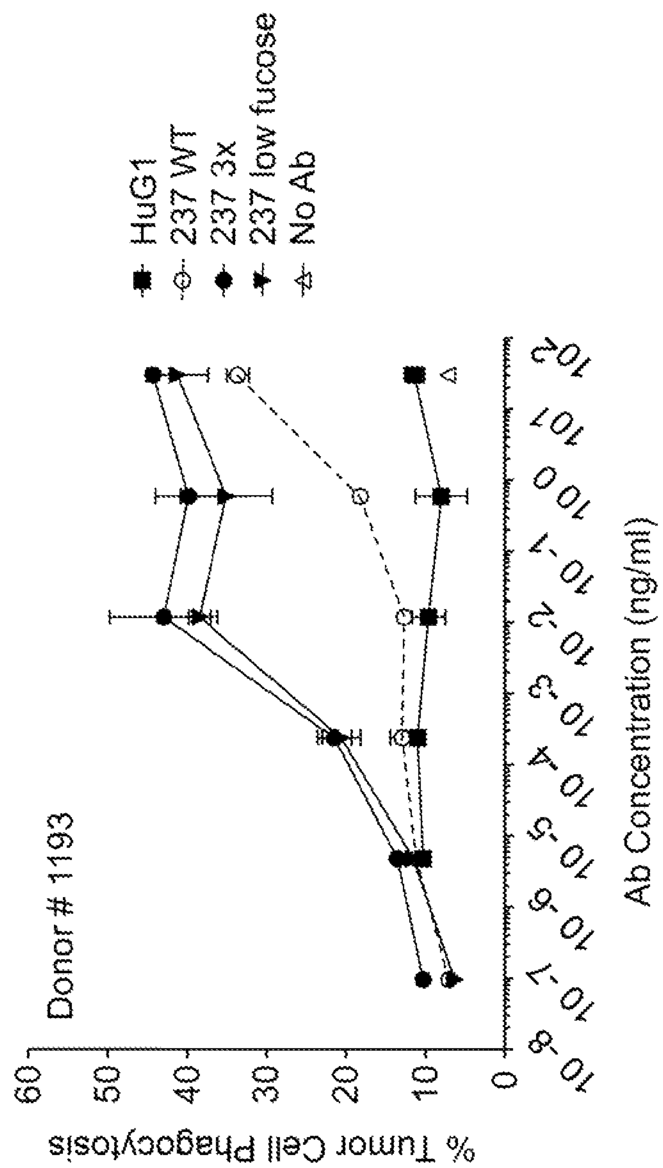
FIG. 14 summarizes anti-MSLN antibody ADCP mediated cell killing data.

Fc-enhanced Anti-Mesothelin HuG1, Clone 237-3× and -Low Fucose Enhance Tumor Cell Phagocytosis Compared to 237 WT in Ovcar 8 After 1 h Incubation Anti-MSLN antibodies mediate ADCP activity by human macrophages. Mesothelin expressing tumor cell line Ovcar 8 was exposed to 237 WT, or Fc enhanced Abs, 237 3× and 237 low fucose or its negative control, HuG1. Then cells were mixed with human macrophages at a ratio of 2:1 (effectors:tumor). After incubation at 37° C., 5% CO2 for 1 hr, macrophages were detected with the marker CD11b. The ADCP activity in Y axis was measured from output feature of ArrayScan VTI reader "% selected objects" to detect % of tumor cells were phagocytized into macrophages. Data are expressed as the mean and standard error of the mean (SEM) for duplicate measurements (n=2). FIG. 11 summarizes these results.

Example 8—Soluble MSLN vs. Surface MSLN Binding

Experiments were run to determine binding affinity of the anti-MSLN antibody ab237 against native surface bound MSLN and soluble MSLN. It was determined that ab237 binds native surface bound MSLN with 30-fold higher selectivity as compared to soluble MSLN. 237 anti MSLN bind with greater affinity to native human MSLN expressed on the cell surface than recombinant soluble MSLN

| | | ab237 |
|---|---|---|
| Binding Affinity | rHuMSLN sol.[#] | 97 pM |
| $K_D$ | Hu MSLN native* | 3.5 pM |

Equilibrium binding of 237 antibody was assessed to native human MSLN expressing N87 tumor cells utilizing KinExA technology. The results of binding of 237 to native human MSLN are reported as the equilibrium binding constant or KD in pM. Binding of 237 to recombinant human soluble MSLN (rHuMSLN sol.) was assessed in solution by Biacore analysis. The 237 antibody was captured on the Biacroe sensor chip and the solution containing rHuMSLN sol was allowed to flow across the chip until binding equilibrium reached. Both the association and dissociation constants were measured and the results reported as the equilibrium binding constant or KD in pM. The results showed that the 237 mAb bound 30-fold better to native MSLN expressed on the cell surface than it did to soluble MSLN in solution.

Example 9—In Vivo Efficacy of Anti-Mesothelin Antibodies

In vivo experiments were performed to evaluate the efficacy of the anti-MSLN antibodies of the invention. The data from these experiments is summarized in FIGS. 15-17.

Figure 16:
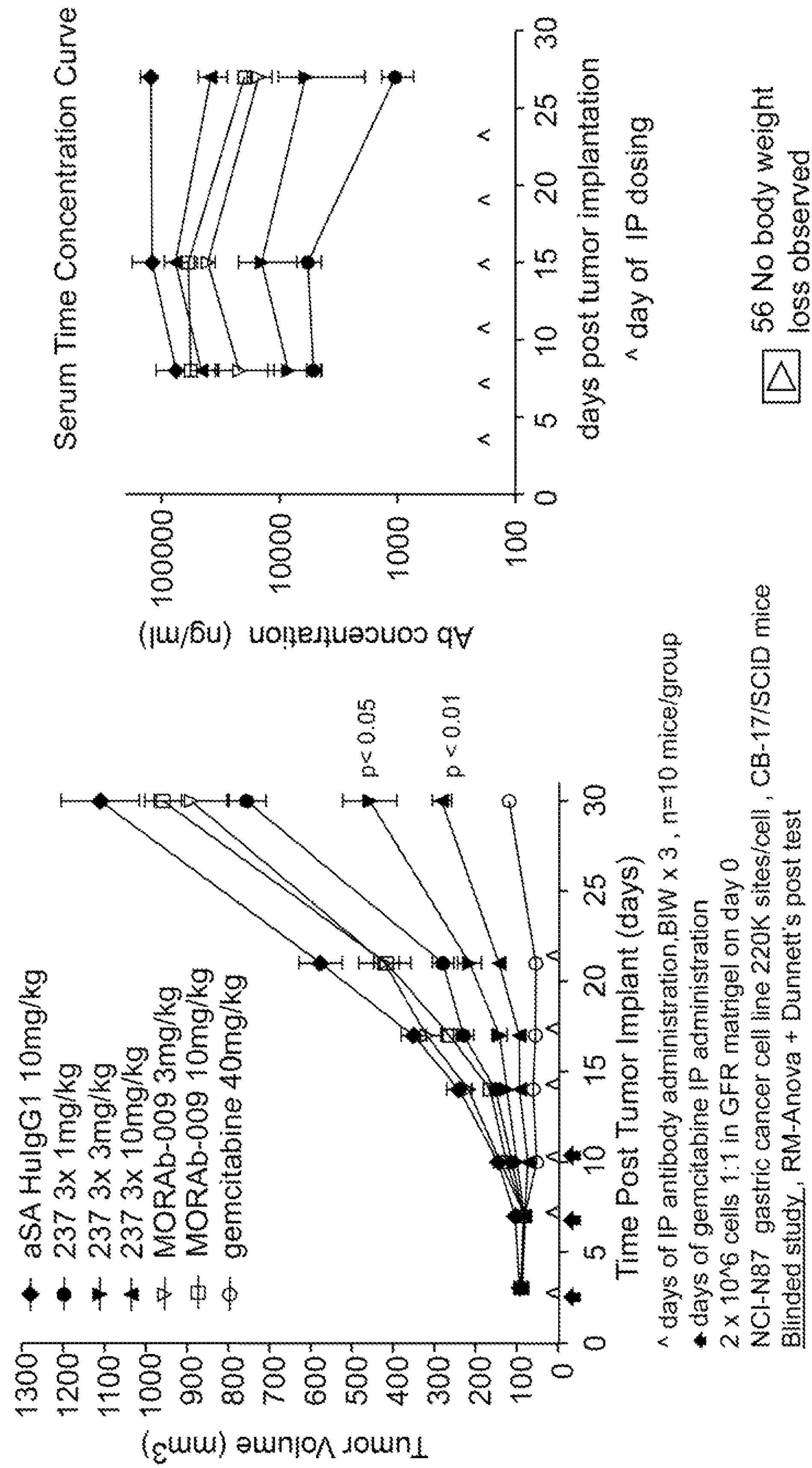
Figure 17:
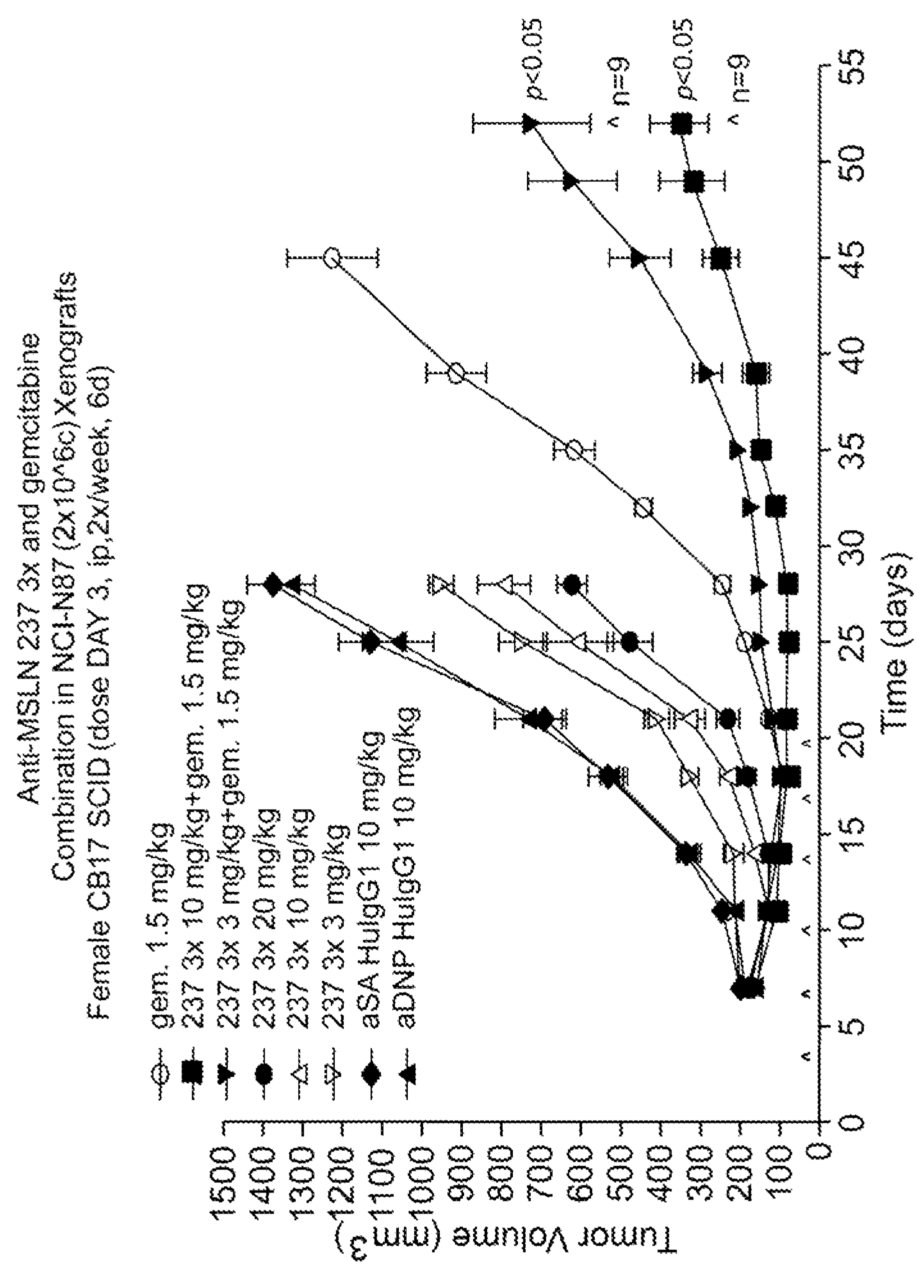
Figure 18:
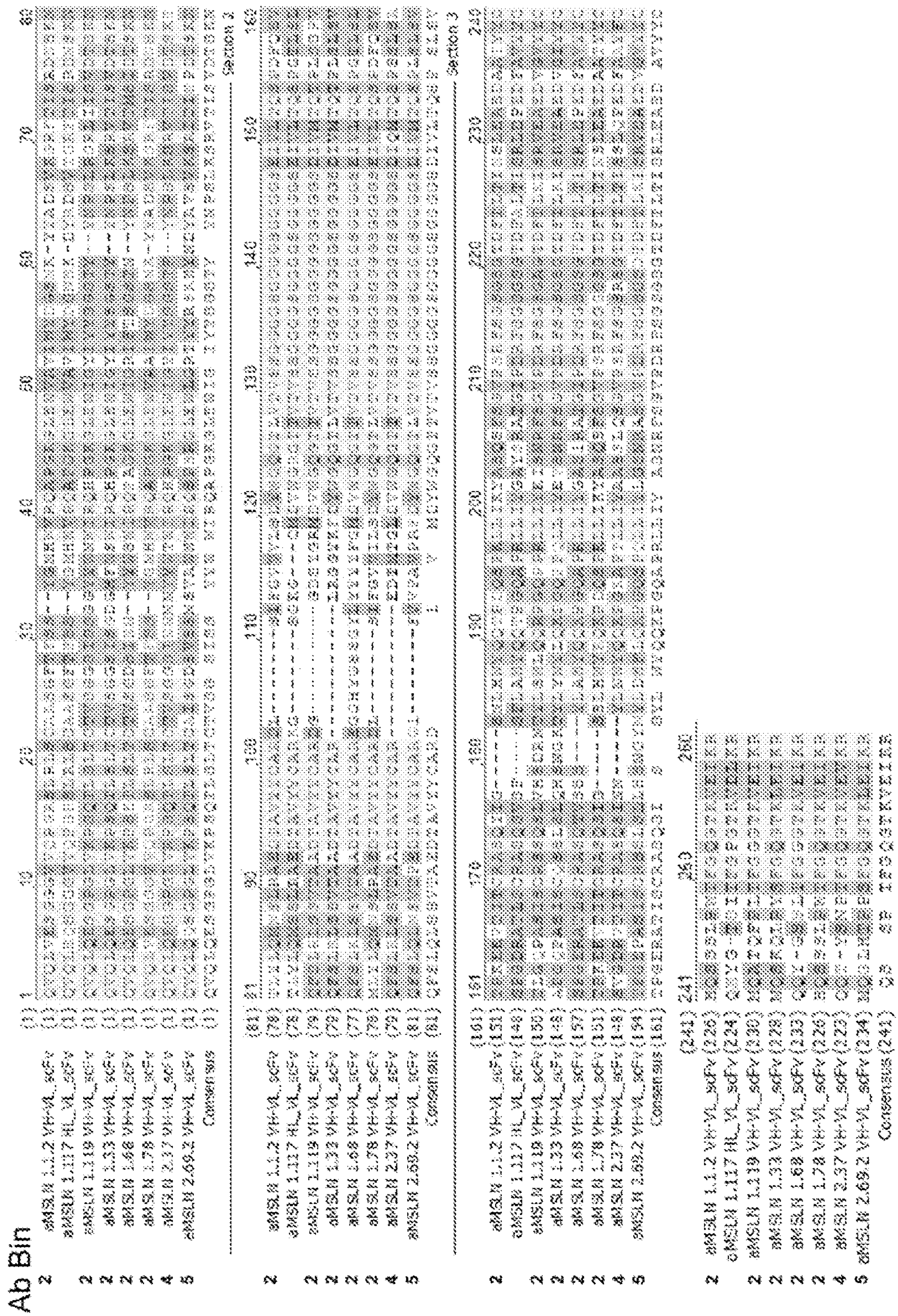
FIG. 18 provides an alignment of several different scFv anti-MSLN molecules uses in the generation of BITE molecules. Sequences identifiers are as follows: aMSLN 1.1.2 VH-VL scFv (SEQ ID NO: 184); aMSLN 1.117 HL VL scFv (SEQ ID NO: 176); aMSLN 1.119 VH-VL scFv (SEQ ID NO: 168); aMSLN 1.33 VH-VL scFv (SEQ ID NO: 162); aMSLN 1.68 VH-VL scFv (SEQ ID NO: 170); aMSLN 1.78 VH-VL scFv (SEQ ID NO: 166); aMSLN 2.37 VH-VL scFv (SEQ ID NO: 160); aMSLN 2.69.2 VH-VL scFv (SEQ ID NO: 172); Consensus (SEQ ID NO: 197).
Figure 19:
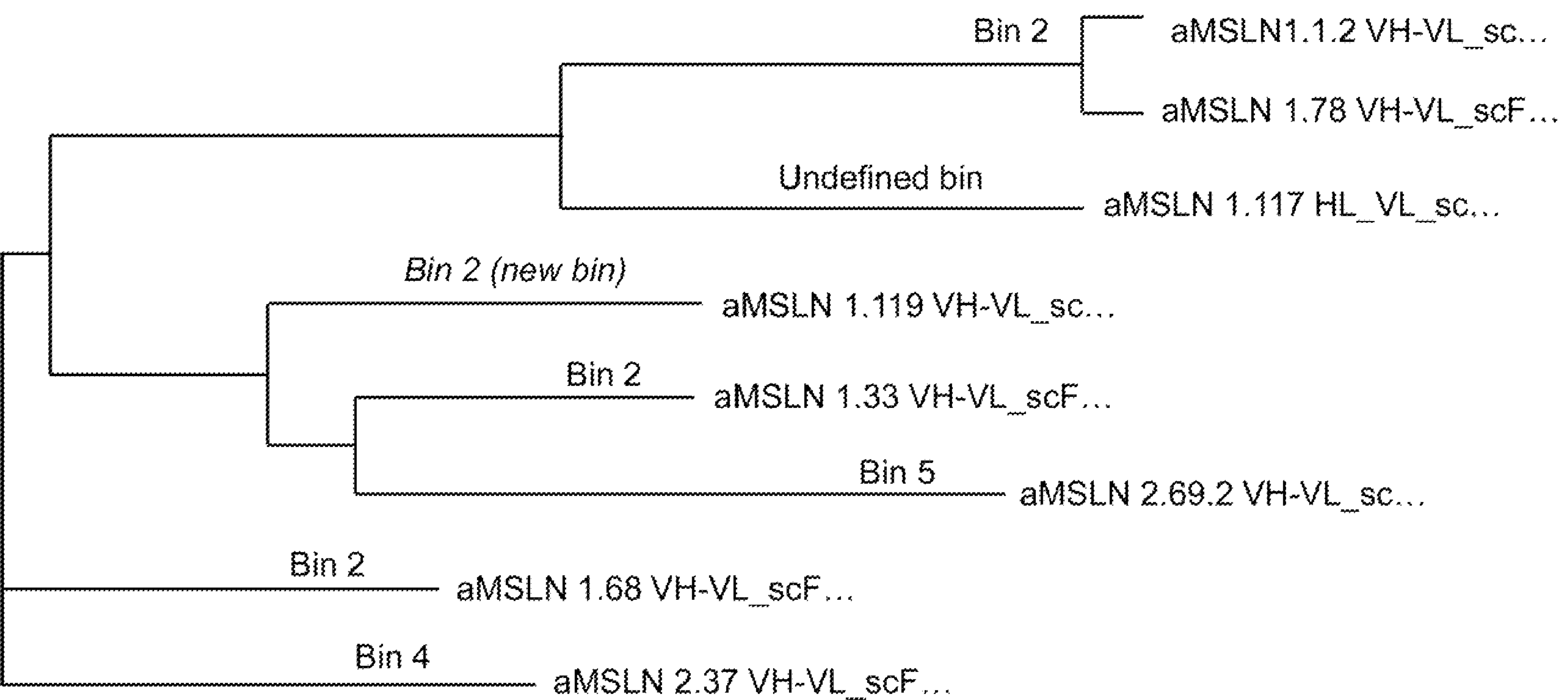
FIG. 19 summarizes anti-MSLN antibody binning based on competitive binding assays and sequence comparisons.

The ability of Fc-enhanced 237 anti MSLN to mediate anti tumor activity in vivo was assessed in the N87 gastric cancer xenograft model. Prior to implantation mice barcode chips were implanted into CB-17/SCID mice that would receive tumor implants. N87 gastric cancer cells (2×10^6) in 100 μl were implanted subcutaneously in an equal volume of growth-factor reduced Matrigel (BD). Following implantation, the animals were either immediately treated with 237 mAb or with control mAb as indicated in FIG. 16 (left panel) or starting on the fourth day post tumor implantation FIG. 16 (right panel), FIG. 17 and FIG. 18. When initiation of treatment was delayed to day 4 post tumor implantation, the tumors were measured and the mice randomized into treatment groups of 10 so that the average tumor volume across the groups was similar prior to the start of treatment.

The control IgG1 antibody, 237 or MorAb-009 (FIG. 17) were administered twice per week i.p. for three weeks at the doses indicated in each figure. Where indicated, Gemcitabine was administered i.p. at the doses indicated on the FIG. 16 (left panel). 17 and 18 on day 4, 7 and 11 post tumor implant. Tumor volume was assessed twice weekly by taking perpendicular measurements, electronic using calipers and recordering the measure associated with the bar code read in an xls spreadsheet. Control treated N87 tumors typically reached >1000 mm^3 by day 28-30 so that is when the studies were designed to end for results presented in FIGS. 16 and 17. In the combination xenograft study (FIG. 18) where 237 was combined with gemcitabine the study was carried out to almost 55 days because the anti tumor effect was more pronounced and one of the outcomes of the experiment was to assess treatment durability. The results are reported as the average tumor volume+/−standard error of the mean over time. Statistical differences between groups was assessed using repeated measures ANOVA followed by post hoc analysis using Dunnett's for multiple comparisons (Graph Pad Prism, 5.0). When comparing the anti-tumor effect of one treatment group to another, a p-value of <0.05 was considered to be indicative a statistical difference between treatment groups.

Example 10—MSLN BiTE Binding

Binding of MSLN-BiTE to membrane-bound target expressed in cells was determined with an on-cell affinity assay. $3\times10^4$ cells per well of a microtiter plate were incubated with MSLN-BiTE protein in a dose response for 16-22 h at 4° C. Cells were washed twice with flow buffer (PBS that contained 2% fetal calf serum and 0.01% sodium azide), and then resuspended in flow buffer and incubated with an anti-His Fab labeled with Alexa Fluor-647 for 50 minutes at 4° C. Cells were fixed after incubation to optimize detection of the fluorescent signal. Cells were then washed twice and resuspended in flow buffer that contained propidium iodide at 1 ug/ml. Cells were analyzed by flow cytometry for live cells that were positive for Alexa Fluor-647. $EC_{50}$ values were determined from the dose response curve of Alexa Fluor-647 positive cells.

Figure 20:
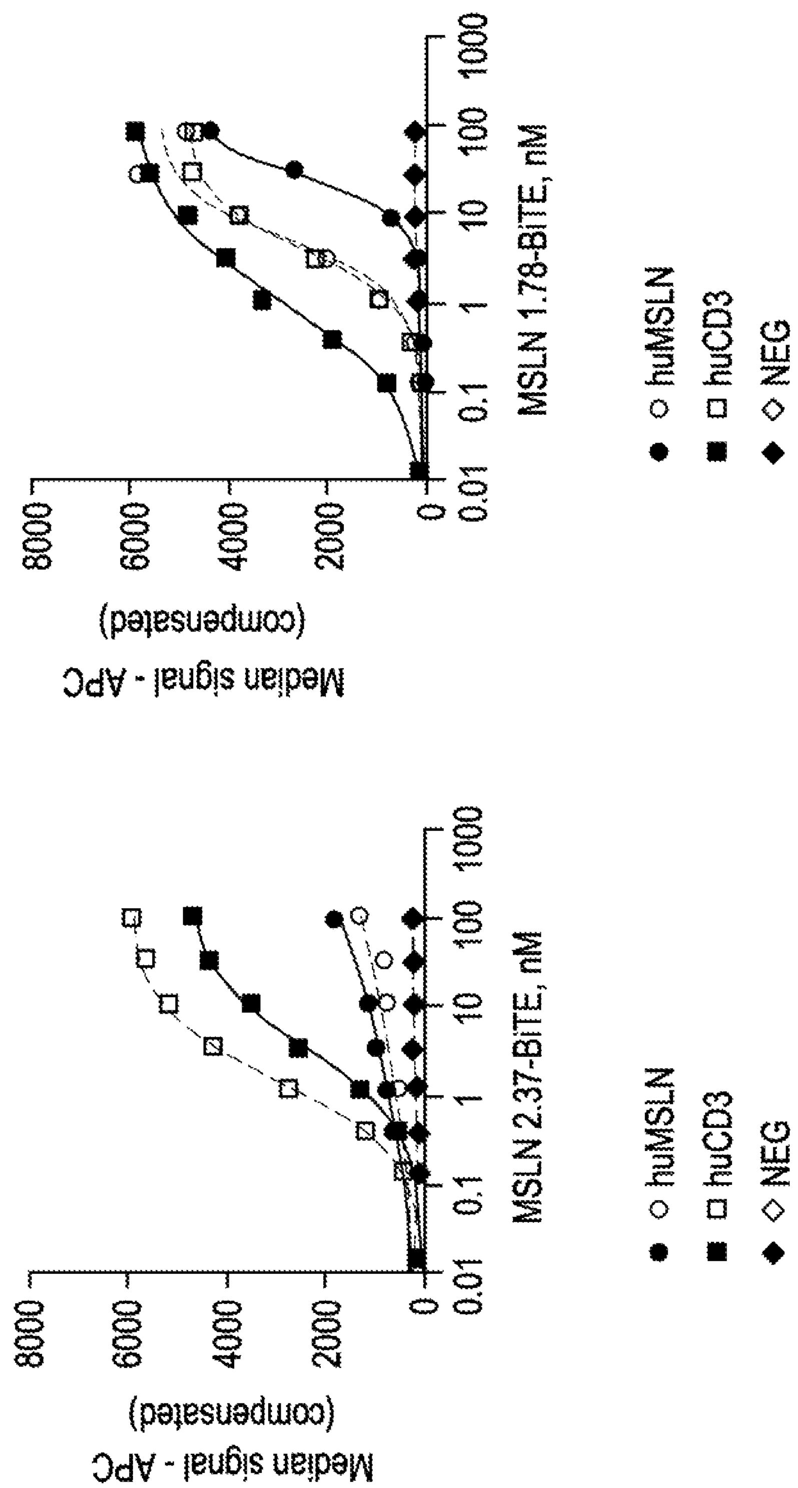
Figure 22:
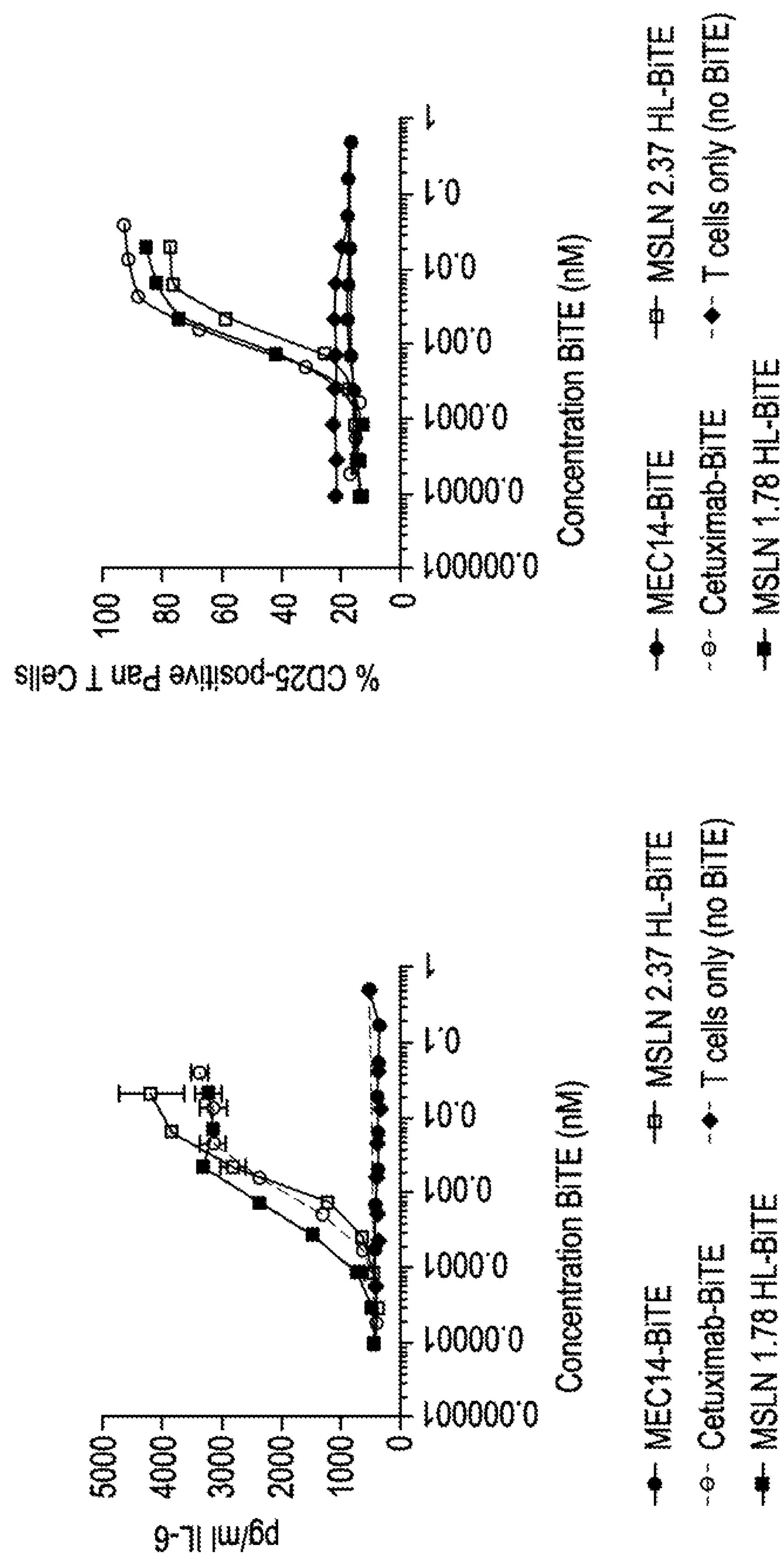
FIG. 22 summarizes an in vitro T-cell activation assay performed with several anti-MSLN/anti-CD3 BiTE molecules as compared to control BiTE molecules, demonstrating T-cell activation by the anti-MSLN/anti-CD3 BiTE molecules.

FIG. 20 shows the results of binding of representative MSLN-BiTE proteins to human MSLN in NCI-N87 gastric cancer cells and to human CD3 in HPB-ALL cells. Solid lines in the graphs below indicate VH-VL orientation and dotted lines indicate the VL-VH orientation. FIG. 22 shows the results of binding of representative MSLN-BiTE proteins to human MSLN in OVCAR-8 ovarian cancer cells and to human or cyno MSLN in 293T cells that are transiently transfected with human MSLN or cyno MSLN.

Example 11—MSLN BiTE T-Cell Activation

OVCAR-8 cells were incubated at 40,000 cells per well with unstimulated pan-T cells (ALL CELLS) at a 10:1 effector to target cells ratio and BiTE proteins. The T cells are pre-labeled with 5 uM CSFE dye. MEC14-BiTE is directed against murine anti-Mecoprop and is a negative control for the assay (Osada et al., Br. J. Cancer 2010). Cetuximab-BiTE is a BiTE generated from the Cetuximab anti-EGFR antibody (Lutterbuese et al., PNAS 2010) that serves as a positive control for this assay due to expression of EGFR in OVCAR-8 cells. Both cytokine production and T cell activation were determined from this assay.

Figure 25:
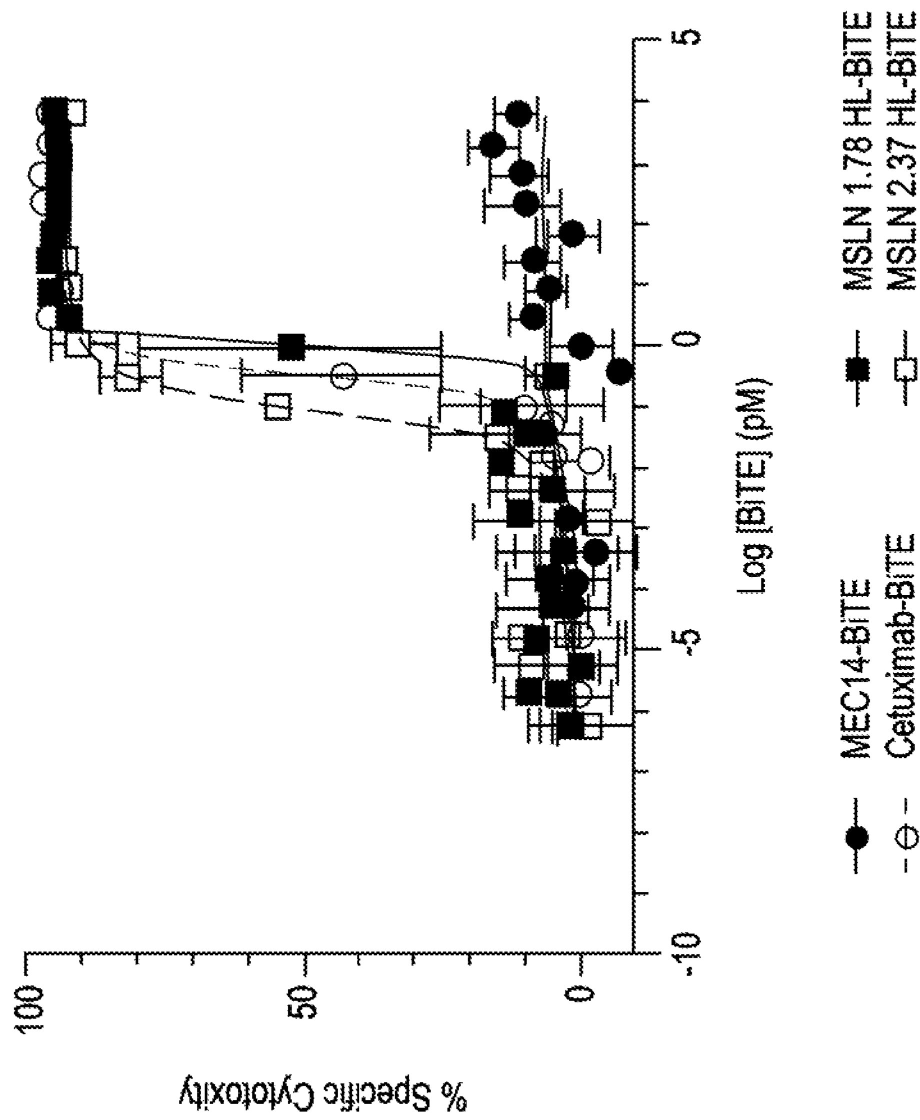

At 24 h, aliquots of supernatants were removed and assayed for the production of cytokines by multiplex ELISA assays (Meso Scale Discovery). Briefly, spots within wells of a microtiter dish are precoated with an antibody against the target cytokine of interest. Supernatants from the incubation of BiTE, tumor cells and T cells are added to the wells of the cytokine assay plate, and then binding of cytokines to the bound antibody is detected by a chemiluminescent detection reagent. The chemiluminescent signal is quantitated with a plate reader and the $EC_{50}$ values are calculated from the dose response curves. Cytokines produced by the reaction of BiTE with target-expressing tumor cells and T cells included: IL-6 (shown in FIGS. 23 and 25), TNF-α, IFN-γ, MCP-1, IL-1B, IL-2, IL-4, IL-10, IL-12 and IL-13. Results from the other cytokine assays are summarized in FIG. 23.

At 48 h, the remaining supernatants were assayed for T cell activation, by increase in $CD25^+$ or $CD69^+$ T cells. T cells were washed in flow buffer and then incubated with monoclonal antibodies to CD25, CD69 or an isotype control antibody for 30 minutes at room temperature. Cells were then washed twice with flow buffer and analyzed by flow cytometry for gain of CD25-positive or CD69-positive T cells. Dose response curves were obtained by graphing the number of $CD25^+$ or $CD69^+$ cells at each dose. The increase in $CD25^+$ cells is shown in FIGS. 22 and 24. T cell proliferation was also assessed in the flow cytometry experiments by measuring the loss of CSFE signal, a marker for mitotic index (data not shown).

Example 12—MSLN-BiTE Cytotoxicity

Cytoxicity assays for the MSLN-BiTE molecules were performed generally as described above in Example 5, except that pan-T cells were used as effector cells. BiTE proteins were incubated with MSLN-expressing tumor cells OVCAR-8 at 2500 cells per well of a microtiter plate, and unstimulated pan-T cells (source: ALL CELLS) in a 10:1 effector to target cells ratio, for 48 h at 37° C., 5% CO2. Cells were then stained with 10 uM Hoechst 33342 to visualize the cell nuclei, and 2 uM propidium iodide to specifically label the nuclei of dead cells. After incubation with the DNA stains for 90 min at 37° C., 5% CO2, the microplate wells were scanned by high content imaging (ArrayScan) to capture images of the cells. Percent specific cytotoxicity was calculated using the formula: [1−live target cell count (+BiTE)/live target cell count (−BiTE)]×100. Results are summarized in FIGS. 25 and 26.

Example 13—In Vivo Efficacy of MSLN-BiTEs

Figure 27:
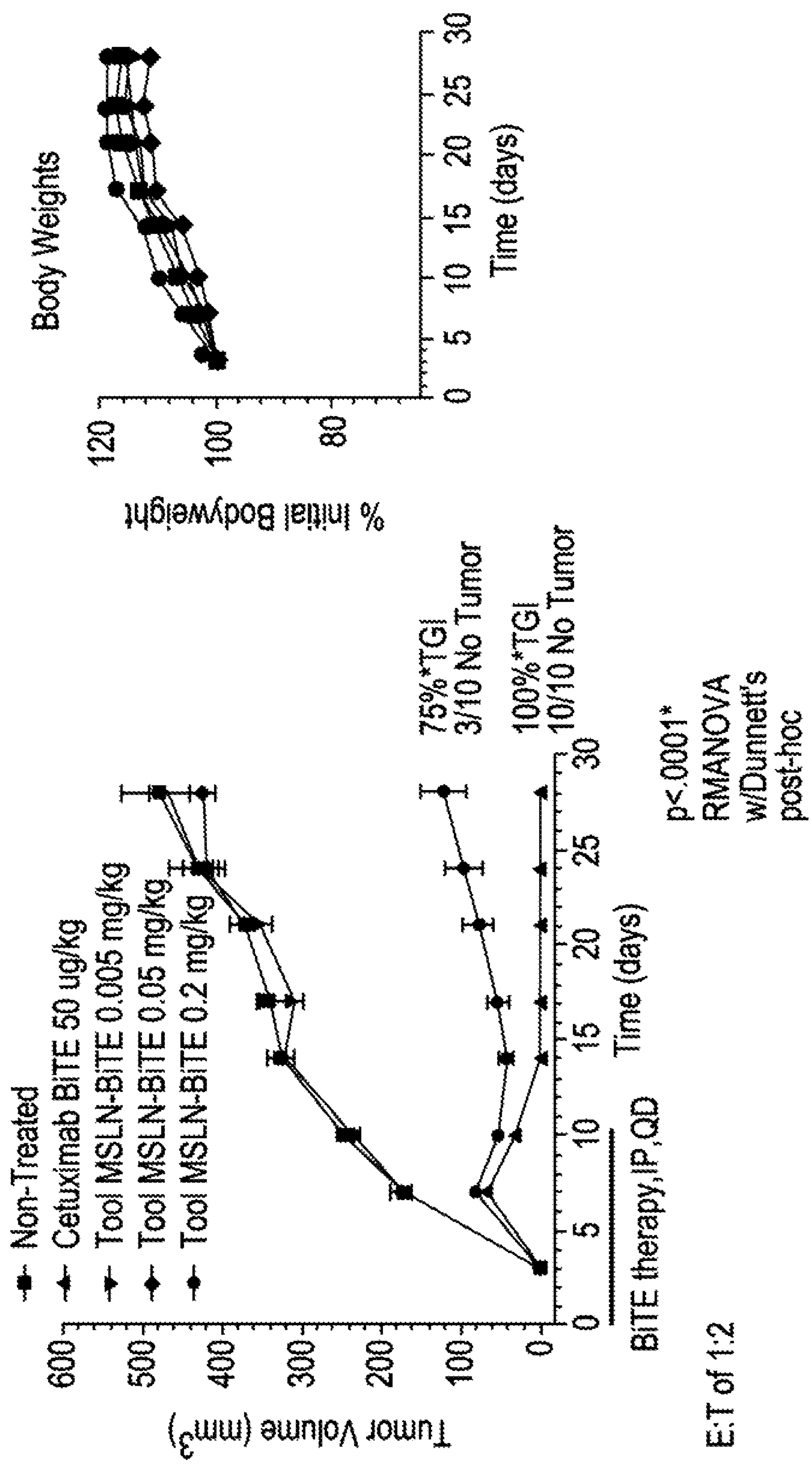
FIG. 27-29 summarize in vivo tumor growth inhibition assay using several different tumor types (gastric cancer cells, SK-OV-3, NCI-N87, OVCAR-8, A-2780) performed with an anti-MSLN/anti-CD3 BiTE molecule as compared to controls, demonstrating a dramatic reduction in tumor growth by the anti-MSLN/anti-CD3 BiTE molecule against MSLN expression tumor cells.

Admixture Model:

Athymic nude female mice (Harlan) are implanted subcutaneously in the flank with a mixture of $5\times10^6$ NCI-N87 gastric cancer cells and $2.5\times10^6$ human PBMCs (1:2 effector:target cell ratio). Mice are dosed with an intraperitoneal (ip) injection of MSLN-BiTE that contains the 2.37 scFv and the 8H9 CD3 (P73362) or vehicle control once a day for 10 days. Each dosing group contains 10 mice. Caliper measurement of tumor size is determined every 3-4 days until day 28 when the study is terminated. Body weights are maintained throughout the study. Results are summarized in FIG. 27.

Figure 29:
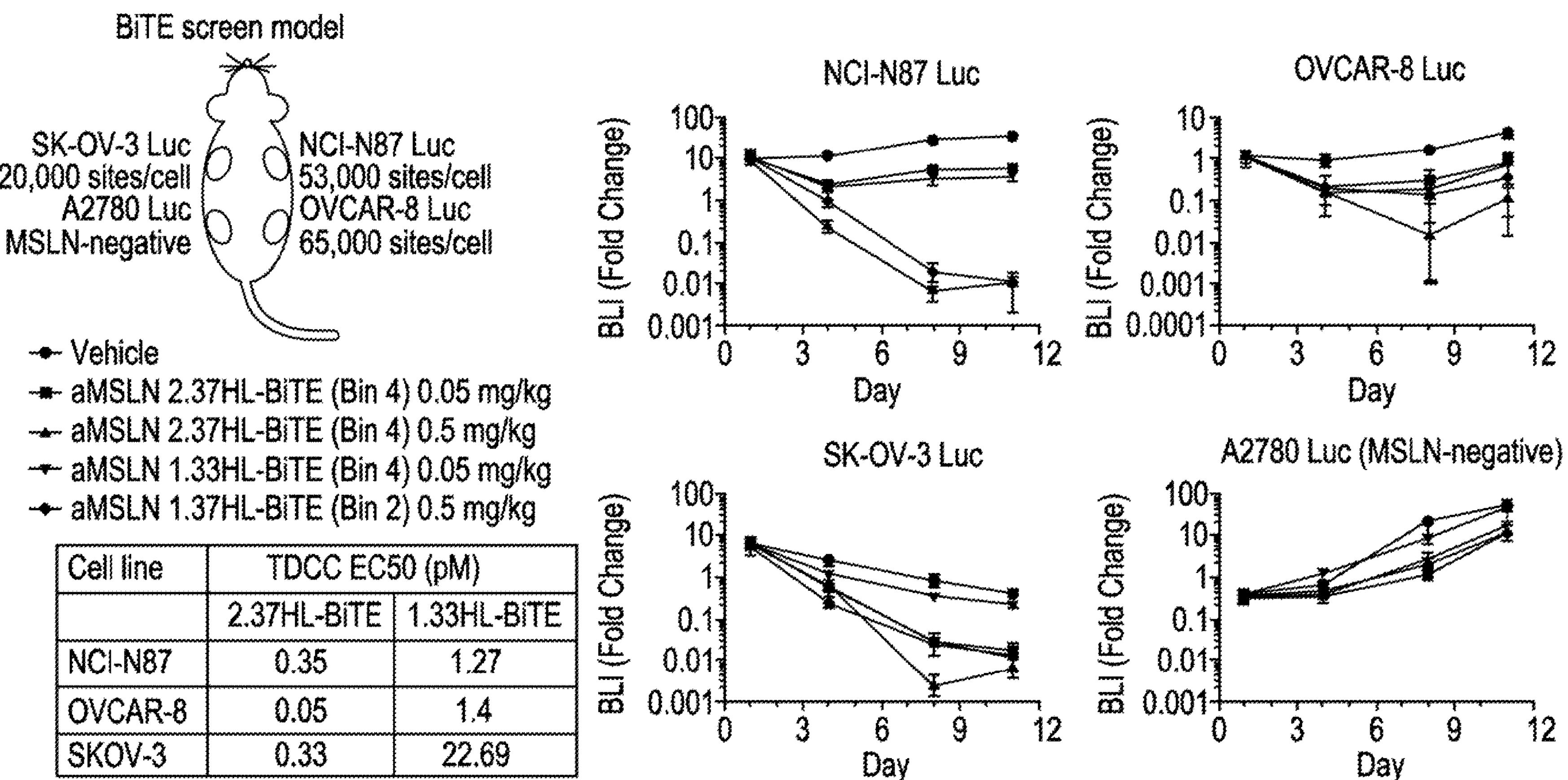
Figure 30:
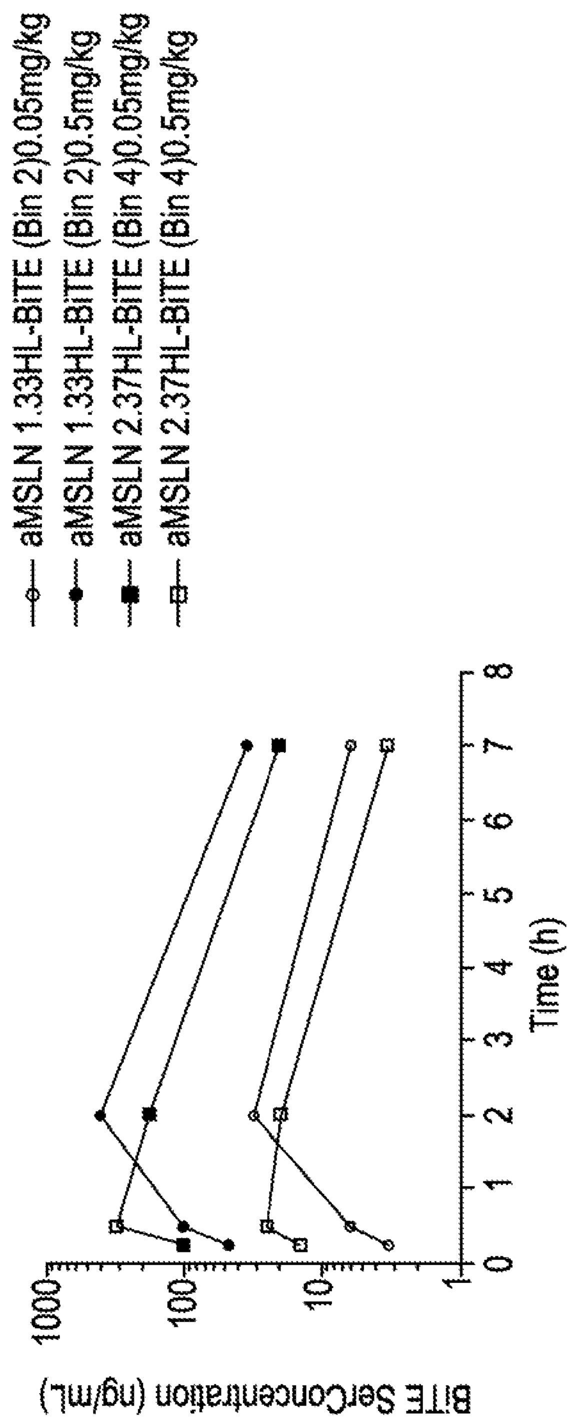
FIG. 30 summarizes the results of an in vivo pharmacokinetic assay using MSLN BiTE molecules, indicating the pharmacokinetics are consistent with inhibition of tumor growth.

BiTE Screen Model:

Athymic nude female mice (Harlan) are implanted subcutaneously with four xenograft model cell lines at different sites on the flank (see diagram in FIGS. 29 and 30). Each cancer cell line is labeled with luciferase and mixed 1:1 ($5\times10^5$ cells each) with human pan-T cells isolated from PBMCs. The BiTE screen model used here tests NCI-N87 cells (53,000 MSLN sites/cell), OVCAR-8 cells (65,000 MSLN sites/cell), SK-OV-3 cells (15,000 MSLN sites/cell) and A2780 cells (MSLN-negative). Baseline cell luciferase signal is measured by Xenogen imaging on Day 1. Mice are dosed intraperitoneally once a day for 11 days with MSLN-BiTE or vehicle, with 5 mice per dosing group. Cell luciferase signal is measured every 3 days (Day 1, 4, 7 and 11) to monitor tumor growth. Tumor growth inhibition is determined by fold change in the luciferase signal.

Figure 28:
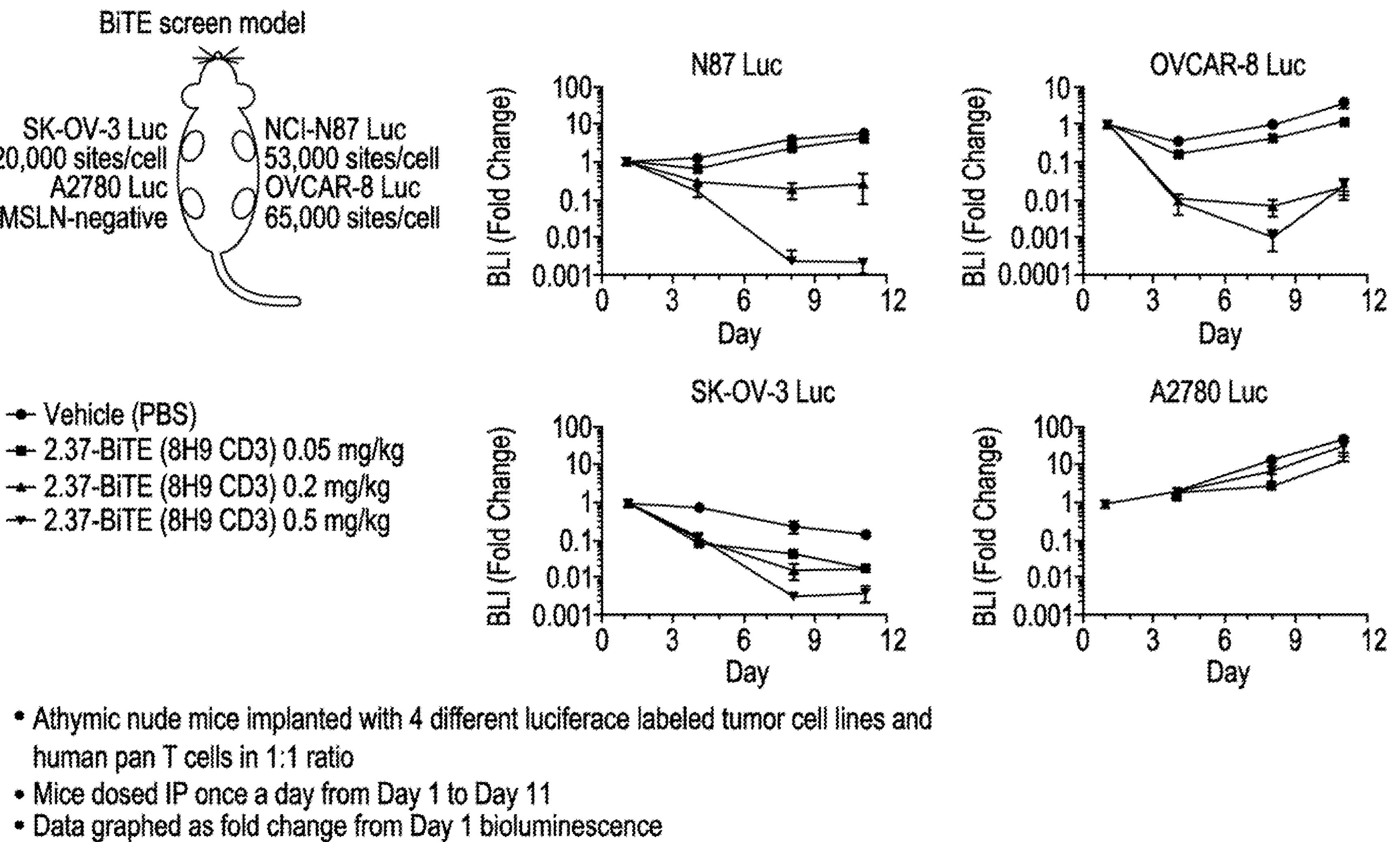

In one study, the effect of the MSLN-BiTE that contains the 2.37 scFv and the 8H9 CD3 (P73362) was tested. This study showed that the MSLN-BiTE is active in the BiTE screen model. Growth of cancer cell lines that express MSLN is inhibited, and growth of the MSLN-negative cell line A2780 was not affected. Results are summarized in FIG. 28.

In another study, in vivo activity of the MSLN-BiTE proteins 2.37HL-BiTE and 1.33HL-BiTE, which use the I2C CD3, were tested. Both MSLN-BiTE proteins were active in the BiTE screen, and inhibited tumor growth of the MSLN-expressing cell lines. Results are summarized in FIG. 29.

Blood plasma pharmacokinetics of the MSLN-BiTE showed increased levels of the BiTE present with higher dose, consistent with the dose-dependent effect on tumor growth (FIG. 30).

Each reference cited herein is hereby incorporated by reference in its entirety for all that it teaches and for all purposes.

The present invention is not to be limited in scope by the specific embodiments described herein, which are intended as single illustrations of individual aspects of the invention, and functionally equivalent methods and components are invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method of determining if a subject has mesothelin expressing tumor cells, comprising:

contacting a tumor sample from the subject with an antibody, antigen binding protein, or fragment thereof, wherein the antibody, antigen binding protein, or fragment thereof comprises a mesothelin binding domain comprising three heavy chain CDRs and three light chain CDRs with sequences selected from the group consisting of:

a) SEQ ID NOs: 45, 46, and 47 of the heavy chain and SEQ ID NOs: 9, 10, and 11 of the light chain;

b) SEQ ID NOs: 48, 49, and 50 of the heavy chain and SEQ ID NOs: 12, 13, and 14 of the light chain;

c) SEQ ID NOs: 51, 52, and 53 of the heavy chain and SEQ ID NOs: 15, 16, and 17 of the light chain;

d) SEQ ID NOs: 51, 52, and 53 of the heavy chain and SEQ ID NOs: 18, 19, and 20 of the light chain;

e) SEQ ID NOs: 54, 55, and 56 of the heavy chain and SEQ ID NOs: 21, 22, and 23 of the light chain;

f) SEQ ID NOs: 57, 58, and 59 of the heavy chain and SEQ ID NOs: 24, 25, and 26 of the light chain;

g) SEQ ID NOs: 60, 61, and 62 of the heavy chain and SEQ ID NOs: 27, 28, and 29 of the light chain;

h) SEQ ID NOs: 63, 64, and 65 of the heavy chain and SEQ ID NOs: 30, 31, and 32 of the light chain:

i) SEQ ID NOs: 63, 64, and 65 of the heavy chain and SEQ ID NOs: 33, 34, and 35 of the light chain:

j) SEQ ID NOs: 63, 64, and 65 of the heavy chain and SEQ ID NOs: 36, 37, and 38 of the light chain, and k) any one of (a)-(j), wherein each of the CDRs are identical to or comprise 1, 2, or 3 amino acid residue substitutions relative to their specified sequence; and detecting binding of the antibody, antigen binding protein, or fragment thereof to the sample, wherein an increase in binding of the antibody, antigen binding protein, or fragment thereof to the sample as compared to binding of the antibody, antigen binding protein, or fragment thereof to a control sample identifies the subject as having mesothelin expressing tumor cells.

2. The method of claim 1, wherein the antibody, antigen binding protein, or fragment thereof is directly labeled.

3. The method of claim 1, wherein the mesothelin binding domain comprises a heavy chain variable domain and a light chain variable domain, each comprising at least 90% identity to the heavy chain variable domain and the light chain variable domain selected from the group consisting of:

a) the heavy chain variable domain comprising the sequence set forth in SEQ ID NO: 86 and the light chain variable domain comprising the sequence set forth in SEQ ID NO: 72;

b) the heavy chain variable domain comprising the sequence set forth in SEQ ID NO: 87 and the light chain variable domain comprising the sequence set forth in SEQ ID NO: 73;

c) the heavy chain variable domain comprising the sequence set forth in SEQ ID NO: 88 and the light chain variable domain comprising the sequence set forth in SEQ ID NO: 74;

d) the heavy chain variable domain comprising the sequence set forth in SEQ ID NO: 88 and the light chain variable domain comprising the sequence set forth in SEQ ID NO: 75;

e) the heavy chain variable domain comprising the sequence set forth in SEQ ID NO: 89 and the light chain variable domain comprising the sequence set forth in SEQ ID NO: 76;

f) the heavy chain variable domain comprising the sequence set forth in SEQ ID NO: 90 and the light chain variable domain comprising the sequence set forth in SEQ ID NO: 77;

g) the heavy chain variable domain comprising the sequence set forth in SEQ ID NO: 91 and the light chain variable domain comprising SEQ ID NO: 78;

h) the heavy chain variable domain comprising the sequence set forth in SEQ ID NO: 92 and the light chain variable domain comprising the sequence set forth in SEQ ID NO: 79;

i) the heavy chain variable domain comprising the sequence set forth in SEQ ID NO: 92 and the light chain variable domain comprising the sequence set forth in SEQ ID NO: 80;

j) the heavy chain variable domain comprising the sequence set forth in SEQ ID NO: 92 and the light chain variable domain comprising the sequence set forth in SEQ ID NO: 81;

k) the heavy chain variable domain comprising the sequence set forth in SEQ ID NO: 93 and the light chain variable domain comprising the sequence set forth in SEQ ID NO: 82; and l) the heavy chain variable domain comprising the sequence set forth in SEQ ID NO: 94 and the light chain variable domain comprising the sequence set forth in SEQ ID NO: 83.

4. The method of claim 1, wherein the mesothelin binding domain comprises a heavy chain variable domain and a light chain variable domain, each comprising at least 95% identity to the heavy chain variable domain and the light chain variable domain selected from the group consisting of:

a) the heavy chain variable domain comprising the sequence set forth in SEQ ID NO: 86 and the light chain variable domain comprising the sequence set forth in SEQ ID NO: 72;

b) the heavy chain variable domain comprising the sequence set forth in SEQ ID NO: 87 and the light chain variable domain comprising the sequence set forth in SEQ ID NO: 73;

c) the heavy chain variable domain comprising the sequence set forth in SEQ ID NO: 88 and the light chain variable domain comprising the sequence set forth in SEQ ID NO: 74;

d) the heavy chain variable domain comprising the sequence set forth in SEQ ID NO: 88 and the light chain variable domain comprising the sequence set forth in SEQ ID NO: 75;

e) the heavy chain variable domain comprising the sequence set forth in SEQ ID NO: 89 and the light chain variable domain comprising the sequence set forth in SEQ ID NO: 76;

f) the heavy chain variable domain comprising the sequence set forth in SEQ ID NO: 90 and the light chain variable domain comprising the sequence set forth in SEQ ID NO: 77;

g) the heavy chain variable domain comprising the sequence set forth in SEQ ID NO: 91 and the light chain variable domain comprising SEQ ID NO: 78;

h) the heavy chain variable domain comprising the sequence set forth in SEQ ID NO: 92 and the light chain variable domain comprising the sequence set forth in SEQ ID NO: 79;

i) the heavy chain variable domain comprising the sequence set forth in SEQ ID NO: 92 and the light chain variable domain comprising the sequence set forth in SEQ ID NO: 80;

j) the heavy chain variable domain comprising the sequence set forth in SEQ ID NO: 92 and the light chain variable domain comprising the sequence set forth in SEQ ID NO: 81;

k) the heavy chain variable domain comprising the sequence set forth in SEQ ID NO: 93 and the light chain variable domain comprising the sequence set forth in SEQ ID NO: 82; and l) the heavy chain variable domain comprising the sequence set forth in SEQ ID NO: 94 and the light chain variable domain comprising the sequence set forth in SEQ ID NO: 83.

5. The method of claim 1, wherein the mesothelin binding domain comprises a heavy chain variable domain and a light chain variable domain, each comprising at least 96%, 97%, 98%, or 99% identity to the heavy chain variable domain and the light chain variable domain selected from the group consisting of:

a) the heavy chain variable domain comprising the sequence set forth in SEQ ID NO: 86 and the light chain variable domain comprising the sequence set forth in SEQ ID NO: 72;

b) the heavy chain variable domain comprising the sequence set forth in SEQ ID NO: 87 and the light chain variable domain comprising the sequence set forth in SEQ ID NO: 73;

c) the heavy chain variable domain comprising the sequence set forth in SEQ ID NO: 88 and the light chain variable domain comprising the sequence set forth in SEQ ID NO: 74;

d) the heavy chain variable domain comprising the sequence set forth in SEQ ID NO: 88 and the light chain variable domain comprising the sequence set forth in SEQ ID NO: 75;

e) the heavy chain variable domain comprising the sequence set forth in SEQ ID NO: 89 and the light chain variable domain comprising the sequence set forth in SEQ ID NO: 76;

f) the heavy chain variable domain comprising the sequence set forth in SEQ ID NO: 90 and the light chain variable domain comprising the sequence set forth in SEQ ID NO: 77;

g) the heavy chain variable domain comprising the sequence set forth in SEQ ID NO: 91 and the light chain variable domain comprising SEQ ID NO: 78;

h) the heavy chain variable domain comprising the sequence set forth in SEQ ID NO: 92 and the light chain variable domain comprising the sequence set forth in SEQ ID NO: 79;

i) the heavy chain variable domain comprising the sequence set forth in SEQ ID NO: 92 and the light chain variable domain comprising the sequence set forth in SEQ ID NO: 80;

j) the heavy chain variable domain comprising the sequence set forth in SEQ ID NO: 92 and the light chain variable domain comprising the sequence set forth in SEQ ID NO: 81;

k) the heavy chain variable domain comprising the sequence set forth in SEQ ID NO: 93 and the light chain variable domain comprising the sequence set forth in SEQ ID NO: 82; and l) the heavy chain variable domain comprising the sequence set forth in SEQ ID NO: 94 and the light chain variable domain comprising the sequence set forth in SEQ ID NO: 83.

6. The method of claim 1, wherein the mesothelin binding domain comprises a heavy chain variable domain and a light chain variable domain selected from the group consisting of:

a) the heavy chain variable domain comprising the sequence set forth in SEQ ID NO: 86 and the light chain variable domain comprising the sequence set forth in SEQ ID NO: 72;

b) the heavy chain variable domain comprising the sequence set forth in SEQ ID NO: 87 and the light chain variable domain comprising the sequence set forth in SEQ ID NO: 73;

c) the heavy chain variable domain comprising the sequence set forth in SEQ ID NO: 88 and the light chain variable domain comprising the sequence set forth in SEQ ID NO: 74;

d) the heavy chain variable domain comprising the sequence set forth in SEQ ID NO: 88 and the light chain variable domain comprising the sequence set forth in SEQ ID NO: 75;

e) the heavy chain variable domain comprising the sequence set forth in SEQ ID NO: 89 and the light chain variable domain comprising the sequence set forth in SEQ ID NO: 76;

f) the heavy chain variable domain comprising the sequence set forth in SEQ ID NO: 90 and the light chain variable domain comprising the sequence set forth in SEQ ID NO: 77;

g) the heavy chain variable domain comprising the sequence set forth in SEQ ID NO: 91 and the light chain variable domain comprising SEQ ID NO: 78;

h) the heavy chain variable domain comprising the sequence set forth in SEQ ID NO: 92 and the light chain variable domain comprising the sequence set forth in SEQ ID NO: 79;

i) the heavy chain variable domain comprising the sequence set forth in SEQ ID NO: 92 and the light chain variable domain comprising the sequence set forth in SEQ ID NO: 80;

j) the heavy chain variable domain comprising the sequence set forth in SEQ ID NO: 92 and the light chain variable domain comprising the sequence set forth in SEQ ID NO: 81;

k) the heavy chain variable domain comprising the sequence set forth in SEQ ID NO: 93 and the light chain variable domain comprising the sequence set forth in SEQ ID NO: 82; and l) the heavy chain variable domain comprising the sequence set forth in SEQ ID NO: 94 and the light chain variable domain comprising the sequence set forth in SEQ ID NO: 83.

7. The method of claim 1, wherein the antibody is a bispecific antibody which comprises a second binding domain in addition to the mesothelin binding domain.

8. The method of claim 7, wherein the second binding domain is a CD3 binding domain.

9. The method of claim 8, wherein the CD3 binding domain binds human, mouse, rat, or cynomolgus CD3.

10. The method of claim 8, wherein the CD3 binding domain comprises a variable heavy chain region (VH) as set forth in SEQ ID NO: 118 and a variable light chain region (VL) as set forth in SEQ ID NO: 120.

11. The method of claim 8, wherein the CD3 binding domain comprises:

a) a VH CDR1 having an amino acid sequence identical to or comprising 1, 2, or 3 amino acid residue substitutions relative to SEQ ID NO: 115;

b) a VH CDR2 having an amino acid sequence identical to or comprising 1, 2, or 3 amino acid residue substitutions relative to SEQ ID NO: 116;

c) a VH CDR3 having an amino acid sequence identical to or comprising 1, 2, or 3 amino acid residue substitutions relative to SEQ ID NO: 117;

d) a VL CDR1 having an amino acid sequence identical to or comprising 1, 2, or 3 amino acid residue substitutions relative to SEQ ID NO: 112;

e) a VL CDR2 having an amino acid sequence identical to or comprising 1, 2, or 3 amino acid residue substitutions relative to SEQ ID NO: 113; and f) a VL CDR3 having an amino acid sequence identical to or comprising 1, 2, or 3 amino acid residue substitutions relative to SEQ ID NO: 114.

12. The method of claim 8, wherein the CD3 binding domain comprises a variable region as set forth in SEQ ID NO: 122.

13. The method of claim 1, wherein the antibody, antigen binding protein, or fragment thereof further comprises an IgG heavy chain constant domain and an IgG light chain constant domain.

14. The method of claim 1, wherein the antibody, antigen binding protein, or fragment thereof is a monoclonal antibody.

15. The method of claim 1, wherein the antibody, antigen binding protein, or fragment thereof is a chimeric antibody, a humanized antibody, or a fully human antibody.

16. The method of claim 1, wherein the subject is human.

17. A method of determining if a subject has mesothelin expressing tumor cells, comprising contacting a tumor sample from the subject with a bispecific single chain antibody, the bispecific single chain antibody comprising a cluster of differentiation 3 (CD3) binding domain and a mesothelin (MSLN) binding domain, wherein the variable heavy chain regions ($V_H$) and the variable light chain regions ($V_L$) regions of the bispecific antibody are arranged, from N-terminus to C-terminus, in the order, $V_H$(MSLN)-$V_L$(MSLN)-$V_H$(CD3)-$V_L$(CD3), $V_H$(CD3)-$V_L$(CD3)-$V_H$(MSLN)-$V_L$(MSLN), $V_L$(MSLN)-$V_H$(MSLN)-$V_H$(CD3)-$V_L$(CD3), $V_H$(CD3)-$V_L$(CD3)-$V_L$(MSLN)-$V_H$(MSLN), $V_L$(MSLN)-$V_H$(MSLN)-$V_L$(CD3)-$V_H$(CD3), $V_L$(CD3)-$V_H$(CD3)-$V_L$(MSLN)-$V_H$(MSLN), $V_H$(MSLN)-$V_L$(MSLN)-$V_L$(CD3)-$V_H$(CD3), or $V_L$(CD3)-$V_H$(CD3)-$V_H$(MSLN)-$V_L$(MSLN), wherein the $V_H$(MSLN) and $V_L$(MSLN) comprise three heavy chain CDRs and three light chain CDRs with sequences selected from the group consisting of:

a) SEQ ID NOs: 45, 46, and 47 of the heavy chain and SEQ ID NOs: 9, 10, and 11 of the light chain;

b) SEQ ID NOs: 48, 49, and 50 of the heavy chain and SEQ ID NOs: 12, 13, and 14 of the light chain;

c) SEQ ID NOs: 51, 52, and 53 of the heavy chain and SEQ ID NOs: 15, 16, and 17 of the light chain;

d) SEQ ID NOs: 51, 52, and 53 of the heavy chain and SEQ ID NOs: 18, 19, and 20 of the light chain;

e) SEQ ID NOs: 54, 55, and 56 of the heavy chain and SEQ ID NOs: 21, 22, and 23 of the light chain;

f) SEQ ID NOs: 57, 58, and 59 of the heavy chain and SEQ ID NOs: 24, 25, and 26 of the light chain;

g) SEQ ID NOs: 60, 61, and 62 of the heavy chain and SEQ ID NOs: 27, 28, and 29 of the light chain;

h) SEQ ID NOs: 63, 64, and 65 of the heavy chain and SEQ ID NOs: 30, 31, and 32 of the light chain;

i) SEQ ID NOs: 63, 64, and 65 of the heavy chain and SEQ ID NOs: 33, 34, and 35 of the light chain;

j) SEQ ID NOs: 63, 64, and 65 of the heavy chain and SEQ ID NOs: 36, 37, and 38 of the light chain, and k) any one of (a)-(j), wherein each of the CDRs are identical to or comprise 1, 2, or 3 amino acid residue substitutions relative to their specified sequence; and detecting binding of the antibody, antigen binding protein, or fragment thereof to the sample, wherein an increase in binding of the antibody, antigen binding protein, or fragment thereof to the sample as compared to binding of the antibody, antigen binding protein, or fragment thereof to a control sample identifies the subject as having mesothelin expressing tumor cells.

18. The method of claim 17, wherein the CD3 binding domain binds human, cynomolgus, mouse, or rat CD3 and the MSLN binding domain binds human, cynomolgus, mouse, or rat MSLN.

19. The method of claim 17, wherein the $V_H$ (MSLN) is set forth in any one of SEQ ID NOs: 86-94, the $V_L$(MSLN) is set forth in SEQ ID NOs: 72-83, the VH (CD3) is set forth in SEQ ID NO: 118, and the VL (CD3) is set forth in SEQ ID NO: 120.

20. The method of claim 17, wherein the VH (MSLN) comprises CDRs 1-3 having the sequences set forth in SEQ ID NOs: 45, 46, and 47, respectively, the VL (MSLN) comprises CDRs 1-3 having the sequences set forth in SEQ ID NOs: 9, 10, and 11, respectively, the VH (CD3) comprises CDRs 1-3 having the sequences set forth in SEQ ID NOs: 115, 116, and 117, respectively, and the VL(CD3) comprises CDRs 1-3 having the sequences set forth in SEQ ID NOs: 112, 113, and 114, respectively.

21. The method of claim 17, wherein the antibody comprises a first VH as set forth in SEQ ID NO: 86, a first VL as set forth in SEQ ID NO: 72, a second VH as set forth in SEQ ID NO: 118, and a second VL as set forth in SEQ ID NO: 120.

22. The method of claim 17, wherein the antibody comprises:

a) a first VH CDR1 having an amino acid sequence identical to or comprising 1, 2, or 3 amino acid residue substitutions relative to SEQ ID NO: 45;

b) a first VH CDR2 having an amino acid sequence identical to or comprising 1, 2, or 3 amino acid residue substitutions relative to SEQ ID NO: 46;

c) a first VH CDR3 having an amino acid sequence identical to or comprising 1, 2, or 3 amino acid residue substitutions relative to SEQ ID NO: 47;

d) a first VL CDR1 having an amino acid sequence identical to or comprising 1, 2, or 3 amino acid residue substitutions relative to SEQ ID NO: 9;

e) a first VL CDR2 having an amino acid sequence identical to or comprising 1, 2, or 3 amino acid residue substitutions relative to SEQ ID NO: 10;

f) a first VL CDR3 having an amino acid sequence identical to or comprising 1, 2, or 3 amino acid residue substitutions relative to SEQ ID NO: 11;

g) a second VH CDR1 having an amino acid sequence identical to or comprising 1, 2, or 3 amino acid residue substitutions relative to SEQ ID NO: 115;

h) a second VH CDR2 having an amino acid sequence identical to or comprising 1, 2, or 3 amino acid residue substitutions relative to SEQ ID NO: 116;

i) a second VH CDR3 having an amino acid sequence identical to or comprising 1, 2, or 3 amino acid residue substitutions relative to SEQ ID NO: 117;

j) a second VL CDR1 having an amino acid sequence identical to or comprising 1, 2, or 3 amino acid residue substitutions relative to SEQ ID NO: 112;

k) a second VL CDR2 having an amino acid sequence identical to or comprising 1, 2, or 3 amino acid residue substitutions relative to SEQ ID NO: 113; and l) a second VL CDR3 having an amino acid sequence identical to or comprising 1, 2, or 3 amino acid residue substitutions relative to SEQ ID NO: 114.

23. The method of claim 17, wherein the antibody comprises the amino acid sequence set forth in SEQ ID NO: 127 or SEQ ID NO: 129.

24. The method of claim 17, wherein the antibody comprises a first binding domain comprising any of SEQ ID NOs: 158-185 and a second binding domain comprising SEQ ID NO: 122.

25. The method of claim 17, wherein the antibody is directly labeled.

26. The method of claim 17, wherein the subject is human.

* * * * *

UNITED STATES PATENT AND TRADEMARK OFFICE

CERTIFICATE OF CORRECTION

PATENT NO. : 11,866,508 B2
APPLICATION NO. : 17/142850
DATED : January 9, 2024
INVENTOR(S) : William Christian Fanslow, III et al.

It is certified that error appears in the above-identified patent and that said Letters Patent is hereby corrected as shown below:

In the Claims

At Column 283, Line 60, "chain:" should be -- chain; --.

At Column 283, Line 62, "chain:" should be -- chain; --.

Signed and Sealed this
Twenty-second Day of October, 2024

Katherine Kelly Vidal

Katherine Kelly Vidal
*Director of the United States Patent and Trademark Office*